US012648354B2

(12) United States Patent
Horiuchi et al.

(10) Patent No.: US 12,648,354 B2
(45) Date of Patent: Jun. 2, 2026

(54) ORGANIC COMPOUND AND ORGANIC LIGHT-EMITTING ELEMENT

(71) Applicant: CANON KABUSHIKI KAISHA, Tokyo (JP)

(72) Inventors: Takayuki Horiuchi, Kanagawa (JP); Hiroki Ohrui, Tokyo (JP); Hironobu Iwawaki, Kanagawa (JP); Yosuke Nishide, Kanagawa (JP); Hirokazu Miyashita, Miyagi (JP); Naoki Yamada, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 381 days.

(21) Appl. No.: 18/331,856

(22) Filed: Jun. 8, 2023

(65) Prior Publication Data

US 2023/0403933 A1 Dec. 14, 2023

(30) Foreign Application Priority Data

Jun. 10, 2022 (JP) ................................ 2022-094225

(51) Int. Cl.

| | |
|---|---|
| ***C07D 493/04*** | (2006.01) |
| ***C09K 11/06*** | (2006.01) |
| ***G03G 15/04*** | (2006.01) |
| ***H01L 51/00*** | (2006.01) |
| ***H10K 85/60*** | (2023.01) |
| *H10K 50/11* | (2023.01) |

(52) U.S. Cl.

CPC ....... *H10K 85/6574* (2023.02); *C07D 493/04* (2013.01); *C09K 11/06* (2013.01); *G03G 15/04036* (2013.01); *H10K 85/626* (2023.02); *C09K 2211/1018* (2013.01); *H10K 50/11* (2023.02)

(58) Field of Classification Search

CPC .. C07D 493/04; H10K 85/6574; H10K 50/00; C07F 15/0033; C07F 15/0086

USPC .......................... 549/382, 212, 275; 313/498

See application file for complete search history.

(56) References Cited

U.S. PATENT DOCUMENTS

2020/0044159 A1 2/2020 Yamatani
2022/0144857 A1 5/2022 Nishide et al.

FOREIGN PATENT DOCUMENTS

DE 4211420 A1 * 7/1993 ........... C07D 493/04
JP 2009533852 A 9/2009
JP 2014139987 A 7/2014

OTHER PUBLICATIONS

Sugiyama Yoko et al., Synthesis and Evaluation of Deuterated OLED Material, Taiyo Nippon Sanso Technical Report No. 32 (2013), p. 5-p. 8.

* cited by examiner

*Primary Examiner* — Charanjit Aulakh
(74) *Attorney, Agent, or Firm* — CANON U.S.A., INC. IP DIVISION

(57) ABSTRACT

An organic compound represented by formula [1]:

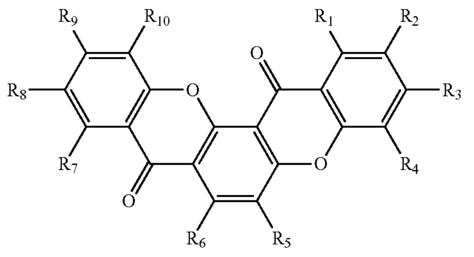

[1]

$R_1$ to $R_{10}$ are each independently selected from the group consisting of a hydrogen atom, a deuterium atom, a substituted or unsubstituted alkyl group, a substituted or unsubstituted aryl group, and a substituted or unsubstituted heterocyclic group. However, at least one of $R_2$, $R_3$, $R_8$, and $R_9$ is selected from the group consisting of a deuterium atom, a substituted or unsubstituted alkyl group, a substituted or unsubstituted aryl group, and a substituted or unsubstituted heterocyclic group.

20 Claims, 7 Drawing Sheets

ORGANIC COMPOUND AND ORGANIC LIGHT-EMITTING ELEMENT

BACKGROUND OF THE INVENTION

Field of the Invention

The present disclosure relates to an organic compound and an organic light-emitting element.

Description of the Related Art

An organic light-emitting element (hereinafter, may be referred to as an "organic electroluminescence element" or an "organic EL element") is an electronic element including a pair of electrodes and an organic compound layer disposed between the electrodes. The injection of electrons and holes from this pair of electrodes generates excitons of a light-emitting organic compound in the organic compound layer, and the organic light-emitting element emits light when the excitons return to the ground state. Recently, organic light-emitting elements have been remarkably progressed, and a low drive voltage, a wide variety of emission wavelengths, a high-speed response, and a reduction in thickness and weight of light-emitting devices have been achieved.

Compounds suitable for organic light-emitting elements have been actively created to date. This is because the creation of compounds having good element lifetime characteristics is important to provide high-performance organic light-emitting elements. An example of a compound that has been created to date is chromeno[2,3-a]xanthene-8,14-dione (CXD) disclosed in U.S. Patent Application Publication No. 2020/44159 (PTL 1).

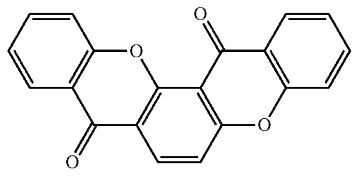

CXD

PTL 1 discloses that CXD is used as a host in a light-emitting layer of an organic light-emitting element. However, further improvements in light emission efficiency and durability characteristics are desired.

SUMMARY OF THE INVENTION

In view of the above disadvantages, the present disclosure provides an organic compound and an organic light-emitting element having good light emission efficiency and durability characteristics.

An organic compound according to an embodiment of the present disclosure is represented by formula [1].

[1]

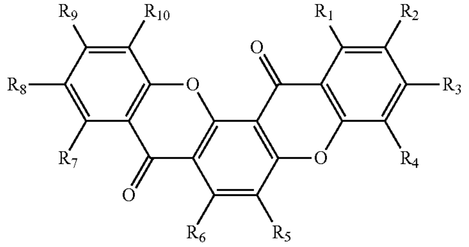

In formula [1], $R_1$ to $R_{10}$ are each independently selected from the group consisting of a hydrogen atom, a deuterium atom, a substituted or unsubstituted alkyl group, a substituted or unsubstituted aryl group, and a substituted or unsubstituted heterocyclic group, provided that at least one of $R_2$, $R_3$, $R_8$, and $R_9$ is selected from the group consisting of a deuterium atom, a substituted or unsubstituted alkyl group, a substituted or unsubstituted aryl group, and a substituted or unsubstituted heterocyclic group.

Further features of the present disclosure will become apparent from the following description of exemplary embodiments with reference to the attached drawings.

DESCRIPTION OF THE EMBODIMENTS

Organic Compound

Figure 1A:
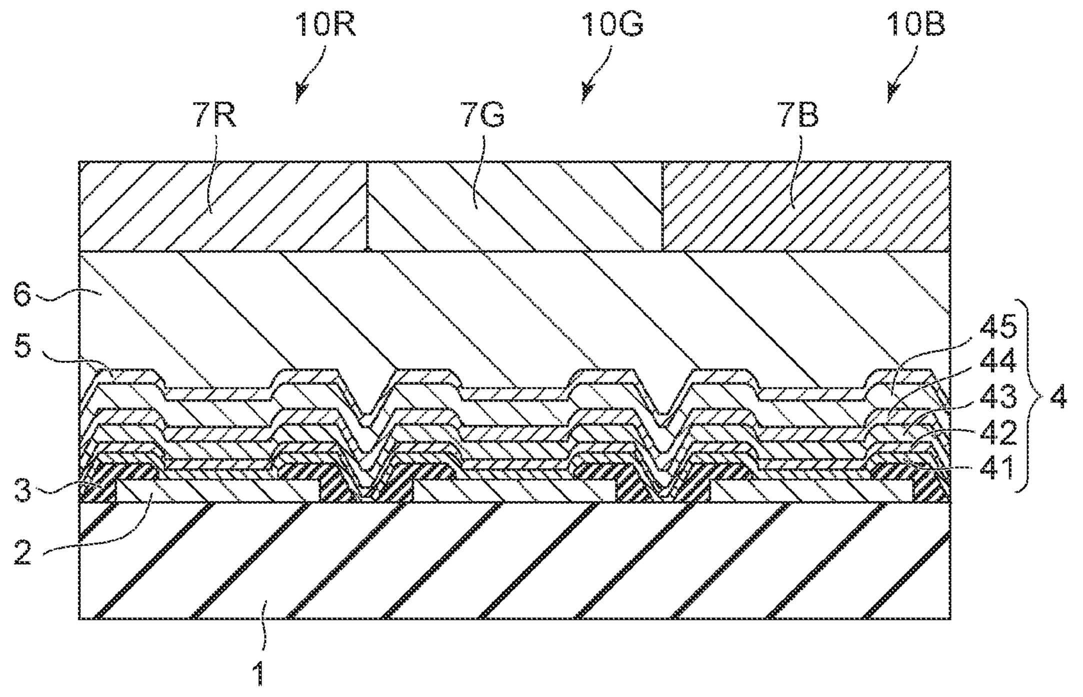
FIG. 1A is a schematic sectional view illustrating an example of a pixel of a display apparatus according to an embodiment of the present disclosure.

An organic compound according to this embodiment is represented by general formula [1].

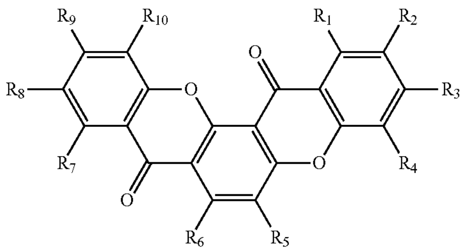
[1]

$R_1$ to $R_{10}$

In general formula [1], $R_1$ to $R_{10}$ are each independently selected from a hydrogen atom, a deuterium atom, a substituted or unsubstituted alkyl group, a substituted or unsubstituted aryl group, and a substituted or unsubstituted heterocyclic group. However, at least one of $R_2$, $R_3$, $R_8$, and $R_9$ is selected from a deuterium atom, a substituted or unsubstituted alkyl group, a substituted or unsubstituted aryl group, and a substituted or unsubstituted heterocyclic group.

At least one or two, preferably two of $R_2$, $R_3$, $R_8$, and $R_9$ are preferably selected from a substituted or unsubstituted alkyl group, a substituted or unsubstituted aryl group, and a substituted or unsubstituted heterocyclic group, and more preferably selected from a substituted or unsubstituted aryl group and a substituted or unsubstituted heterocyclic group. Furthermore, at least one of $R_2$ and $R_3$ and at least one of $R_8$ and $R_9$ are preferably selected from a substituted or unsubstituted alkyl group, a substituted or unsubstituted aryl group, and a substituted or unsubstituted heterocyclic group, and more preferably selected from a substituted or unsubstituted aryl group and a substituted or unsubstituted heterocyclic group. Most preferably, $R_2$ and $R_8$ are preferably selected from a substituted or unsubstituted alkyl group, a substituted or unsubstituted aryl group, and a substituted or unsubstituted heterocyclic group, and more preferably selected from a substituted or unsubstituted aryl group and a substituted or unsubstituted heterocyclic group.

Examples of the alkyl group include, but are not limited to, a methyl group, an ethyl group, a normal propyl group, an isopropyl group, a normal butyl group, a tertiary butyl group, an isobutyl group, a secondary butyl group, an octyl group, a dodecyl group, a cyclohexyl group, a 1-adamantyl group, and a 2-adamantyl group. Of these, a methyl group and a tertiary butyl group are preferred.

Examples of the aryl group include, but are not limited to, a phenyl group, a naphthyl group, an indenyl group, a biphenyl group, a terphenyl group, a fluorenyl group, an anthracenyl group, a phenanthryl group, a fluoranthenyl group, a pyrenyl group, a chrysenyl group, a triphenylenyl group, and a perylenyl group. Of these, a phenyl group, a biphenyl group, a terphenyl group, a fluorenyl group, and a phenanthryl group are preferred.

Examples of the heterocyclic group include, but are not limited to, a pyridyl group, a pyrimidyl group, a pyrazyl group, a triazyl group, a triazolyl group, an oxazolyl group, an oxadiazolyl group, a thiazolyl group, a thiadiazolyl group, a quinolyl group, an acridinyl group, a phenanthrolyl group, a dibenzofuranyl group, and a dibenzothienyl group. Of these, a pyridyl group, a pyrimidyl group, a pyrazyl group, a triazyl group, a phenanthrolyl group, a dibenzofuranyl group, and a dibenzothienyl group are preferred. The heterocyclic group is preferably a heteroaryl group and preferably a group bonded through a carbon atom.

Examples of substituents that may be further contained in the alkyl group, the aryl group, and the heterocyclic group include, but are not limited to, a deuterium atom; alkyl groups such as a methyl group, an ethyl group, a normal propyl group, an isopropyl group, a normal butyl group, a tertiary butyl group, a secondary butyl group, an octyl group, a cyclohexyl group, a 1-adamantyl group, and a 2-adamantyl group; aryl groups such as a phenyl group, a naphthyl group, an indenyl group, a biphenyl group, a terphenyl group, a fluorenyl group, a phenanthryl group, a fluoranthenyl group, and a triphenylenyl group; heterocyclic groups such as a pyridyl group, a pyrimidyl group, a pyrazyl group, a triazyl group, a triazolyl group, an oxazolyl group, an oxadiazolyl group, a thiazolyl group, a thiadiazolyl group, an acridinyl group, a phenanthrolyl group, a dibenzofuranyl group, and a dibenzothienyl group; and a cyano group.

The organic compound according to this embodiment has a structure in which a specific group other than a hydrogen atom is introduced at a specific position in the CXD skeleton. As a result, chemical stability is improved compared with CXD, and good durability characteristics can be achieved when the organic compound is used as a host molecule in a light-emitting layer of an organic light-emitting element. The mechanism of the operation and effect will be described in detail below Hydrocarbon-based or heterocyclic-based fused polycyclic compounds have a high electron density on the plane of the rings and have high chemical reactivity. It is known that, in particular, such compounds have high reactivity to an electrophilic substitution reaction and react with an electrophilic chemical species in a state of lack of electrons. In addition, in a light-emitting layer of an organic light-emitting element, a host molecule in a radical cation state is present as a hole carrier. This molecule in a one-electron oxidation state behaves as an electrophilic chemical species and may react with another host molecule. In view of this, stability of compounds in an oxidation state was evaluated by cyclic voltammetry (CV).

In CXD, when sweeping was repeatedly conducted on the oxidation side, a peak was newly observed. This is probably because an electrophilic chemical species such as a radical cation generated by oxidation of CXD causes a chemical reaction such as an electrophilic substitution reaction to generate a new molecule. On the other hand, in exemplary compounds A-1 and A-40 in which groups other than hydrogen atoms are introduced at $R_2$ and $R_8$ in general formula [1] and exemplary compounds C-1 and C-19 in which groups other than hydrogen atoms are introduced at $R_3$ and $R_9$ in general formula [1], no new peak with repeated sweeping was observed. Table 1 summarizes these results.

The cyclic voltammetry (CV) was performed in an acetonitrile solution of 0.1 M tetrabutylammonium perchlorate and measured using $Ag/Ag^+$ as a reference electrode, Pt as a counter electrode, and glassy carbon as a working electrode. The sweep rate in the repeated sweeping was 1.0 V/s. The measuring device used was an electrochemical analyzer, model 660C manufactured by ALS Co., Ltd.

TABLE 1

| Name of compound | Structure | Appearance of new peak in repeated measurements of CV |
|---|---|---|
| CXD | 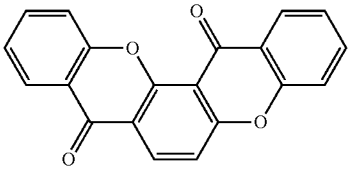 [SMILES: O=c1c2ccccc2oc2c1ccc1oc3ccccc3c(=O)c12] | Appear |
| Exemplary compound A-1 | 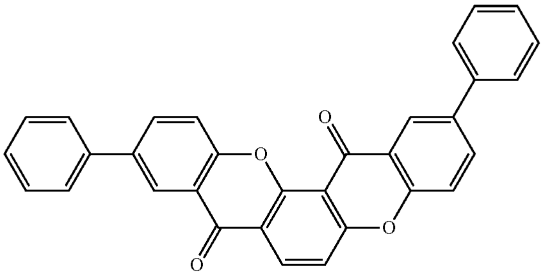 [SMILES: O=c1c2cc(-c3ccccc3)ccc2oc2c1ccc1oc3ccc(-c4ccccc4)cc3c(=O)c12] | Not appear |
| Exemplary compound A-40 | 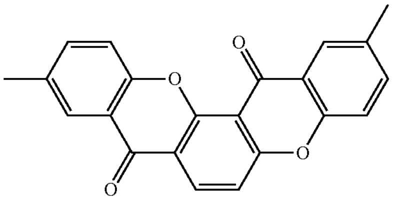 | Not appear |
| Exemplary compound C-1 | 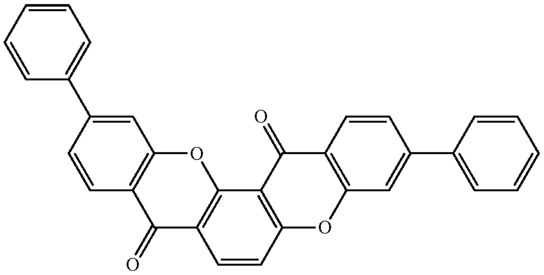 [SMILES: O=c1c2ccc(-c3ccccc3)cc2oc2c1ccc1oc3cc(-c4ccccc4)ccc3c(=O)c12] | Not appear |
| Exemplary compound C-19 | 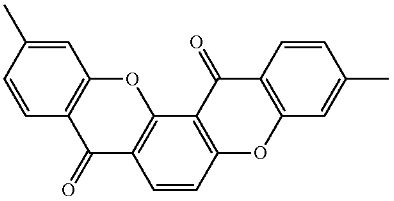 [SMILES: Cc1ccc2c(=O)c3ccc4oc5cc(C)ccc5c(=O)c4c3oc2c1] | Not appear |

Thus, stability in the oxidation state was improved by introducing groups other than hydrogen atoms at specific positions of the CXD skeleton. The factor of this is presumed as follows. The CXD skeleton has phenolic oxygen atoms and has a particularly high electron density at the para-positions of the phenolic oxygen atoms, that is, on carbon atoms (respectively referred to as C2 and C10) to which $R_2$ and $R_8$ in general formula [1] are bonded. Accordingly, C2 and C10 are in a state of easily forming a bond when attacked by an electrophilic chemical species. In the case of CXD, since only hydrogen atoms are bonded to carbon atoms adjacent to C2 and C10, an electrophilic chemical species can attack C2 and C10 without any steric hindrance. On the other hand, in compounds in which groups other than hydrogen atoms are introduced at $R_2$ and $R_8$ in general formula [1], and compounds in which groups other than hydrogen atoms are introduced at $R_3$ and $R_9$ in general formula [1], the attack on C2 and C10 by an electrophilic chemical species is reduced by the steric hindrance of the groups other than hydrogen atoms. It is considered that, as a result, the compounds according to this embodiment were stable without undergoing a chemical reaction in the oxidation state.

It is known that the electron density is high not only at the para-positions of the phenolic oxygen atoms but also at the ortho-positions. However, due to the steric hindrance of the phenolic oxygen atoms themselves, carbon atoms at the ortho-positions are less likely to be attacked by an electrophilic chemical species having a large size. In fact, referring to the results in Table 1, in the compounds having the CXD skeleton, even when groups other than hydrogen atoms are not introduced at the ortho-positions, an appearance of a new peak is not observed in CV (exemplary compounds A-1, A-40, C-1, and C-19). Accordingly, from the viewpoint of decomposition by an electrophilic chemical species, groups other than hydrogen atoms can be introduced at least the para-positions (C2 and C10) or carbon atoms adjacent to C2 or C10 because a high effect is obtained.

The carbon atoms adjacent to C2 or C10 are carbon atoms to which $R_3$ and $R_9$ in general formula [1] are bonded and carbon atoms (respectively referred to as C1 and C9) to which $R_1$ and $R_7$ are bonded. If groups other than hydrogen atoms are introduced to C1 and C9, steric repulsion with the oxygen atoms of the carbonyl groups is caused, distortion is generated in the whole molecule, and the bond energy of the molecule may decrease. Consequently, when high excitation energy is provided in a light-emitting layer of an organic light-emitting element, the molecule may be decomposed by breakage of the bond, resulting in a decrease in durability performance. Accordingly, from the viewpoint of durability performance, groups other than hydrogen atoms can be introduced to the carbon atoms to which $R_3$ and $R_9$ are bonded.

A group other than a hydrogen atom introduced at least one of $R_2$, $R_3$, $R_8$, and $R_9$ may be bonded to the CXD skeleton through a carbon-carbon bond with a high bond energy. Examples of such a group other than a hydrogen atom include substituted or unsubstituted alkyl groups, substituted or unsubstituted aryl groups, and substituted or unsubstituted heterocyclic groups. In this carbon-carbon bond, the carbon atom of the CXD skeleton has an $sp^2$ hybrid orbital. Thus, the carbon atom of the group other than a hydrogen atom can have an $sp^2$ hybrid orbital rather than an $sp^3$ hybrid orbital because of its higher bond energy. Examples of such a group other than a hydrogen atom include substituted or unsubstituted aryl groups and substituted or unsubstituted heterocyclic groups.

Thus, the organic compound according to this embodiment is more chemically stable than CXD in the oxidation state and achieves improved durability performance when used as a host molecule in a light-emitting layer of an organic light-emitting element.

Furthermore, not only durability performance of the organic light-emitting element but also the light emission efficiency thereof was found to be improved. Although the detailed mechanism is not clear, this is presumably because excessive aggregation and stacking of the CXD skeleton are reduced by introducing the groups other than hydrogen atoms, and an exciton deactivation site is less likely to be generated.

Specific structural formulae of the organic compound according to this embodiment are shown below. However, the present disclosure is not limited to these.

A-1

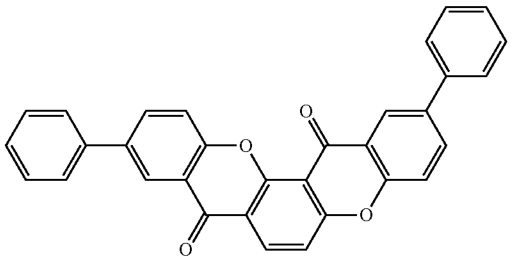

A-2

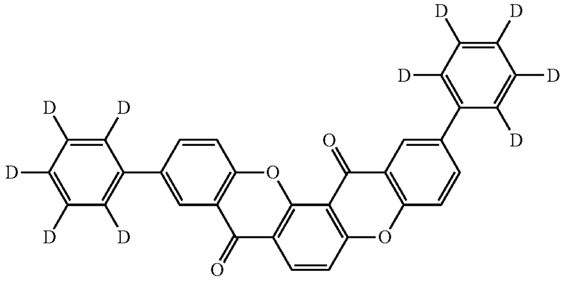

A-3

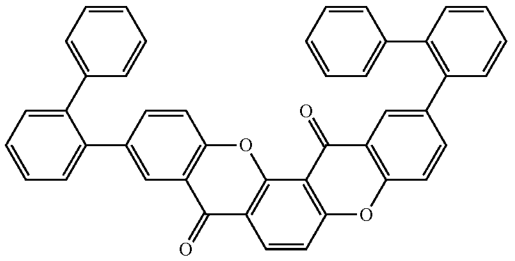

A-4

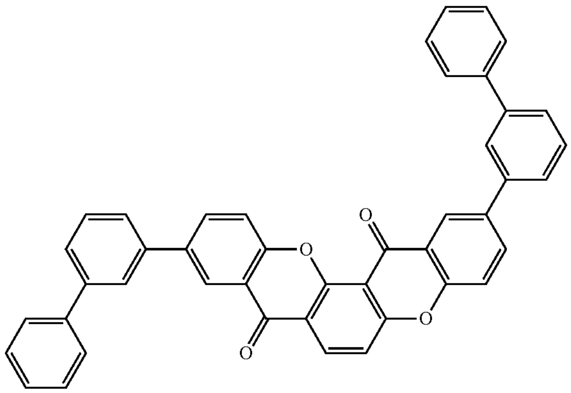

-continued
A-5
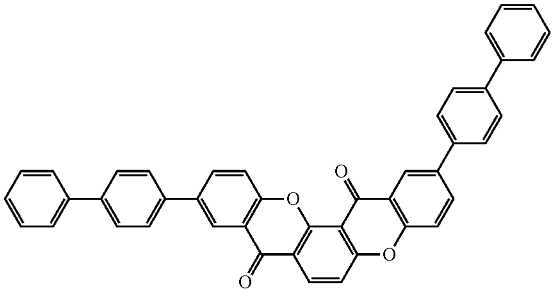
A-6
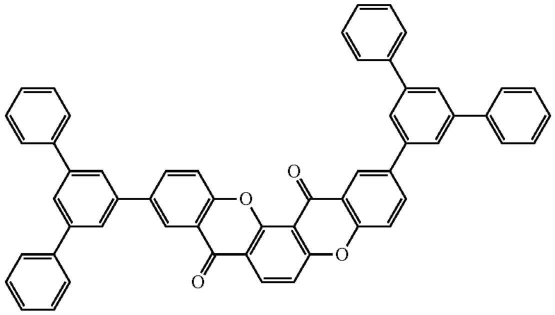
A-7
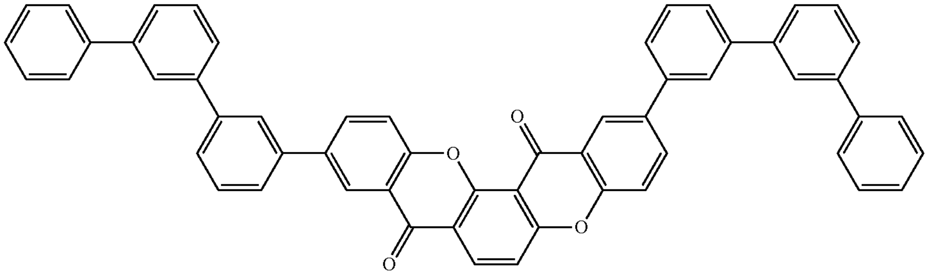
A-8
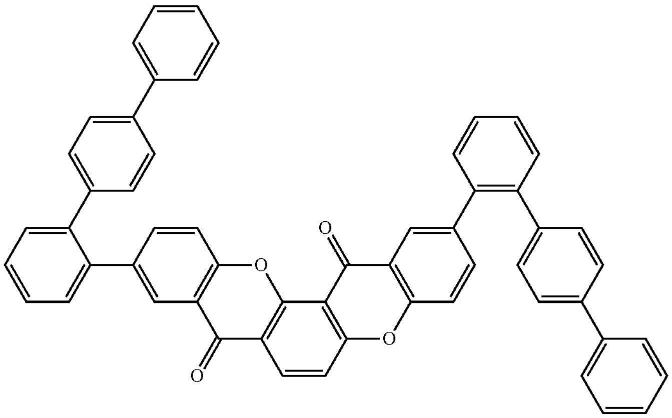
A-9
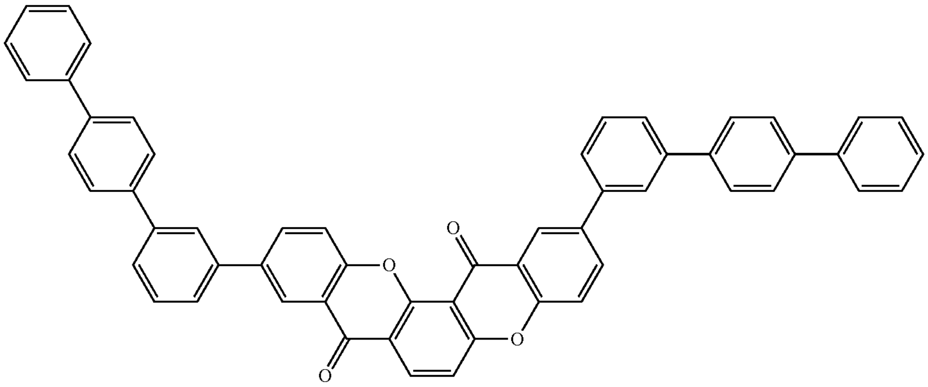

-continued
A-10
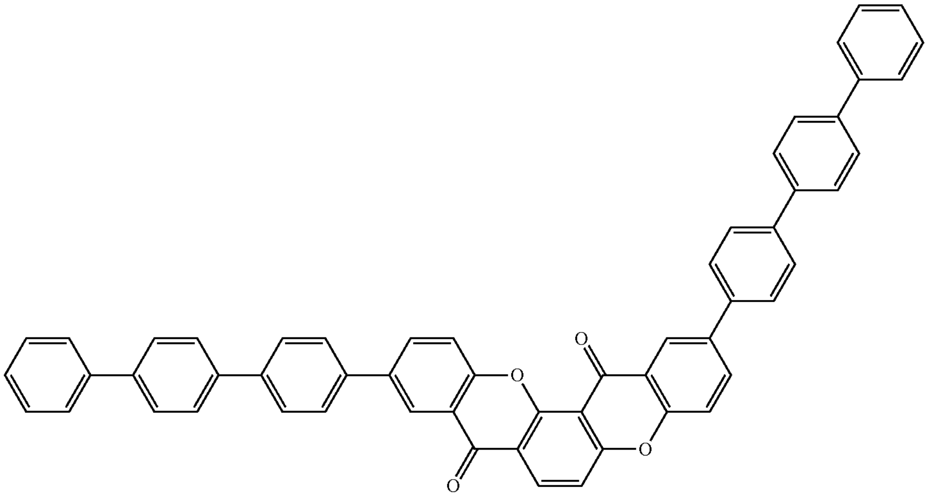
A-11
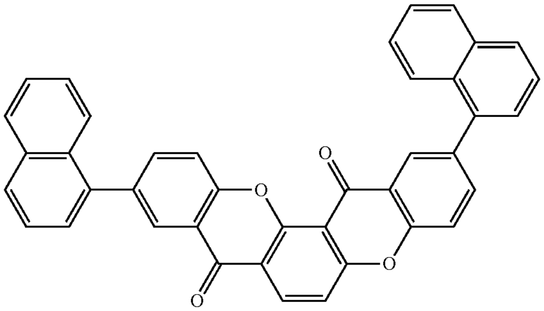
A-12
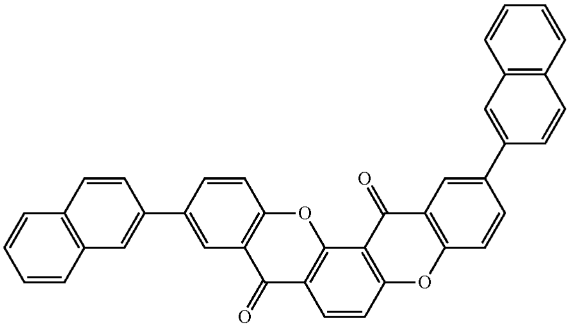
A-13
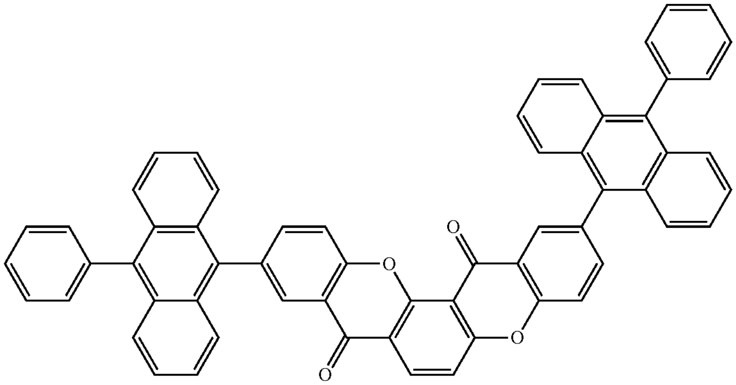

-continued
A-14
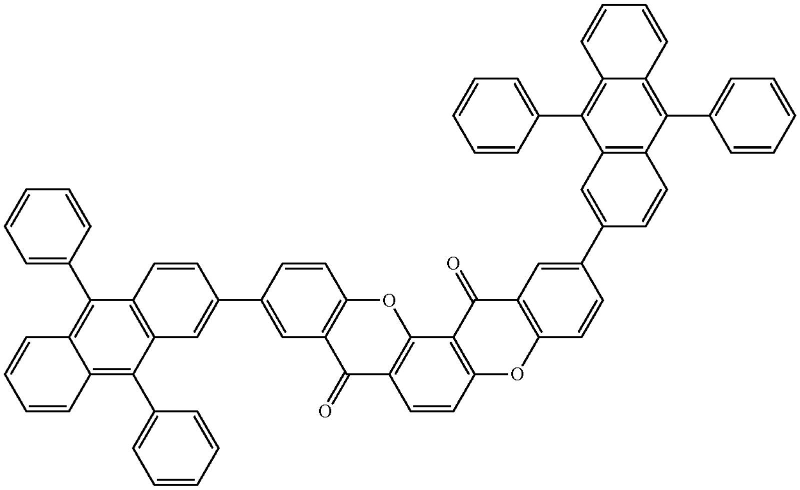
A-15
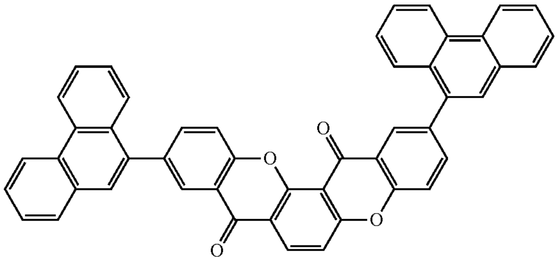
A-16
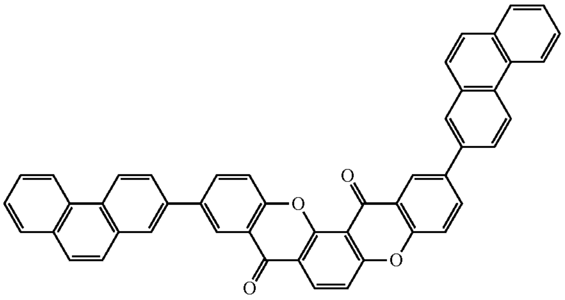
A-17
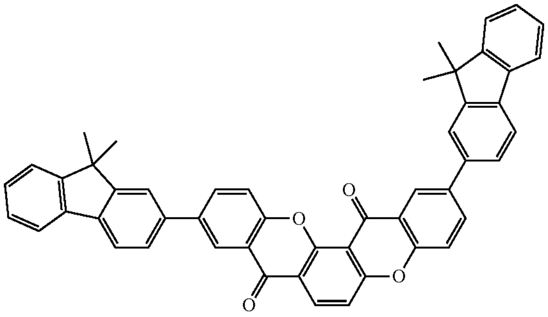
A-18
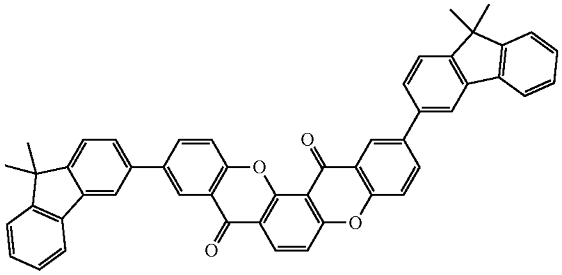
A-19
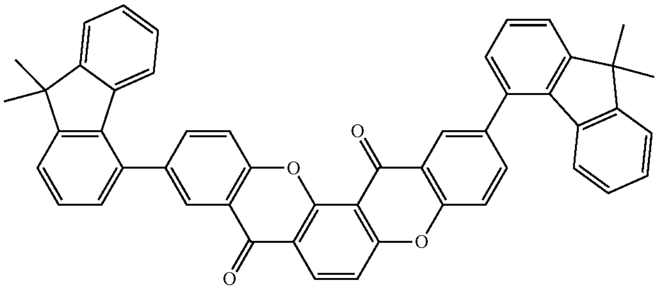

-continued
A-20
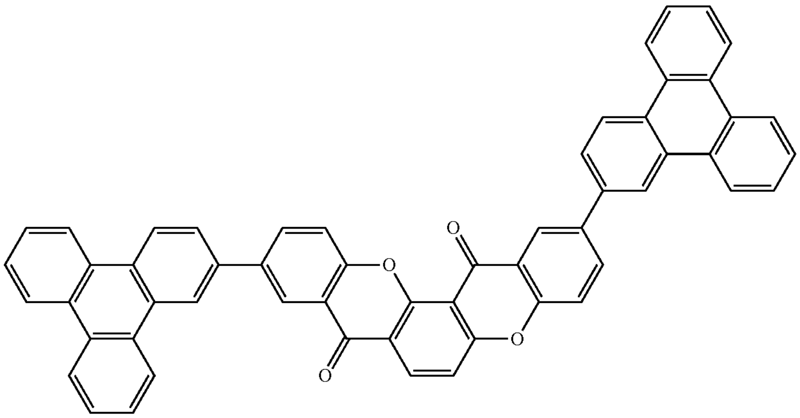
A-21
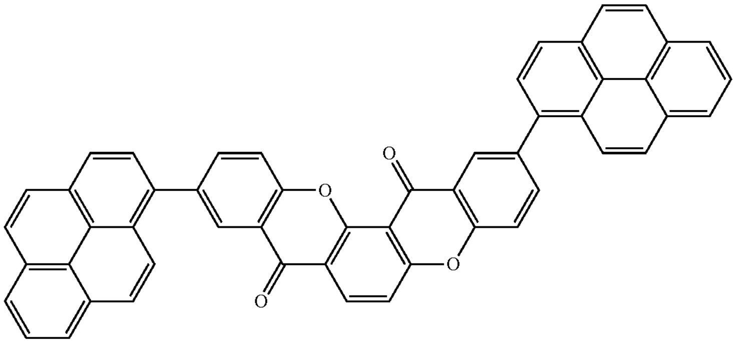
A-22
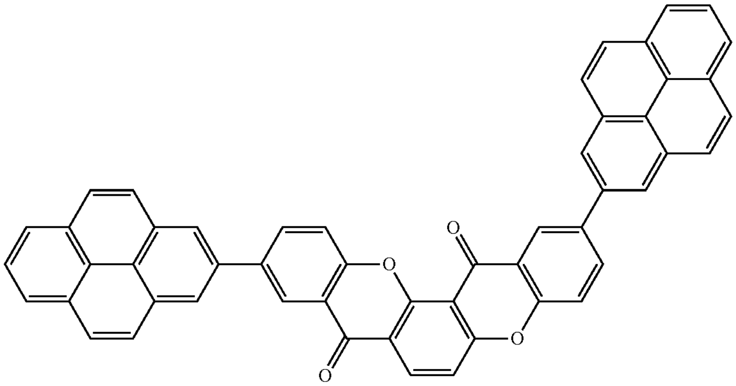
A-23
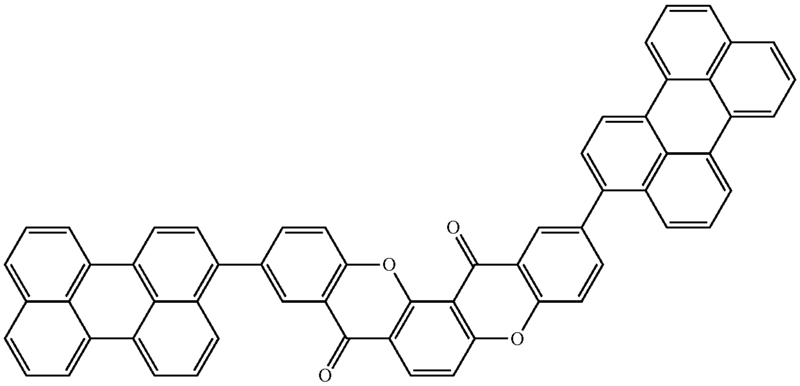

-continued
A-24
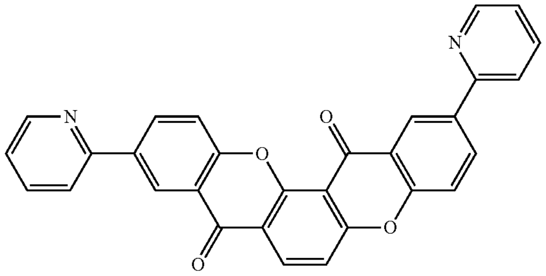
A-25
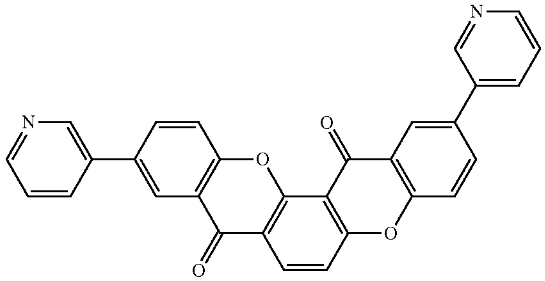
A-26
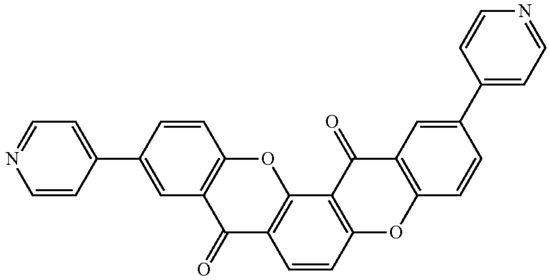
A-27
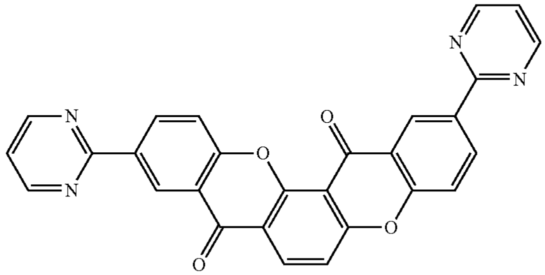
A-28
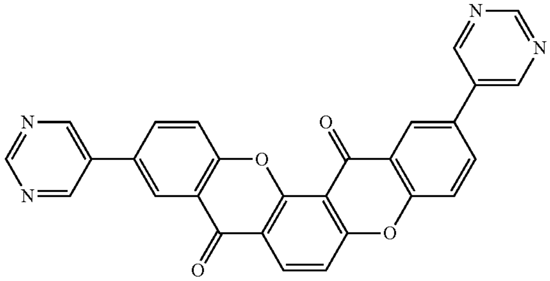
A-29
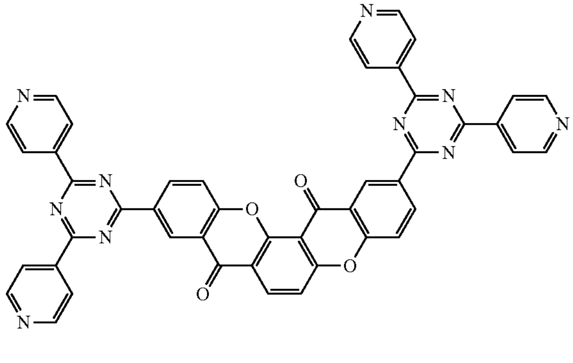
A-30
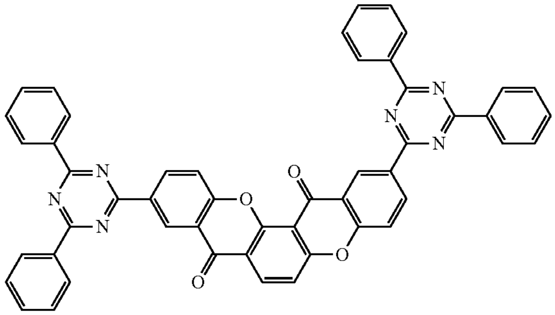
A-31
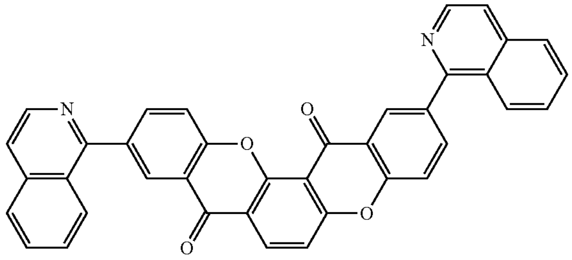

-continued
A-32
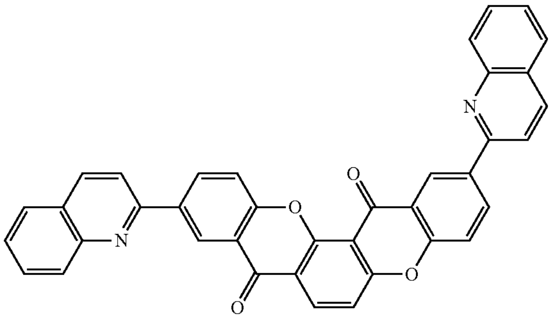
A-33
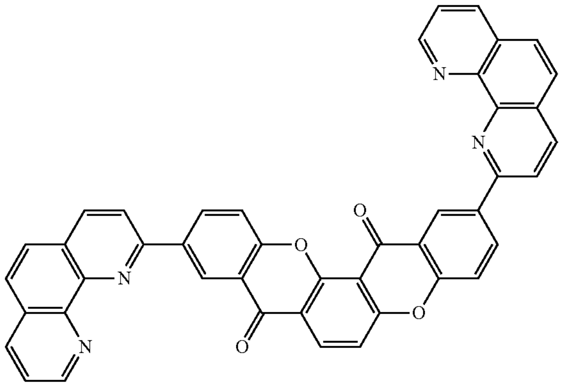
A-34
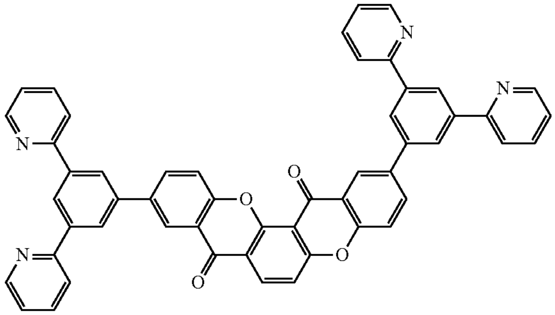
A-35
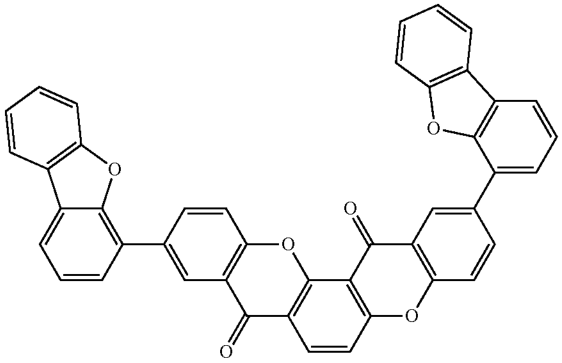
A-36
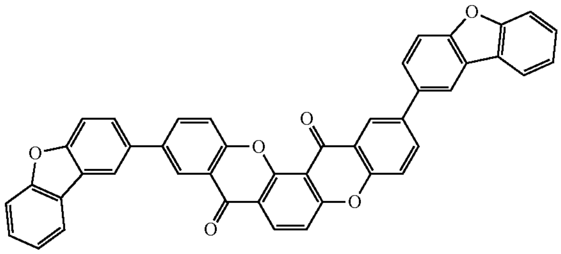
A-37
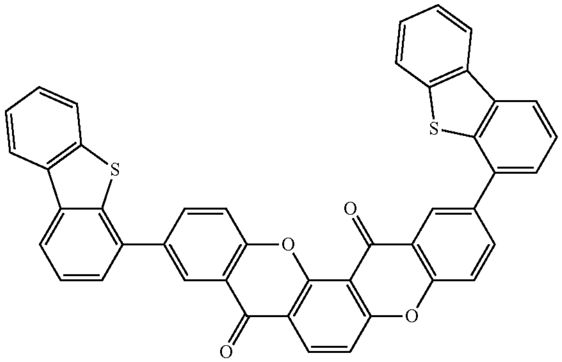
A-38
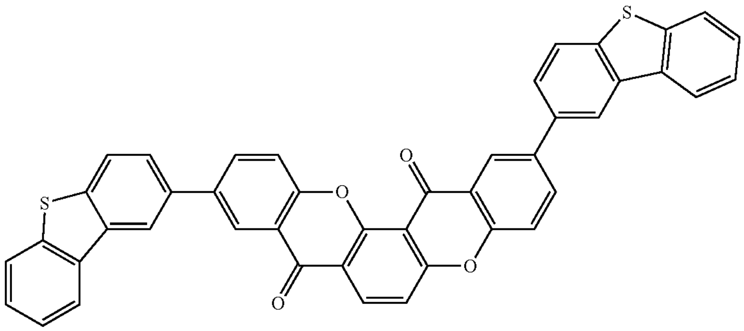

-continued
A-39
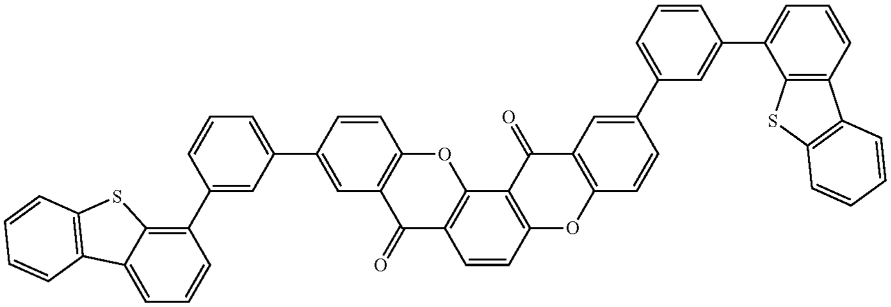
A-40
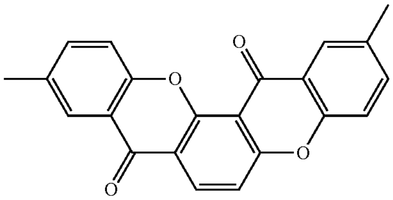
A-41
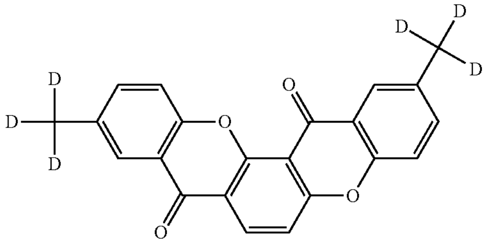
A-42
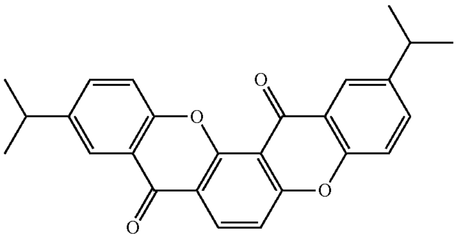
A-43
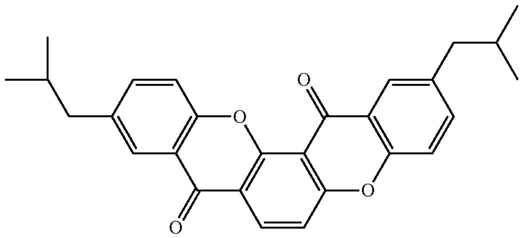
A-44
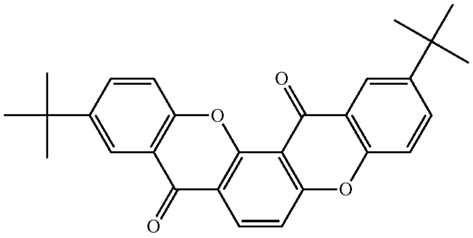
A-45
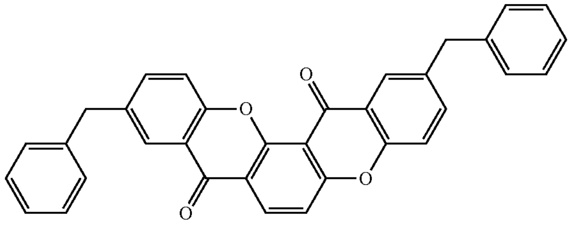
A-46
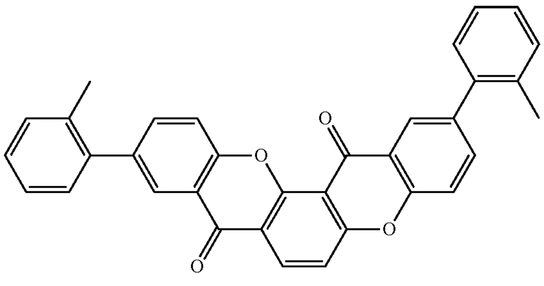
A-47
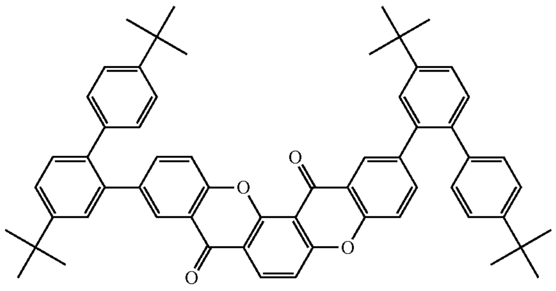

-continued
A-48
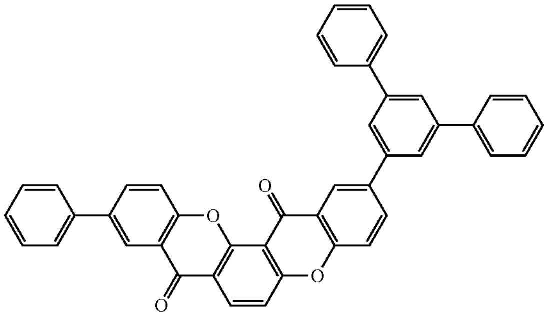
A-49
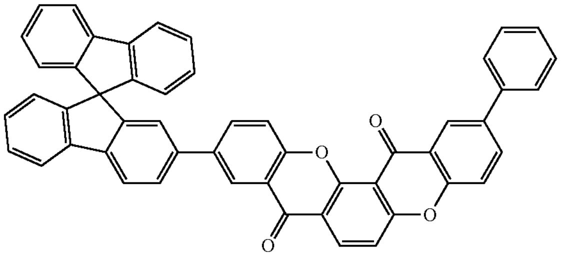
A-50
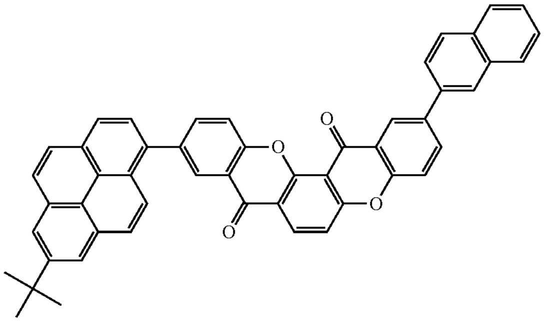
A-51
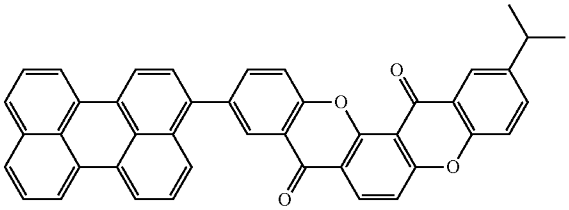
A-52
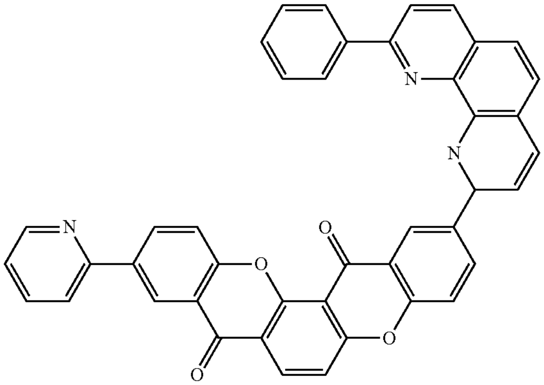
A-53
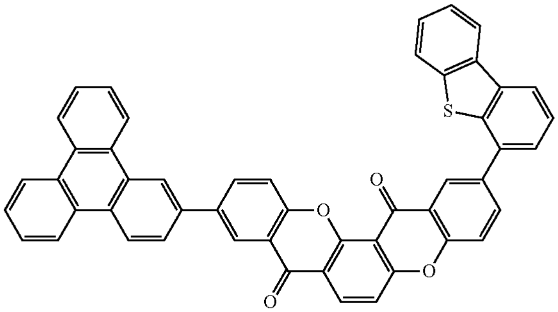
A-54
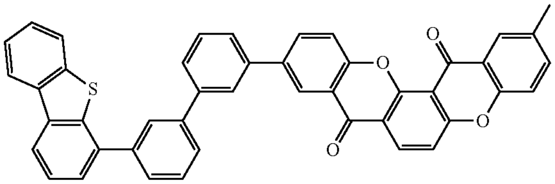
B-1
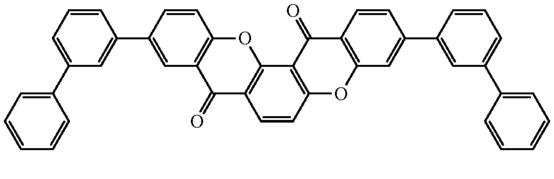

-continued
B-2
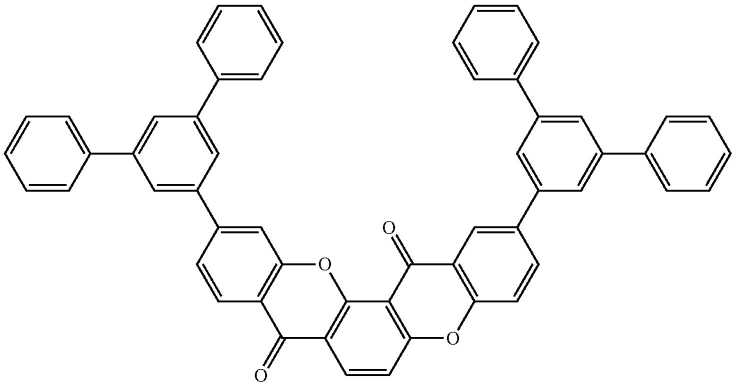
B-3
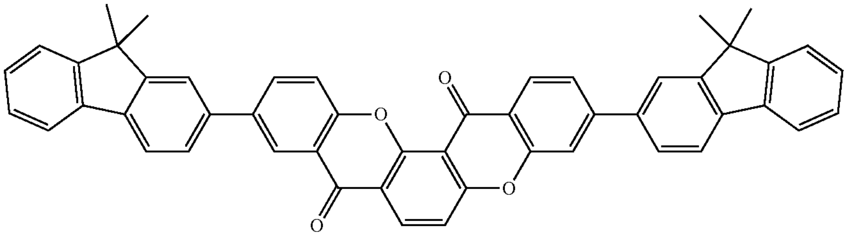
B-4
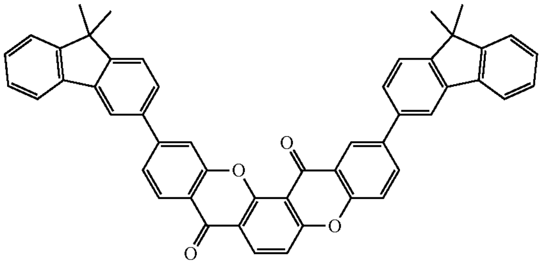
B-5
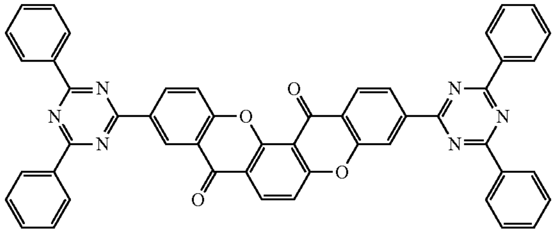
B-6
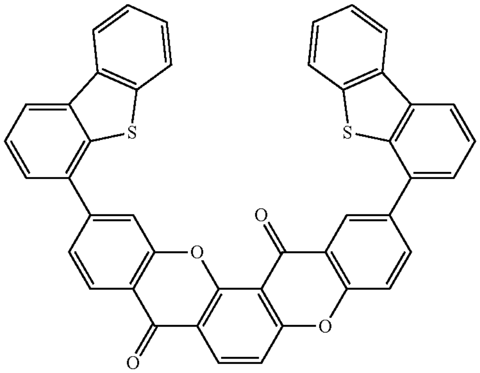
B-7
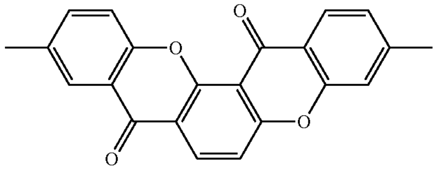
B-8
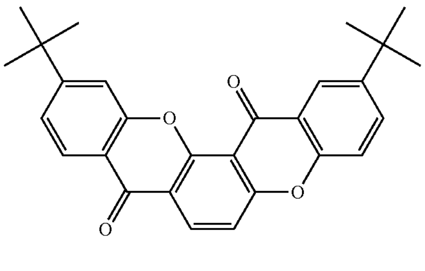
B-9
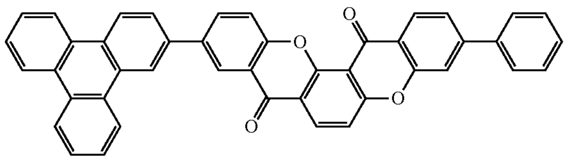

-continued
B-10
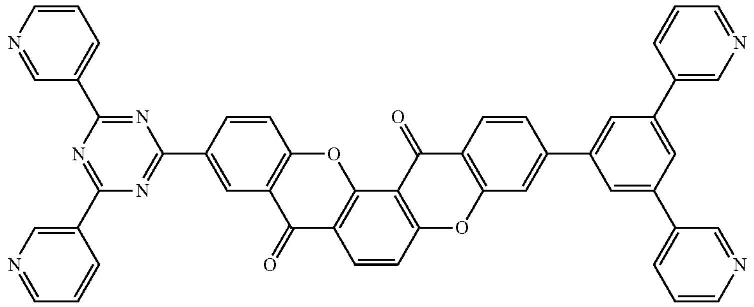
B-11
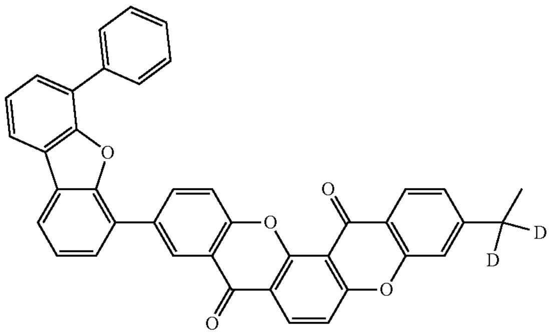
C-1
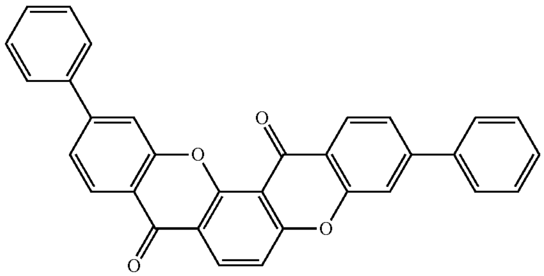
C-2
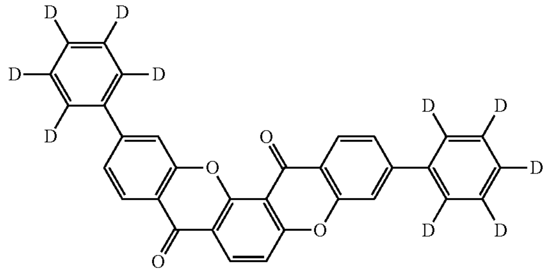
C-3
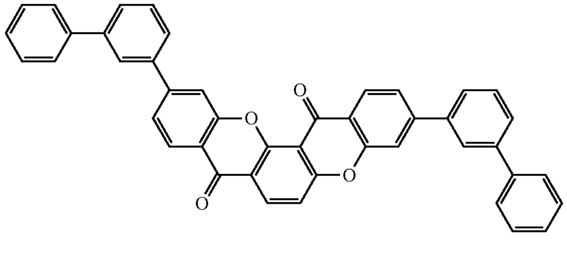
C-4
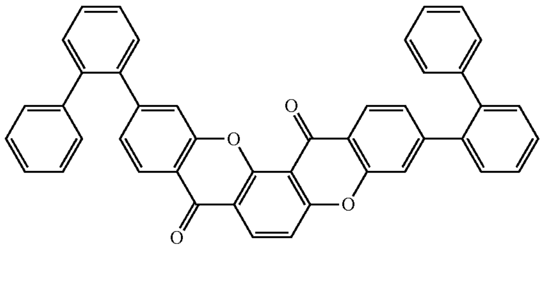
C-5
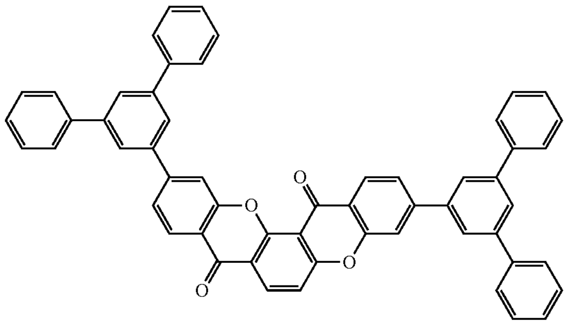

-continued
C-6
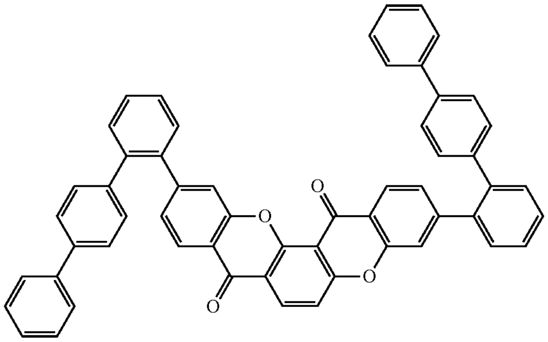
C-7
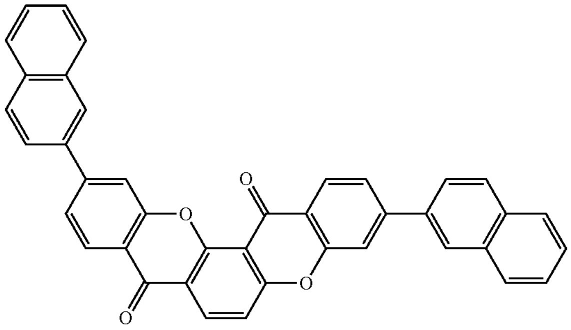
C-8
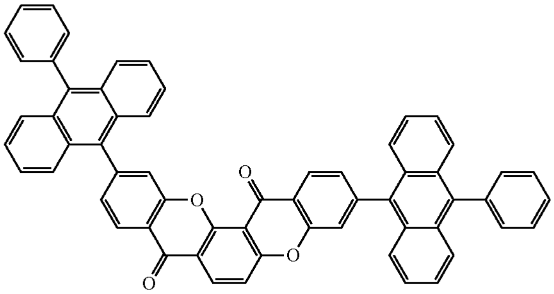
C-9
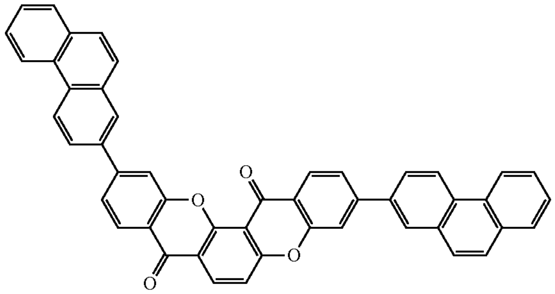
C-10
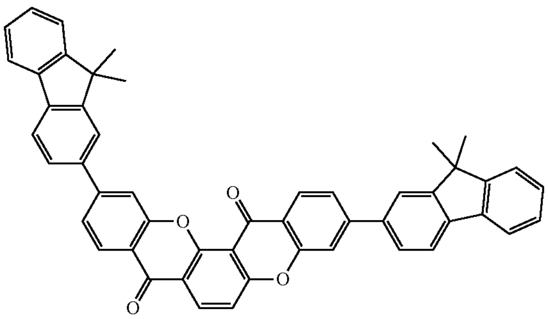
C-11
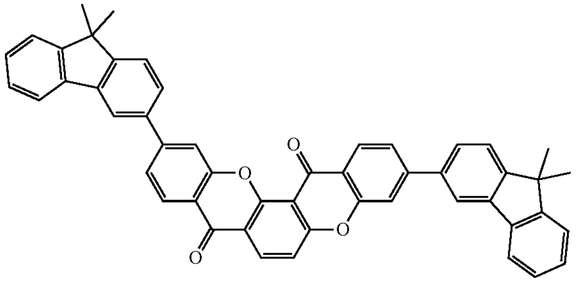
C-12
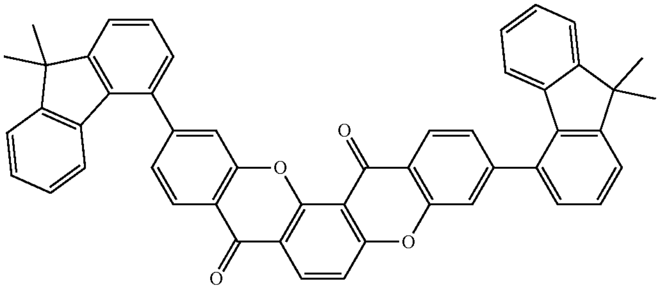

-continued
C-13
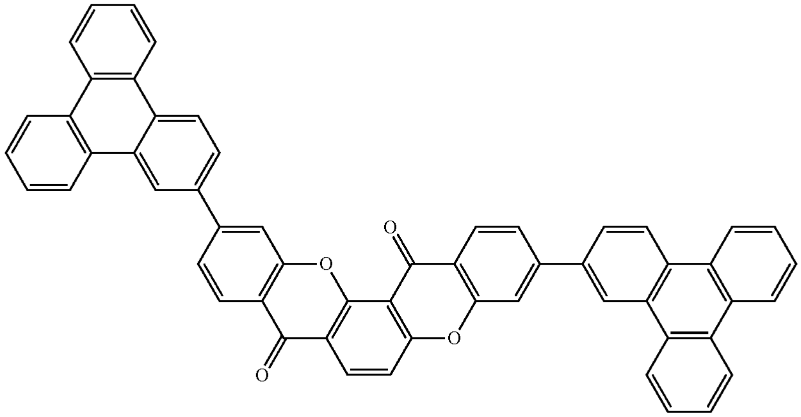
C-14
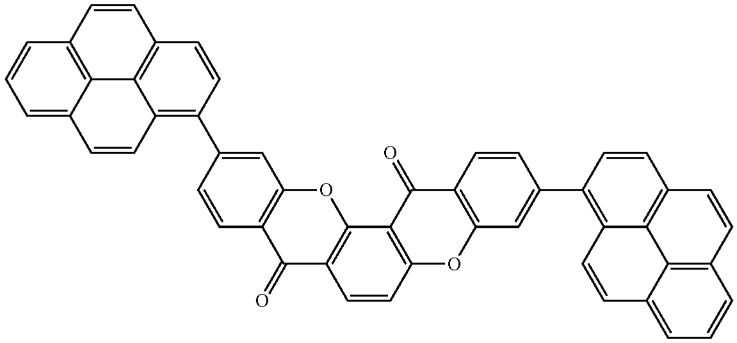
C-15
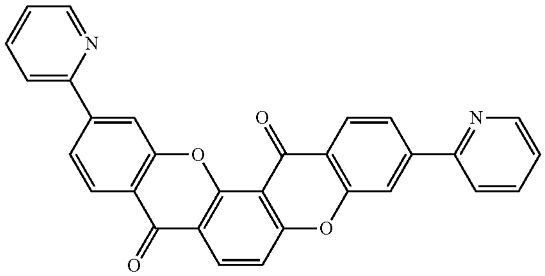
C-16
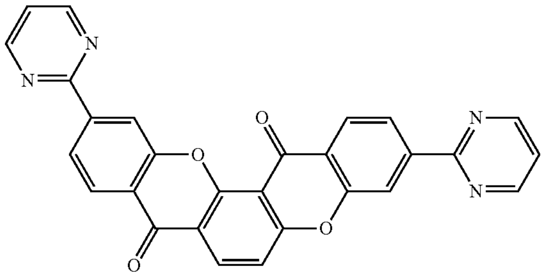
C-17
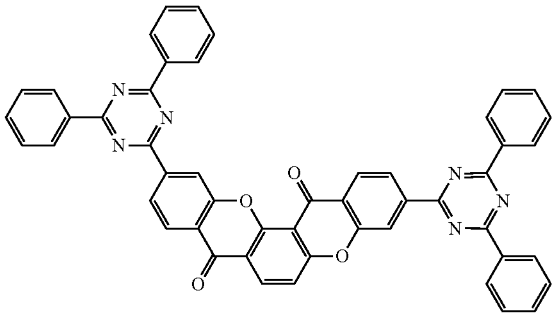
C-18
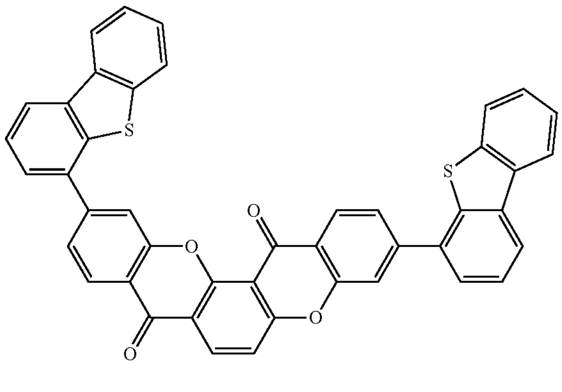

-continued
C-19
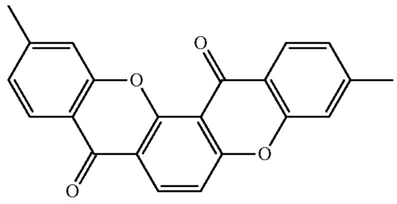
C-20
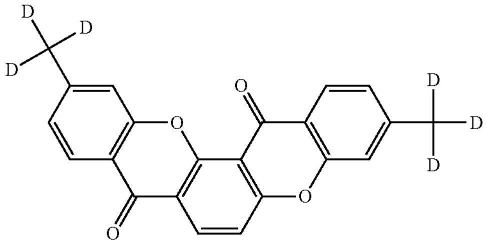
C-21
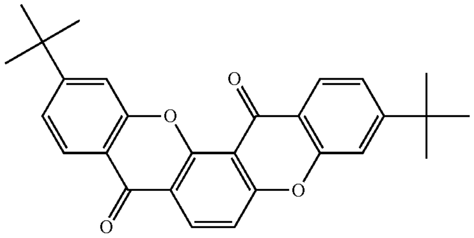
C-22
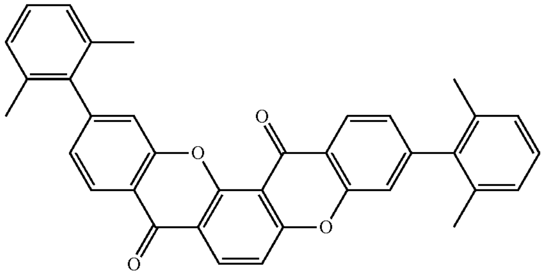
C-23
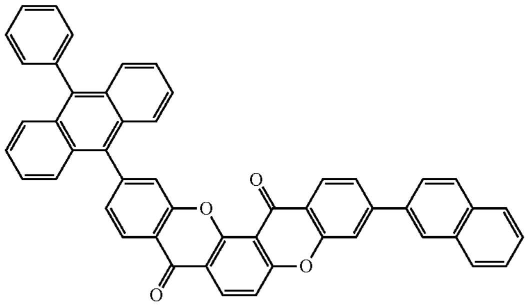
C-24
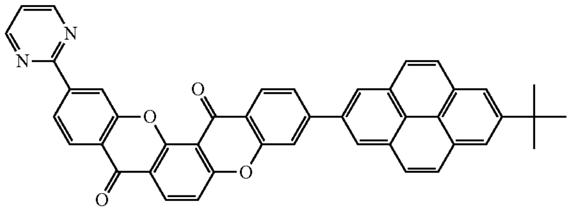
C-25
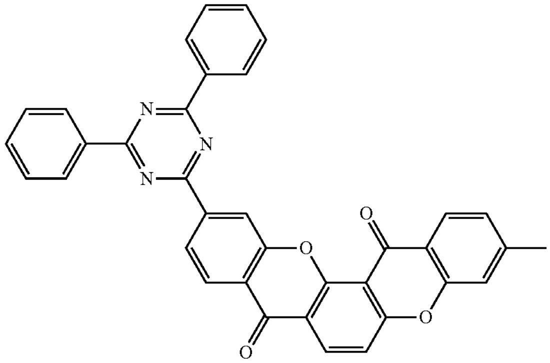
C-26
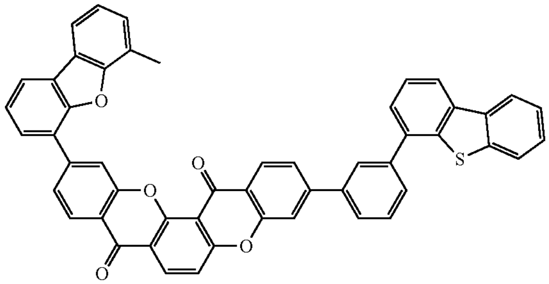

-continued
D-1
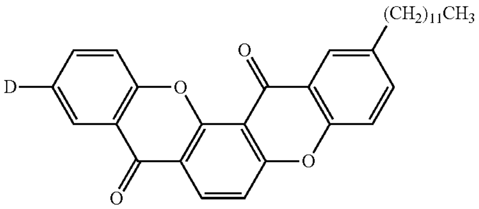
D-2
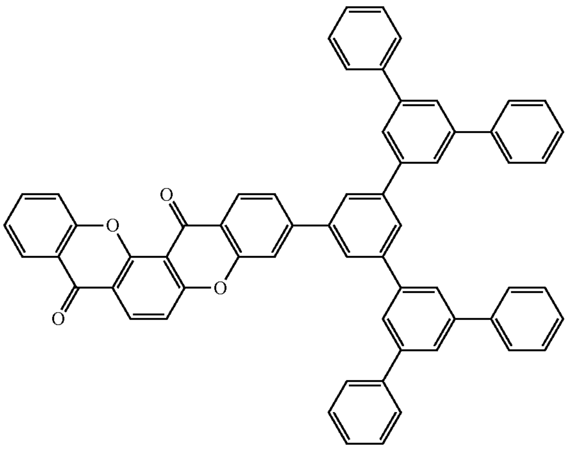
D-3
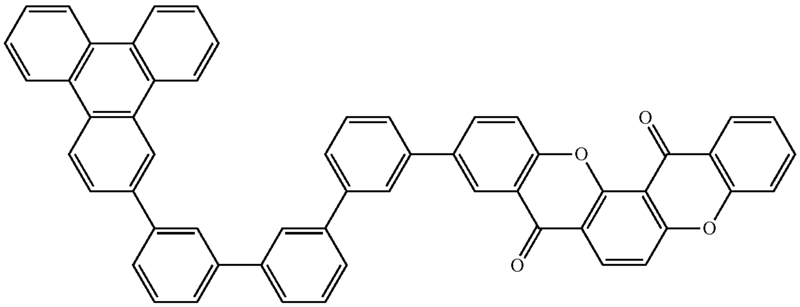
D-4
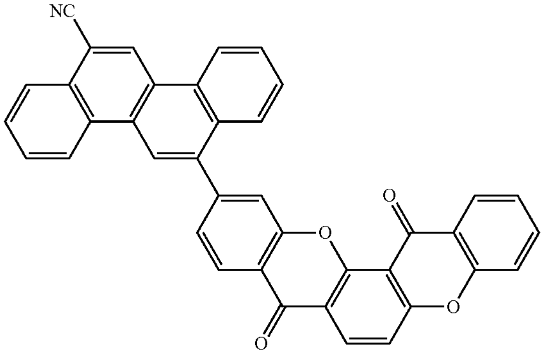
D-5
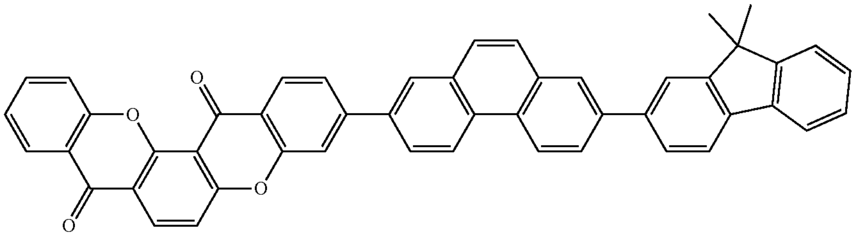
D-6
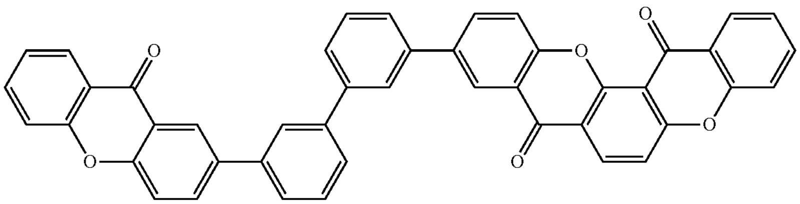

-continued

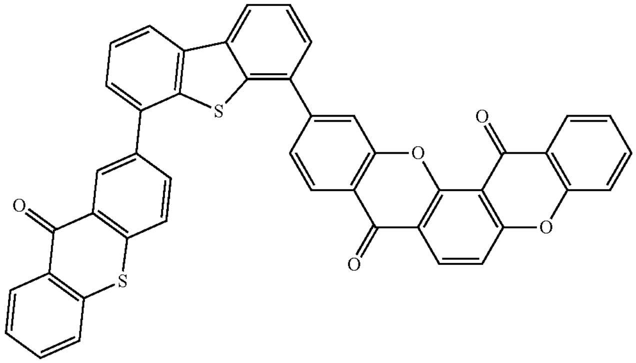

D-7

The compounds belonging to group A are compounds in which $R_2$ and $R_8$ are each an alkyl group, an aryl group, or a heterocyclic group. The compounds belonging to group A have higher chemical stability because groups other than hydrogen atoms are directly bonded to the para-positions of phenolic oxygen atoms. That is, group A is a group of compounds that have even higher durability performance when used in an organic light-emitting element. A-24 to A-39 and A-52 to A-54 are compounds having a heterocyclic group, and the HOMO level and the LUMO level of these compounds can be adjusted.

The compounds belonging to group B are compounds in which $R_2$ and $R_9$, or $R_3$ and $R_8$ are each an alkyl group, an aryl group, or a heterocyclic group. In the compounds belonging to group B, a group other than a hydrogen atom is bonded to one para-position of a phenolic oxygen atom, and a group other than a hydrogen atom is bonded to one carbon atom adjacent to another para-position. Thus, group B is a group of compounds that have the second highest chemical stability after group A and that have higher durability performance when used in an organic light-emitting element. B-5, B-6, B-10, and B-11 are compounds having a heterocyclic group, and the HOMO level and the LUMO level of these compounds can be adjusted.

The compounds belonging to group C are compounds in which $R_3$ and $R_9$ are each an alkyl group, an aryl group, or a heterocyclic group. In group C, groups other than hydrogen atoms are bonded to carbon atoms adjacent to para-positions with respect to phenolic oxygen atoms. Thus, group C is a group of compounds that have the second highest chemical stability after group B and that have higher durability performance when used in an organic light-emitting element. C-15 to C-18 and C-24 to C-26 are a group of compounds having a heterocyclic group, and the HOMO level and the LUMO level of these compounds can be adjusted.

The compounds belonging to group D are compounds in which one of $R_2$, $R_3$, $R_8$, and $R_9$ is an alkyl group, an aryl group, or a heterocyclic group. In group D, in particular, D-2 to D-7, a para-position of a phenolic oxygen atom, the para-position not being protected by a group other than a hydrogen atom, is present. Thus, group D has chemical stability that is not as high as that in groups A to C but is a group of compounds whose sublimability is easily improved and whose HOMO and LUMO levels can be easily adjusted.

Organic Light-Emitting Element

An organic light-emitting element according to this embodiment includes a pair of electrodes and a light-emitting layer disposed between the pair of electrodes. The light-emitting layer may contain a first compound which may be a host, and a second compound which may be a guest.

A specific element configuration of the organic light-emitting element according to this embodiment may be a multilayer element configuration in which electrode layers and organic compound layers described in any of (a) to (f) below are sequentially stacked on a substrate.

Note that, in any of the element configurations, the organic compound layers includes a light-emitting layer containing a light-emitting material without exception.

(a) anode/light-emitting layer/cathode
(b) anode/hole transport layer/light-emitting layer/electron transport layer/cathode
(c) anode/hole transport layer/light-emitting layer/electron transport layer/electron injection layer/cathode
(d) anode/hole injection layer/hole transport layer/light-emitting layer/electron transport layer/cathode
(e) anode/hole injection layer/hole transport layer/light-emitting layer/electron transport layer/electron injection layer/cathode
(f) anode/hole transport layer/electron-blocking layer/light-emitting layer/hole-blocking layer/electron transport layer/cathode However, these examples of the element configuration are merely very basic element configurations, and the element configuration is not limited to these configurations. Various layer configurations are possible. For example, an insulating layer, an adhesive layer, or an interference layer may be formed at an interface between an electrode and an organic compound layer, the electron transport layer or the hole transport layer may be composed of two layers having different ionization potentials, or the light-emitting layer may be composed of two layers formed of different light-emitting materials.

The light-emitting layer may have a single-layer structure or a multilayer structure. The multilayer structure refers to a state in which the light-emitting layer and another light-emitting layer are stacked. For example, a light-emitting layer containing the organic compound according to this embodiment represented by general formula [1] and serving as a host molecule and a guest molecule, and another light-emitting layer that emits light of a color different from the color of light emitted from this light-emitting layer may be stacked. In this case, the emission color may be white or a neutral color.

Among the element configurations described in (a) to (f) above, the configuration (f) has both an electron-blocking layer and a hole-blocking layer. That is, in (f) having the electron-blocking layer and the hole-blocking layer, both carriers of holes and electrons can be reliably confined in the light-emitting layer. Thus, the resulting organic light-emitting element has no carrier leakage and has high light emission efficiency.

The mode (element form) of extracting light output from a light-emitting layer may be what is called a bottom-emission mode in which light is extracted from an electrode on the substrate side or what is called a top-emission mode in which light is extracted from the side opposite from the substrate. Alternatively, a double-sided extraction mode in which light is extracted from the substrate side and from the side opposite from the substrate may also be used.

In the organic light-emitting element according to this embodiment, an organic compound according to this embodiment may be contained in the light-emitting layer among the organic compound layers. In this case, the use of compounds contained in the light-emitting layer depends on the concentrations of the compounds in the light-emitting layer. Specifically, the compounds are classified into a main component and an auxiliary component depending on the concentrations of the compounds in the light-emitting layer.

A compound serving as the main component is a compound having the maximum mass ratio (concentration) among a compound group contained in the light-emitting layer and is also referred to as a host. The host is a compound that is present as a matrix around a light-emitting material in the light-emitting layer and that is mainly responsible for carrier transport to the light-emitting material and excitation energy supply to the light-emitting material.

A compound serving as the auxiliary component is a compound other than the main component and can be referred to as a guest (dopant), a light-emitting assist material, or an electric charge injection material depending on the function of the compound. The guest, which is an auxiliary component, is a compound (light-emitting material) responsible for main light emission in the light-emitting layer. The light-emitting assist material, which is an auxiliary component, is a compound that assists the light emission of the guest and is a compound having a lower mass ratio (concentration) than the host in the light-emitting layer. The light-emitting assist material is also referred to as a second host because of its function.

The concentration of the host is preferably 50% by mass or more and 99% by mass or less, and more preferably 70% by mass or more and 99% by mass or less based on the total amount of the constituent materials of the light-emitting layer.

The concentration of the guest is 0.01% by mass or more and less than 50% by mass, preferably 0.1% by mass or more and 20% by mass or less based on the total amount of the constituent materials of the light-emitting layer. The concentration of the guest is particularly preferably 10% by mass or less from the viewpoint of reducing concentration quenching. The concentration of the light-emitting assist material is 0.1% by mass or more and less than 50% by mass, preferably 1% by mass or more and less than 50% by mass based on the total amount of the constituent materials of the light-emitting layer.

The guest may be uniformly contained or may be contained so as to have a concentration gradient in the entire layer in which the host serves as a matrix. Alternatively, the guest may be partially contained in a specific region in the layer, and the light-emitting layer may have a region that contains no guest but contains the host alone.

In this embodiment, the light-emitting layer may contain an organic compound according to this embodiment as a host. In order to assist the transfer of excitons or carriers, the light-emitting layer may further contain a third compound (second host) in addition to the first compound and the second compound.

(1) First Compound

The first compound may be the host. The first compound may be an organic compound according to this embodiment represented by general formula [1].

(2) Second Compound

The second compound may be the guest. Examples of a guest molecule that is mainly related to the light-emitting function include fused-ring compounds (such as fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives. Specific examples of the compound used as a light-emitting material are shown below but are not limited to these, as a matter of course.

BD1

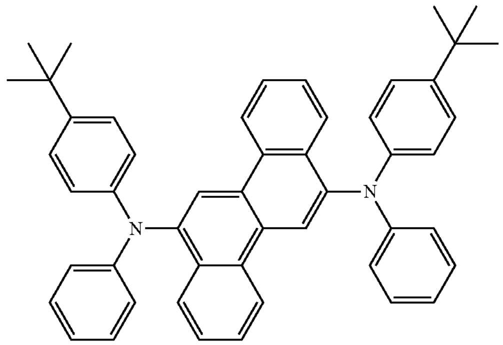

BD2

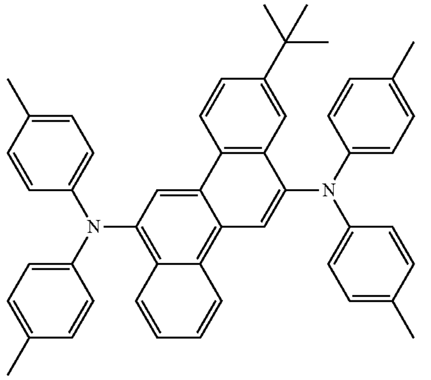

-continued
BD3
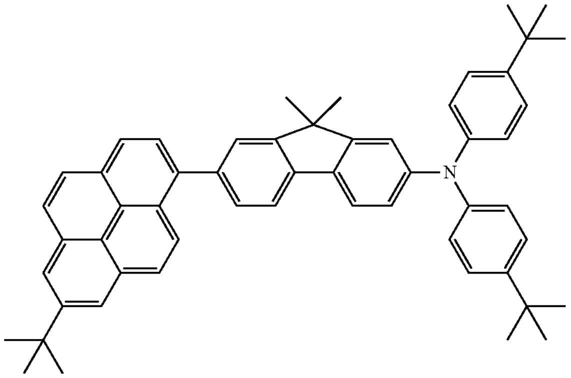
BD4
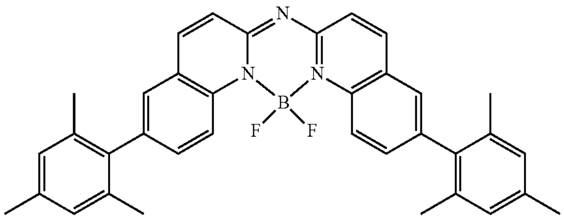
BD5
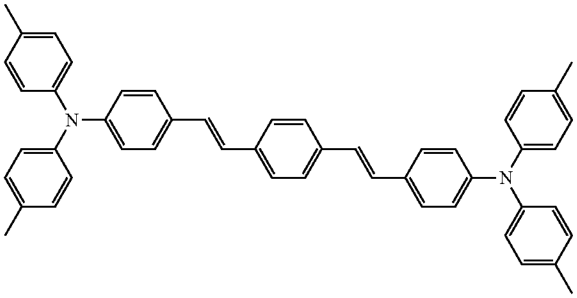
BD6
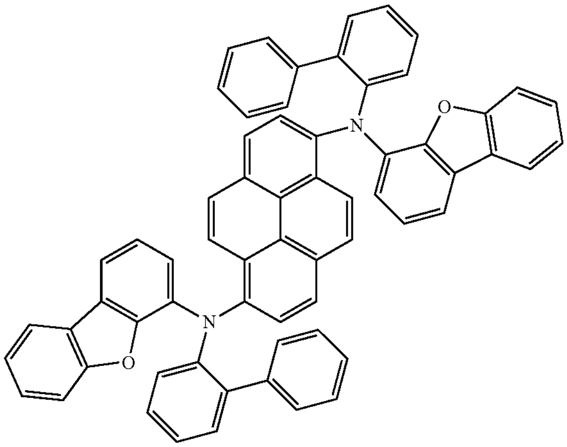
-continued
BD7
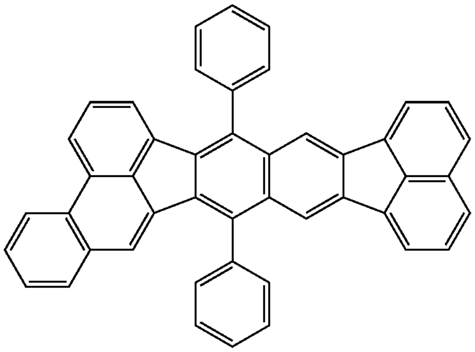
BD8
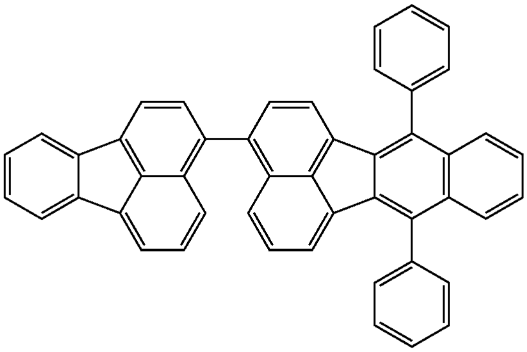
BD9
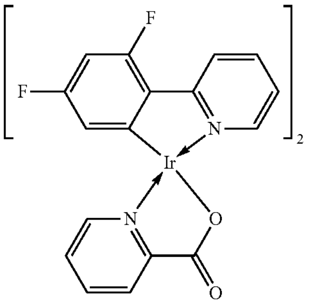
BD10
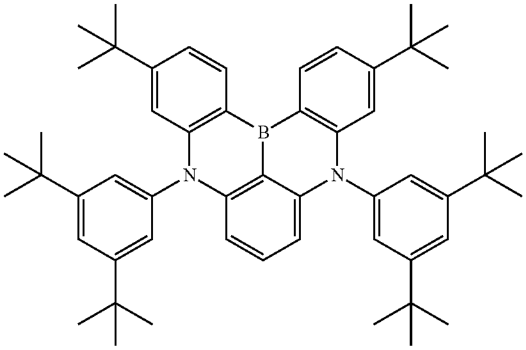

-continued
GD1
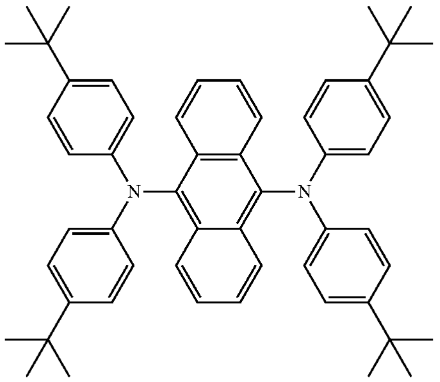
GD2
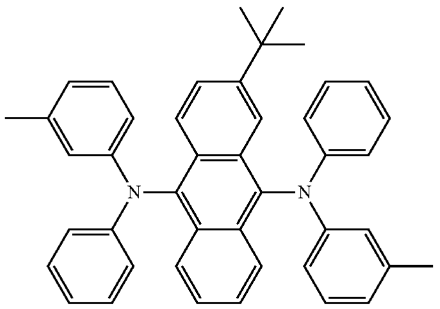
GD3
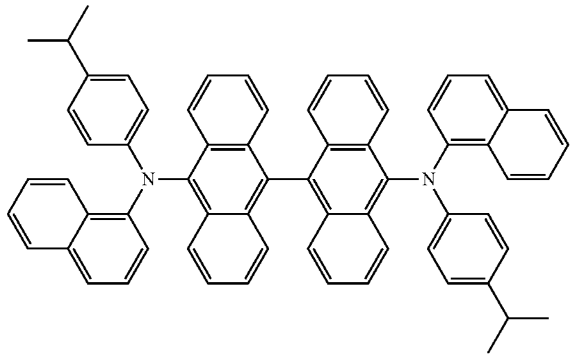
GD4
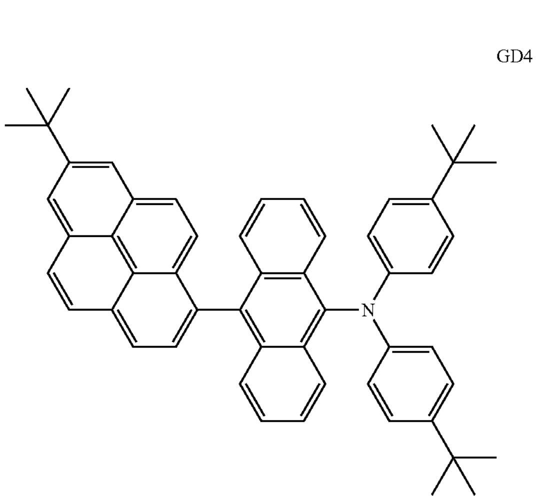
-continued
GD5
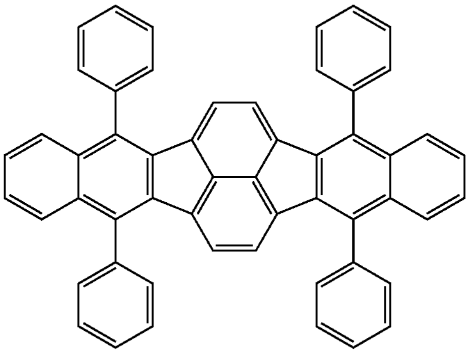
GD6
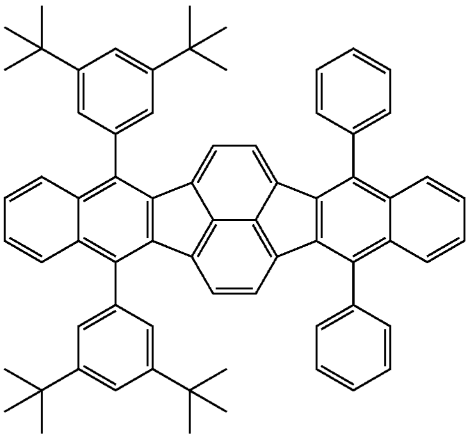
GD7
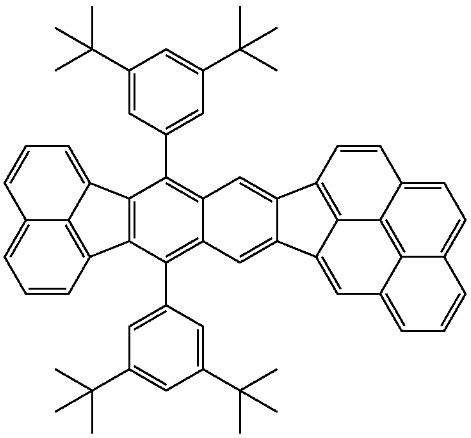
GD8
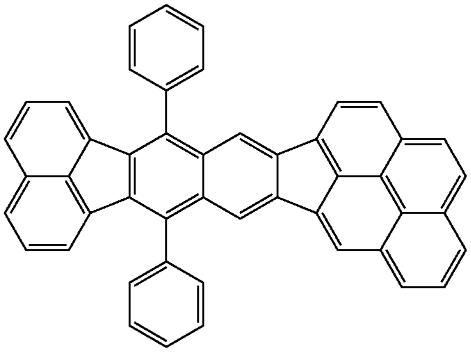

-continued
GD9
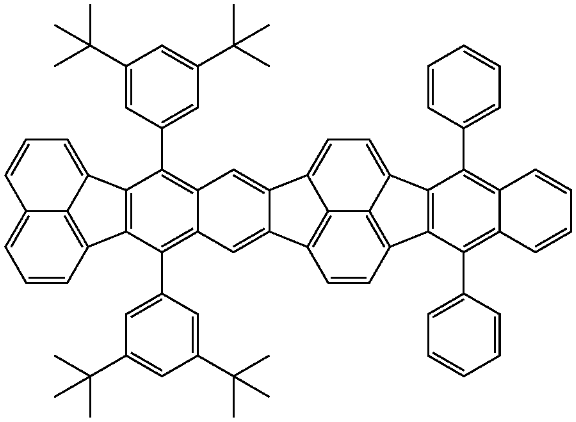
GD10
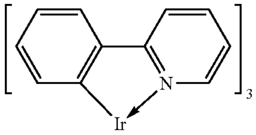
GD11
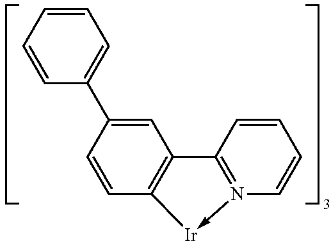
GD12
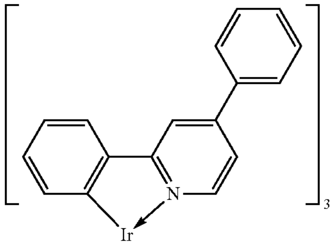
GD13
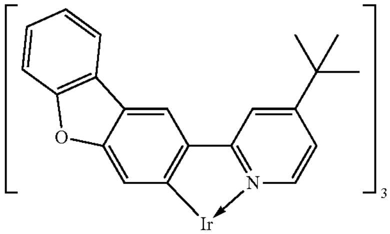
-continued
GD14
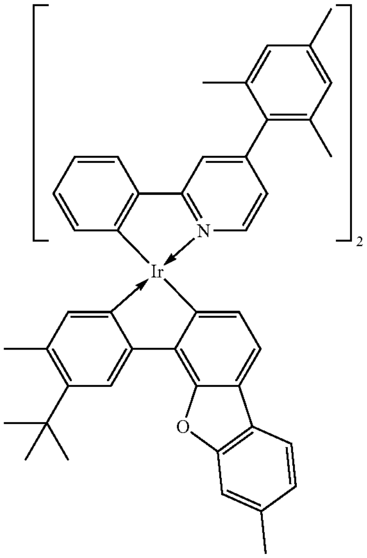
GD15
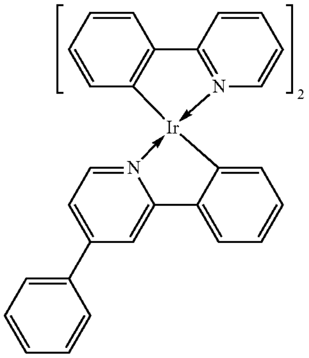
RD1
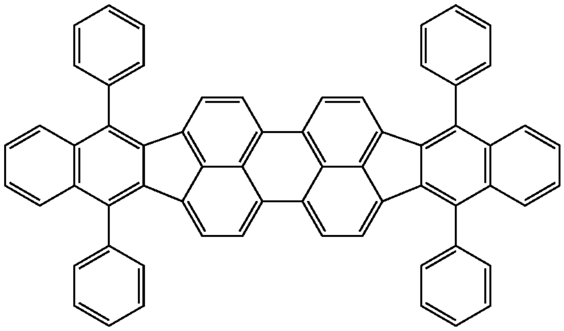
RD2
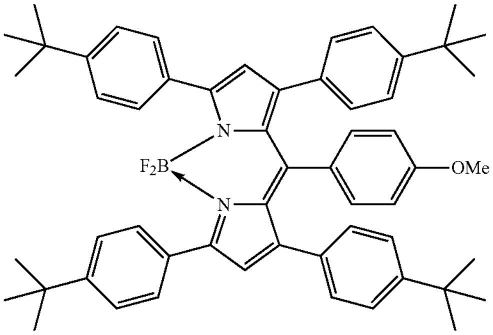

-continued

RD3

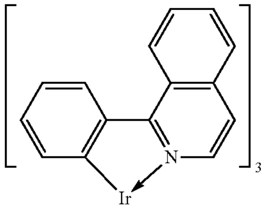

RD4

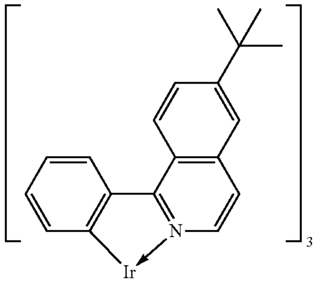

RD5

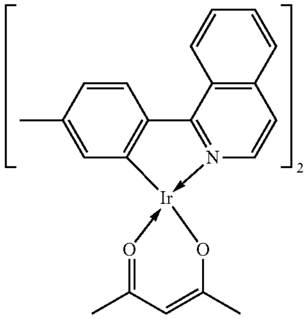

RD6

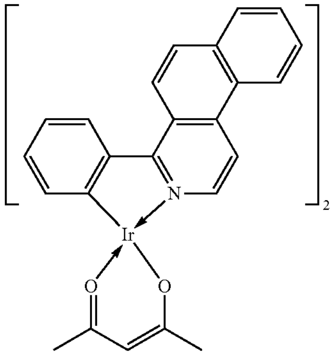

RD7

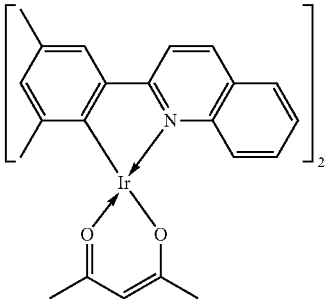

-continued

RD8

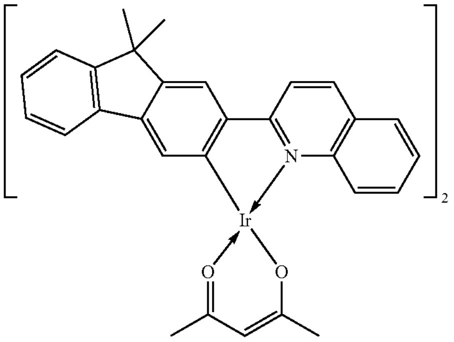

RD9

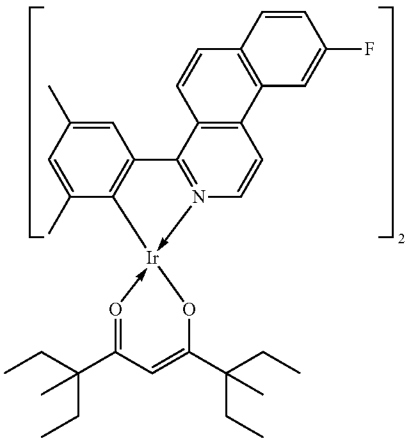

RD10

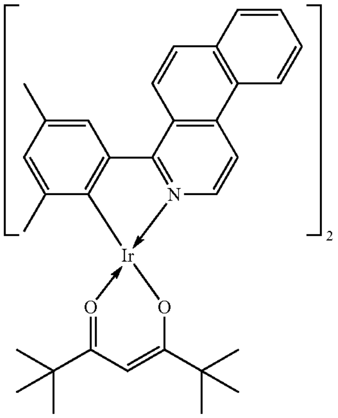

In view of the light emission efficiency in the organic light-emitting element, the guest molecule is preferably a phosphorescent organometallic complex. Specific examples thereof include iridium complexes, platinum complexes, rhenium complexes, copper complexes, europium complexes, and ruthenium complexes.

In view of emission quantum yield, the guest molecule is more preferably an organometallic complex represented by general formula [2].

$$M(L)_m(L')_n \quad [2]$$

In formula [2], M is selected from iridium and platinum.

L and L' represent bidentate ligands different from each other. In a case that m is greater than 1, Ls may be the same or different, and in a case that n is greater than 1, L's may be the same or different.

m is selected from an integer of 1 to 3, and n is selected from an integer of 0 to 2. However, when M is iridium, m+n=3, and when M is platinum, m+n=2.

A partial structure $M(L)_m$ is represented by general formula [2-1].

[2-1]

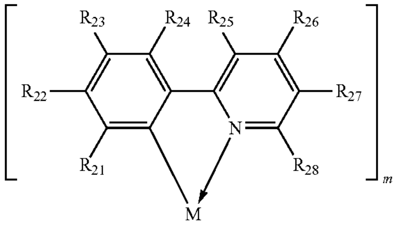

In formula [2-1], $R_{21}$ to $R_{28}$ are each independently selected from a hydrogen atom, a deuterium atom, a halogen atom, a substituted or unsubstituted alkyl group, a substituted or unsubstituted alkoxy group, a substituted or unsubstituted silyl group, a substituted or unsubstituted aryl group, a substituted or unsubstituted heterocyclic group, a substituted or unsubstituted amino group, a substituted or unsubstituted aryloxy group, a substituted or unsubstituted heteroaryloxy group, and a cyano group. Adjacent $R_{21}$ to $R_{28}$ are optionally bonded together to form a ring.

Examples of the halogen atom include, but are not limited to, fluorine, chlorine, bromine, and iodine. Of these, a fluorine atom is preferred.

Examples of the alkyl group include, but are not limited to, a methyl group, an ethyl group, a n-propyl group, an isopropyl group, a n-butyl group, a tert-butyl group, a sec-butyl group, an octyl group, a cyclohexyl group, a 1-adamantyl group, and a 2-adamantyl group.

Examples of the alkoxy group include, but are not limited to, a methoxy group, an ethoxy group, a propoxy group, a 2-ethyl-octyloxy group, and a benzyloxy group.

Examples of the silyl groups include, but are not limited to, a trimethylsilyl group and a triphenylsilyl group.

Examples of the aryl group include, but are not limited to, a phenyl group, a naphthyl group, an indenyl group, a biphenyl group, a terphenyl group, a fluorenyl group, a phenanthryl group, a fluoranthenyl group, and a triphenylenyl group.

Examples of the heterocyclic group include, but are not limited to, a pyridyl group, a pyrimidyl group, a pyrazyl group, a triazolyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group. The heterocyclic group is preferably a heteroaryl group and preferably a group bonded through a carbon atom.

Examples of the amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, an N-phenyl-N-(4-trifluoromethylphenyl)amino group, an N-piperidyl group, and a carbazolyl group.

Examples of the aryloxy group and the heteroaryloxy group include, but are not limited to, a phenoxy group and a thienyloxy group.

Examples of substituents that may be further contained in the alkyl group, the alkoxy group, the silyl group, the aryl group, the heterocyclic group, the amino group, the aryloxy group, and the heteroaryloxy group include, but are not limited to, a deuterium atom; halogen atoms such as fluorine, chlorine, bromine, and iodine; alkyl groups such as a methyl group, an ethyl group, a n-propyl group, an isopropyl group, a n-butyl group, and a tert-butyl group; alkoxy groups such as a methoxy group, an ethoxy group, and a propoxy group; amino groups such as a dimethylamino group, a diethylamino group, a dibenzylamino group, a diphenylamino group, and a ditolylamino group; aryloxy groups such as a phenoxy group; aromatic hydrocarbon groups such as a phenyl group and a biphenyl group; heterocyclic groups such as a pyridyl group and a pyrrolyl group; a cyano group, a hydroxy group, and a thiol group.

Adjacent $R_{21}$ to $R_{28}$, in particular, adjacent $R_{21}$ to $R_{24}$ or adjacent $R_{25}$ to $R_{28}$ are optionally bonded together to form a ring. The phrase "adjacent $R_{21}$ to $R_{28}$ are bonded together to form a ring" means that a ring formed by bonding $R_{21}$ and $R_{22}$, $R_{22}$ and $R_{23}$, or $R_{23}$ and $R_{24}$ together and a benzene ring to which $R_{21}$ to $R_{24}$ are bonded form a fused ring, or that a ring formed by bonding $R_{25}$ and $R_{26}$, $R_{26}$ and $R_{27}$, or $R_{27}$ and $R_{28}$ together and a pyridine ring to which $R_{25}$ to $R_{28}$ are bonded form a fused ring. The ring formed by bonding adjacent $R_{21}$ to $R_{28}$ together may be an aromatic ring.

A partial structure $M(L')_n$ is represented by general formula [2-2].

[2-2]

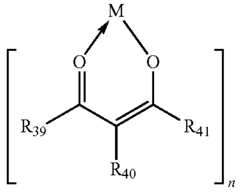

In formula [2-2], $R_{39}$ to $R_{41}$ are each independently selected from a hydrogen atom, a deuterium atom, a halogen atom, a substituted or unsubstituted alkyl group, a substituted or unsubstituted alkoxy group, a substituted or unsubstituted silyl group, a substituted or unsubstituted aryl group, a substituted or unsubstituted heterocyclic group, a substituted or unsubstituted amino group, a substituted or unsubstituted aryloxy group, a substituted or unsubstituted heteroaryloxy group, and a cyano group.

Specific examples of the halogen atom, the alkyl group, the alkoxy group, the silyl group, the aryl group, the heterocyclic group, the amino group, the aryloxy group, and the heteroaryloxy group include, but are not limited to, those described for $R_{21}$ to $R_{28}$. Specific examples of substituents that may be further contained in the alkyl group, the alkoxy group, the silyl group, the aryl group, the heterocyclic group, the amino group, the aryloxy group, and the heteroaryloxy group include, but are not limited to, those described for $R_{21}$ to $R_{28}$.

Among the organometallic complexes represented by general formula [2], organometallic complexes that include a partial structure $M(L)_m$ having a fused ring including three or more rings are preferred. This is because a fused-ring skeleton including three or more rings improves the planarity and promotes energy transfer from a host molecule, resulting in an increase in efficiency and an improvement in durability. Examples of the fused ring including three or more rings include a phenanthrene ring, a triphenylene ring, a benzofluorene ring, a dibenzofuran ring, a dibenzothiophene ring, a benzonaphthofuran ring, a benzonaphthothiophene ring, a benzoisoquinoline ring, and a naphthoisoquinoline ring.

In general formula [2-1], at least one of $R_{22}$, $R_{23}$, $R_{26}$, and $R_{27}$ may be a substituted or unsubstituted aryl group or a substituted or unsubstituted heterocyclic group. This is because the planarity of the organometallic complex is improved as described above.

Specific examples of the partial structure $M(L)_m$ of an organometallic complex serving as a guest are shown below but are not limited to these. Note that, in the specific examples shown below, a coordinate bond is indicated by a straight line, a dotted line, or an arrow.

[Ir-1]

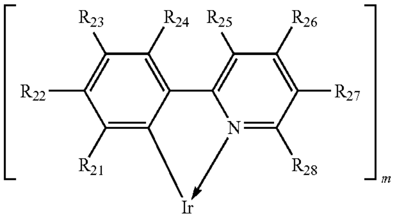

[Ir-2]

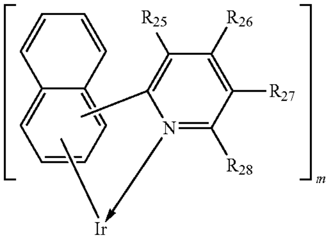

[Ir-3]

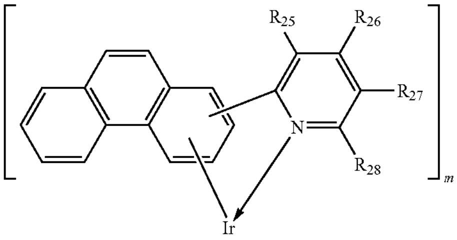

[Ir-4]

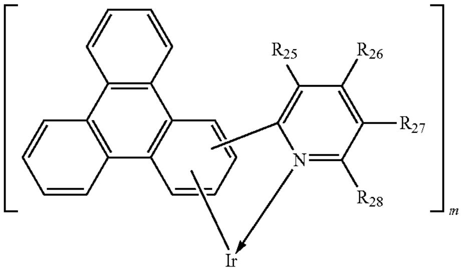

-continued

[Ir-5]

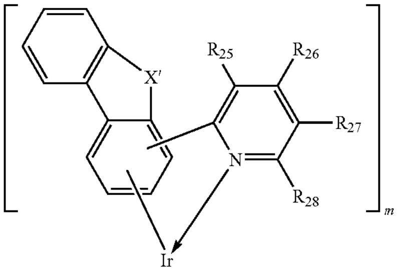

[Ir-6]

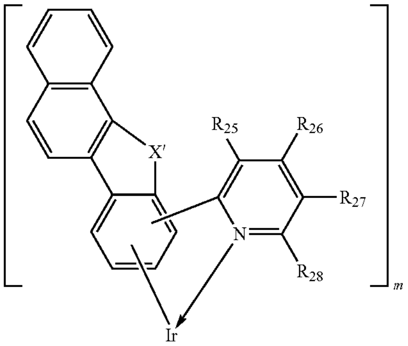

[Ir-7]

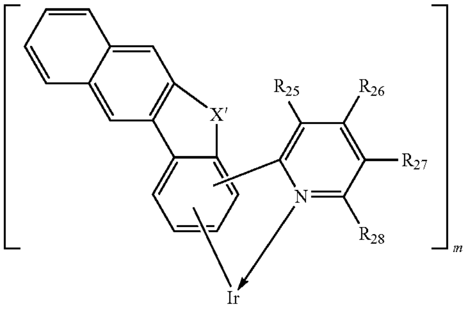

[Ir-8]

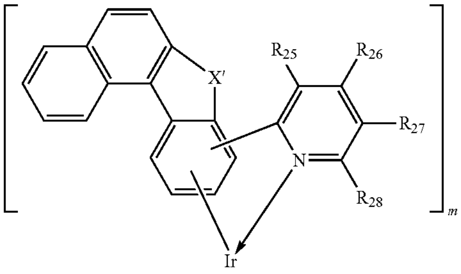

[Ir-9]

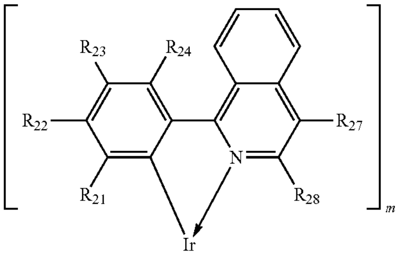

-continued

[Ir-10]

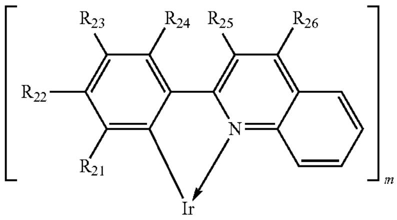

[Ir-11]

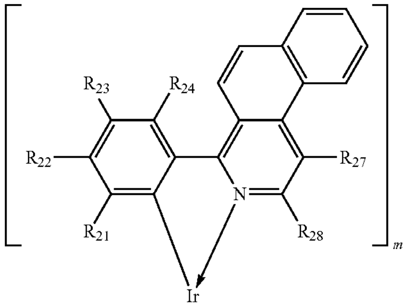

[Ir-12]

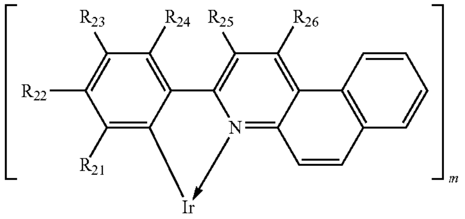

[Ir-13]

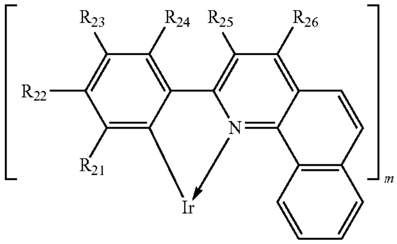

[Ir-14]

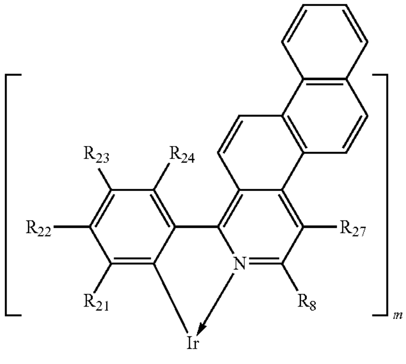

-continued

[Ir-15]

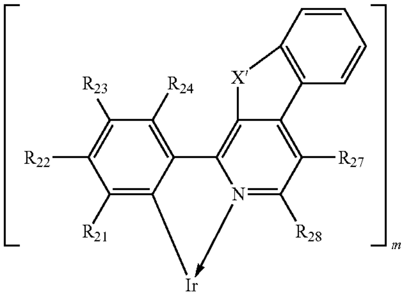

[Ir-16]

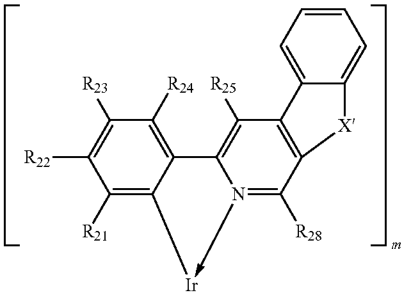

In general formulae [Ir-5] to [Ir-8], and [Ir-15] and [Ir-16] above, X' is selected from an oxygen atom, a sulfur atom, a substituted or unsubstituted carbon atom, and a substituted or unsubstituted nitrogen atom.

In general formulae [Ir-2] to [Ir-8], adjacent $R_{21}$ to $R_{24}$ are bonded together to form a ring. In general formulae [Ir-9] to [Ir-16], adjacent $R_{25}$ to $R_{28}$ are bonded together to form a ring. In general formulae [Ir-3] to [Ir-8], at least one of $R_{21}$ to $R_{24}$ is a phenyl group or a naphthyl group and forms a ring with an adjacent group. In general formulae [Ir-11] to [r-16], at least one of $R_{25}$ to $R_{28}$ is a phenyl group or a naphthyl group and forms a ring with an adjacent group. Thus, general formulae [Ir-3] to [Ir-8] and [Ir-11] to [Ir-16] may or may not further have an aryl group or a heterocyclic group.

Among metal complexes that include a partial structure $M(L)_m$ represented by one of general formulae [r-1] to [r-16] above, metal complexes having a fused ring including three or more rings in the ligand are more preferred. Specifically, metal complexes that include a partial structure $M(L)_m$ represented by one of general formulae [r-3] to [r-8] and [Ir-11] to [r-16] are more preferred. Specific examples thereof are shown below but are not limited to these, as a matter of course.

AA1

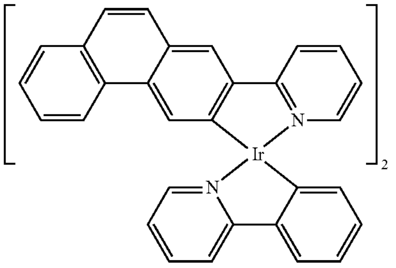

-continued
AA2
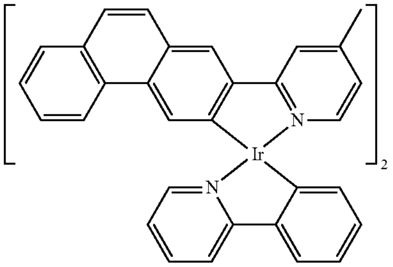
AA3
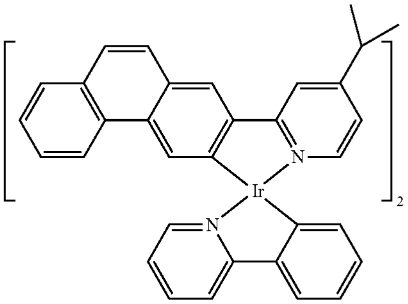
AA4
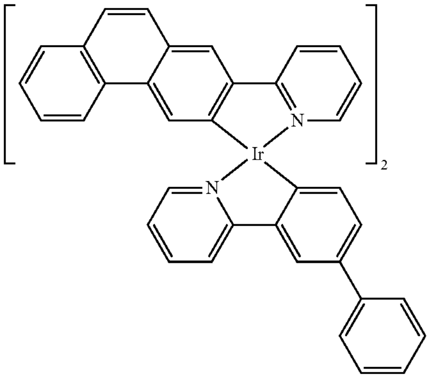
AA5
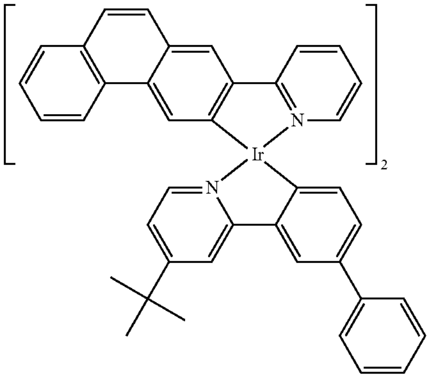
-continued
AA6
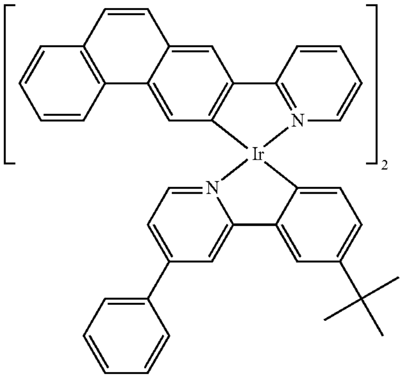
AA7
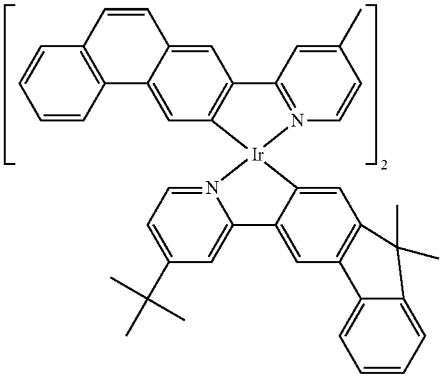
AA8
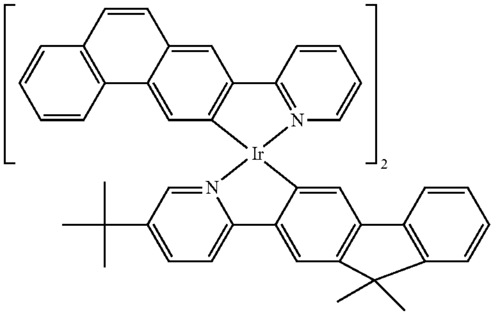
AA9
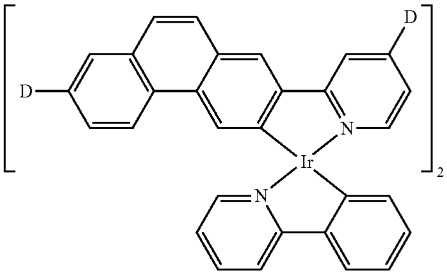

-continued
AA10
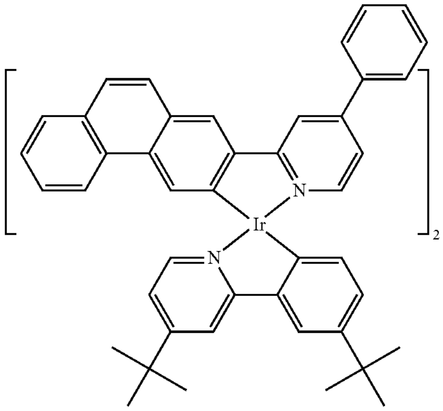
A11
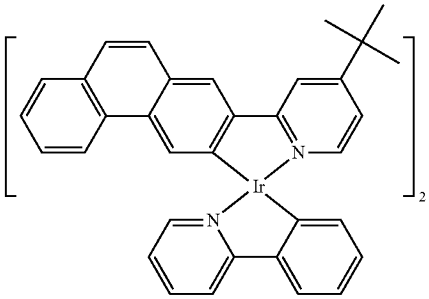
A12
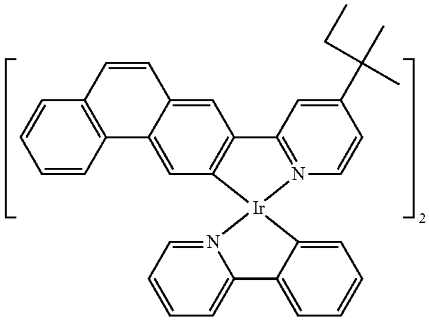
AA13
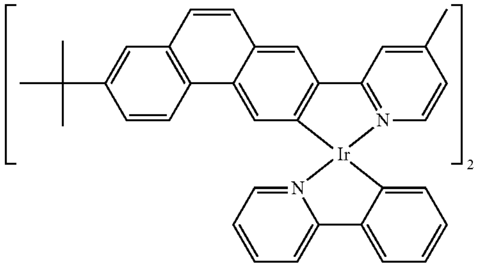
AA14
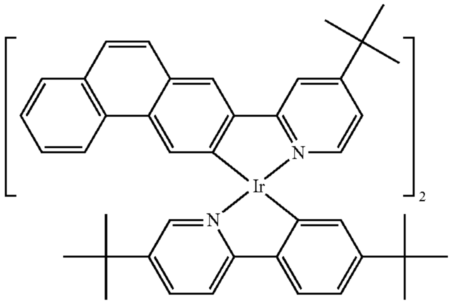
-continued
AA15
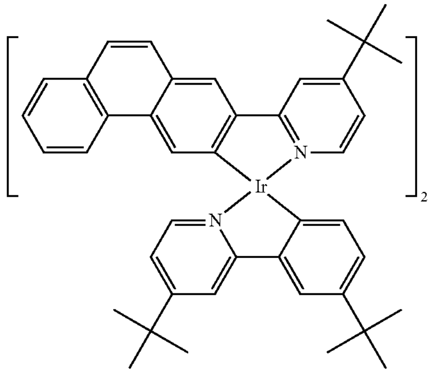
AA16
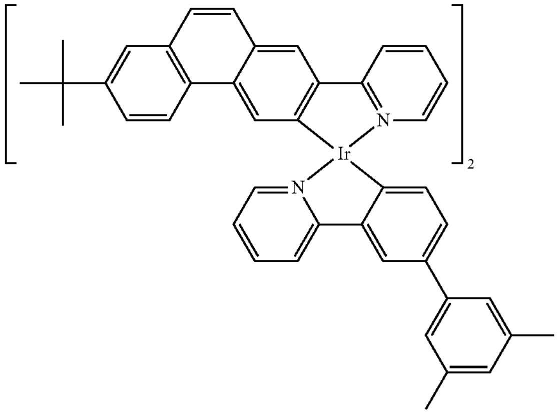
AA17
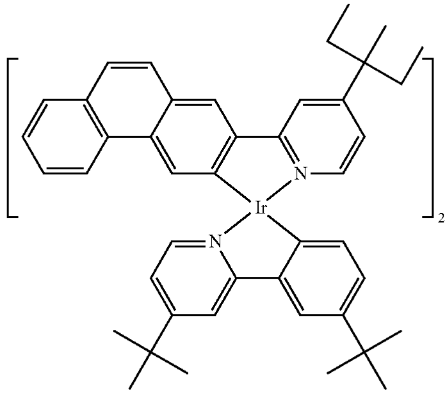
AA18
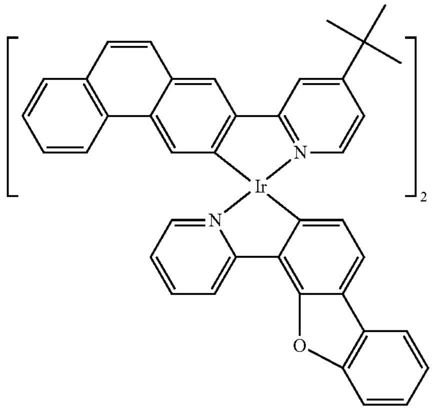

AA19
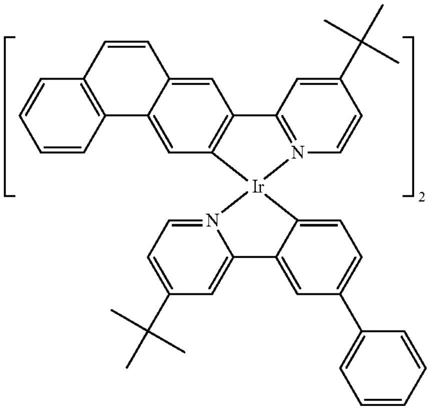
AA20
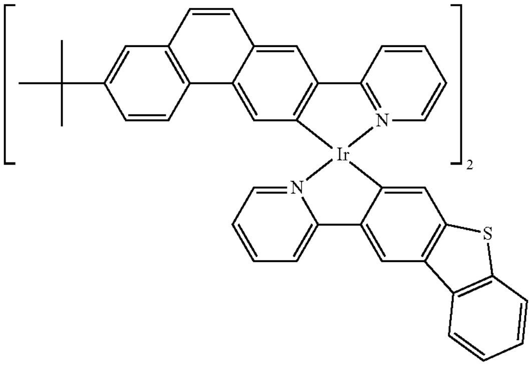
AA21
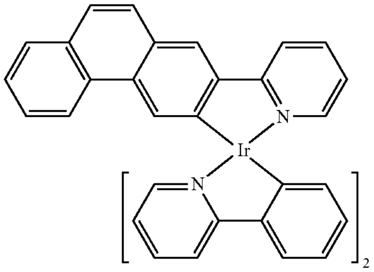
AA22
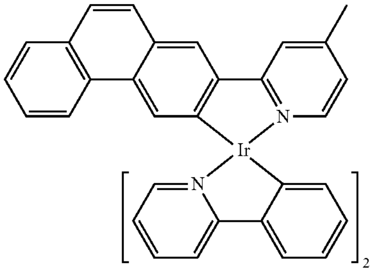
AA23
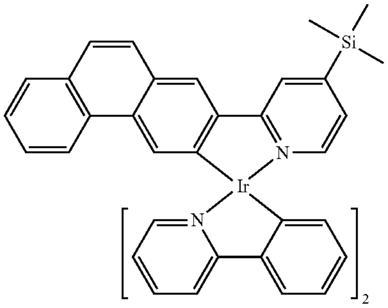
AA24
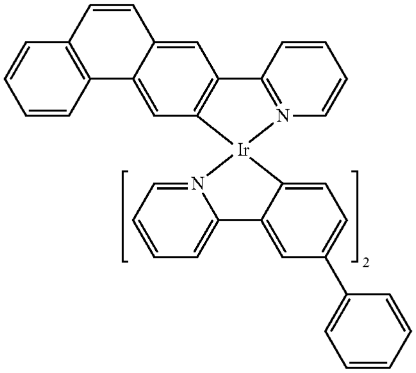
AA25
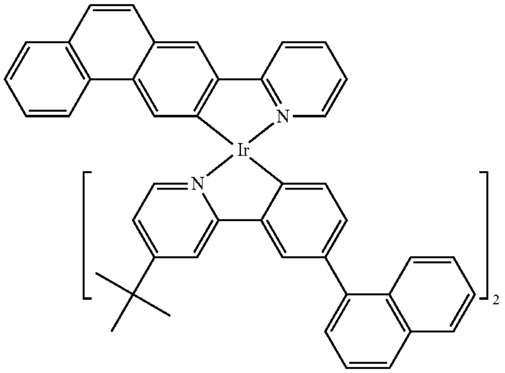
AA26
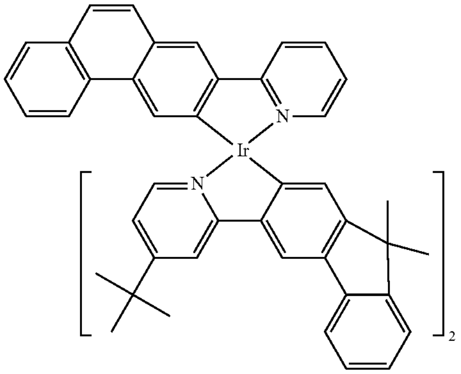

-continued
AA27
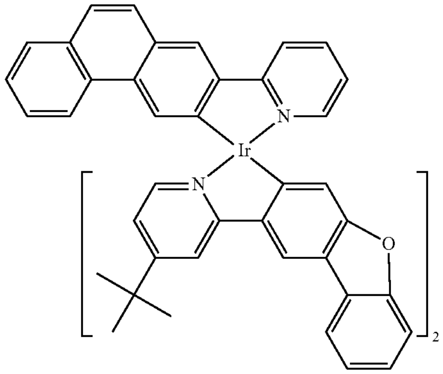
AA28
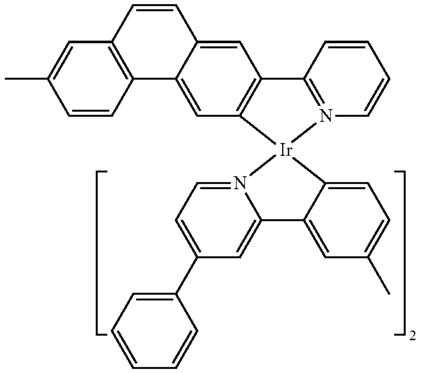
AA29
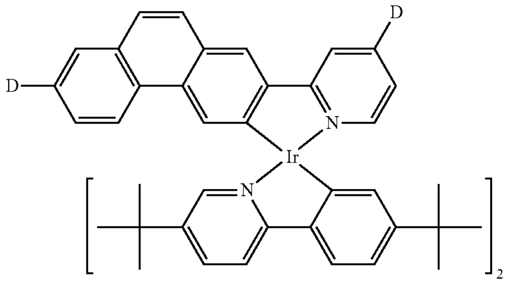
AA30
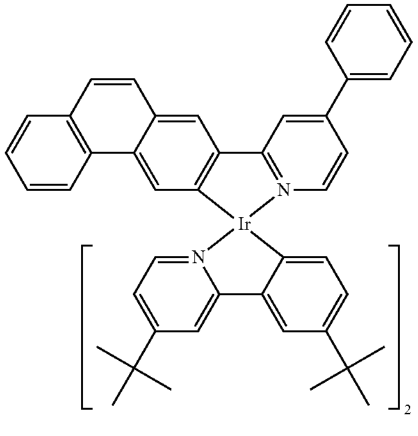
-continued
BB1
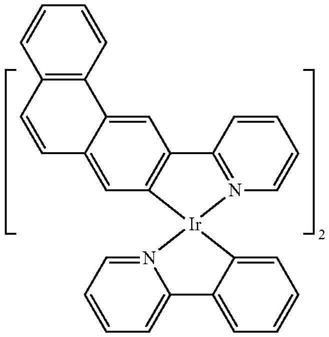
BB2
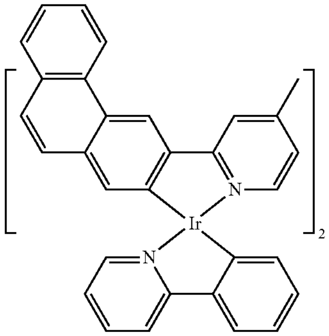
BB3
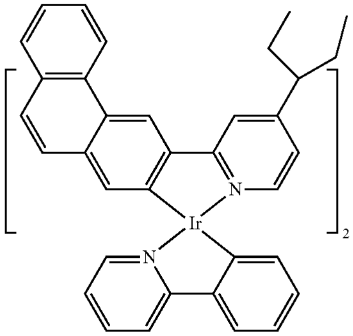
BB4
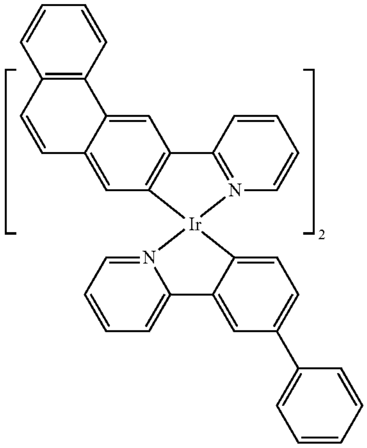

-continued
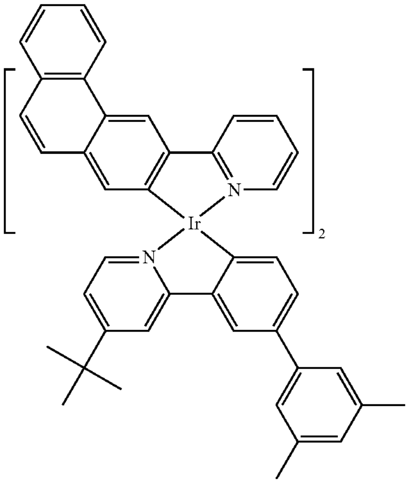
BB5
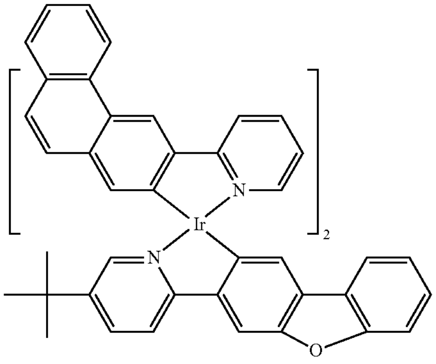
BB8
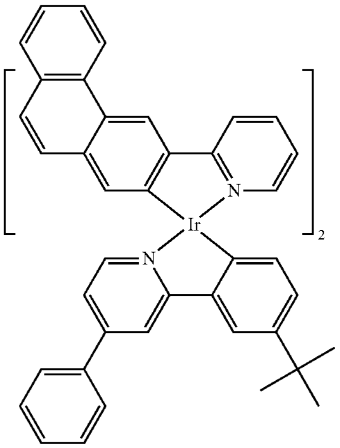
BB6
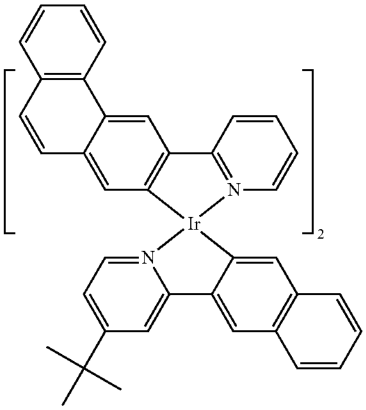
BB9
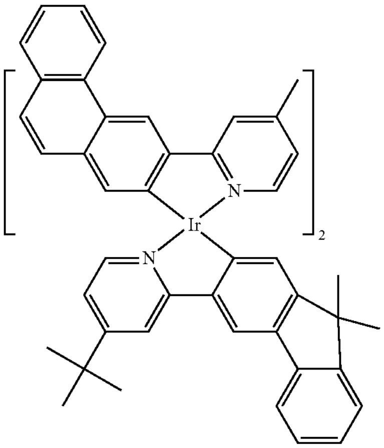
BB7
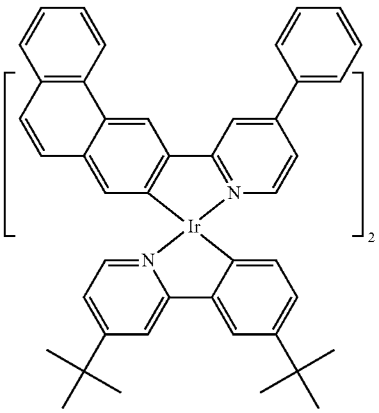
BB10

BB11
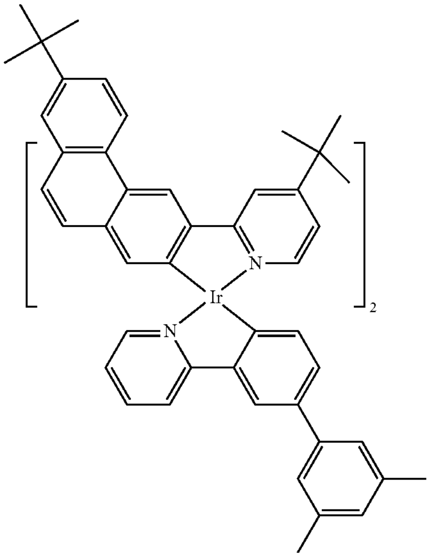
BB12
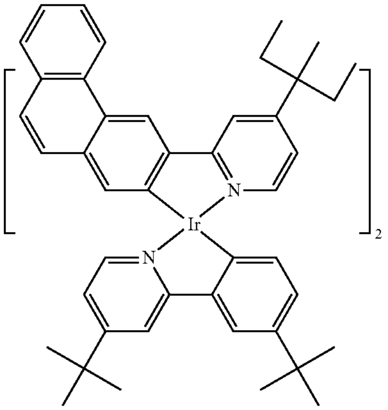
BB13
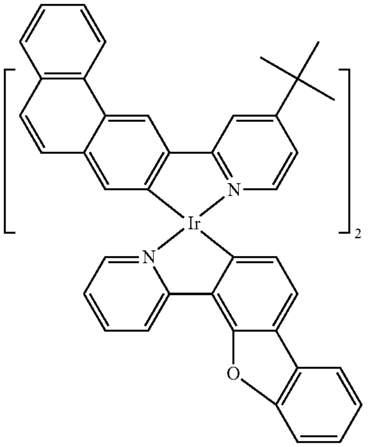
BB14
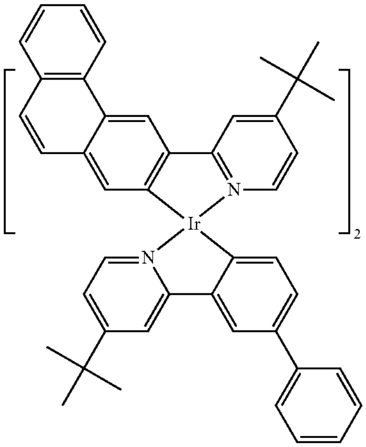
BB15
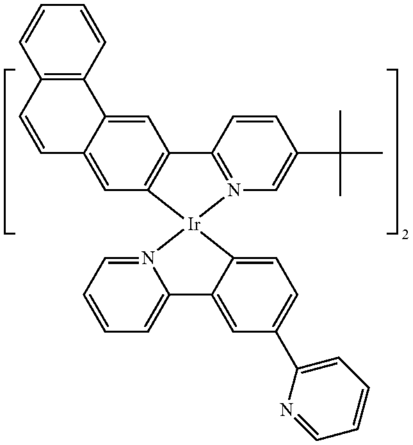
BB16
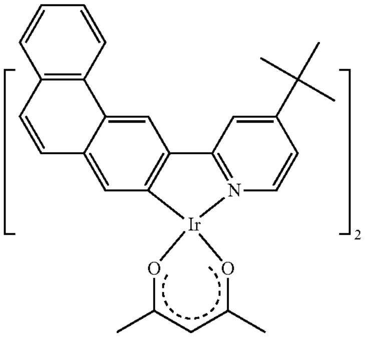
BB17
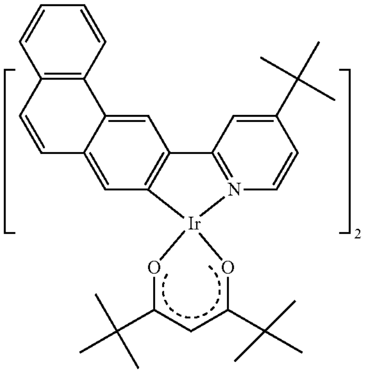

-continued
BB18
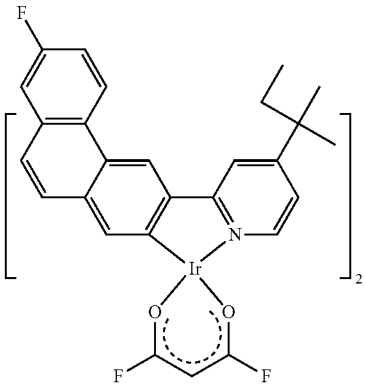
BB19
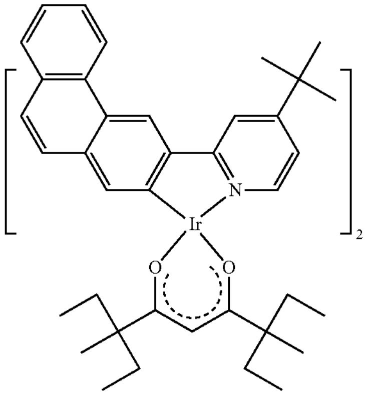
BB21
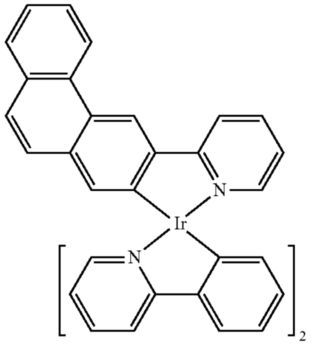
BB22
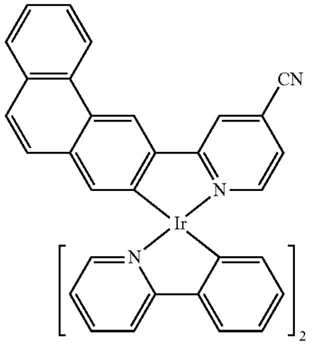
-continued
BB23
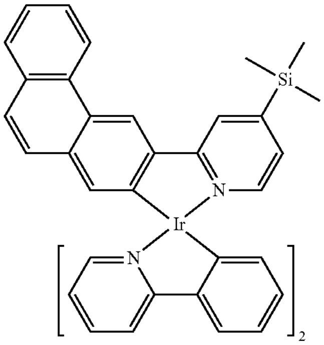
BB24
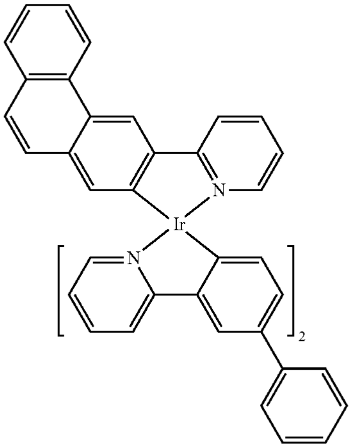
BB25
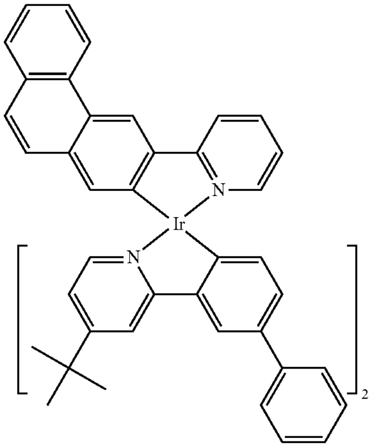

-continued
BB26
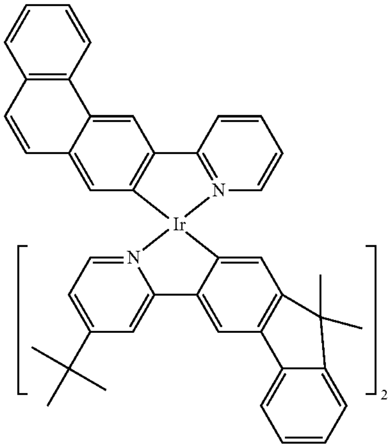
BB27
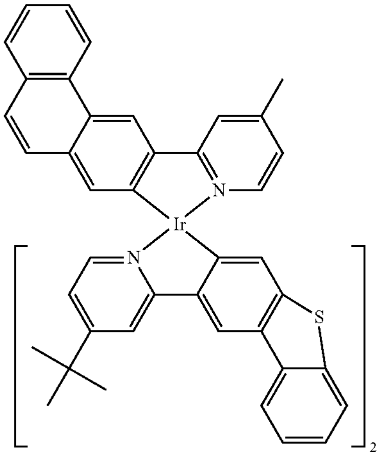
BB28
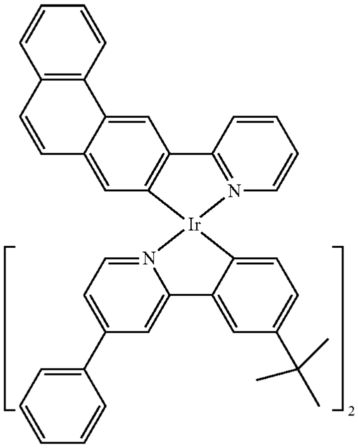
-continued
BB29
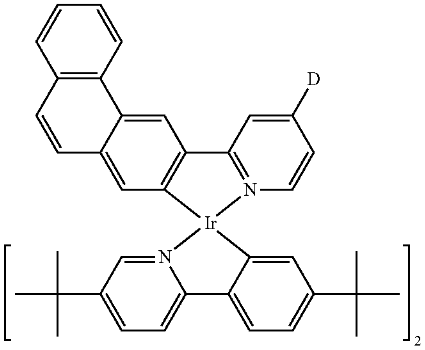
BB30
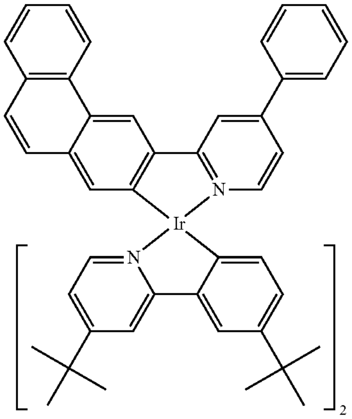
CC1
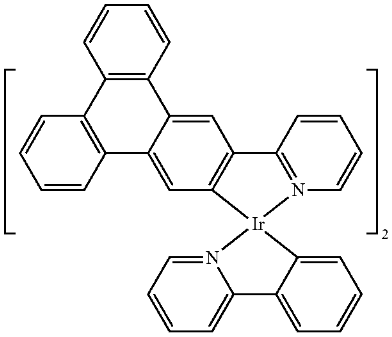
CC2
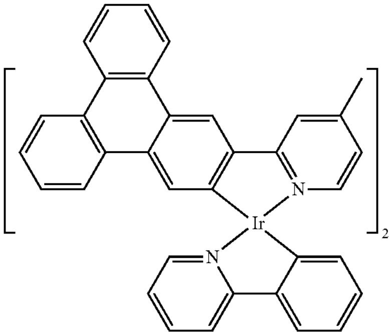

-continued
CC3
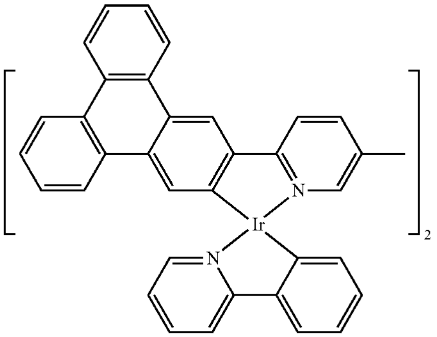
CC4
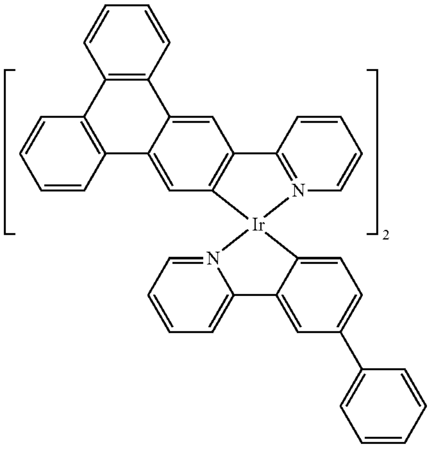
CC5
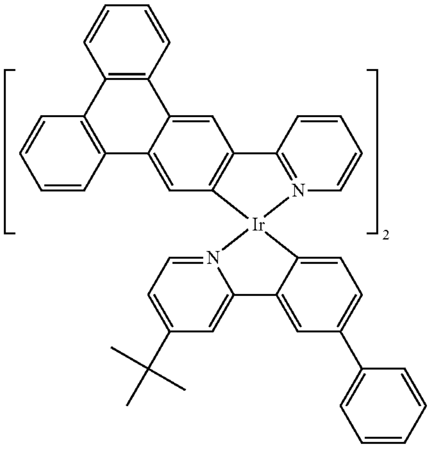
-continued
CC6
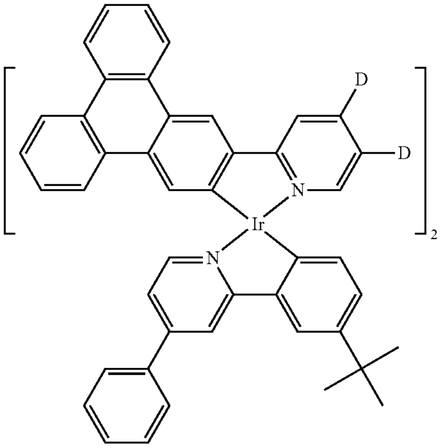
CC7
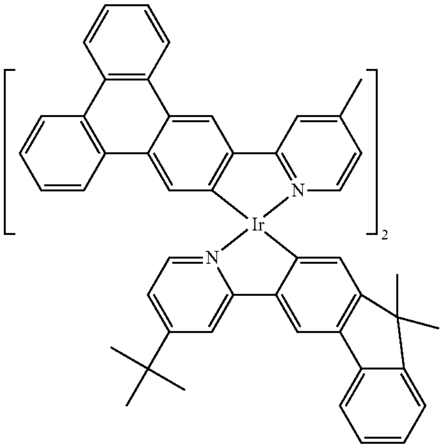
CC8
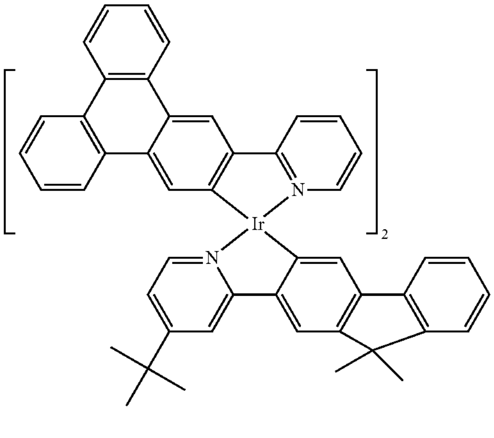

-continued
CC9
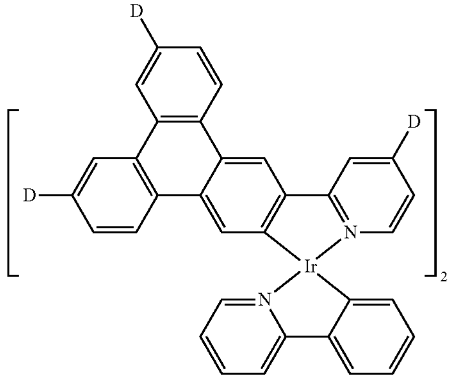
CC10
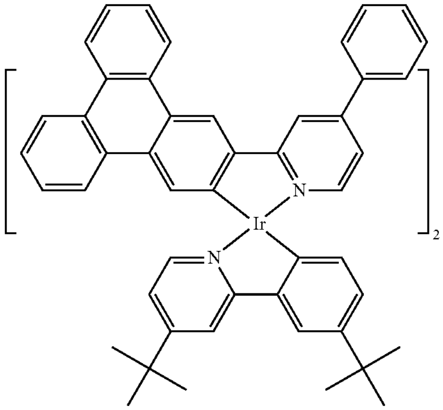
CC11
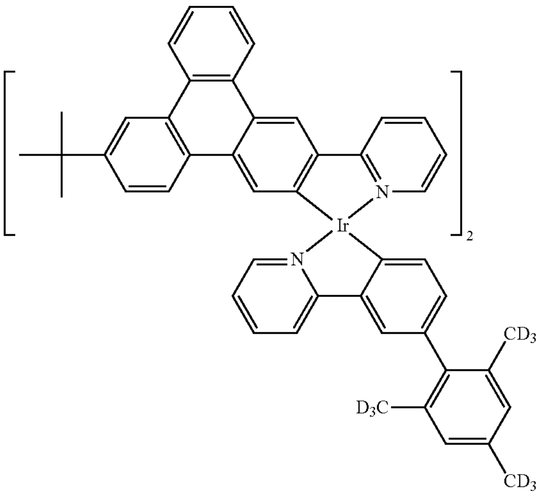
-continued
CC12
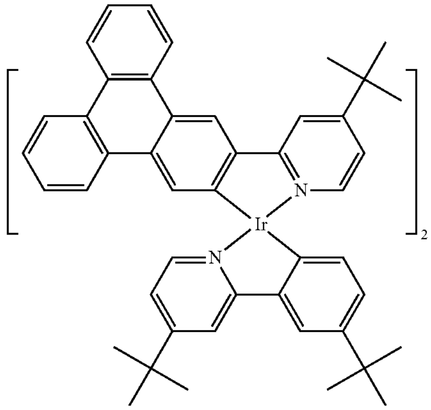
CC13
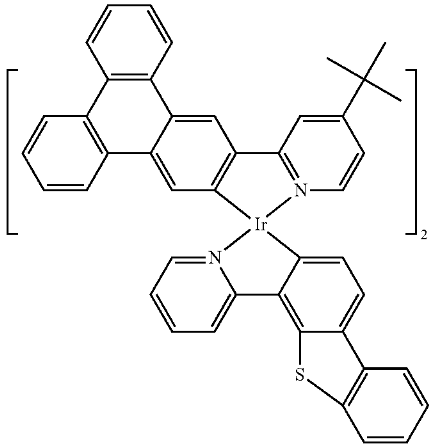
CC14
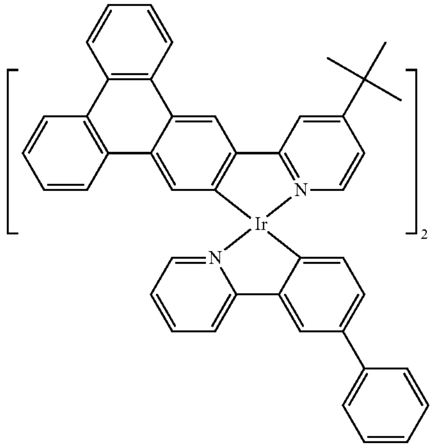

CC15
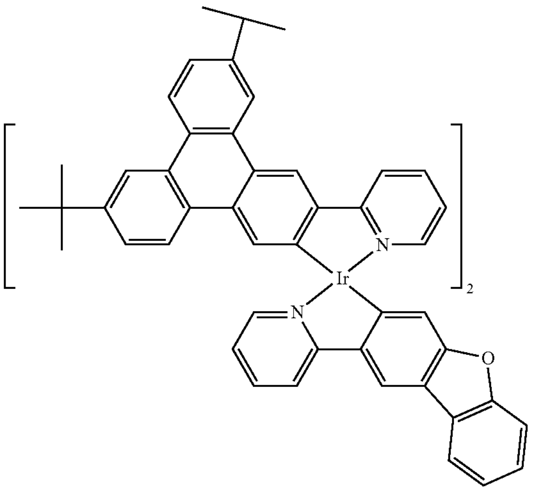
CC16
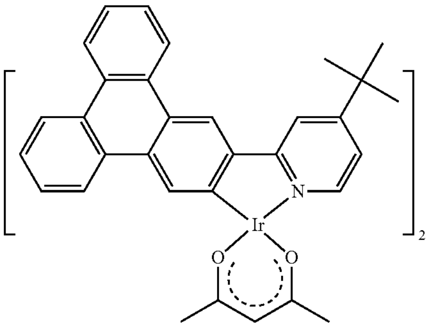
CC17
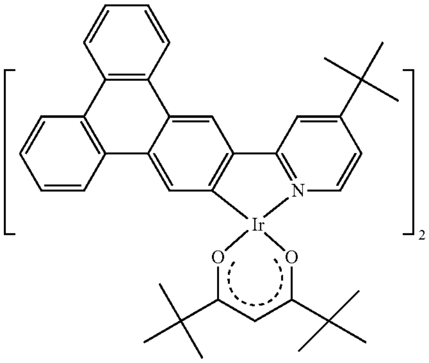
CC18
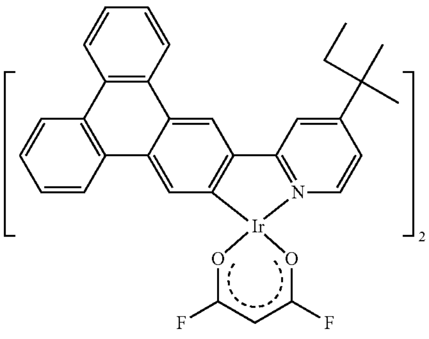
CC19
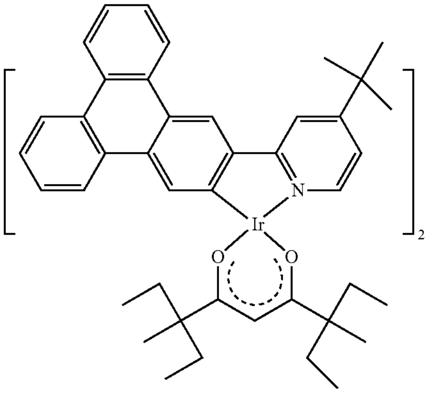
CC20
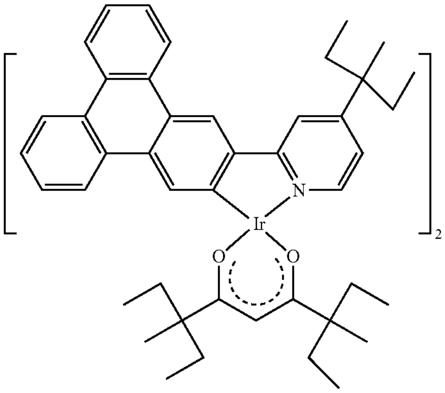
CC21
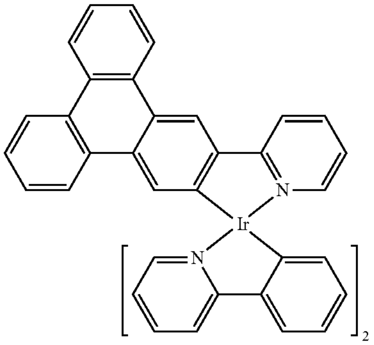
CC22
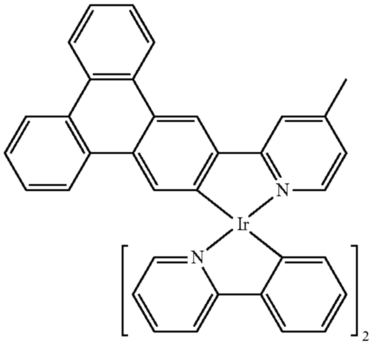

-continued
CC23
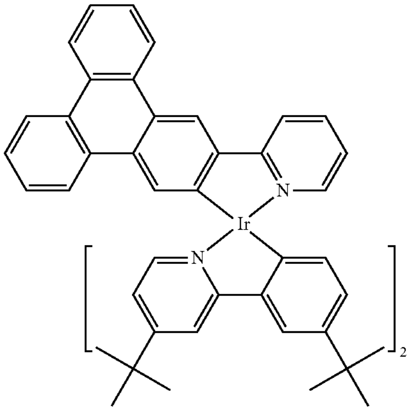
CC24
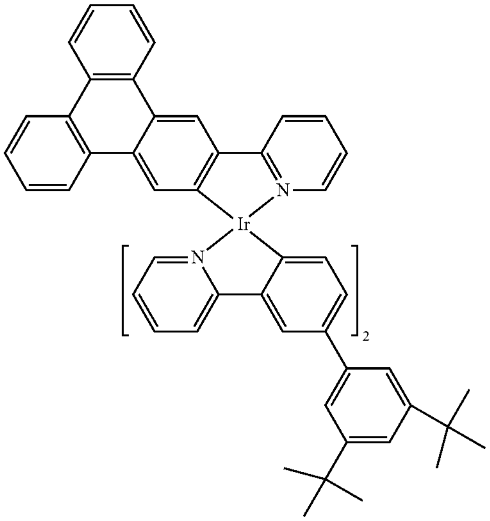
CC25
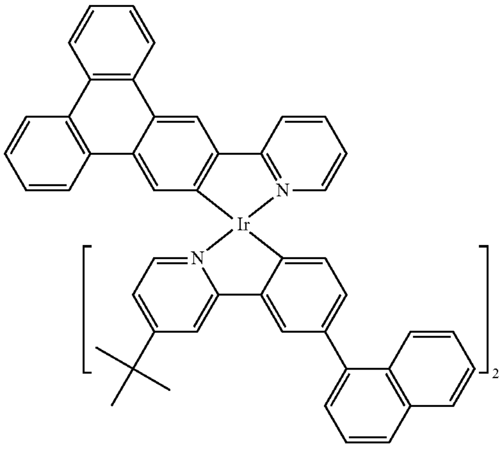
-continued
CC26
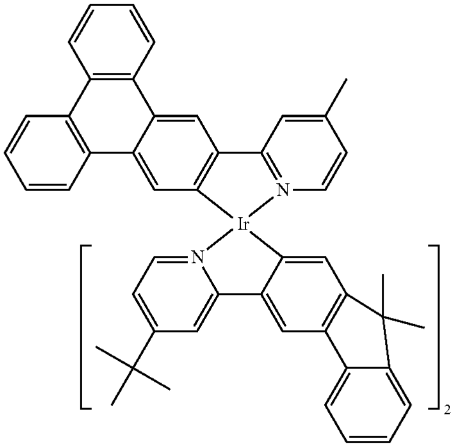
CC27
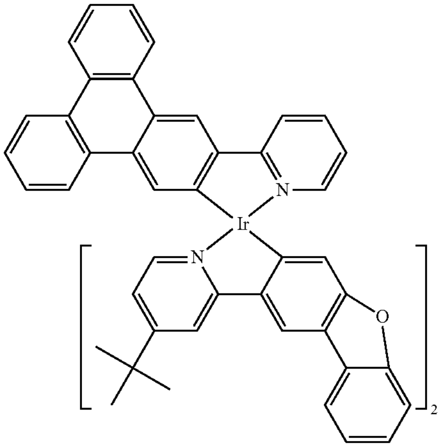
CC28
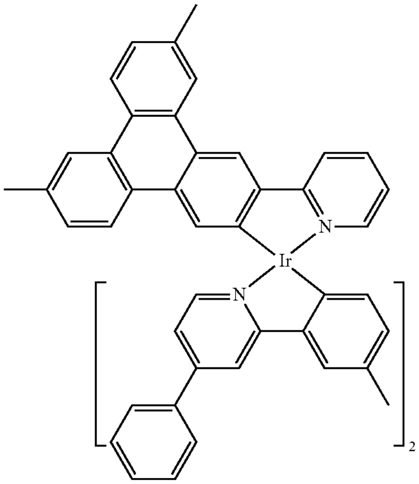

-continued
CC29
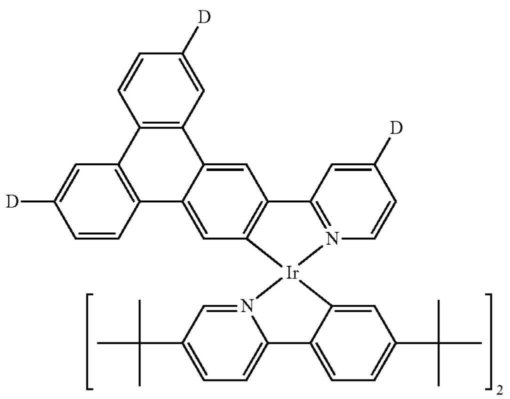
CC30
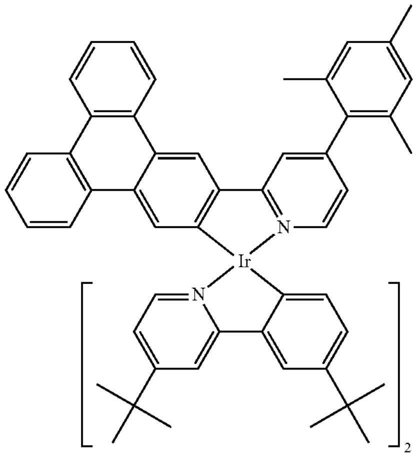
DD1
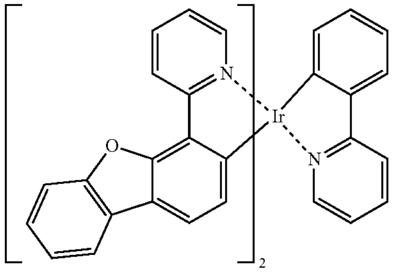
DD2
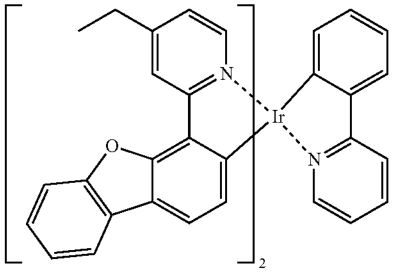
-continued
DD3
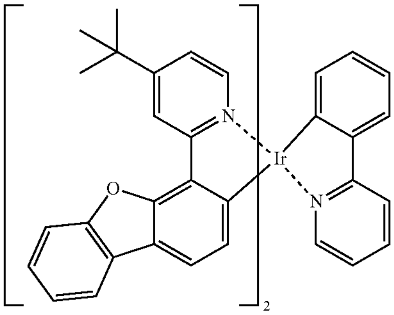
DD4
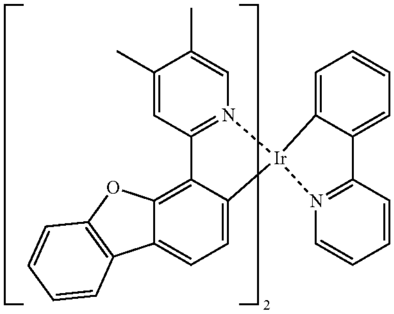
DD5
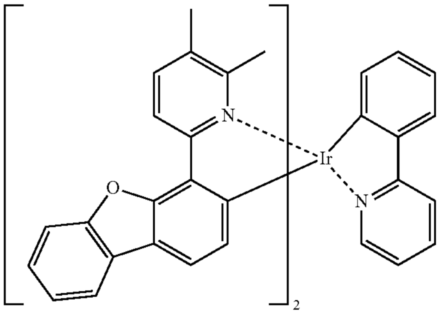
DD6
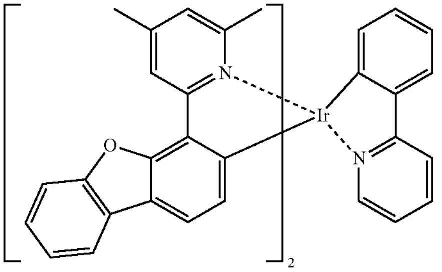
DD7
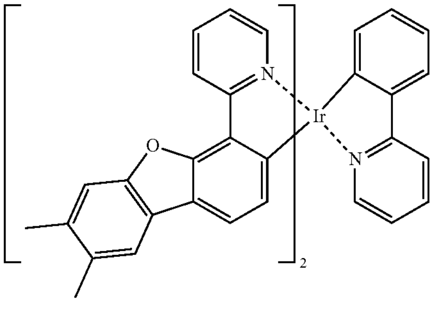

-continued
DD8
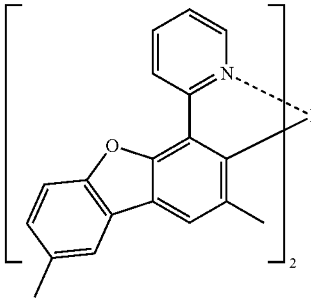
DD9
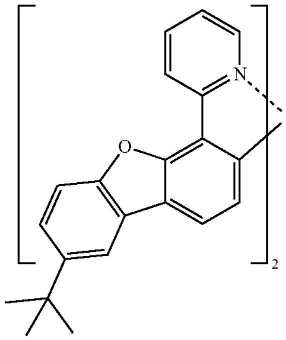
DD10
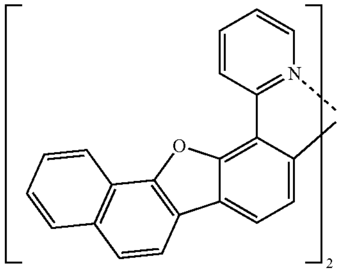
DD11
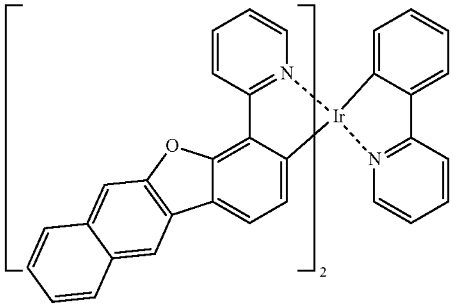
DD12
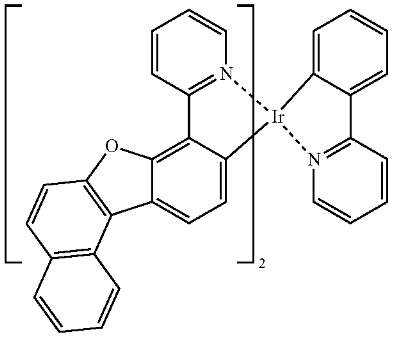
-continued
DD13
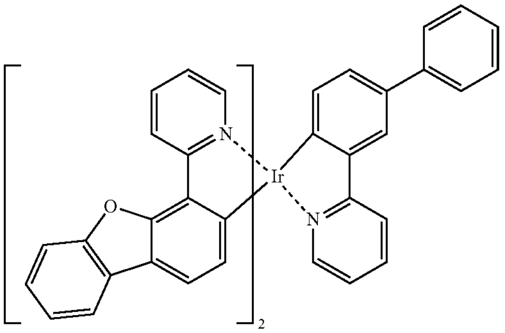
DD14
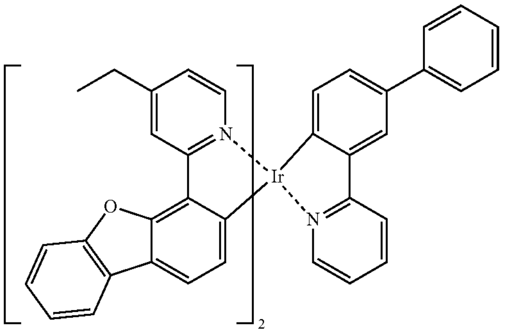
DD15
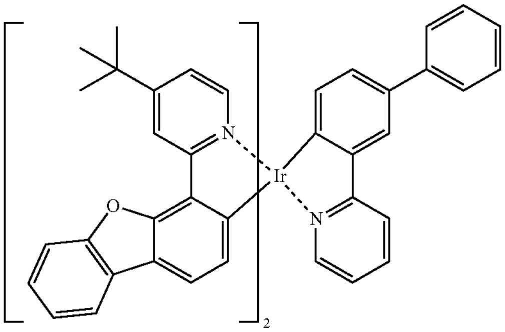
DD16
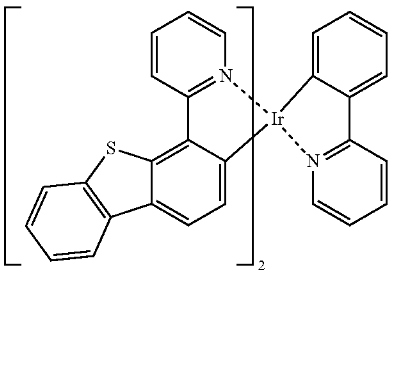

-continued
DD17
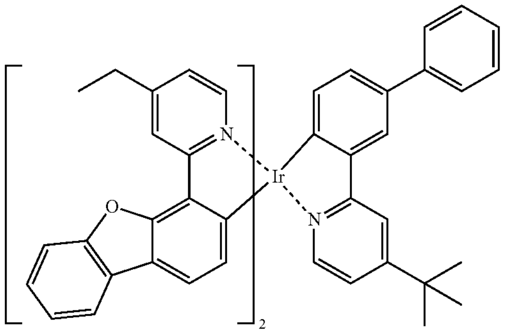
DD18
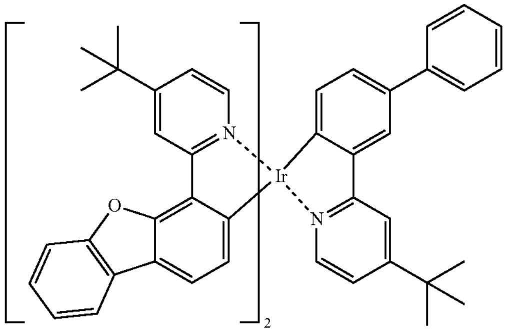
DD20
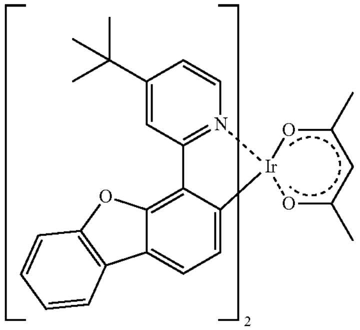
DD21
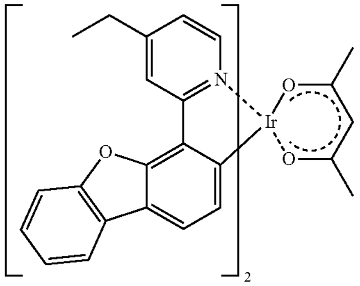
-continued
DD22
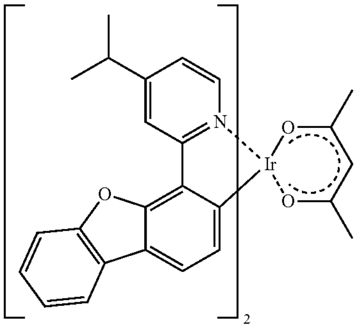
DD23
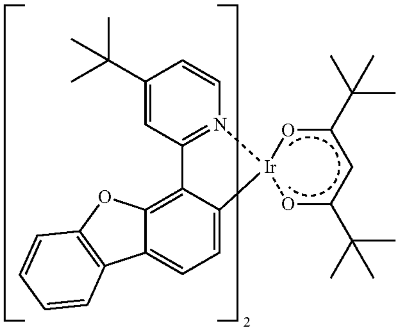
DD24
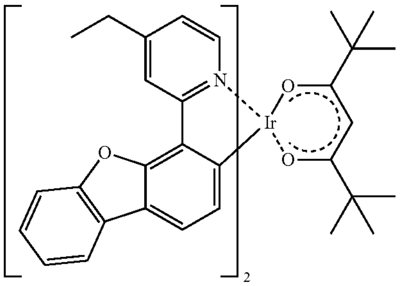
DD25
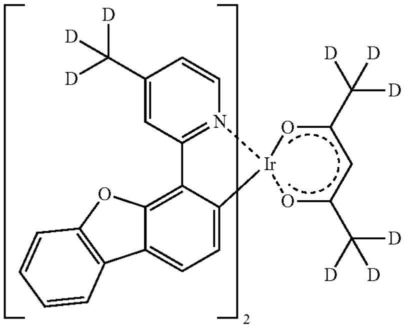

-continued
DD26
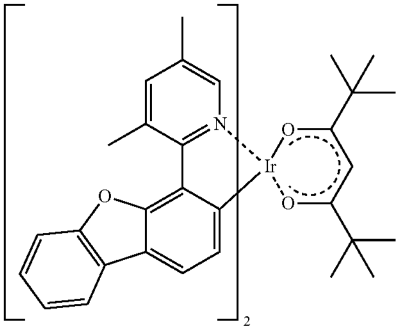
DD27
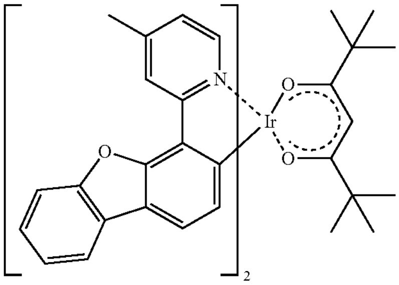
DD28
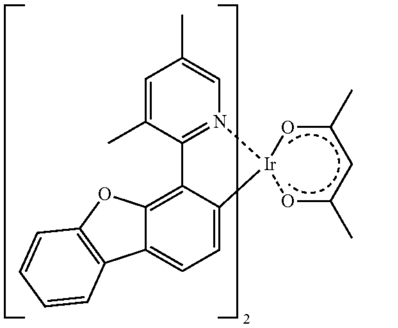
DD29
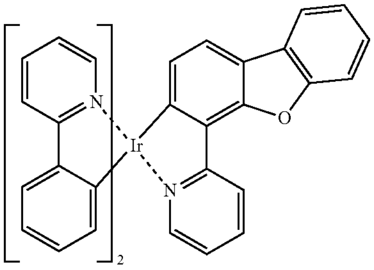
DD30
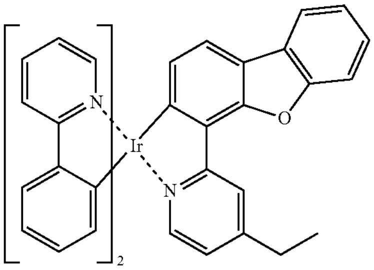
-continued
DD31
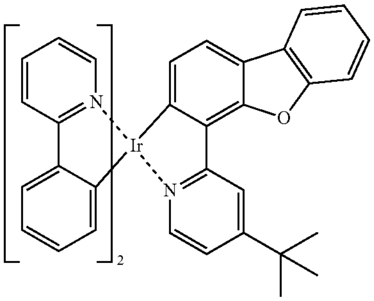
DD32
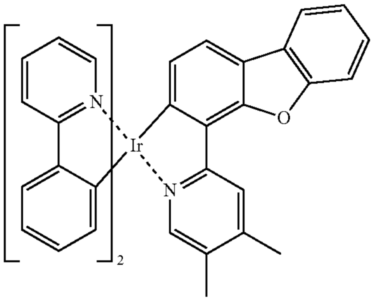
DD33
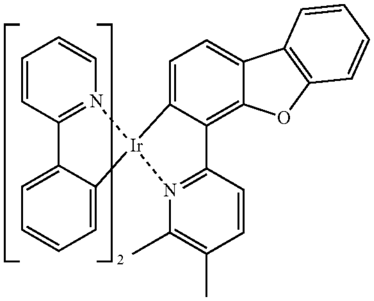
DD34
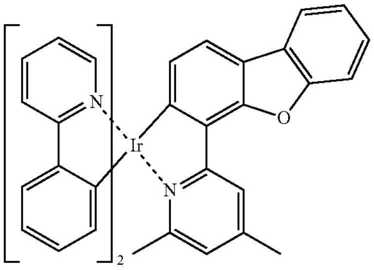
DD35
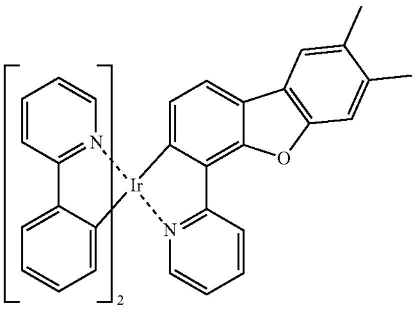

-continued
DD36
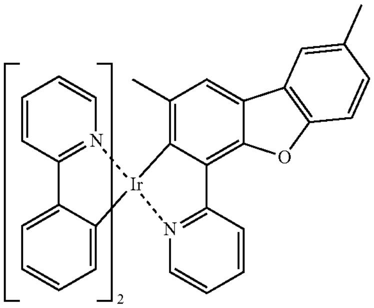
DD37
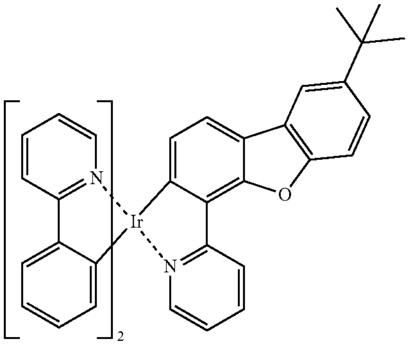
DD38
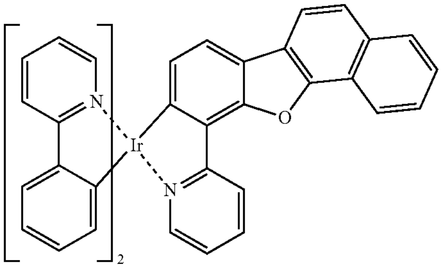
DD39
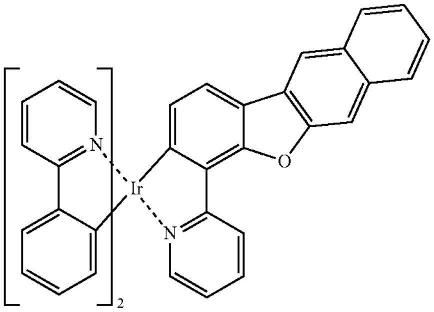
DD40
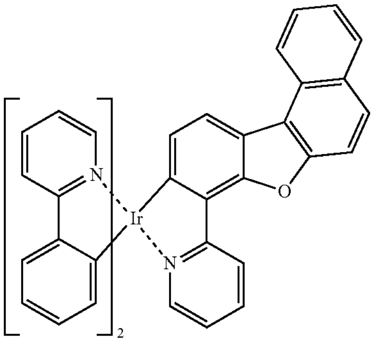
-continued
DD41
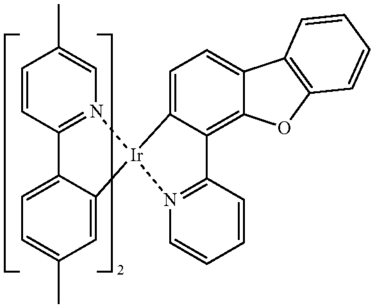
DD42
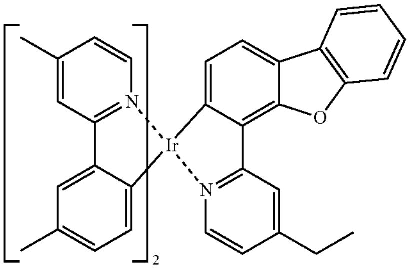
DD43
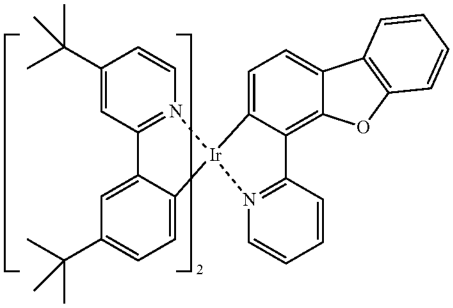
DD44
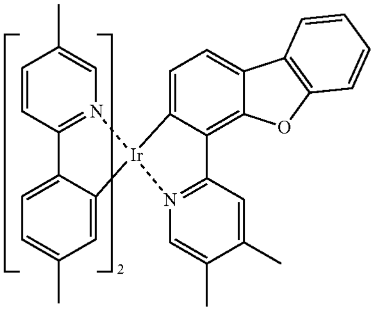
DD45
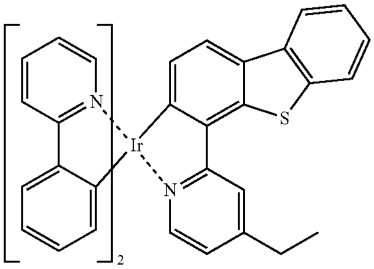

-continued
DD46
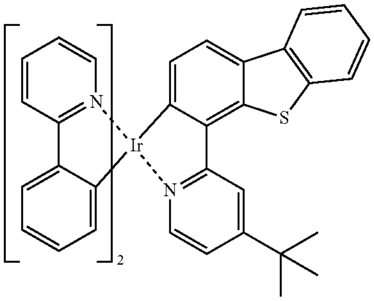
DD47
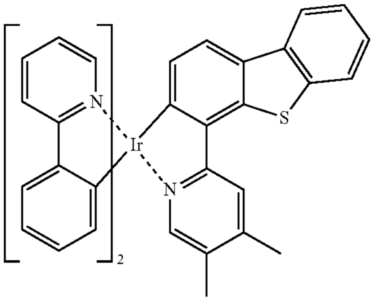
DD48
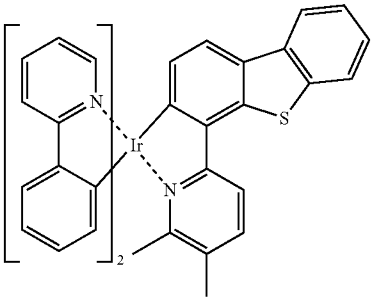
DD49
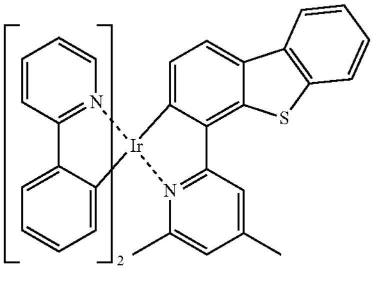
DD50
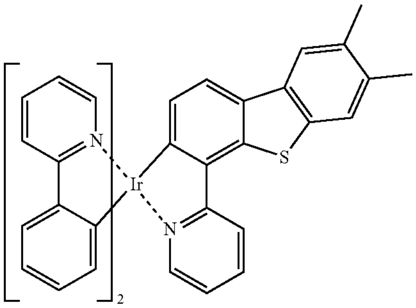
-continued
DD51
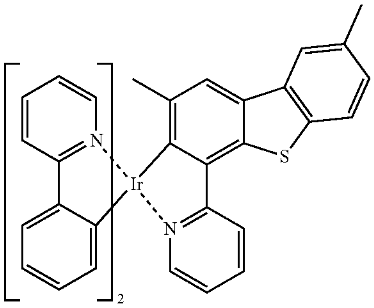
DD52
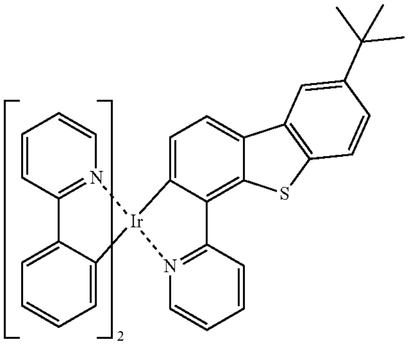
DD53
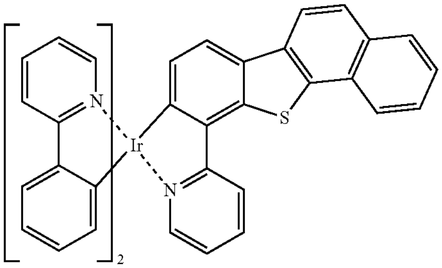
DD54
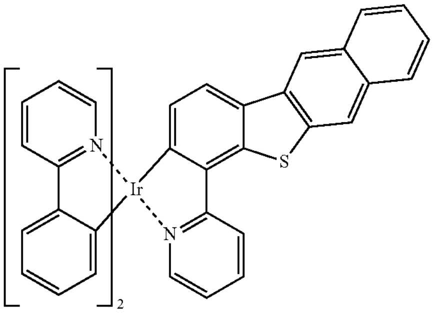
DD55
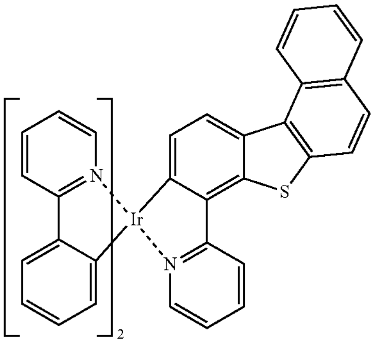

-continued
DD56
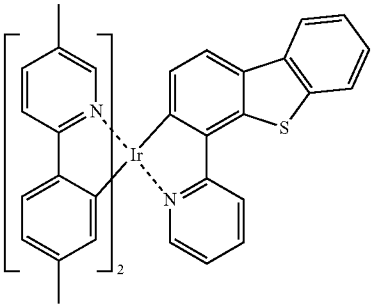
EE1
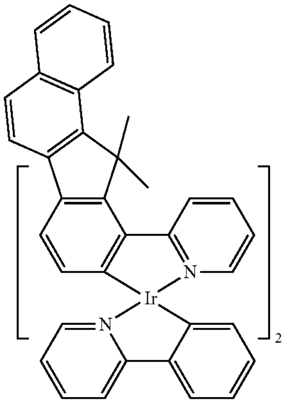
EE2
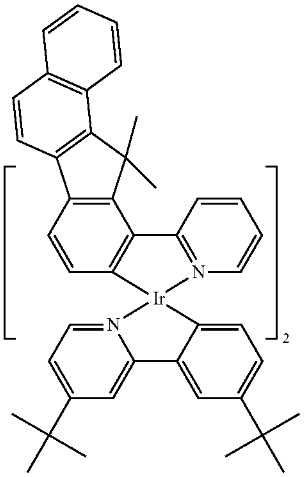
EE3
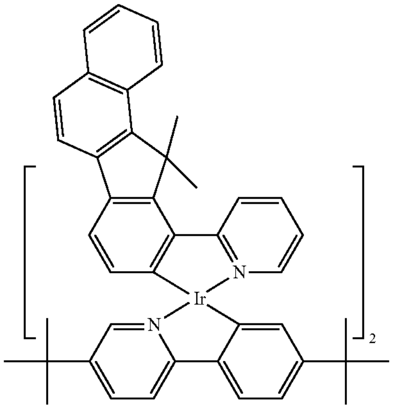
-continued
EE4
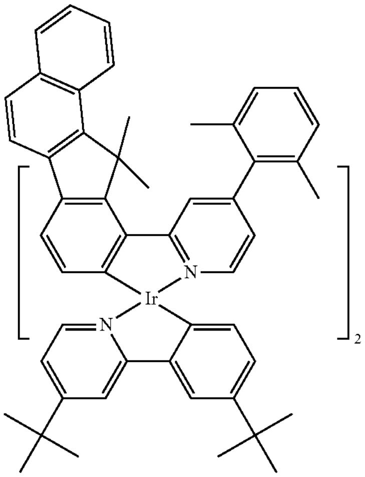
EE5
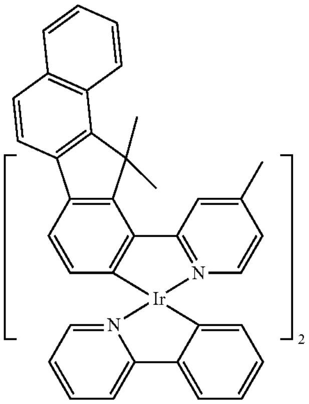
EE6
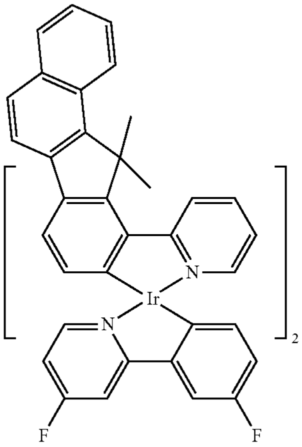

-continued
EE7
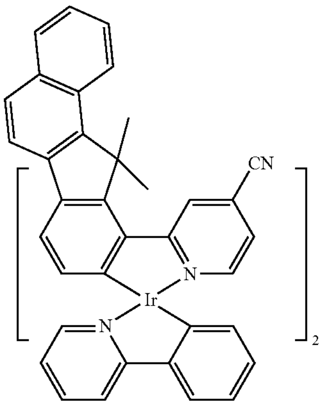
EE8
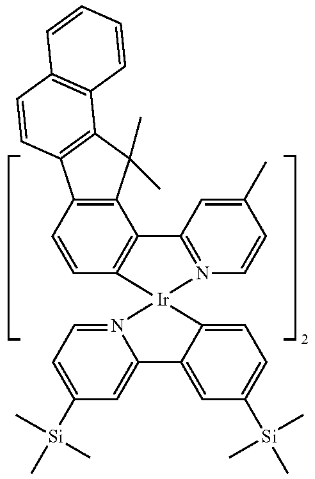
EE9
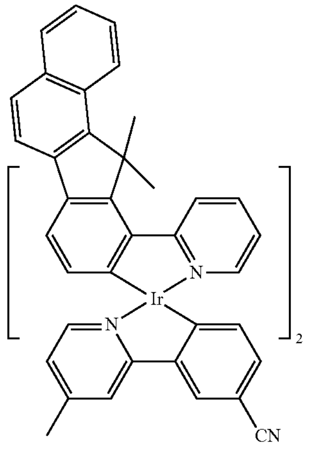
-continued
EE10
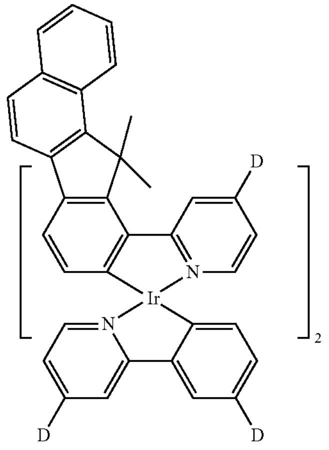
EE11
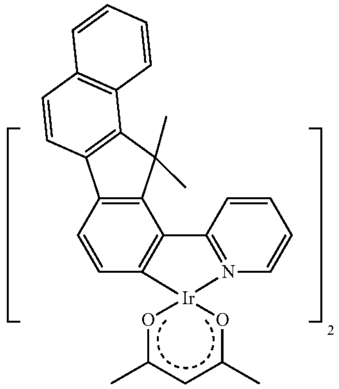
EE12
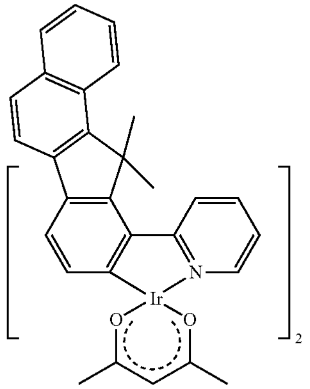

-continued
EE13
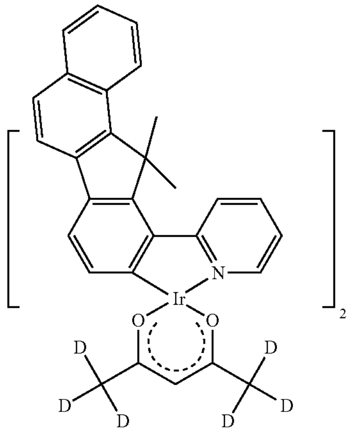
EE14
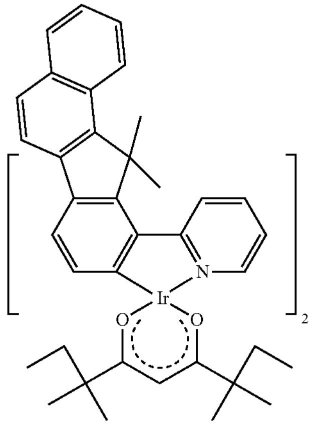
EE15
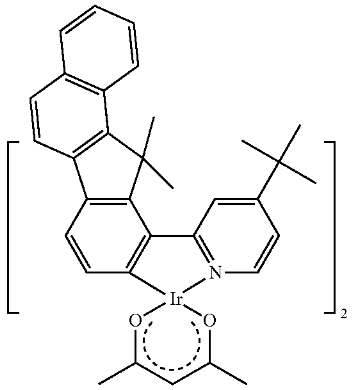
-continued
EE16
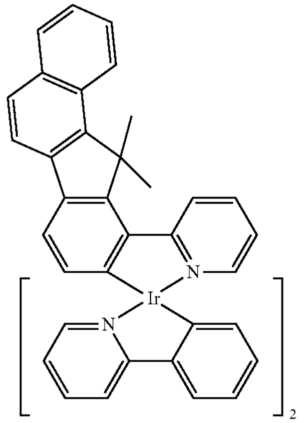
EE17
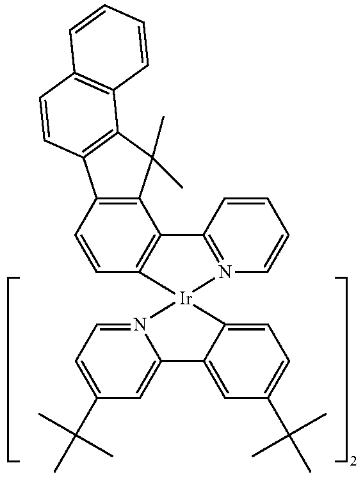
EE18
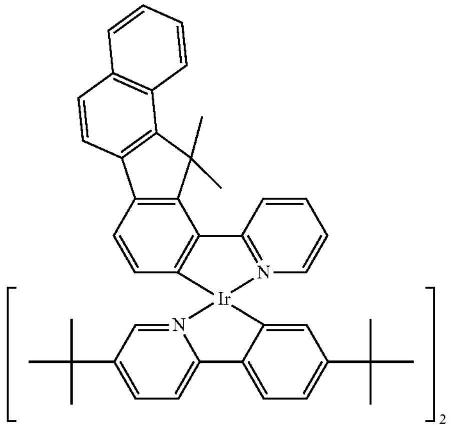

-continued
EE19
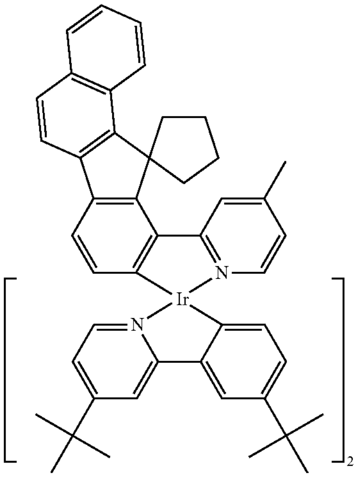
EE20
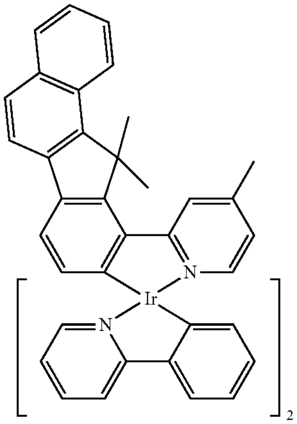
EE21
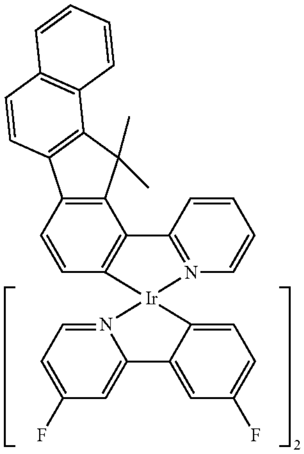
-continued
EE22
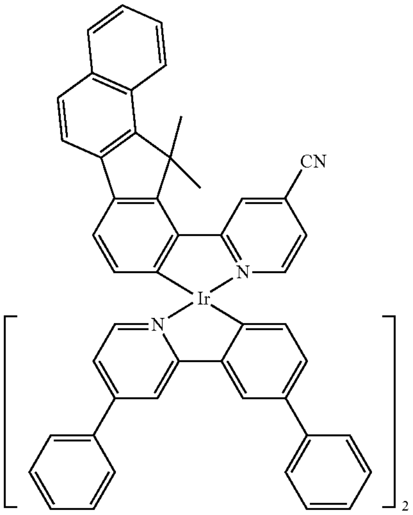
EE23
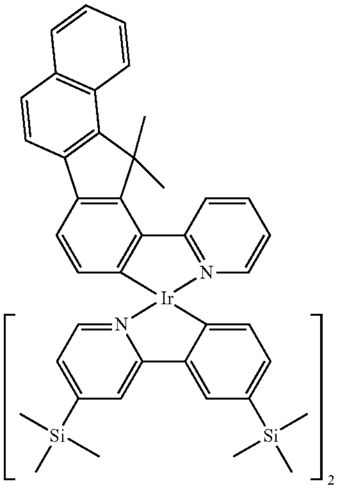
EE24
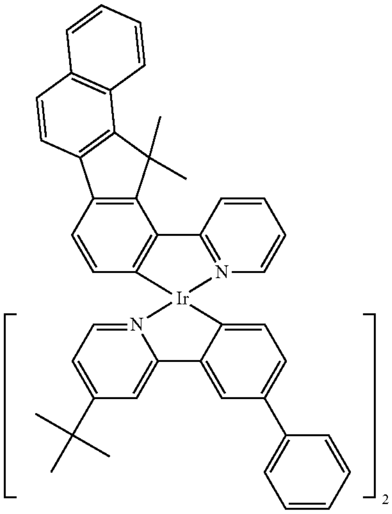

-continued
EE25
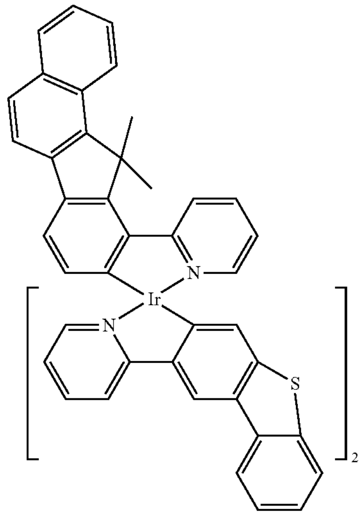
EE26
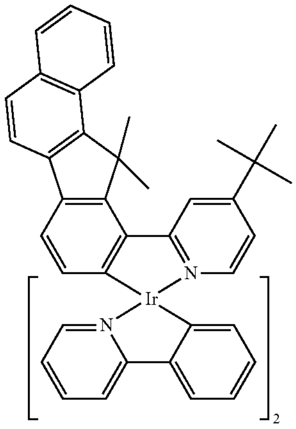
EE27
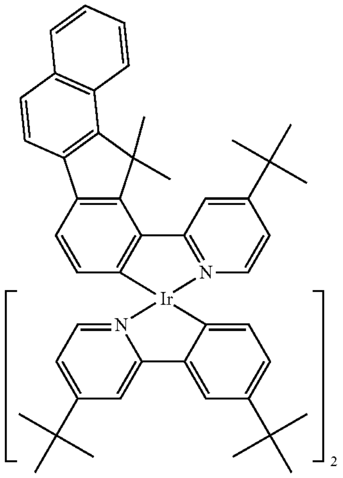
-continued
EE28
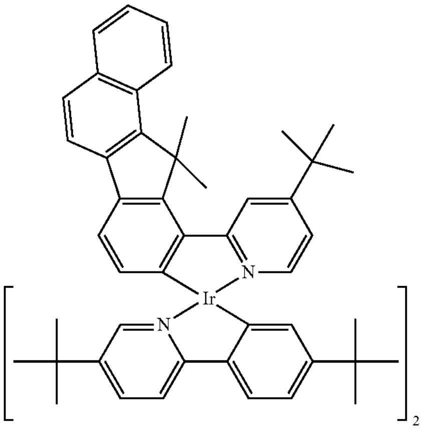
EE29
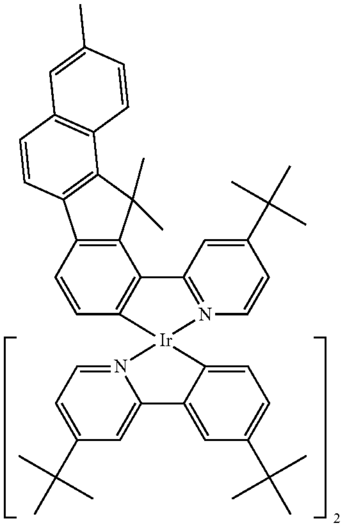
EE30
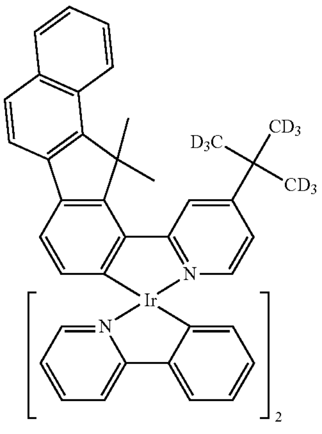

-continued
FF1
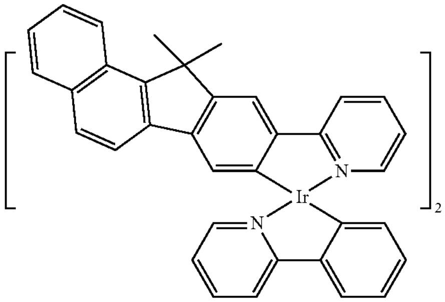
FF2
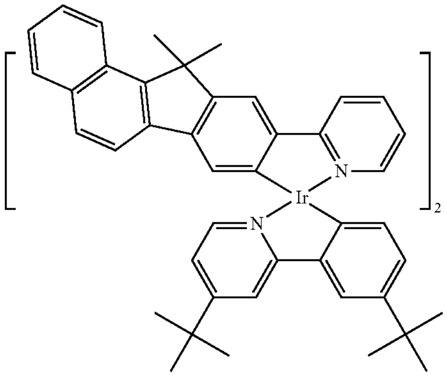
FF3
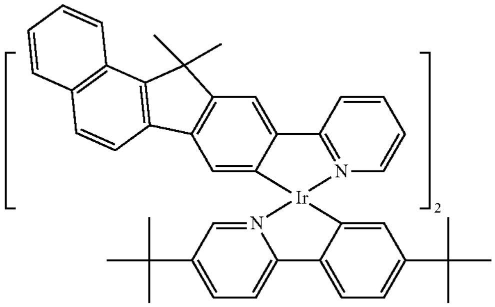
FF4
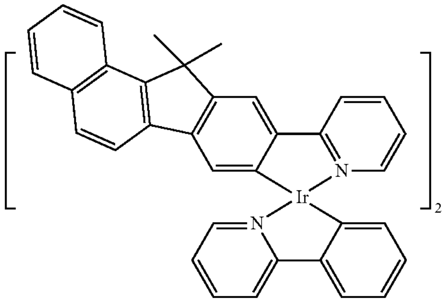
-continued
FF5
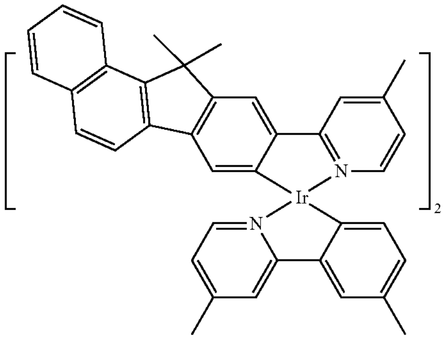
FF6
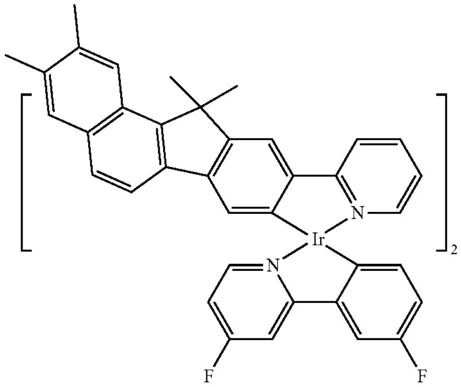
FF7
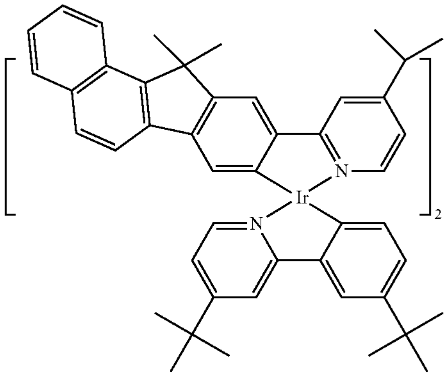
FF8
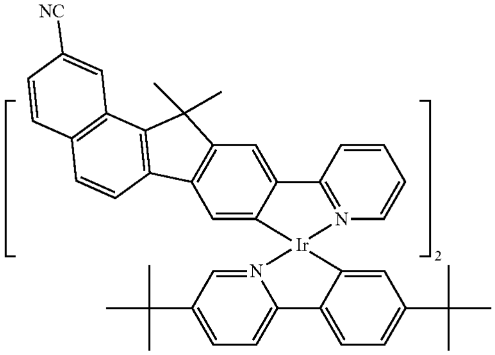

-continued
FF9
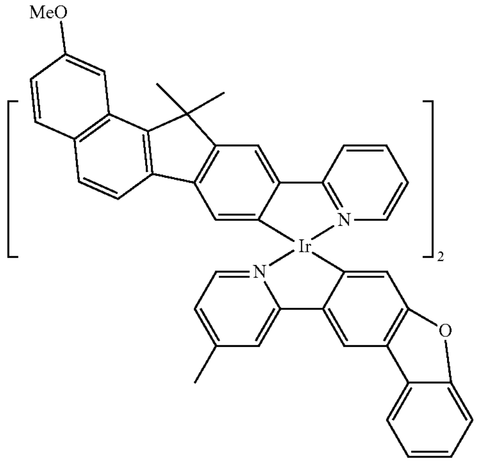
FF10
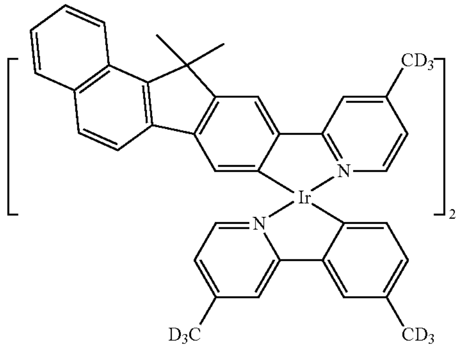
FF11
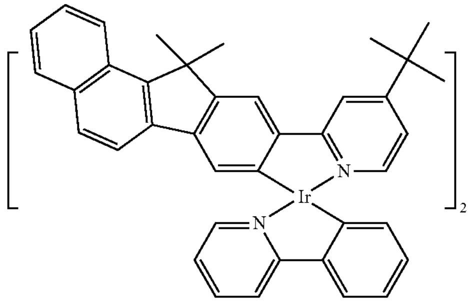
FF12
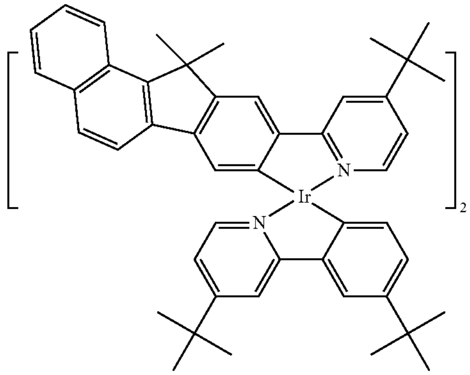
-continued
FF13
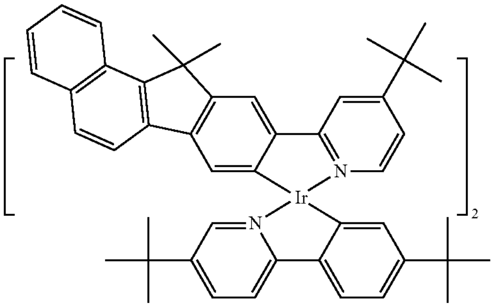
FF14
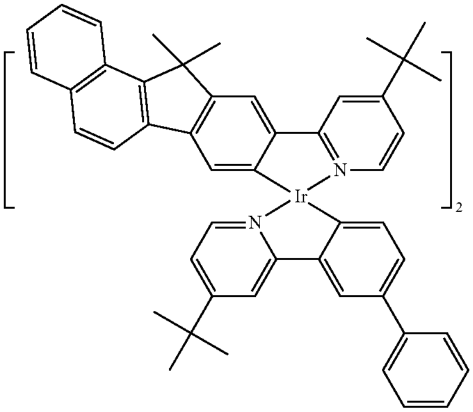
FF15
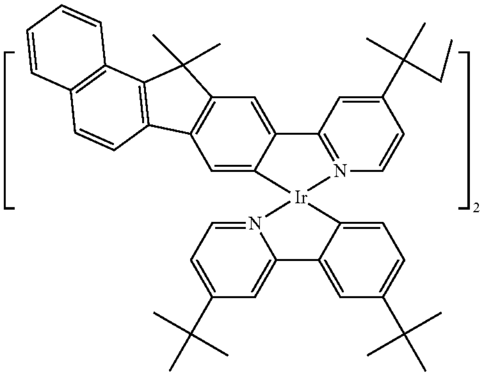
FF16
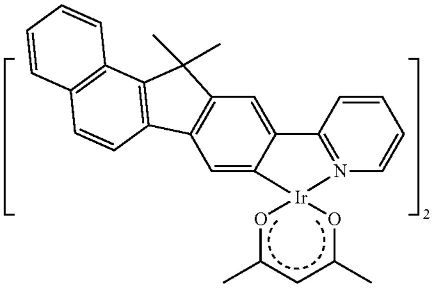

-continued
FF17
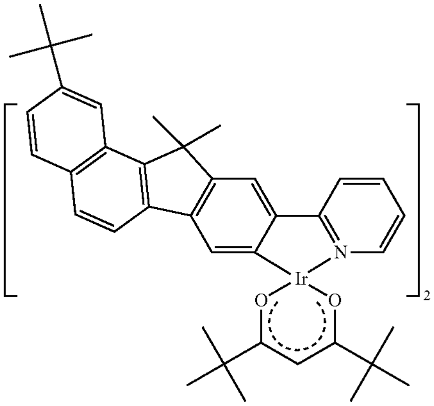
FF18
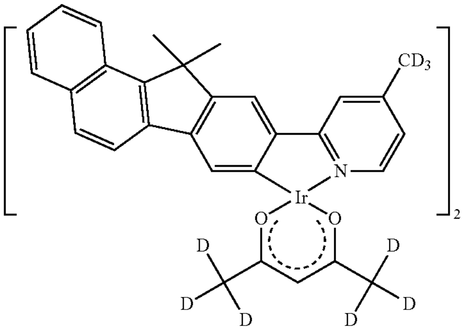
FF19
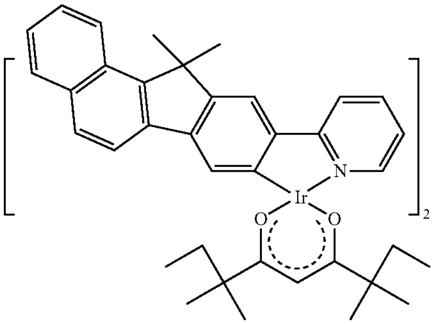
FF20
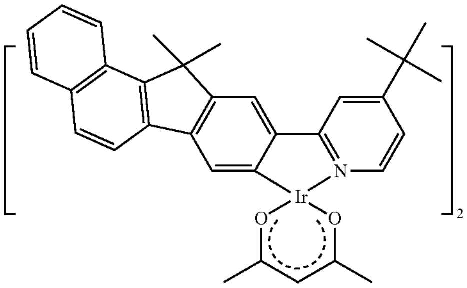
-continued
FF21
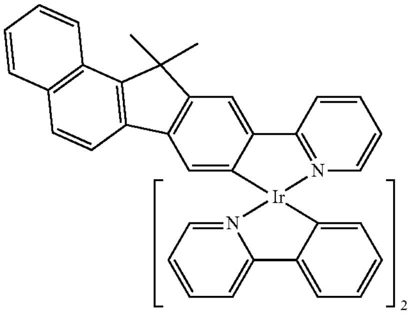
FF22
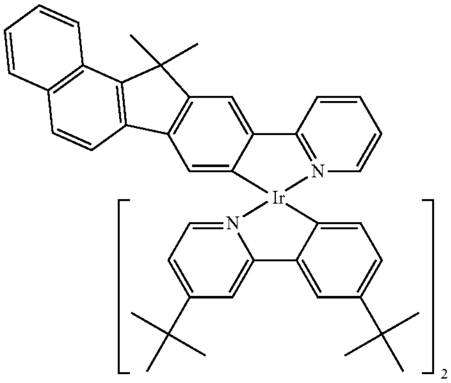
FF23
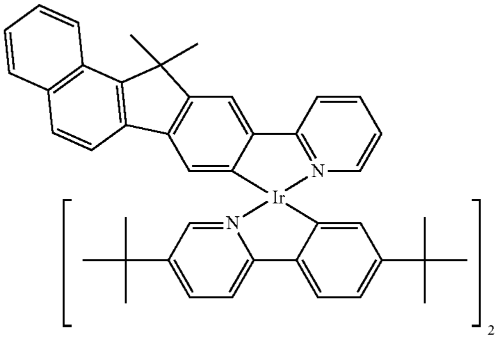
FF24
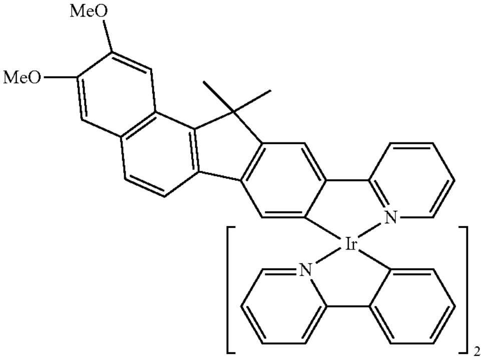

-continued
FF25
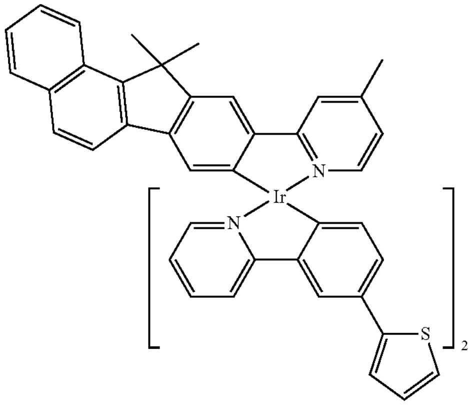
FF26
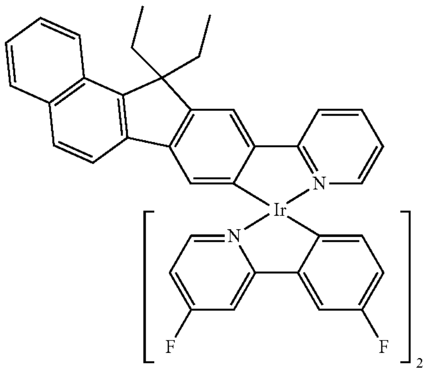
FF27
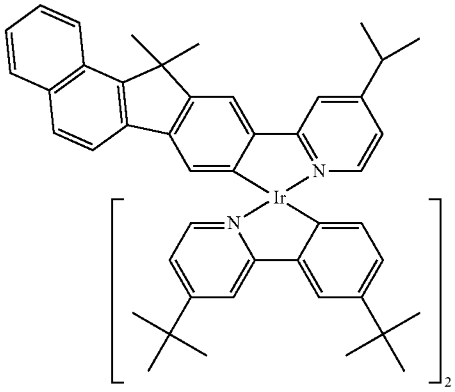
FF28
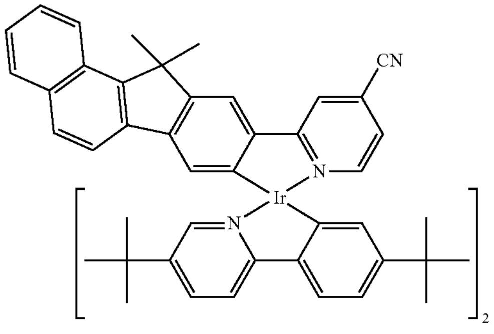
-continued
FF29
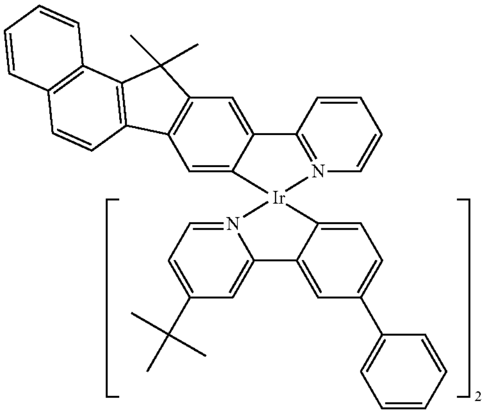
FF30
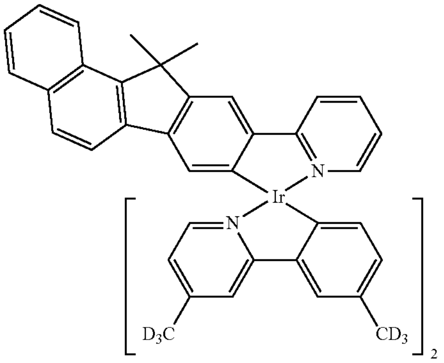
FF31
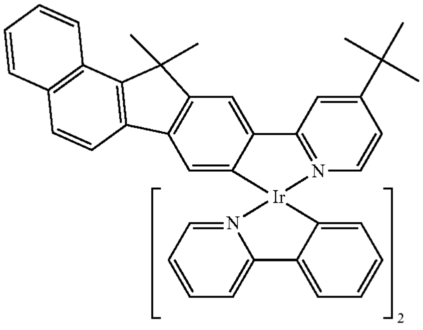
FF32
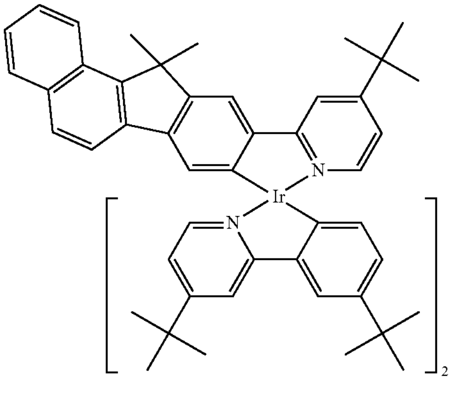

-continued
FF33
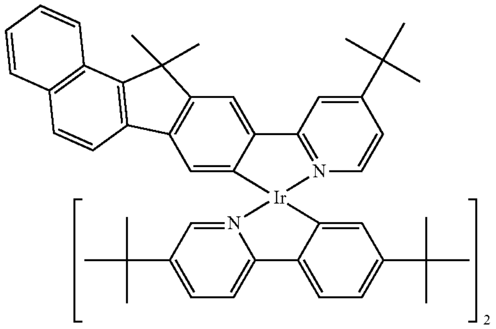
FF34
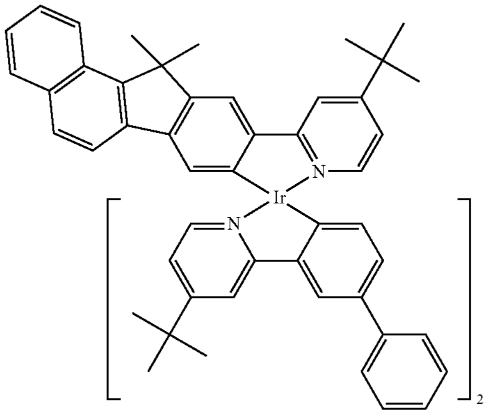
FF35
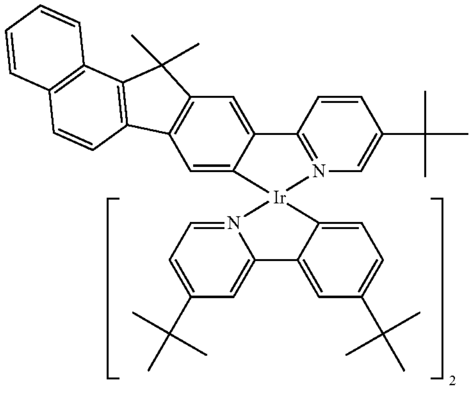
GG1
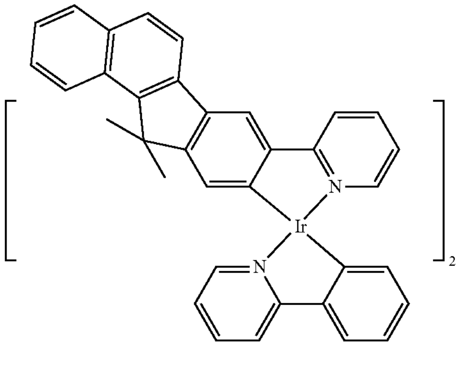
-continued
GG2
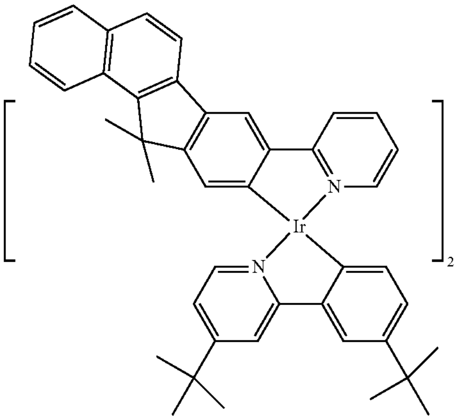
GG3
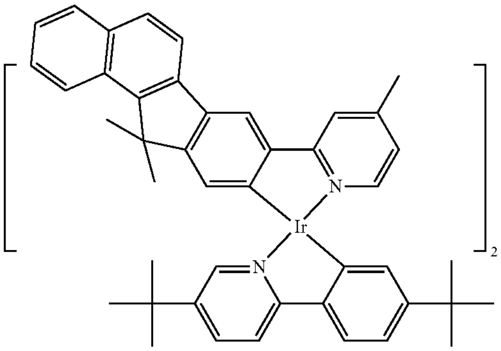
GG4
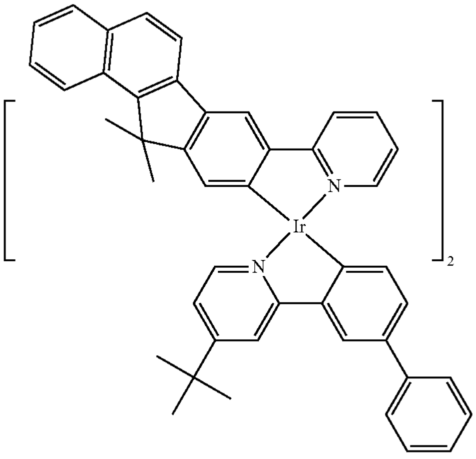
GG5
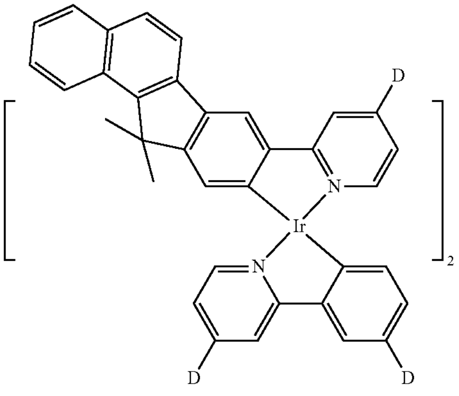

-continued
GG6
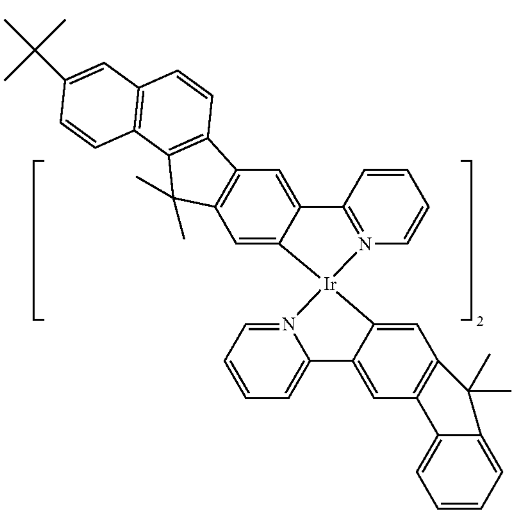
GG7
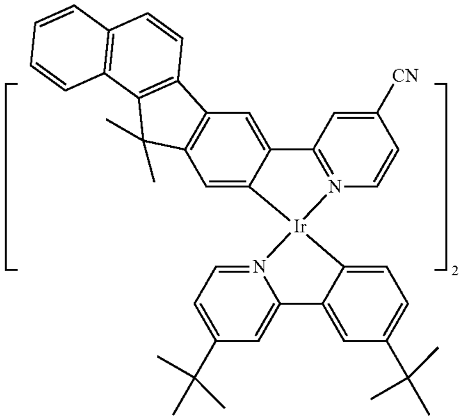
GG8
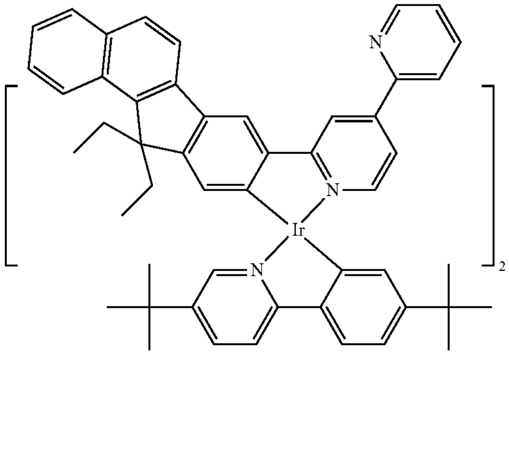
-continued
GG9
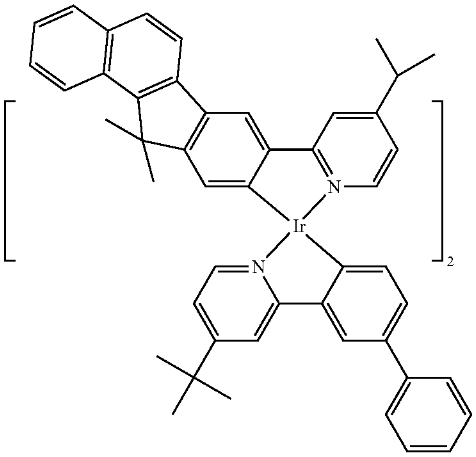
GG10
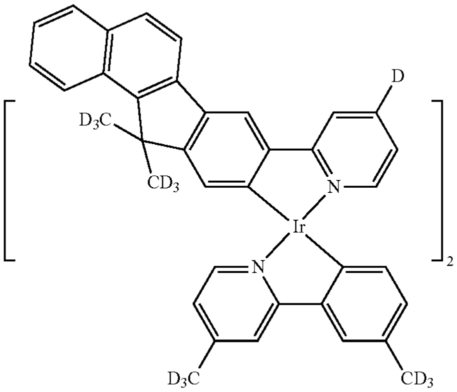
GG11
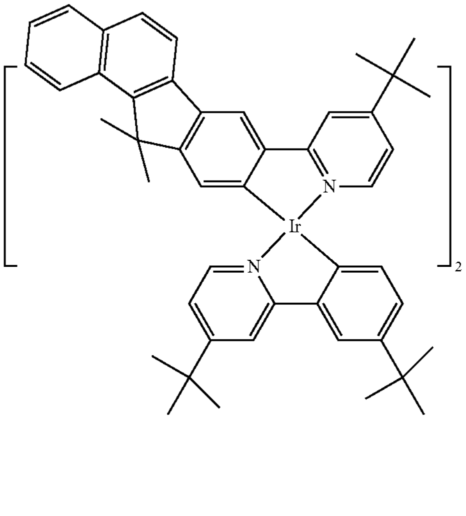

-continued
GG12
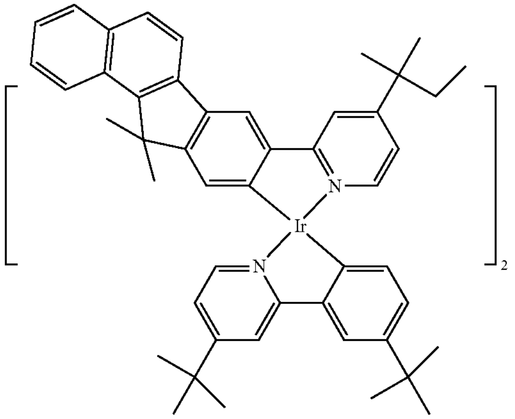
GG13
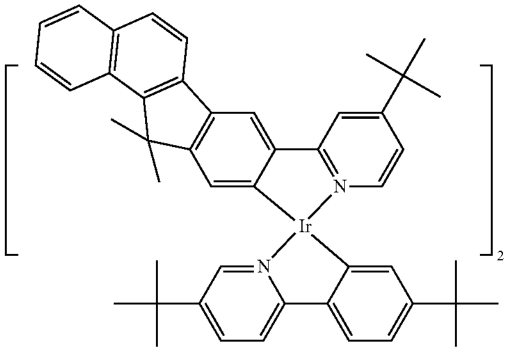
GG14
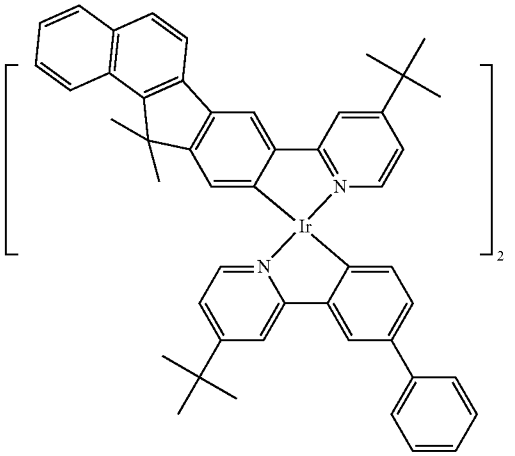
-continued
GG15
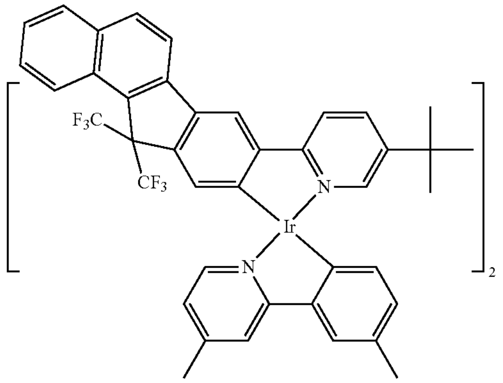
GG16
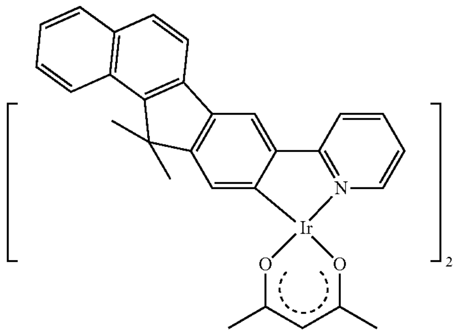
GG17
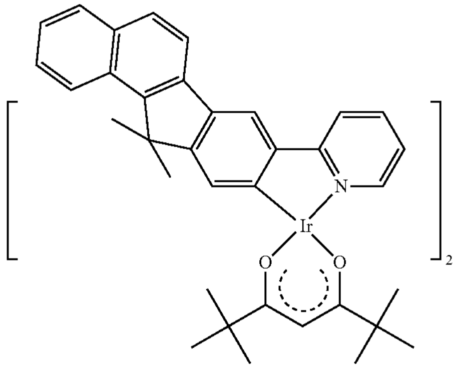
GG18
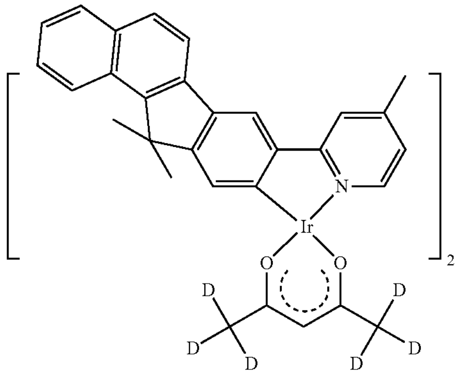

-continued
GG19
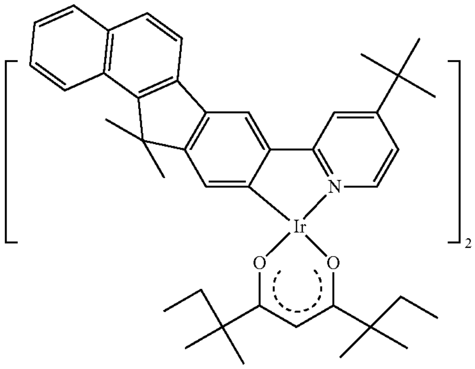
GG20
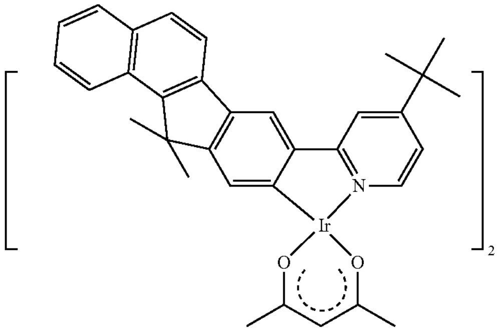
GG21
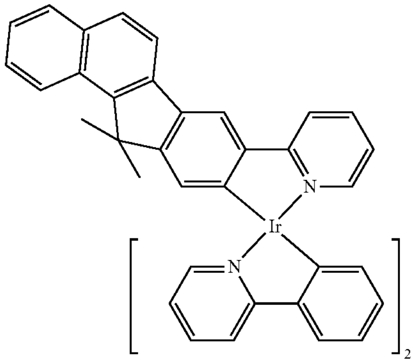
GG22
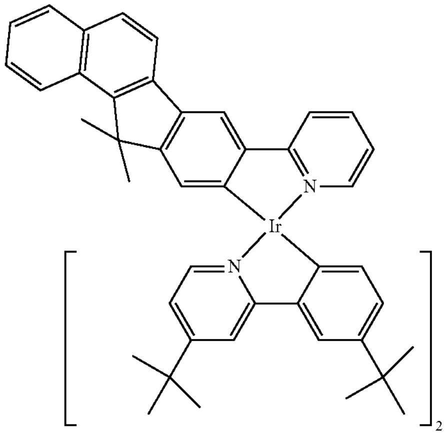
-continued
GG23
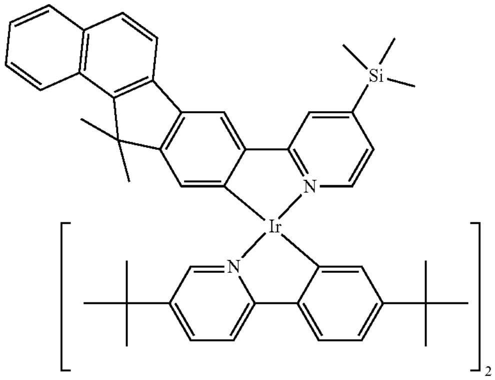
GG24
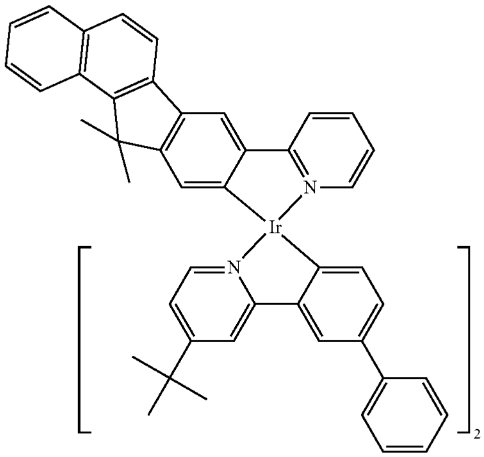
GG25
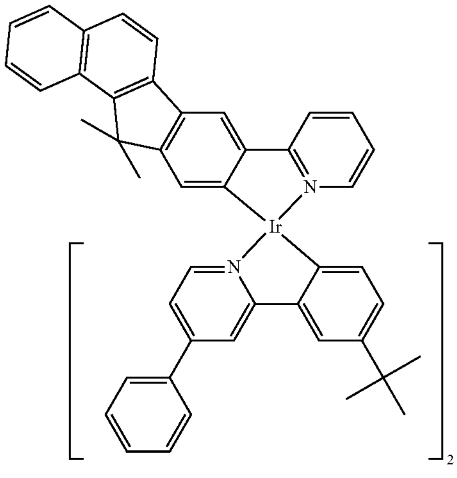

GG26
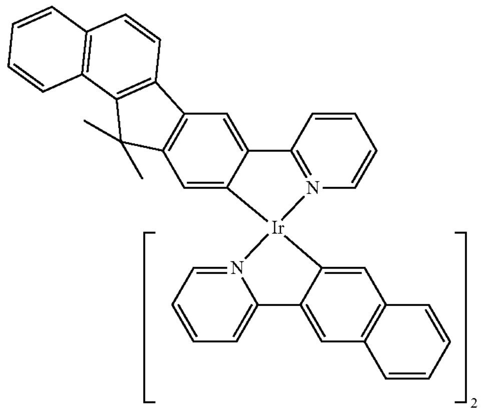
GG27
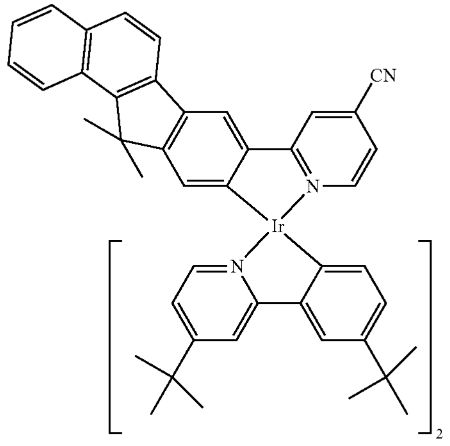
GG28
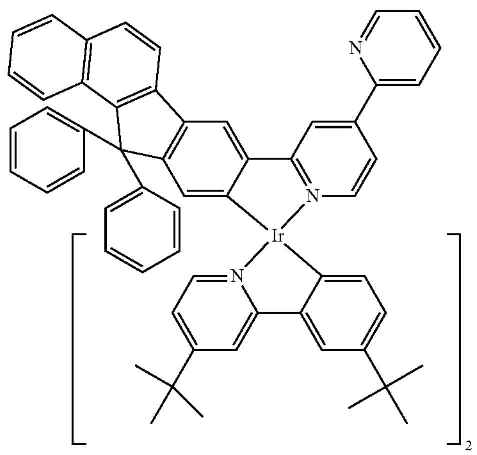
GG29
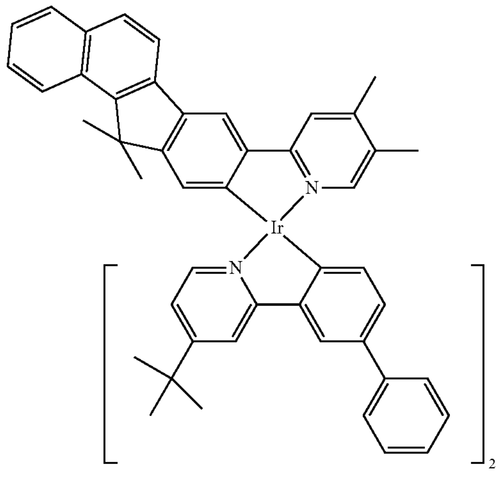
GG30
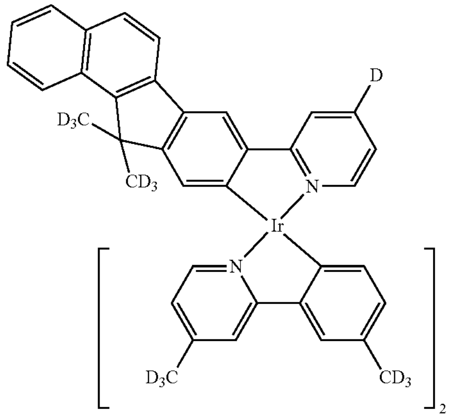
GG31
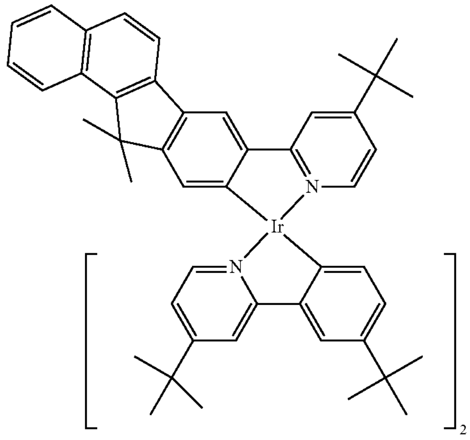

GG32
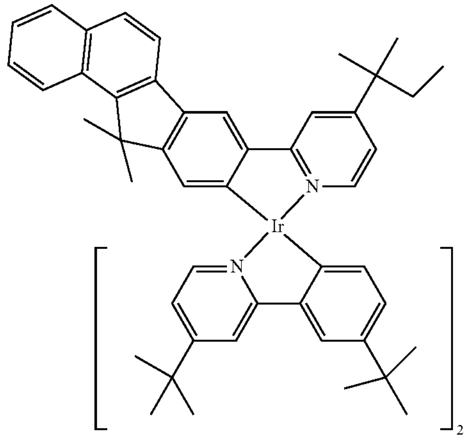
GG33
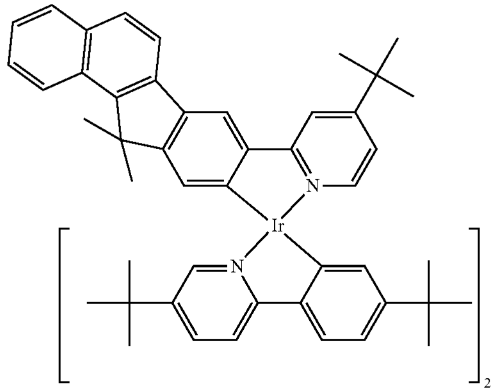
GG34
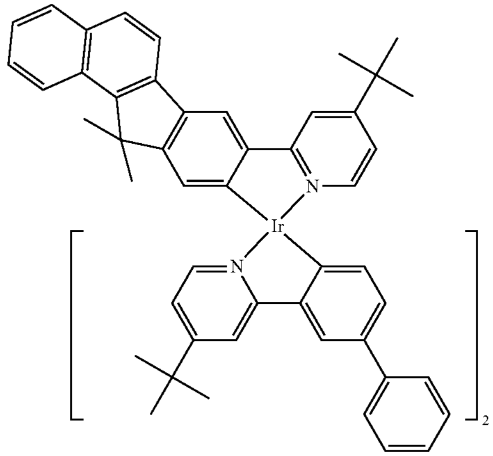
GG35
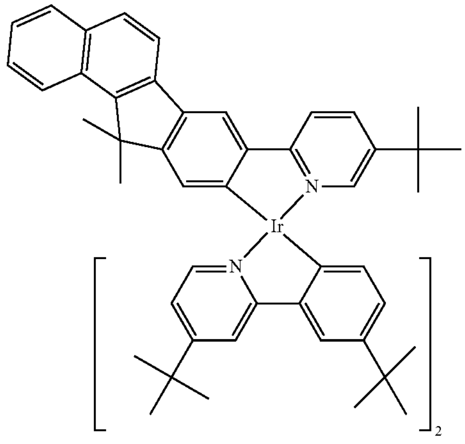
HH1
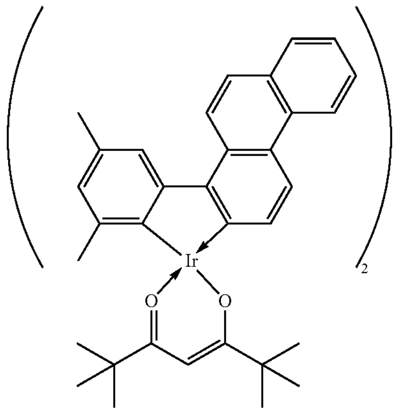
HH2
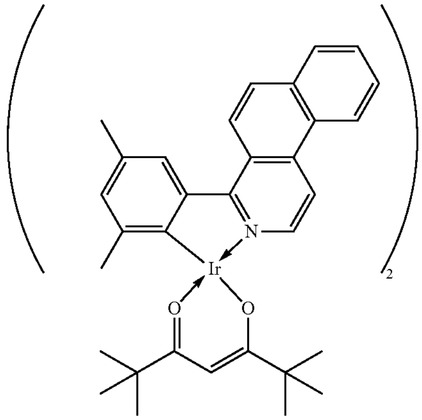

-continued
HH3
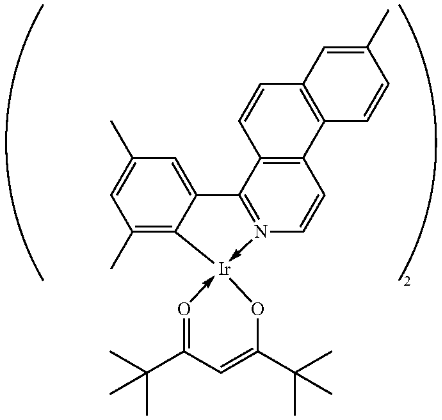
HH4
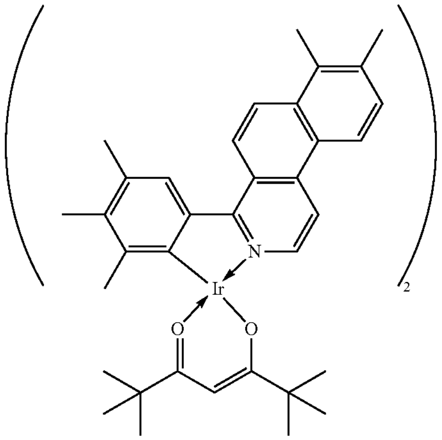
HH5
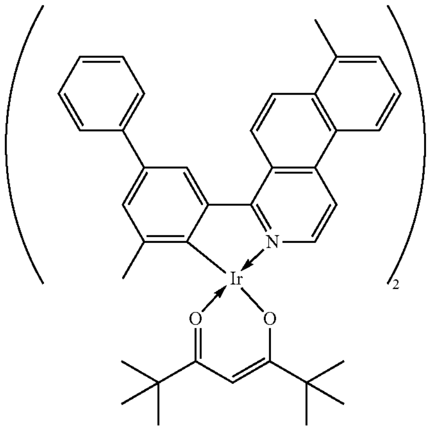
-continued
HH6
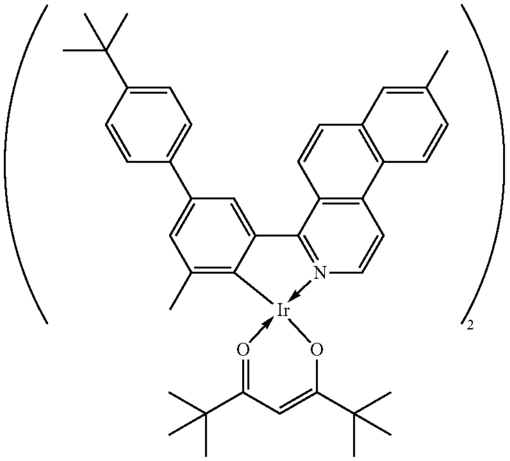
HH7
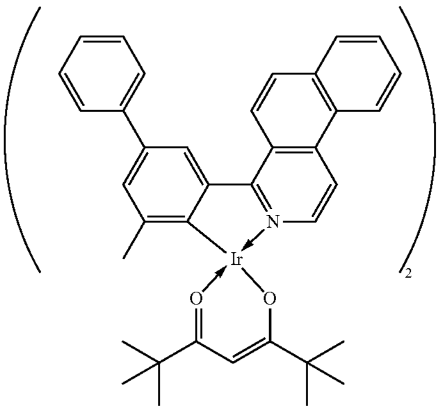
HH8
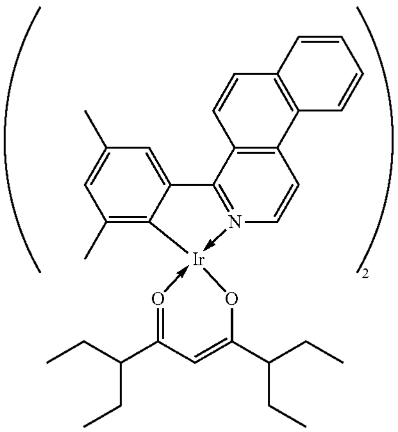

-continued
HH9
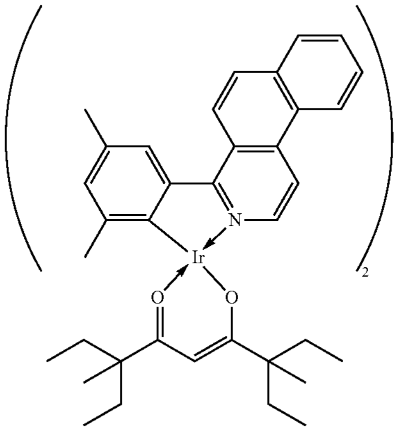
HH10
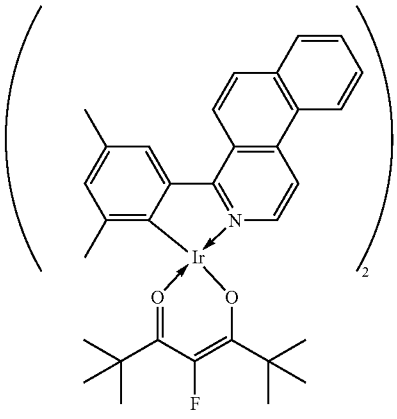
HH11
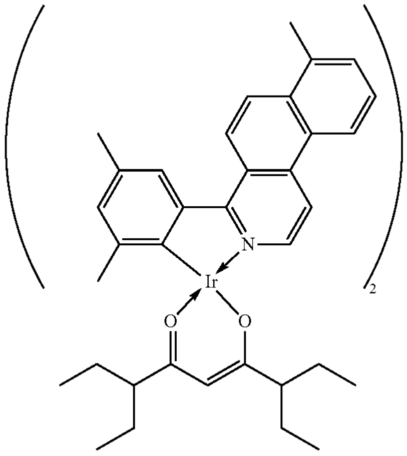
-continued
HH12
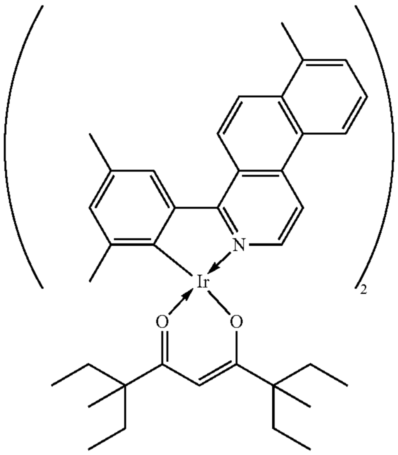
HH13
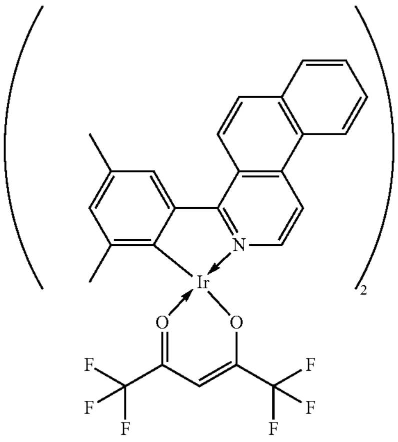
HH14
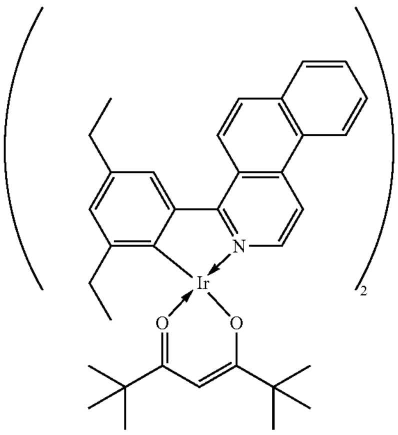

-continued
HH15
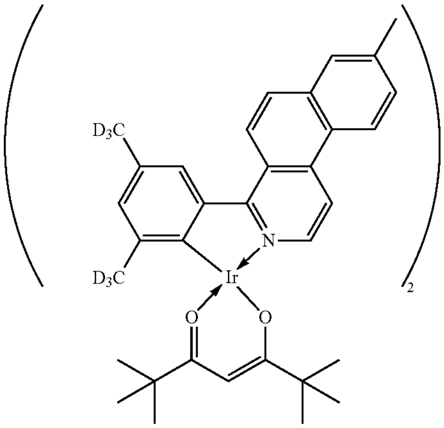
HH16
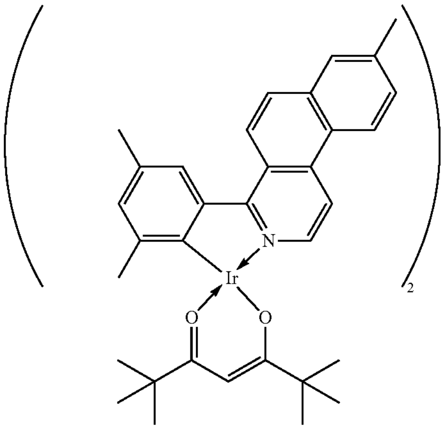
HH17
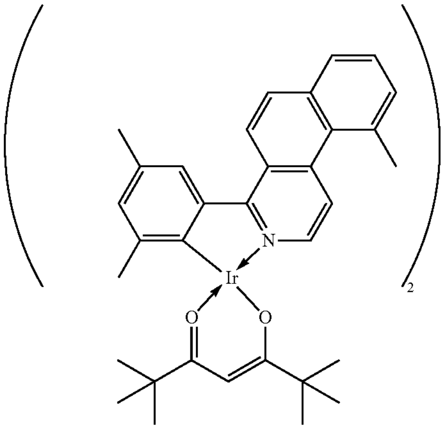
-continued
HH18
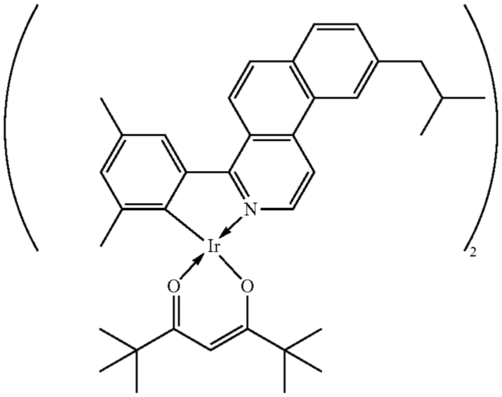
HH19
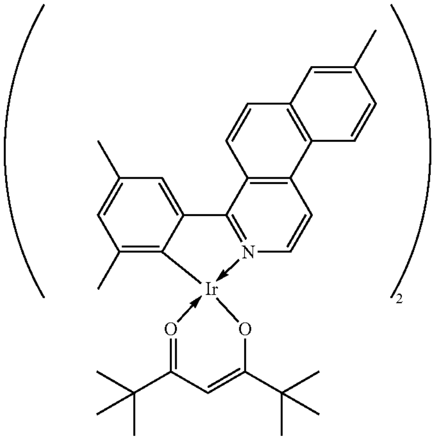
HH20
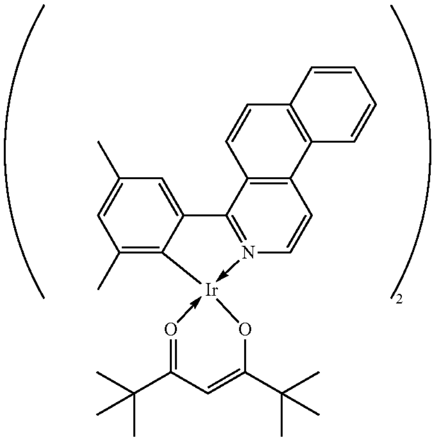

-continued
HH21
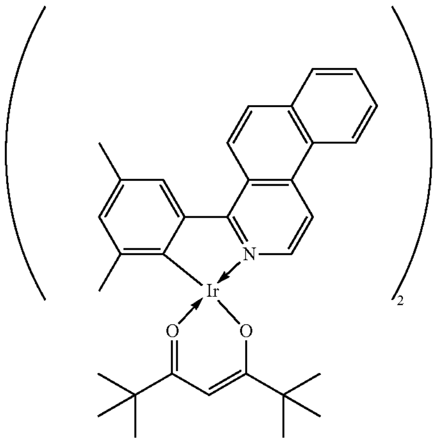
HH22
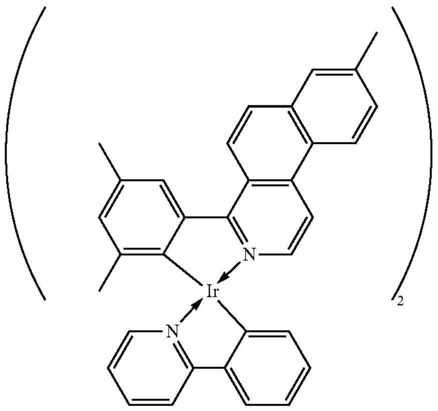
HH23
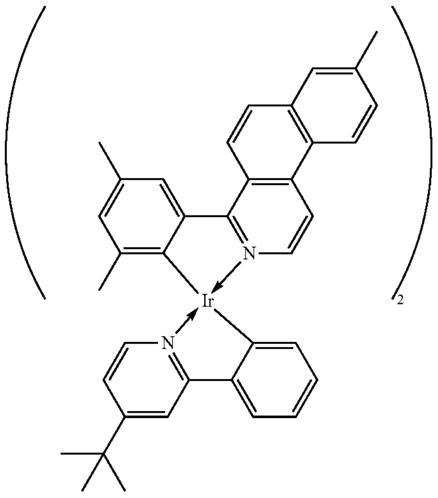
-continued
HH24
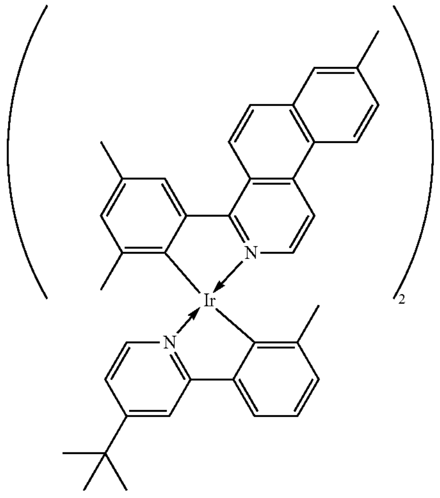
HH25
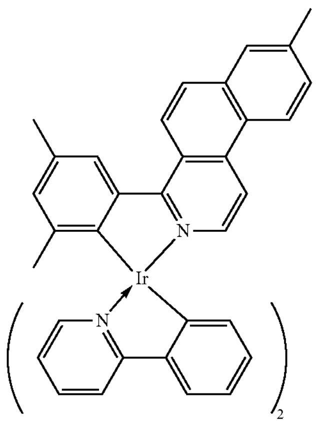
HH26
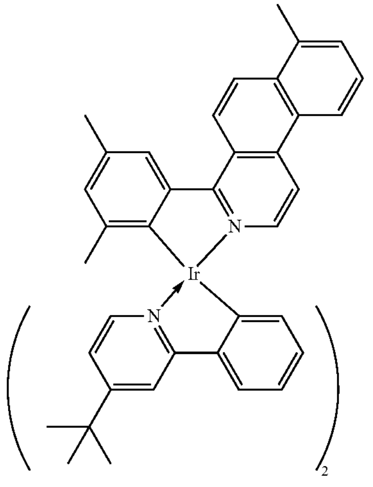

-continued
HH27
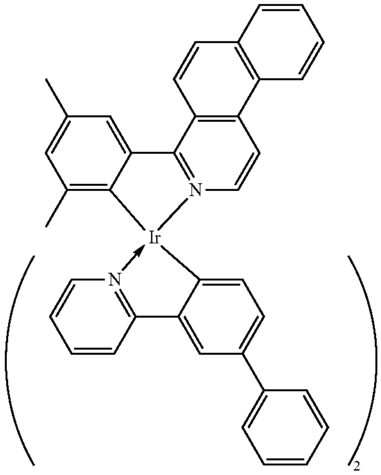
HH28
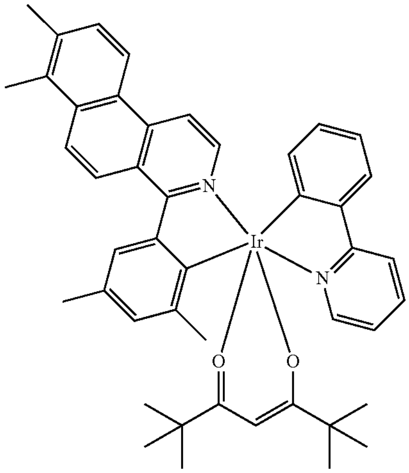
HH29
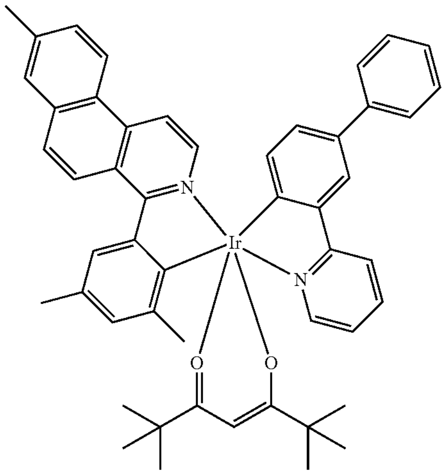
-continued
HH30
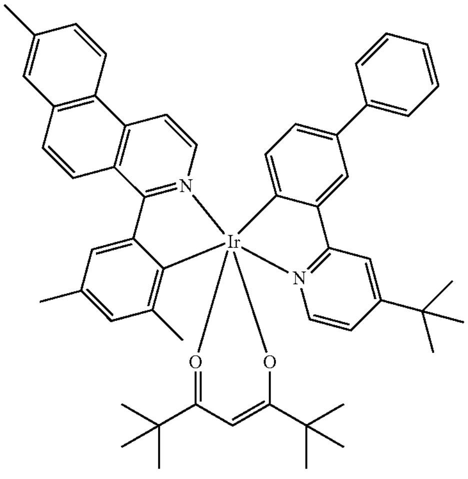
HH31
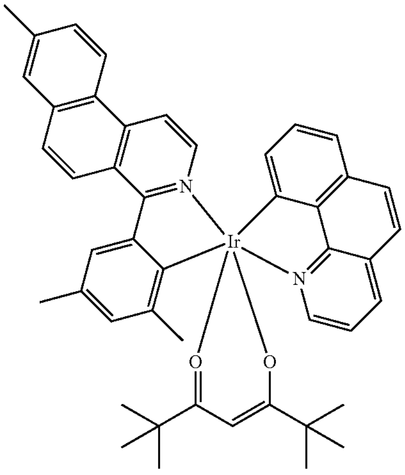
HH32
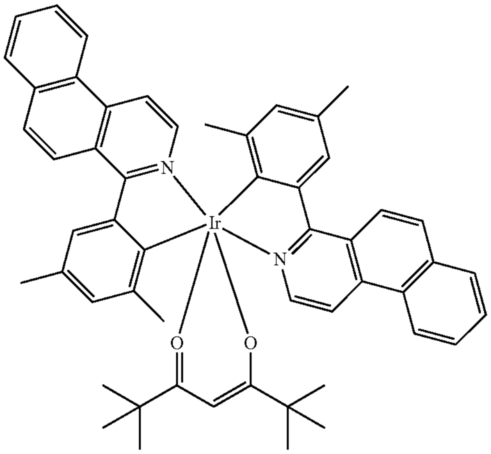

HH33
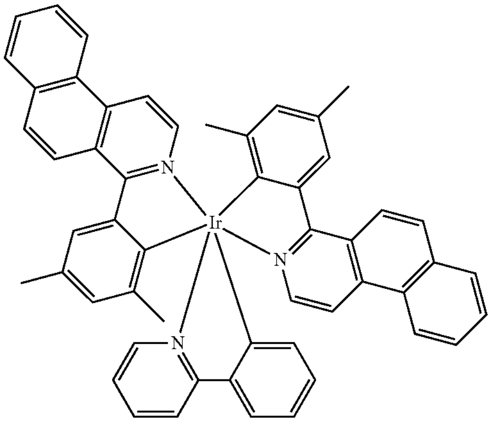
HH34
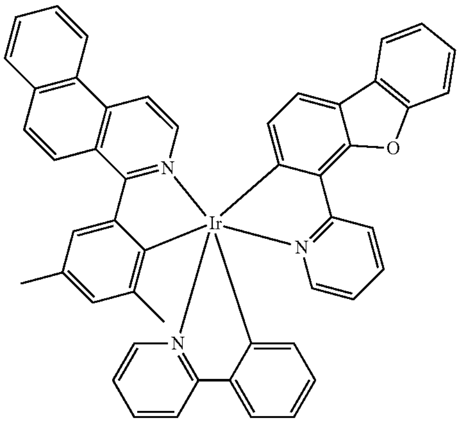
HH35
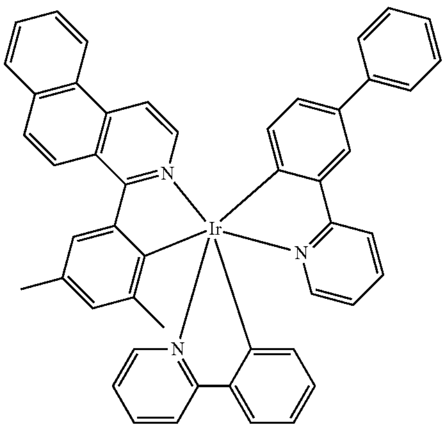
II1
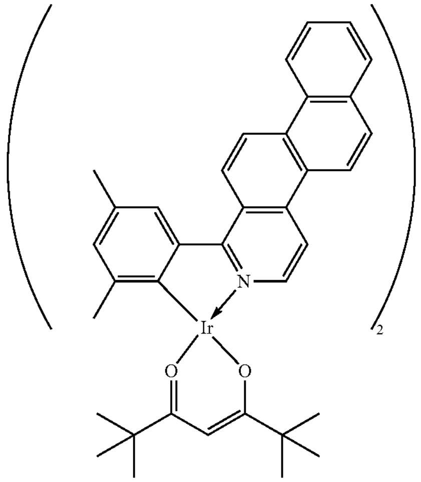
II2
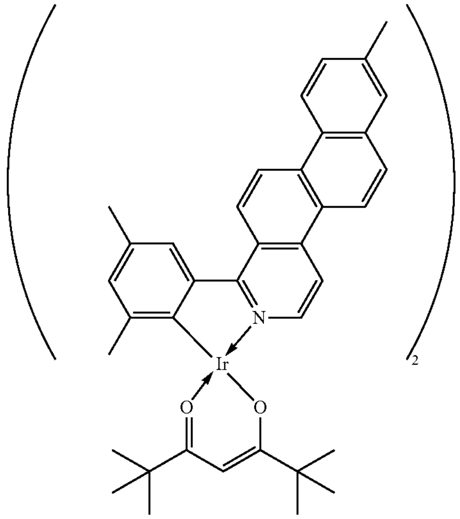
II3
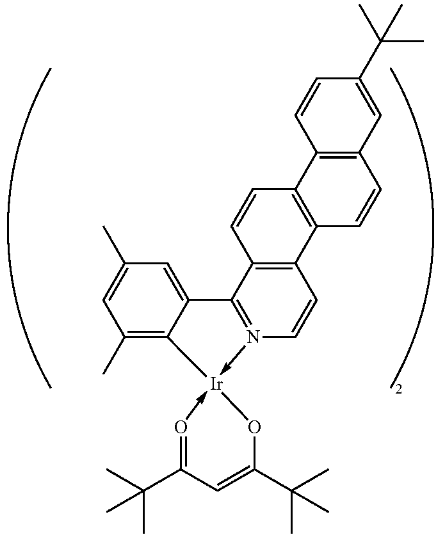

-continued
II4
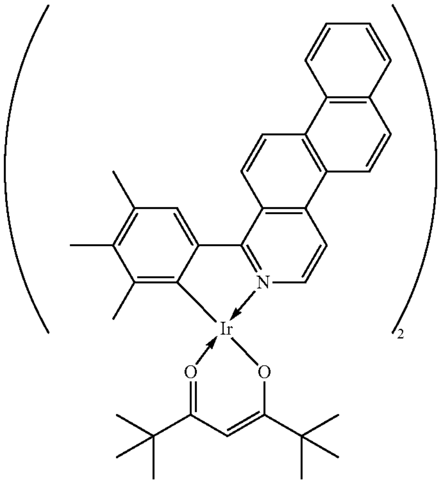
II5
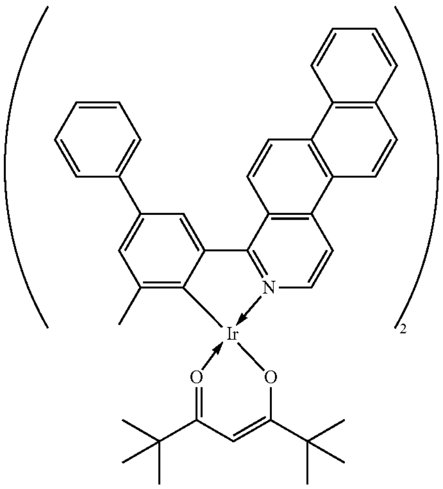
II6
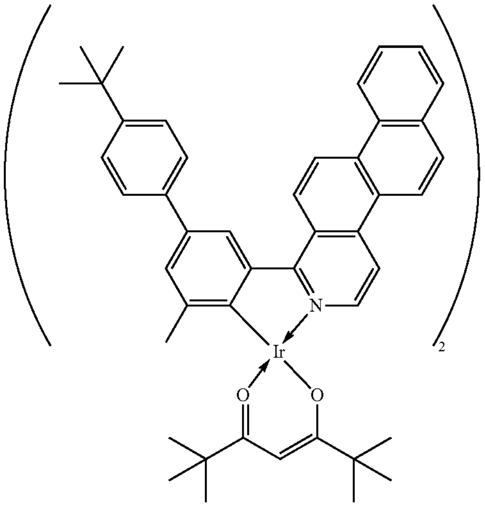
-continued
II7
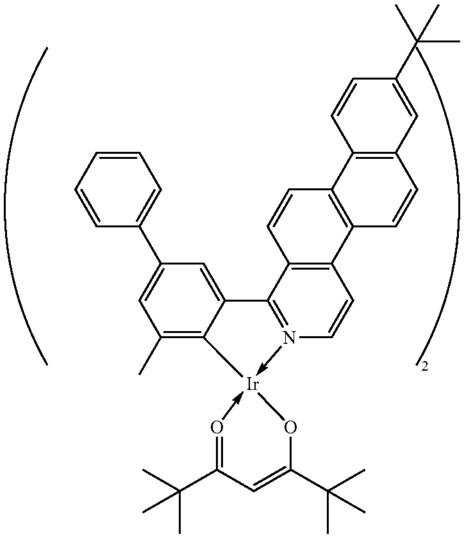
II8
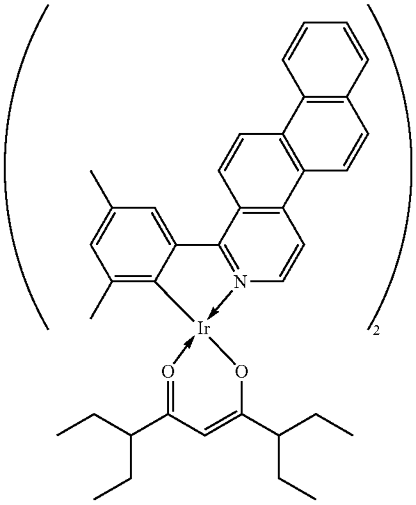
II9
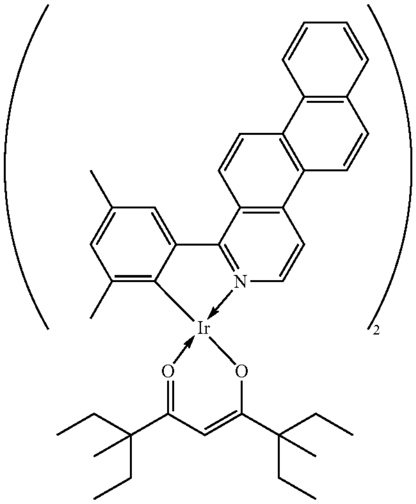

II10
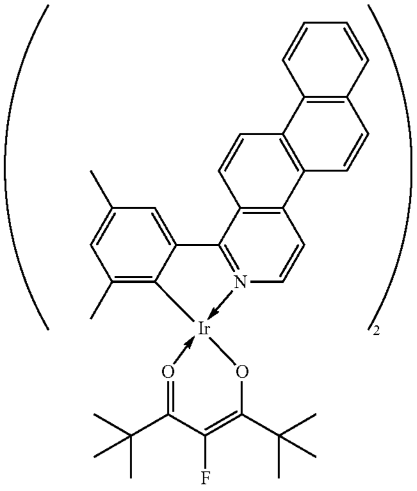
II11
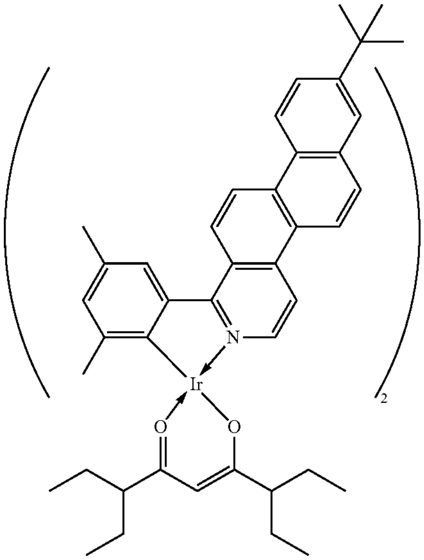
II12
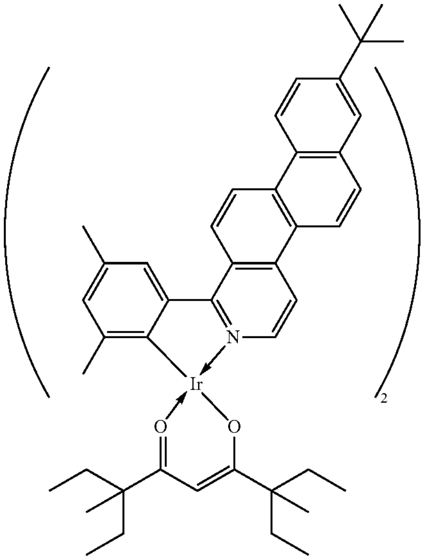
II13
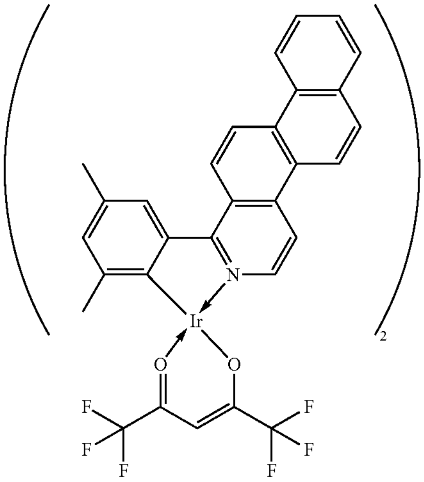
II14
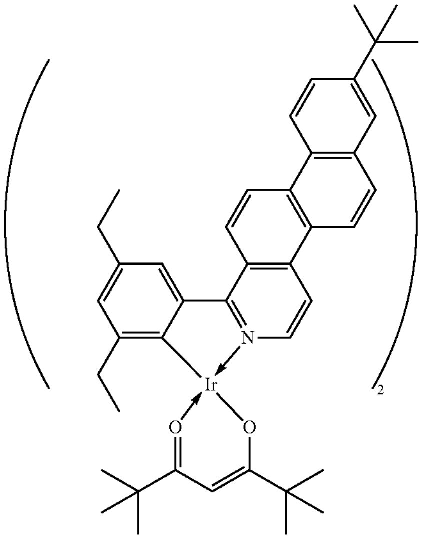
II15
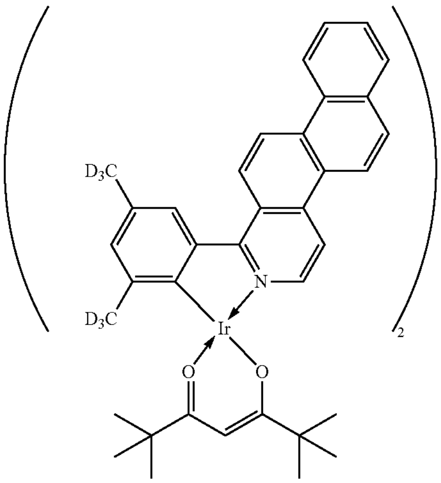

-continued
II16
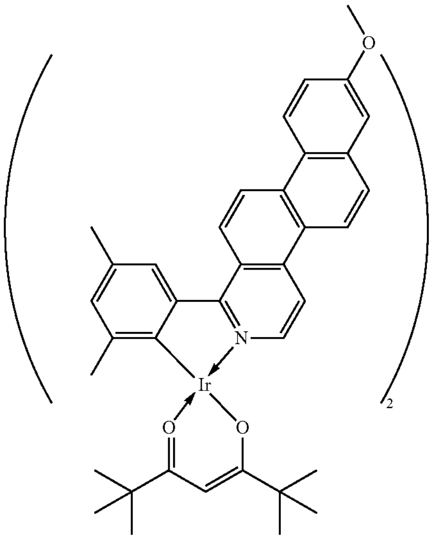
II17
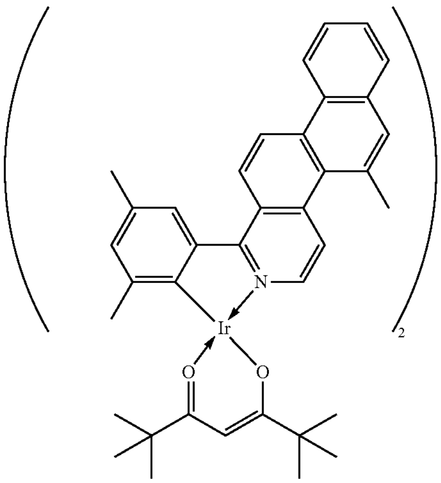
II18
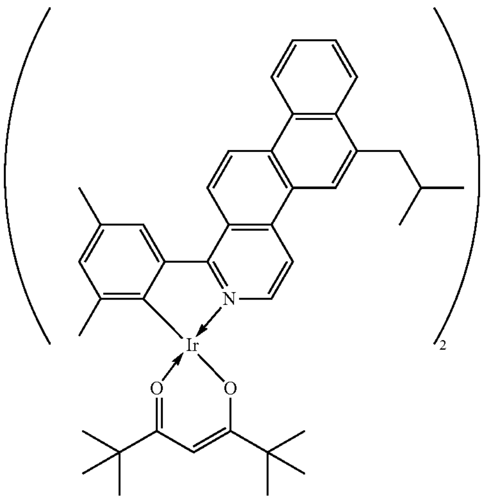
-continued
II19
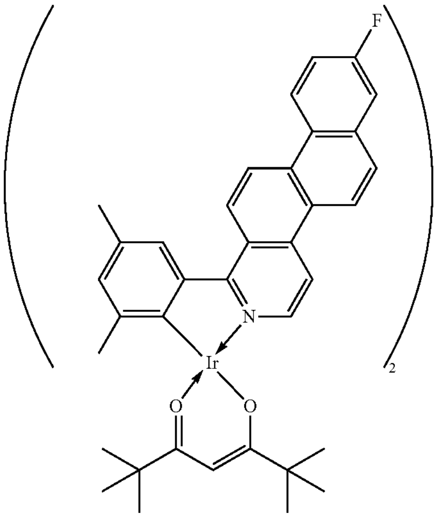
II20
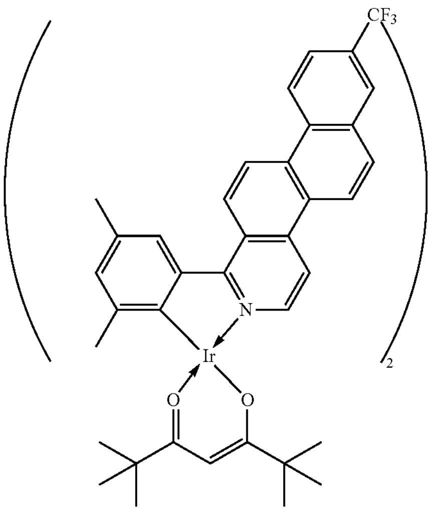
II21
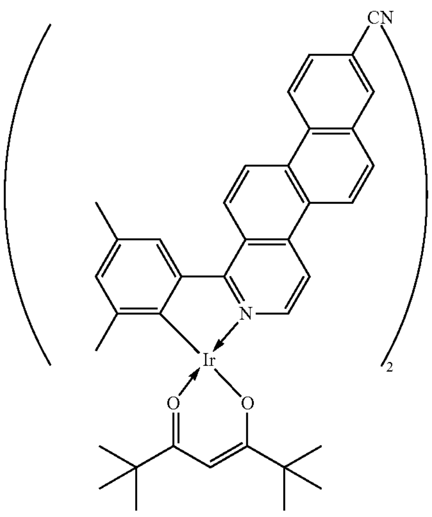

-continued
II22
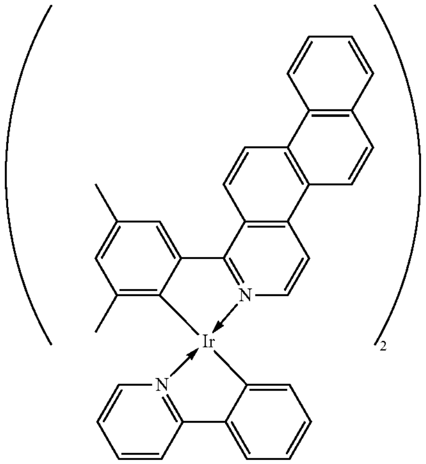
II23
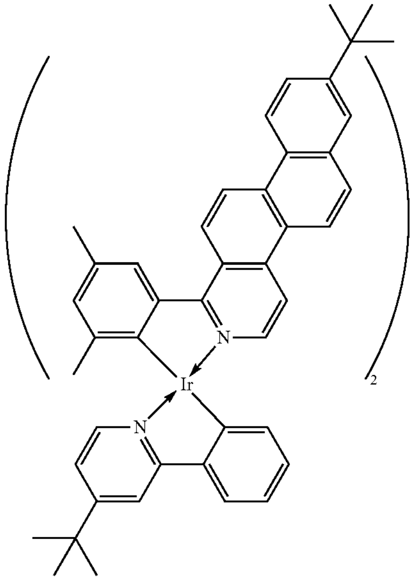
II24
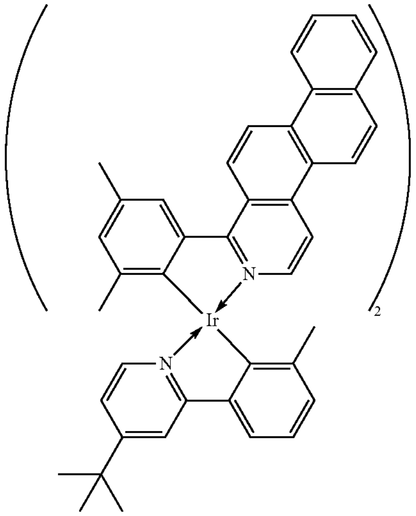
-continued
II25
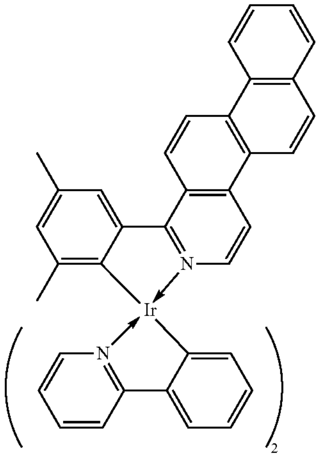
II26
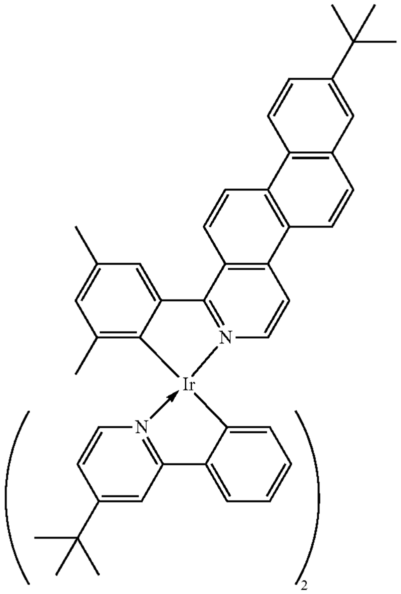
II27
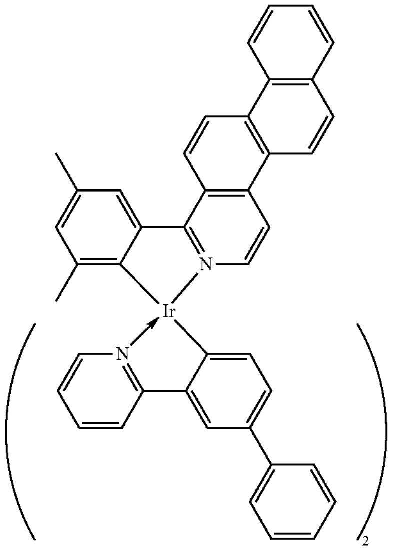

II28
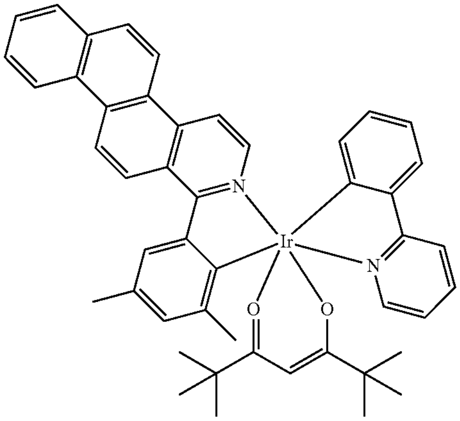
II29
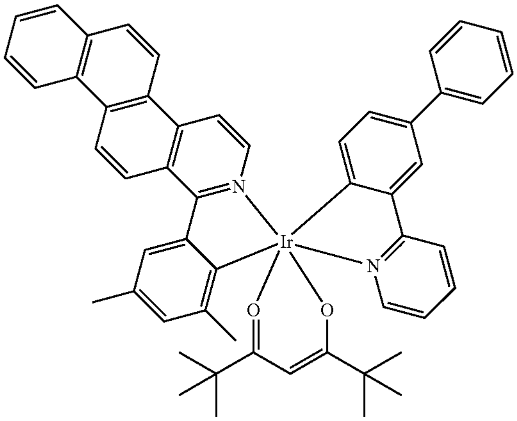
II30
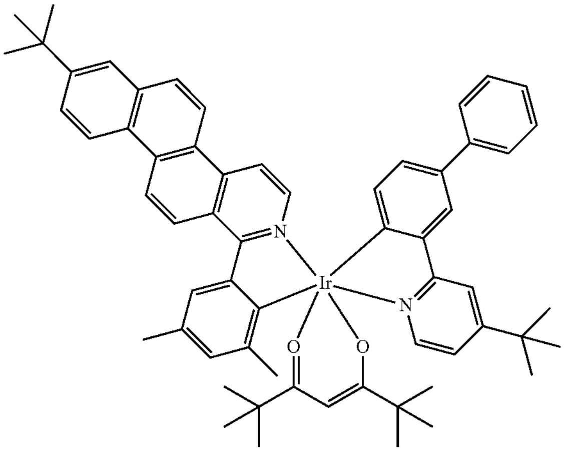
II31
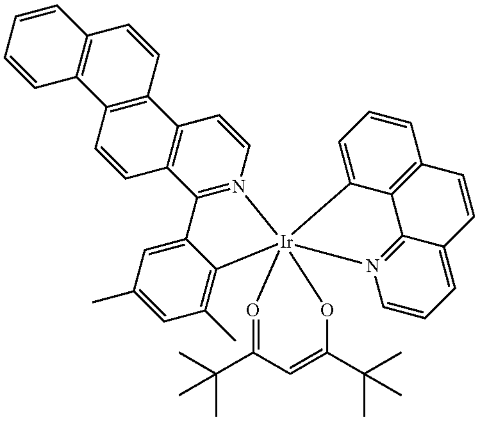
II32
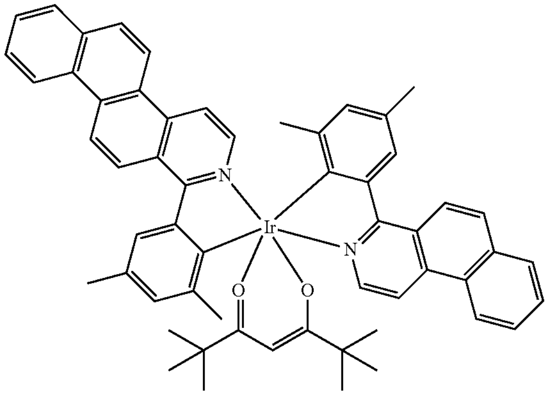
II33
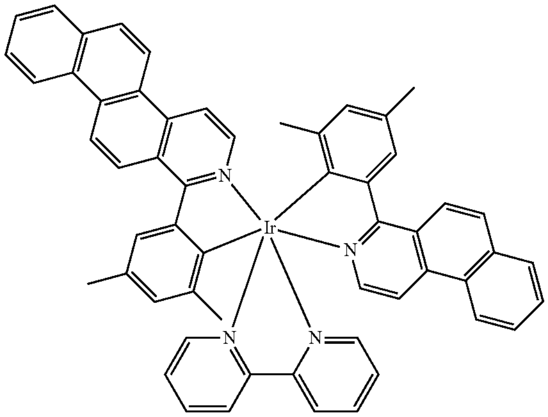

-continued

II34

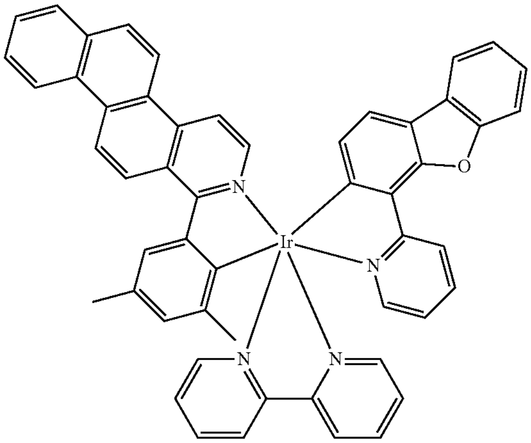

II35

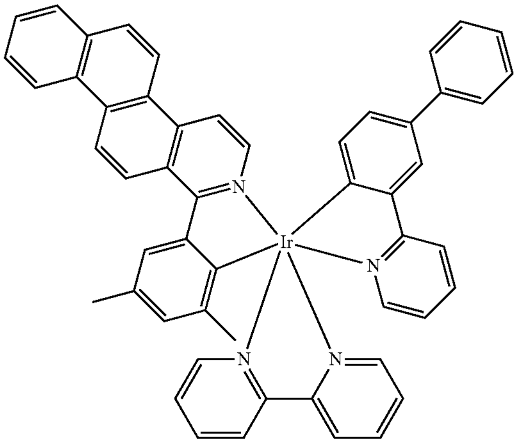

The exemplary compounds belonging to groups AA and BB are metal complexes in which the partial structure $M(L)_m$ is represented by general formula [Ir-3], and are compounds having at least a phenanthrene ring in the ligand.

These compounds particularly have good stability because their fused rings are composed of $sp^2$ hybrid orbitals.

The exemplary compounds belonging to group CC are metal complexes in which the partial structure $M(L)_m$ is represented by general formula [Ir-4], and are compounds having at least a triphenylene ring in the ligand. These compounds particularly have good stability because their fused rings are composed of $sp^2$ hybrid orbitals.

The exemplary compounds belonging to group DD are metal complexes in which the partial structure $M(L)_m$ is represented by one of general formulae [Ir-5] to [Ir-8], and are compounds having at least a dibenzofuran ring, a dibenzothiophene ring, a benzonaphthofuran ring, or a benzonaphthothiophene ring in the ligand.

These compounds contain an oxygen atom or a sulfur atom in the fused ring, and a charge transport ability can be enhanced by abundant unshared electron pairs of these atoms. Thus, in particular, the carrier balance of the compounds is easily adjusted.

The exemplary compounds belonging to groups EE to GG are metal complexes in which the partial structure $M(L)_m$ is represented by one of general formulae [Ir-6] to [Ir-8], and are compounds having at least a benzofluorene ring in the ligand. These compounds have a substituent at the 9-position of the fluorene ring in the direction perpendicular to the in-plane direction of the fluorene ring and thus can particularly reduce the overlap between fused rings. Accordingly, the compounds have particularly high sublimability.

The exemplary compounds belonging to group HH are metal complexes in which the partial structure $M(L)_m$ is represented by one of general formulae [Ir-11] to [Ir-13], and are compounds having at least a benzoisoquinoline ring in the ligand. These compounds contain a N atom in the fused ring, and a charge transport ability can be enhanced by unshared electron pairs and high electronegativity of the atom. Thus, in particular, the carrier balance of the compounds is easily adjusted.

The exemplary compounds belonging to group II are metal complexes in which the partial structure $M(L)_m$ is represented by general formula [Ir-14], and are compounds having at least a naphthoisoquinoline ring in the ligand. These compounds contain a N atom in the fused ring, and a charge transport ability can be enhanced by unshared electron pairs and high electronegativity of the atom. Thus, in particular, the carrier balance of the compounds is easily adjusted.

(3) Other Compounds

In the organic light-emitting element according to this embodiment, a publicly known low-molecular-weight or high-molecular-weight hole injection compound or hole transport compound, compound serving as a host, light-emitting compound, electron injection compound or electron transport compound, and the like may be used in combination, as required. Examples of these compounds will be described below.

A hole injection/transport material may be a material having a high hole mobility so as to facilitate hole injection from the anode and to enable the injected holes to be transported to the light-emitting layer. From the viewpoint of reducing deterioration of the film quality, such as crystallization, in the organic light-emitting element, a material having a high glass transition temperature may be used. Examples of the low-molecular-weight or high-molecular-weight material having a hole injection/transport ability include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection/transport material is also suitably used as an electron-blocking layer. Specific examples of the compound used as the hole injection/transport material are shown below but are not limited to these, as a matter of course.

HT1
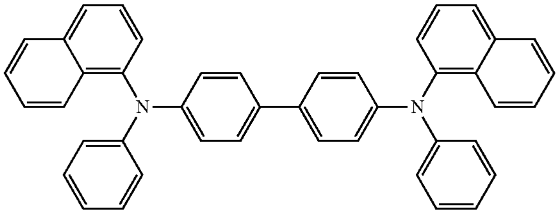
HT2
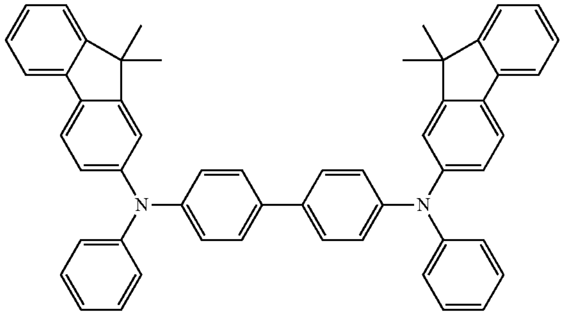
HT3
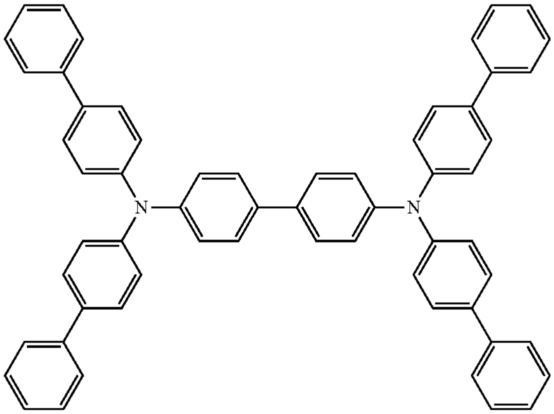
HT4
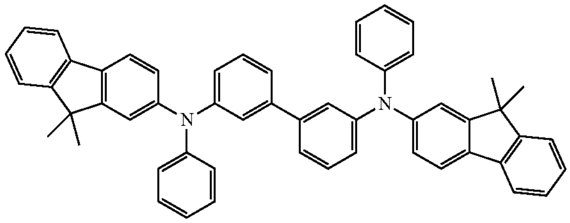
HT5
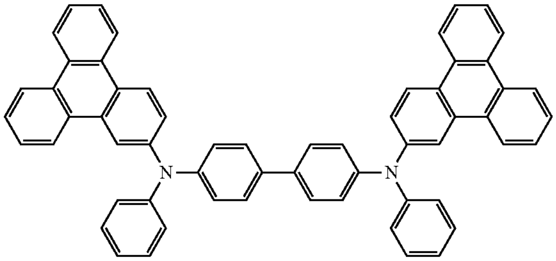
HT6
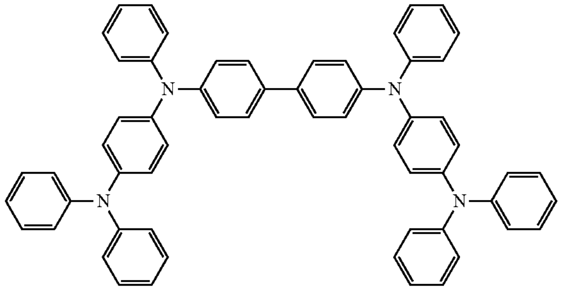
HT7
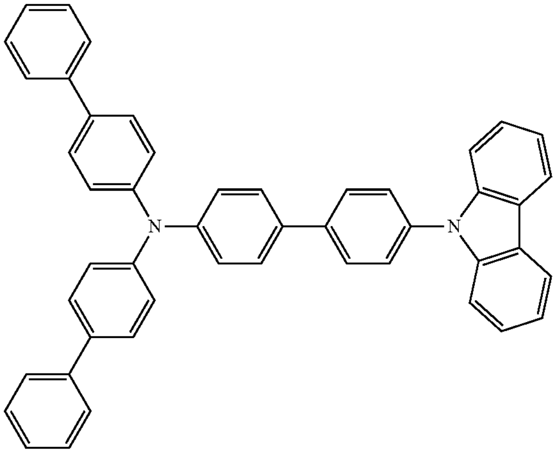
HT8
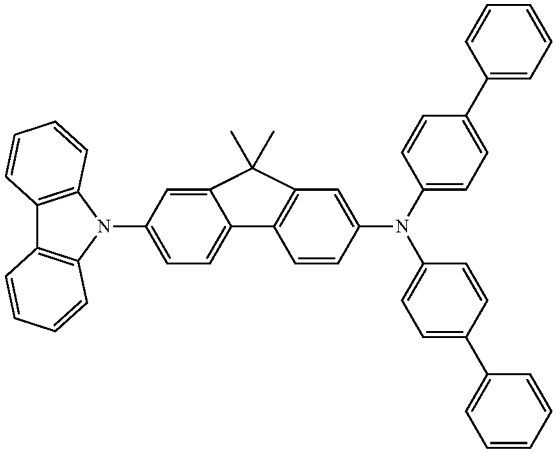

-continued
HT9
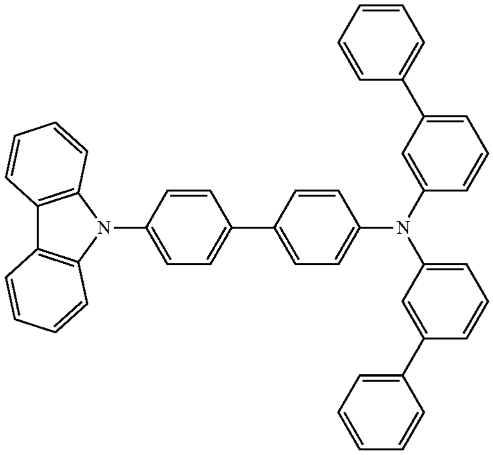
HT10
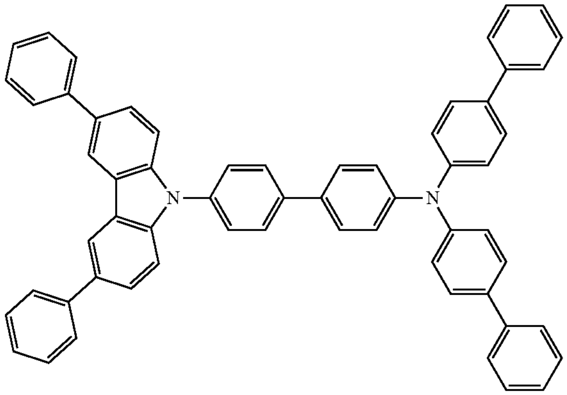
HT11
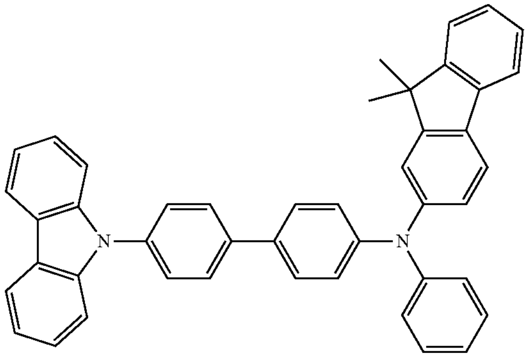
HT12
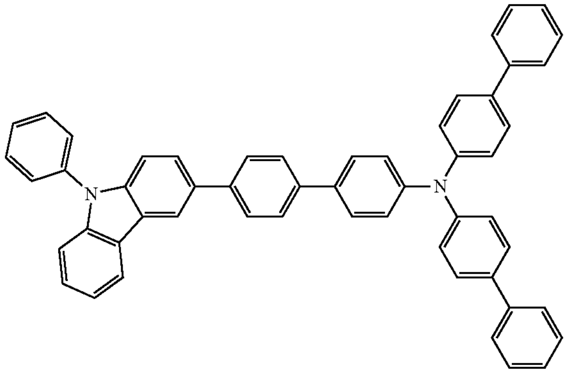
HT13
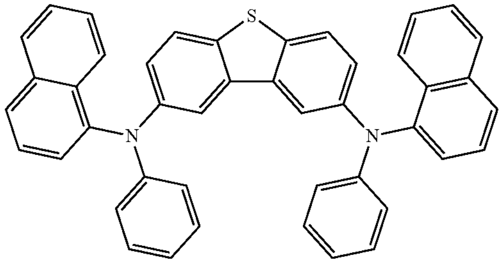
HT14
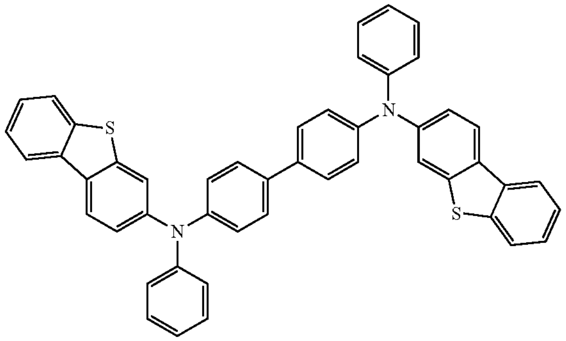
HT15
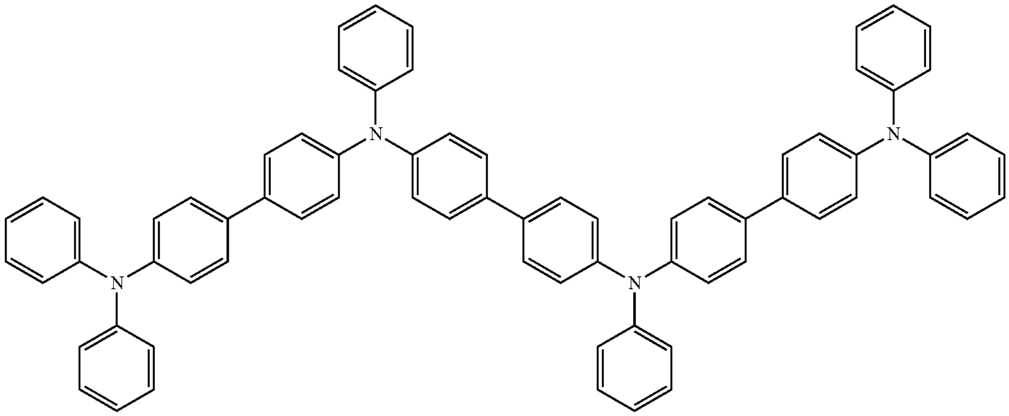

-continued

HT16

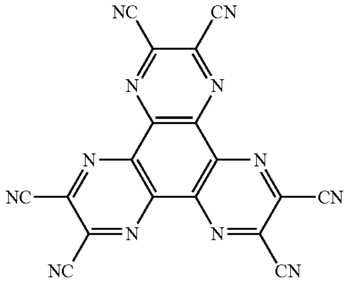

HT17

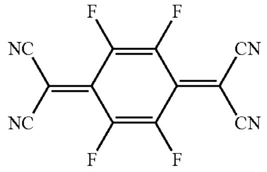

HT18

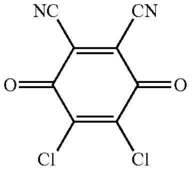

HT19

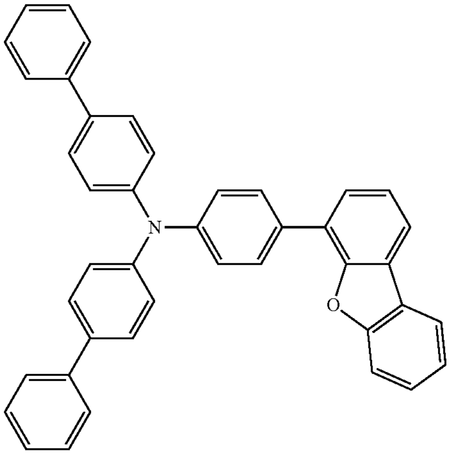

As a light-emitting layer host or a light-emitting assist material contained in the light-emitting layer, a compound other than the organic compound according to this embodiment may be contained as a third compound. Examples of the third compound include aromatic hydrocarbon compounds and derivatives thereof, carbazole derivatives, azine derivatives, xanthone derivatives, dibenzofuran derivatives, dibenzothiophene derivatives, organoaluminum complexes such as tris(8-quinolinolato)aluminum, and organoberyllium complexes.

In particular, the assist material can be a material having a carbazole skeleton, a material having a triphenylene ring in the skeleton, or a material having a dibenzothiophene skeleton. This is because these materials have a high electron-donating ability or electron-withdrawing ability, and the HOMO level and the LUMO level can be easily adjusted. Since the organic compound according to this embodiment has the CXD skeleton, the HOMO level and the LUMO level tend to decrease. In view of this, in particular, a material having the skeleton that can adjust the HOMO or LUMO level can be used as the assist material. A combination of such an assist material with the organic compound according to this embodiment can achieve a good carrier balance.

Specific examples of the compound used as the light-emitting layer host or light-emitting assist material contained in the light-emitting layer are shown below but are not limited to these, as a matter of course. Among the following specific examples, materials that have a carbazole skeleton and can serve as assist materials are EM32 to EM38. Materials that have a triphenylene ring in the skeleton and can serve as assist materials are EM10 to EM14, EM32, and EM39. Materials that have a dibenzothiophene skeleton and can serve as assist materials are EM13, EM14, and EM28.

EM1

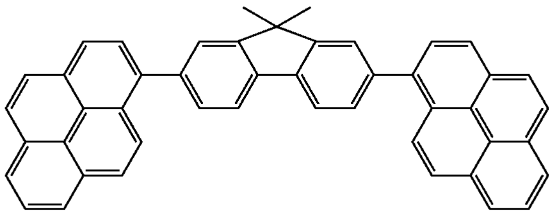

EM2

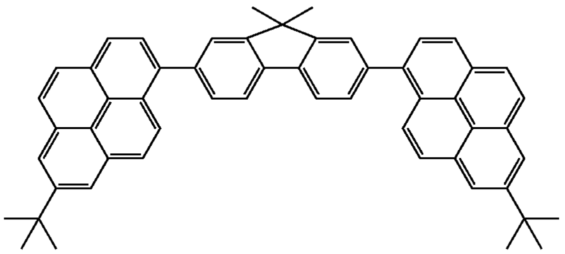

-continued
EM3
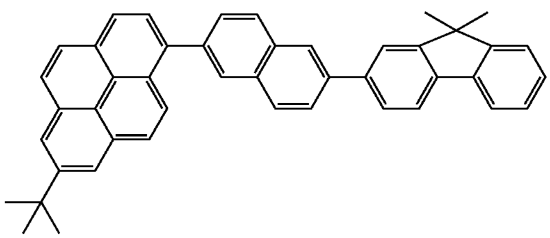
EM4
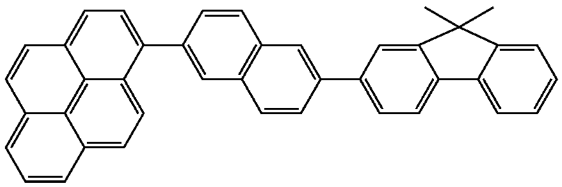
EM5
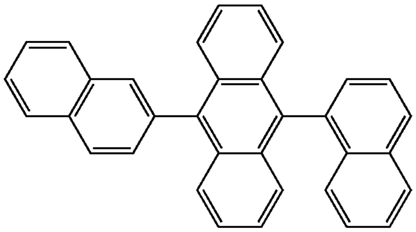
EM6
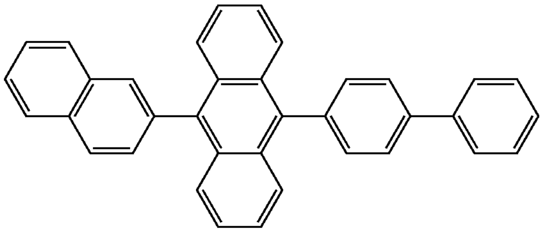
EM7
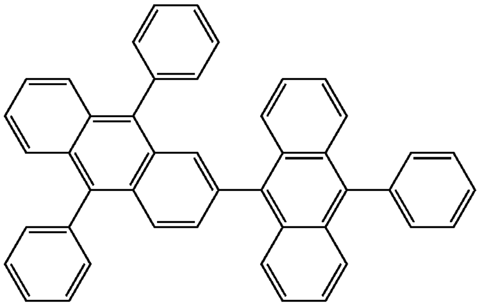
EM8
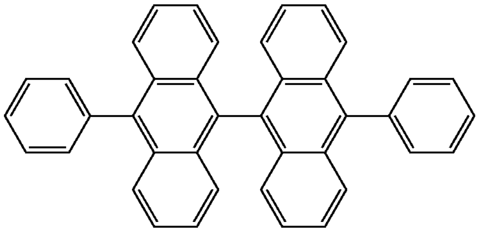
EM9
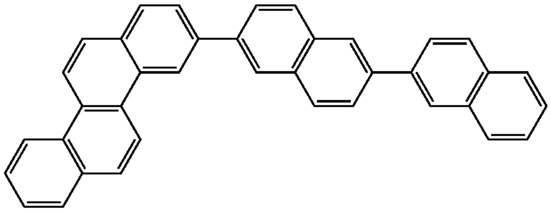
EM10
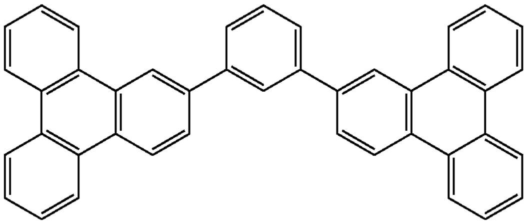
EM11
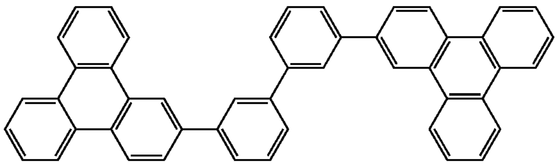
EM12
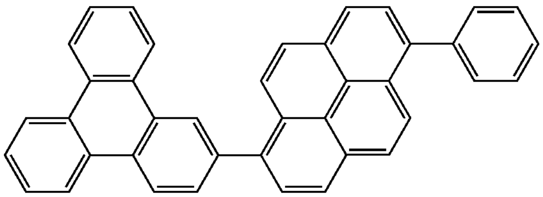
EM13
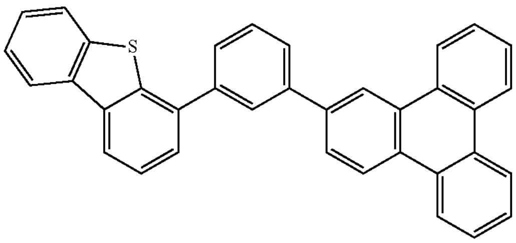
EM14
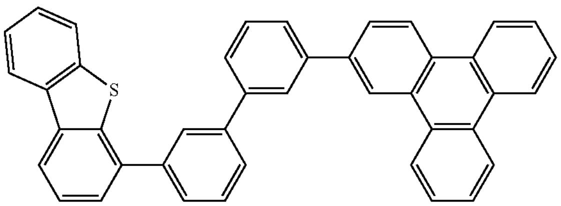

-continued
EM15
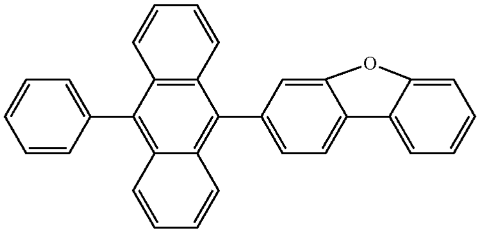
EM16
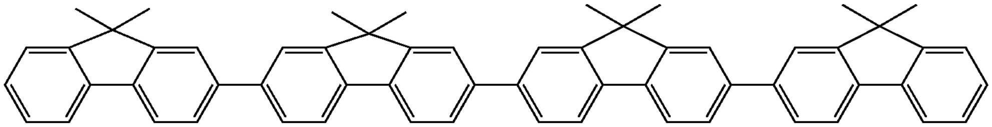
EM17
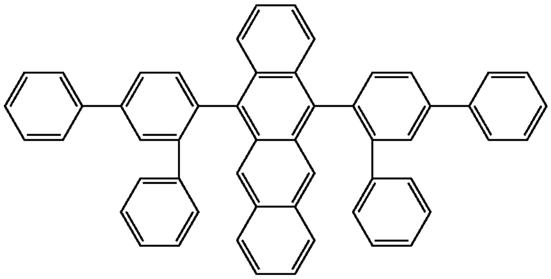
EM18
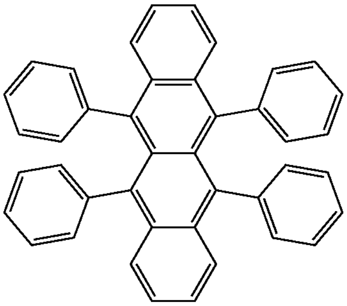
EM19
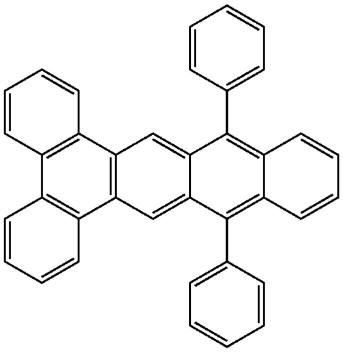
EM20
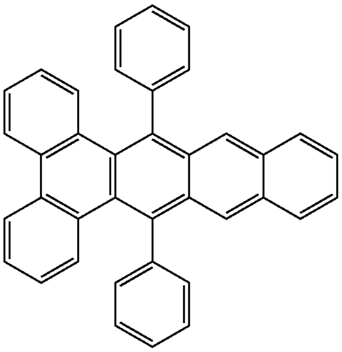
EM21
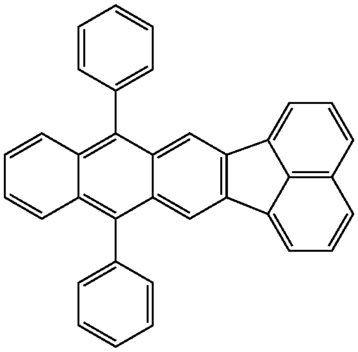
EM22
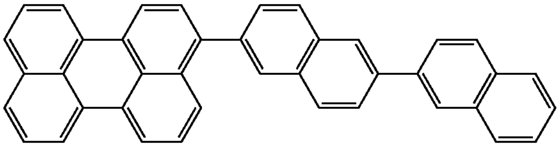

-continued
EM23
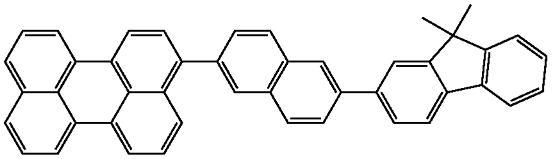
EM24
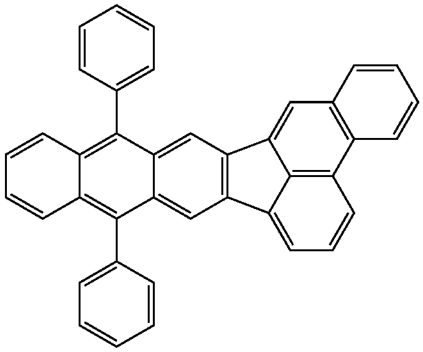
EM25
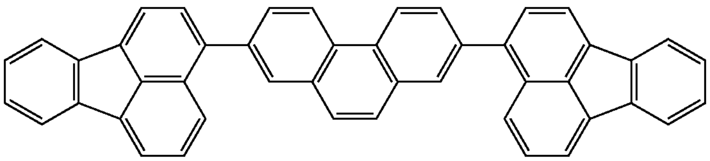
EM26
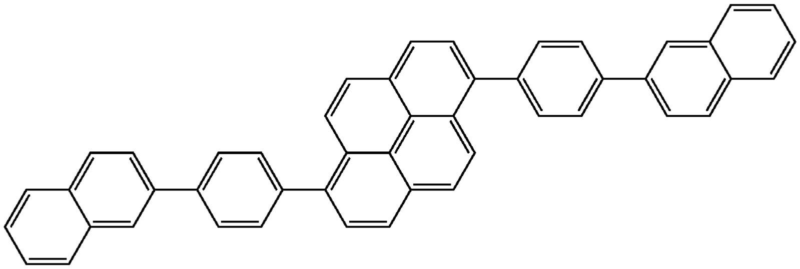
EM27
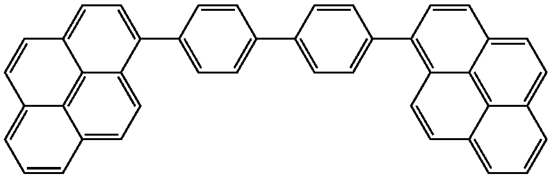
EM28
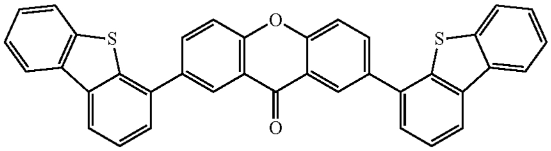
EM30
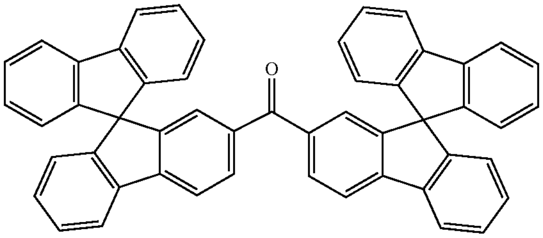
EM29
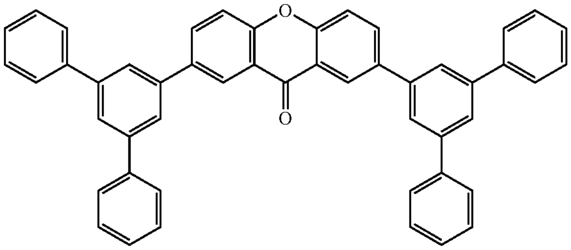
EM31
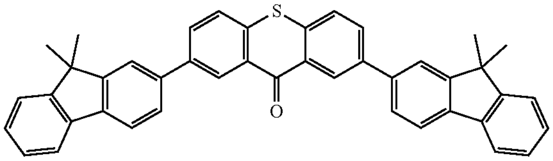
EM32
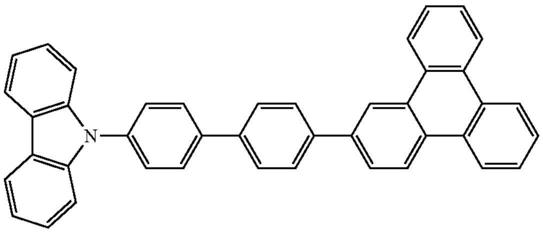

-continued
EM33
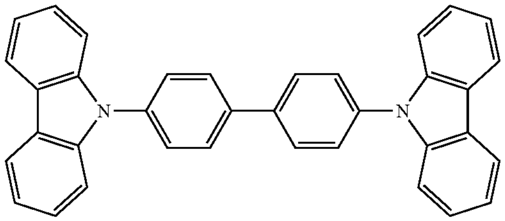
EM34
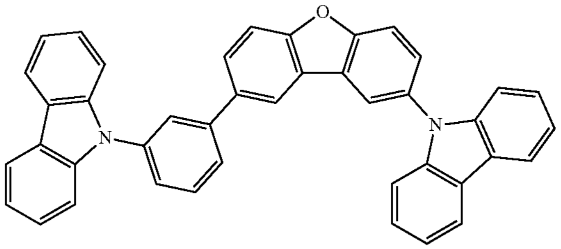
EM35
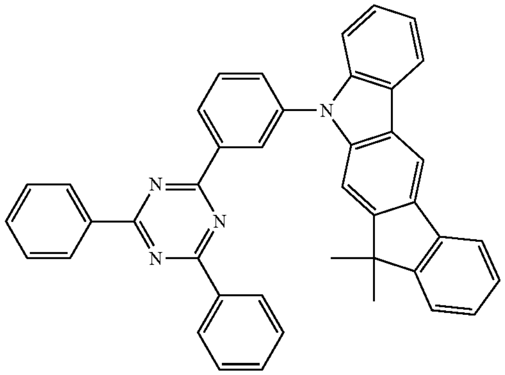
EM36
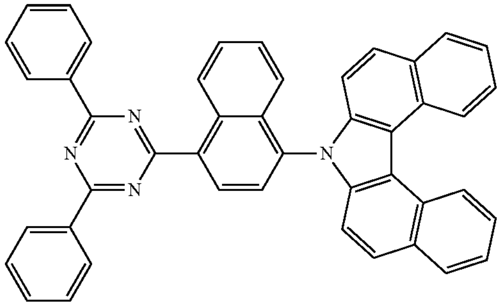
EM37
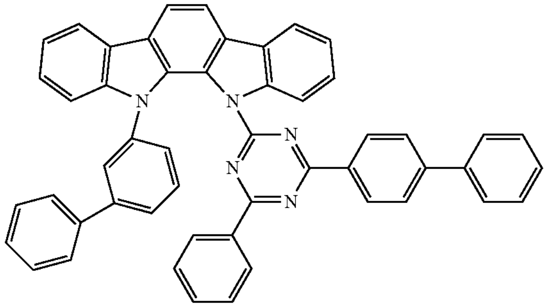
EM38
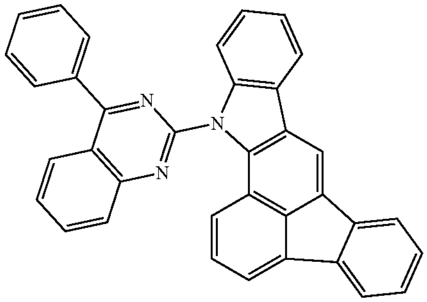
EM39
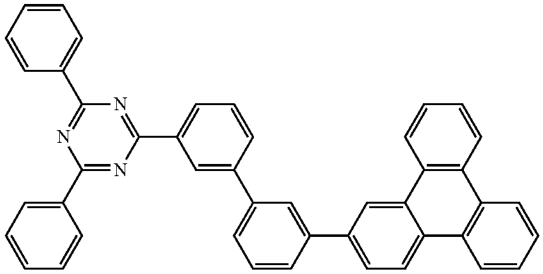
EM40
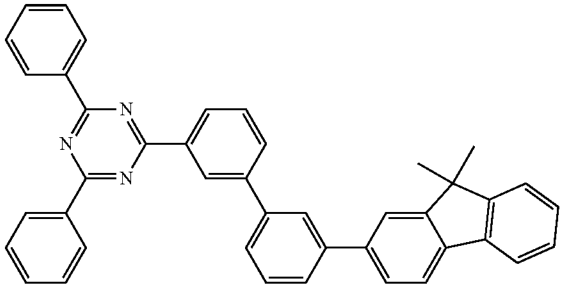

The electron transport material can be freely selected from materials capable of transporting electrons injected from the cathode to the light-emitting layer and is selected in consideration of, for example, the balance with the hole mobility of the hole transport material. Examples of the material having an electron transport ability include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (such as fluorene derivatives, naphthalene derivatives, chrysene derivatives, and anthracene derivatives). The above electron transport material is also suitably used as a hole-blocking layer. Specific examples of the compound used as the electron transport material are shown below but are not limited to these, as a matter of course.

ET1

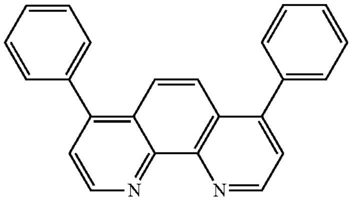

ET2

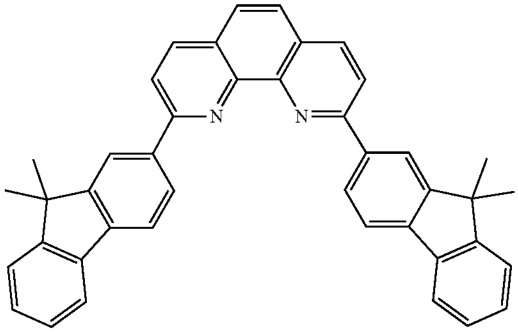

ET3

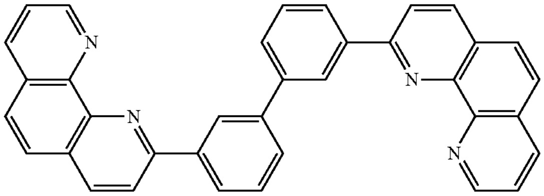

ET4

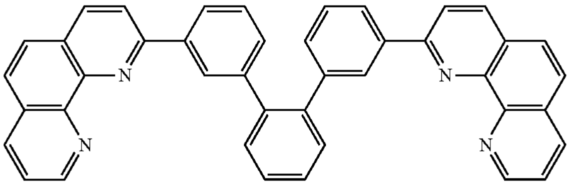

ET5

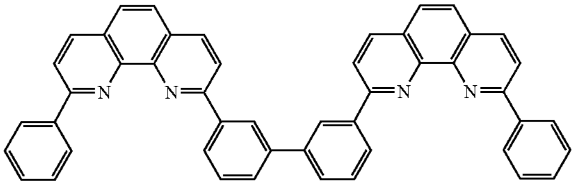

-continued

ET6

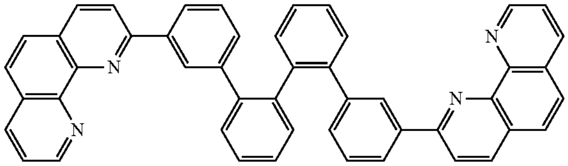

ET7

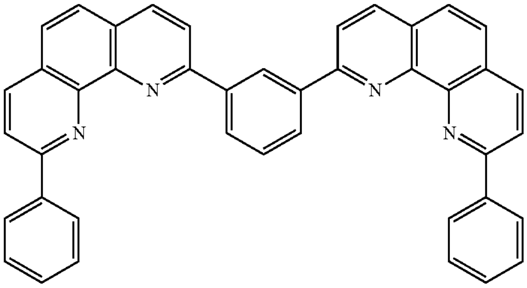

ET8

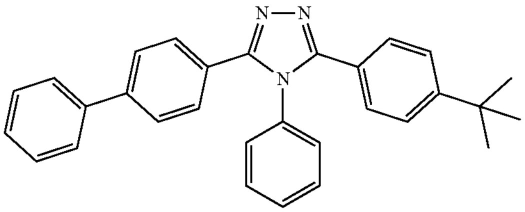

ET9

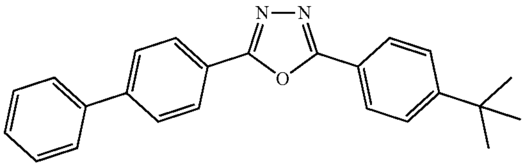

ET10

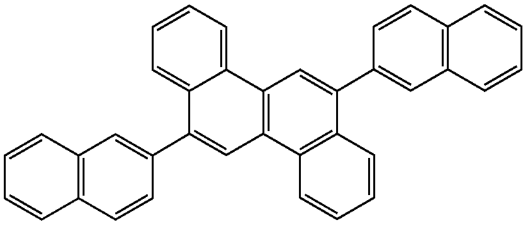

ET11

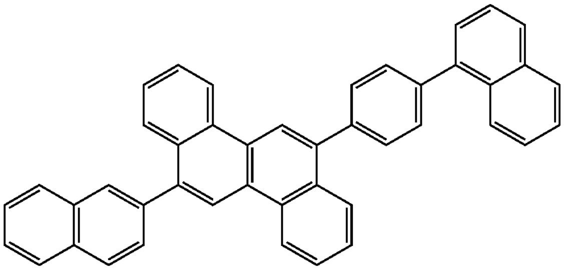

ET12
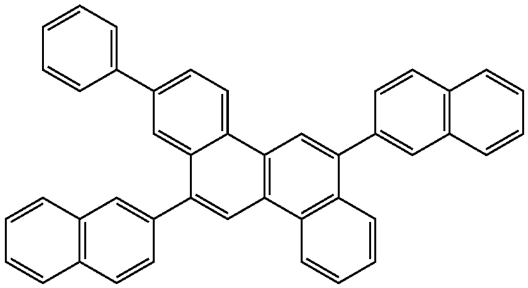
ET13
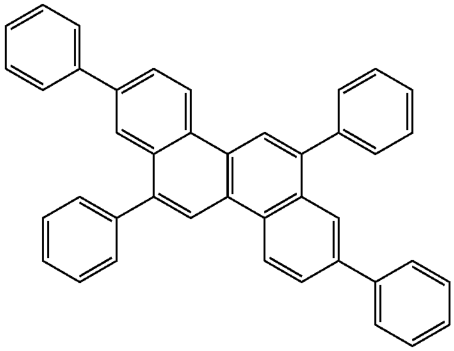
ET14
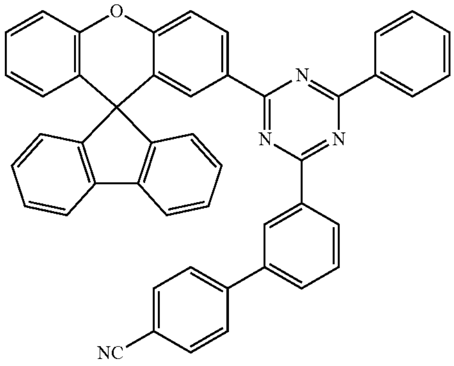
ET15
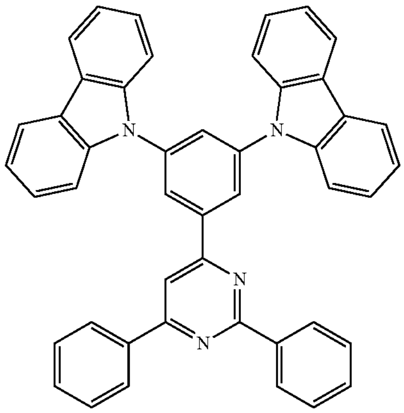
ET16
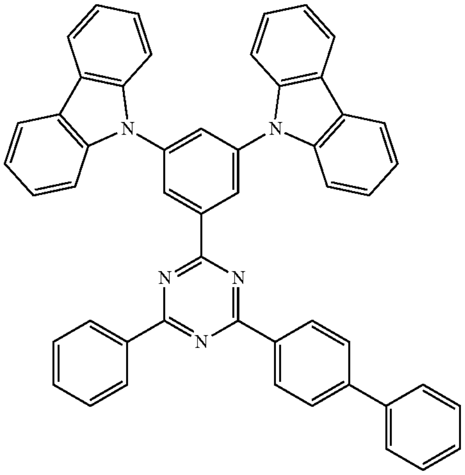
ET17
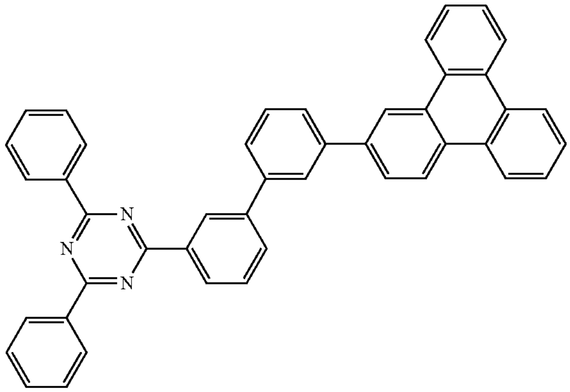
ET18
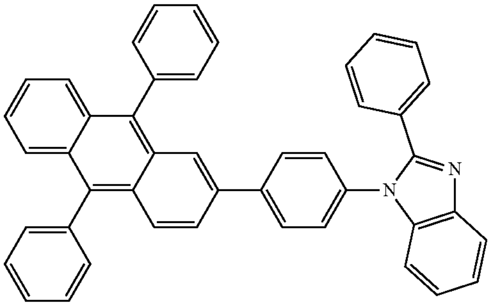
ET19
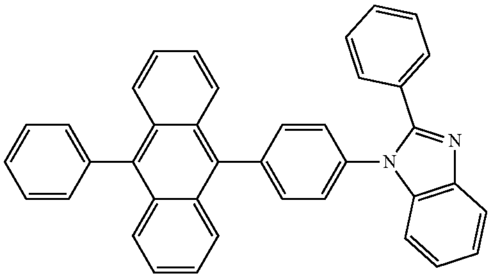

-continued
ET20
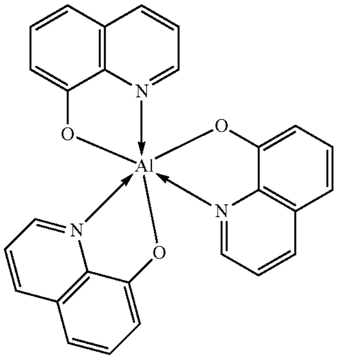
ET21
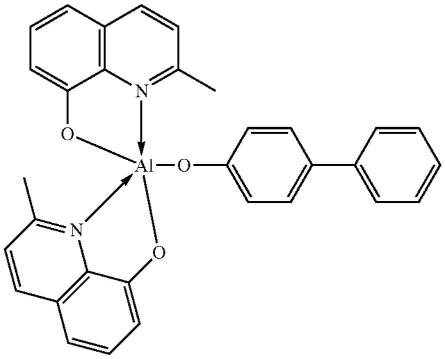
ET22
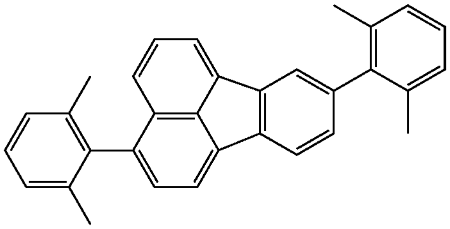
ET23
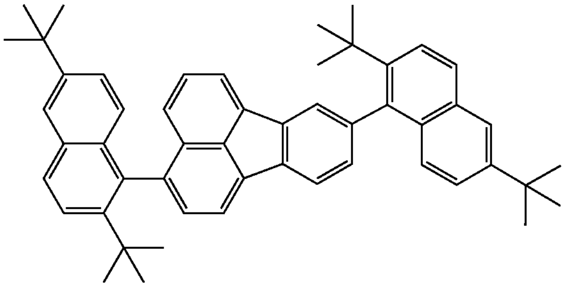
-continued
ET24
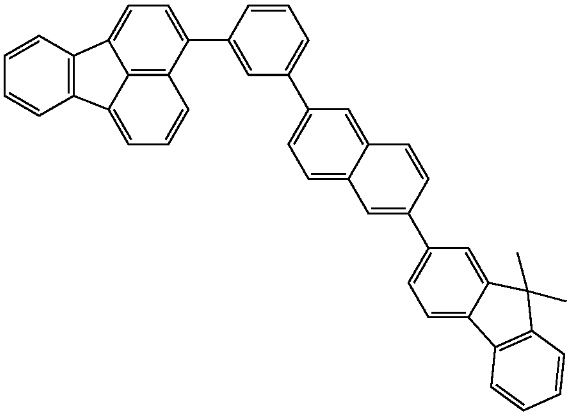
ET25
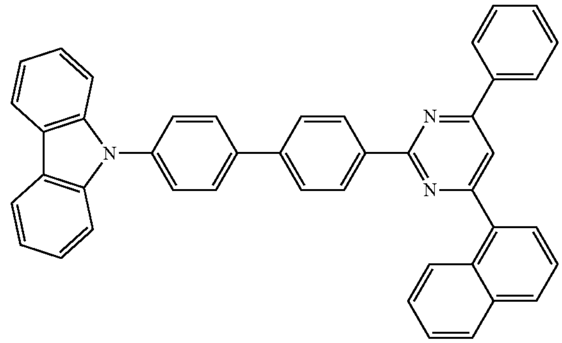
ET26
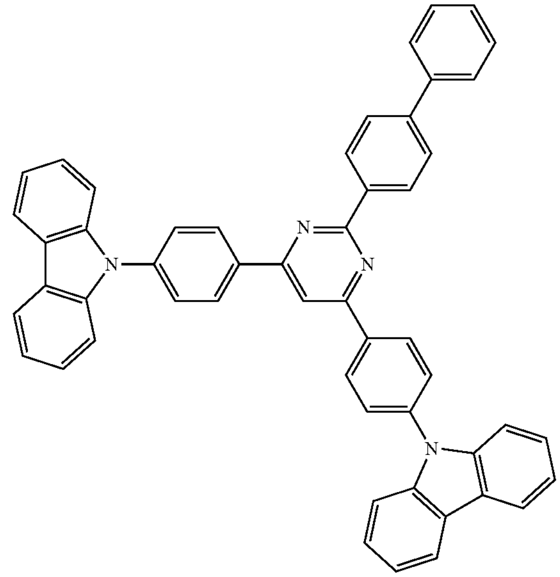

-continued

ET27

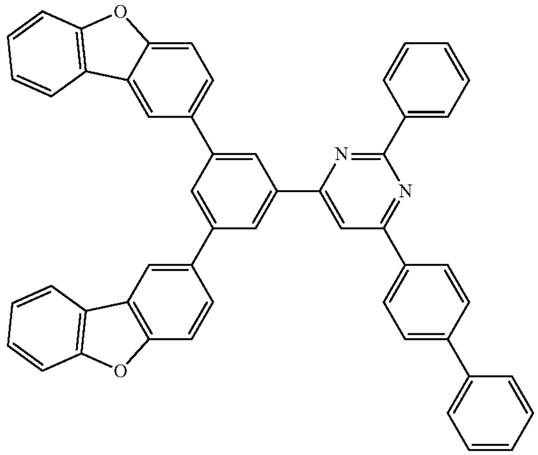

(4) Configuration of Organic Light-Emitting Element

An organic light-emitting element is produced by forming an insulating layer, a first electrode, an organic compound layer, and a second electrode on a substrate. A protective layer, a color filter, a microlens, etc., may be disposed on the second electrode. When a color filter is provided, a planarization layer may be disposed between the color filter and the protective layer. The planarization layer can be formed of an acrylic resin or the like. The same applies to the case where a planarization layer is disposed between the color filter and the microlens.

Substrate

Examples of the substrate include quartz substrates, glass substrates, silicon wafers, resin substrates, and metal substrates. Furthermore, switching elements, such as transistors, and conductive lines may be disposed on the substrate, and an insulating layer may be disposed thereon. The insulating layer may be formed of any material as long as a contact hole can be formed therein so as to form a conductive line connected to the first electrode and as long as the material can provide insulation from a conductive line that is not connected. Examples of the material include resins such as polyimide, silicon oxide, and silicon nitride.

Electrode

A pair of electrodes can be used as the electrodes. The pair of electrodes may be an anode and a cathode.

In the case where an electric field is applied in a direction in which the organic light-emitting element emits light, the electrode with a higher electric potential is the anode, and the other electrode is the cathode. To put it differently, the electrode that supplies holes to the light-emitting layer is the anode, and the electrode that supplies electrons is the cathode.

The material constituting the anode can have a work function that is as large as possible. Examples of the material include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Examples thereof further include conductive polymers such as polyaniline, polypyrrole, and polythiophene.

These electrode substances may be used alone or in combination of two or more thereof. The anode may be formed of a single layer or a plurality of layers.

When the anode is used as a reflective electrode, for example, chromium, aluminum, silver, titanium, tungsten, molybdenum, an alloy thereof, or a layered structure thereof can be used. The above materials may be used to function as a reflective film that does not have a role of an electrode. When the anode is used as a transparent electrode, a transparent conductive oxide layer such as an indium tin oxide (ITO) or indium zinc oxide layer may be used; however, the anode is not limited to these.

The electrodes may be formed by photolithography.

In contrast, the material constituting the cathode can have a small work function. Examples of the material of the cathode include alkali metals such as lithium; alkaline earth metals such as calcium; elemental metals such as aluminum, titanium, manganese, silver, lead, and chromium; and mixtures containing these metals. Alternatively, alloys of these elemental metals may also be used. For example, magnesium-silver, aluminum-lithium, aluminum-magnesium, silver-copper, and zinc-silver may be used. Metal oxides such as indium tin oxide (ITO) may also be used. These electrode substances may be used alone or in combination of two or more thereof. The cathode may have a single-layer structure or a multilayer structure. In particular, silver can be used, and a silver alloy can be used to reduce the aggregation of silver. The alloying ratio is not limited as long as the aggregation of silver can be reduced. The ratio of silver to another metal may be, for example, 1:1 or 3:1.

The cathode is not particularly limited. The cathode may be a conductive oxide layer made of ITO or the like to provide a top-emission element. Alternatively, the cathode may be a reflective electrode made of aluminum (Al) or the like to provide a bottom-emission element. The method for forming the cathode is not particularly limited. For example, a direct-current or alternating-current sputtering method can be used because good film coverage is achieved and thus the resistance is easily reduced.

Organic Compound Layer

The organic compound layer may be formed of a single layer or a plurality of layers. When the organic compound layer is formed of a plurality of layers, the layers may be referred to as a hole injection layer, a hole transport layer, an electron-blocking layer, a light-emitting layer, a hole-blocking layer, an electron transport layer, or an electron injection layer depending on their functions. The organic compound layer is mainly composed of an organic compound and may contain inorganic atoms and an inorganic compound. For example, the organic compound layer may contain copper, lithium, magnesium, aluminum, iridium, platinum, molybdenum, zinc, or the like. The organic compound layer may be disposed between the first electrode and the second electrode and may be disposed in contact with the first electrode and the second electrode.

Organic compound layers (such as a hole injection layer, a hole transport layer, an electron-blocking layer, a light-emitting layer, a hole-blocking layer, an electron transport layer, and an electron injection layer) constituting the organic light-emitting element according to one embodiment of the present disclosure are formed by the methods described below.

The organic compound layers constituting the organic light-emitting element according to one embodiment of the present disclosure can be formed by a dry process, such as a vacuum evaporation method, an ionized deposition method, sputtering, or plasma. Instead of the dry process, a wet process involving dissolving a material in an appropriate solvent, and then forming a layer by a publicly known coating method (for example, spin coating, dipping, a casting method, a Langmuir-Blodgett (LB) method, or an ink jet method) can also be employed.

When a layer is formed by a vacuum evaporation method, a solution coating method, or the like, for example, crystallization is unlikely to occur, and good stability over time is obtained. When a film is formed by a coating method, a material can be combined with an appropriate binder resin to form the film.

Examples of the binder resin include, but are not limited to, polyvinylcarbazole resins, polycarbonate resins, polyester resins, acrylonitrile-butadiene-styrene (ABS) resins, acrylic resins, polyimide resins, phenolic resins, epoxy resins, silicone resins, and urea resins.

These binder resins may be used alone as a homopolymer or a copolymer or in combination as a mixture of two or more thereof. Furthermore, publicly known additives such as a plasticizer, an oxidation inhibitor, and an ultraviolet absorbent may be optionally used in combination.

Protective Layer

A protective layer may be disposed on the second electrode. For example, a glass member with a moisture absorbent can be bonded onto the second electrode to reduce the entry of, for example, water into the organic compound layer, thereby reducing the occurrence of display defects. In another embodiment, a passivation film composed of silicon nitride or the like may be disposed on the second electrode to reduce the entry of, for example, water into the organic compound layer. For example, after the formation of the second electrode, the resulting substrate may be transferred to another chamber without breaking the vacuum, and a protective layer may be formed thereon by forming a silicon nitride film having a thickness of 2 μm by a chemical vapor deposition (CVD) method. A protective layer may be formed by an atomic layer deposition (ALD) method after the film deposition by a CVD method. The material of the film formed by the ALD method is not limited and may be, for example, silicon nitride, silicon oxide, or aluminum oxide. Silicon nitride may be further deposited by the CVD method on the film formed by the ALD method. The film formed by the ALD method may have a smaller thickness than the film formed by the CVD method. Specifically, the film thickness may be 50% or less, even 10% or less.

Color Filter

A color filter may be disposed on the protective layer. For example, a color filter that takes into account the size of the organic light-emitting element may be disposed on another substrate, and the substrate may be bonded to a substrate having the organic light-emitting element thereon. Alternatively, a color filter may be formed on the aforementioned protective layer by photolithographic patterning. The color filter may be formed of a polymer.

Planarization Layer

A planarization layer may be disposed between the color filter and the protective layer. The planarization layer is formed in order to reduce unevenness of the underlying layer. The planarization layer may be referred to as a material resin layer without limiting the purpose thereof. The planarization layer may be formed of an organic compound and may have a low molecular weight or a high molecular weight. The planarization layer can have a high molecular weight.

The planarization layer may be disposed above and below the color filter, and both the planarization layers may be formed of the same material or different materials. Specific examples of the material include polyvinylcarbazole resins, polycarbonate resins, polyester resins, ABS resins, acrylic resins, polyimide resins, phenolic resins, epoxy resins, silicone resins, and urea resins.

Microlens

An organic light-emitting element or an organic light-emitting apparatus may include an optical member such as a microlens on the light-emitting side. The microlens can be composed of an acrylic resin, an epoxy resin, or the like. The microlens may be used to increase the amount of light extracted from the organic light-emitting element or the organic light-emitting apparatus and to control the direction of the extracted light. The microlens may have a hemispherical shape. In the case of a hemispherical shape, among tangents in contact with the hemisphere, there is a tangent parallel to the insulating layer, and the contact point between the tangent and the hemisphere is the vertex of the microlens. The vertex of the microlens can be determined in the same manner in any sectional view. That is, among the tangents in contact with the semicircle of the microlens in the sectional view, there is a tangent parallel to the insulating layer, and the contact point between the tangent and the semicircle is the vertex of the microlens.

The midpoint of the microlens can also be defined. In a section of the microlens, a line segment from one end point to the other end point of the arc is assumed, and the midpoint of the line segment can be referred to as the midpoint of the microlens. The section in which the vertex and the midpoint are determined may be a section perpendicular to the insulating layer.

Opposite Substrate

An opposite substrate may be disposed on the planarization layer. The opposite substrate is disposed at a position corresponding to the aforementioned substrate and thus is referred to as an opposite substrate. The opposite substrate may be composed of the same material as the aforementioned substrate. When the aforementioned substrate is defined as a first substrate, the opposite substrate may be defined as a second substrate.

Pixel Circuit

A light-emitting apparatus having a light-emitting element may include a pixel circuit connected to the light-emitting element. The pixel circuit may be an active matrix-type circuit that independently controls light emission of a first light-emitting element and a second light-emitting element. The active matrix-type circuit may be a voltage programming or current programming circuit. A driving circuit has a pixel circuit for each pixel. The pixel circuit may have a light-emitting element, a transistor that controls the emission luminance of the light-emitting element, a transistor that controls the timing of light emission, a capacitor that holds the gate voltage of the transistor that controls the emission luminance, and a transistor for connecting to GND without through the light-emitting element.

The light-emitting apparatus has a display region and a peripheral region around the display region. The display region includes a pixel circuit, and the peripheral region includes a display control circuit. The mobility of transistors constituting the pixel circuit may be smaller than the mobility of transistors constituting the display control circuit.

The slope of the current-voltage characteristics of the transistors constituting the pixel circuit may be smaller than the slope of the current-voltage characteristics of the transistors constituting the display control circuit. The slope of the current-voltage characteristics can be measured by the so-called Vg-Ig characteristics. The transistors constituting the pixel circuit are transistors connected to light-emitting elements including the first light-emitting element.

Pixel

The light-emitting apparatus having a light-emitting element may include a plurality of pixels. Each pixel includes subpixels that emit light of a color different from the other colors. The subpixels may have, for example, respective red, green, and blue (RGB) emission colors.

The pixels each emit light from an area that is also called a pixel aperture. This area is the same as a first area. The pixel aperture may have a size of 15 μm or less and 5 μm or more. More specifically, the pixel aperture may have a size of, for example, 11 μm, 9.5 μm, 7.4 μm, or 6.4 μm. The distance between the subpixels may be 10 μm or less and may be specifically 8 μm, 7.4 μm, or 6.4 μm.

The pixels can have a publicly known arrangement form in plan view. For example, the arrangement form may be the stripe arrangement, the delta arrangement, the PenTile arrangement, or the Bayer arrangement. The subpixels may have any publicly known shape in plan view. For example, the shape may be a quadrangle such as a rectangle or a rhombus, or a hexagon. As a matter of course, figures that are not exactly rectangles but are close to rectangles are also regarded as rectangles. The shape of the subpixels and the pixel array can be used in combination.

(5) Apparatus Including Organic Light-Emitting Element

The organic light-emitting element according to this embodiment can be used as a constituent member of a display apparatus or an illumination apparatus. Other applications include an exposure light source for an electrophotographic image forming apparatus, a backlight of a liquid crystal display apparatus, and a light-emitting apparatus having a color filter in a white light source.

The display apparatus may be an image information processing apparatus that includes an image input unit to which image information is input from an area CCD, a linear CCD, a memory card, or the like and an information processing unit configured to process the input information, and that displays an input image on a display unit. The display apparatus may have a plurality of pixels, and at least one of the pixels may include the organic light-emitting element according to this embodiment and a transistor connected to the organic light-emitting element. In this case, the substrate may be a semiconductor substrate composed of, for example, silicon, and the transistor may be a MOSFET formed on the substrate.

The display unit included in an image pickup apparatus or an ink jet printer may have a touch panel function. The touch panel function may be driven by any method such as a method that uses infrared radiation, an electrostatic capacitance, a resistive film, or electromagnetic induction. The display apparatus may be used in a display unit of a multifunctional printer.

Figure 1B:
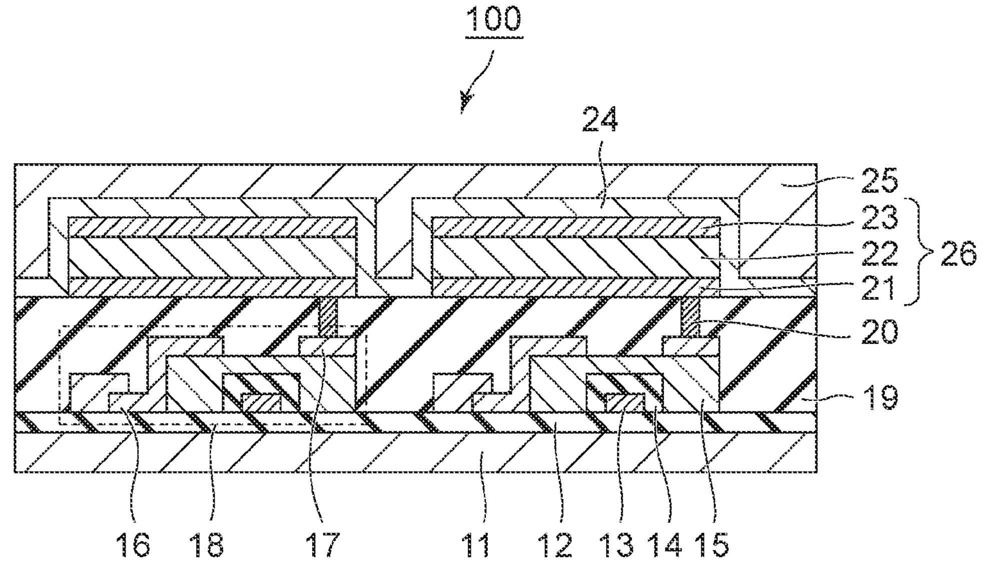
FIG. 1B is a schematic sectional view illustrating an example of a display apparatus including organic light-emitting elements according to an embodiment of the present disclosure.

Next, a display apparatus according to this embodiment will be described with reference to the drawings. FIGS. 1A and 1B are schematic sectional views illustrating an example of a display apparatus including organic light-emitting elements and transistors connected to the organic light-emitting elements. Each of the transistors is one example of an active element. The transistors may be thin-film transistors (TFT).

FIG. 1A illustrates an example of a pixel which is a component of the display apparatus according to this embodiment. A pixel has subpixels 10. The subpixels are separated into 10R, 10G, and 10B according to their light emission. The emission color may be distinguished on the basis of the wavelength of light emitted from the light-emitting layer, or the light emitted from the subpixels may be selectively subjected to transmission or color conversion through a color filter or the like. Each of the subpixels 10 includes, on an interlayer insulating layer 1, a reflective electrode serving as a first electrode 2, an insulating layer 3 covering ends of the first electrode 2, an organic compound layer 4 covering the first electrode 2 and the insulating layer 3, a transparent electrode serving as a second electrode 5, a protective layer 6, and a color filter 7.

The interlayer insulating layer 1 may have transistors and capacitor elements disposed in a layer disposed thereunder or inside thereof.

Each transistor and the first electrode 2 may be electrically connected to each other through a contact hole or the like not illustrated in the drawing.

The insulating layer 3 is also referred to as a bank or a pixel isolation film. The insulating layer 3 covers ends of the first electrode 2 and is disposed so as to surround the first electrode 2. A portion that is not covered with the insulating layer 3 is in contact with the organic compound layer 4 and serves as a light-emitting region.

The organic compound layer 4 includes a hole injection layer 41, a hole transport layer 42, a first light-emitting layer 43, a second light-emitting layer 44, and an electron transport layer 45.

The second electrode 5 may be a transparent electrode, a reflective electrode, or a semi-transparent electrode.

The protective layer 6 reduces the entry of moisture into the organic compound layer 4. Although the protective layer 6 is illustrated as a single layer in the drawing, the protective layer 6 may be formed of a plurality of layers. Each layer may be an inorganic compound layer or an organic compound layer.

The color filter 7 is separated into 7R, 7G, and 7B according to the colors thereof. The color filter 7 may be formed on a planarizing film not illustrated in the drawing. Furthermore, a resin protective layer not illustrated in the drawing may be disposed on the color filter 7. The color filter 7 may be formed on the protective layer 6. Alternatively, the color filter 7 may be formed on an opposite substrate, such as a glass substrate, and may then be bonded.

A display apparatus 100 illustrated in FIG. 1B includes organic light-emitting elements 26 and TFTs 18, which are one example of transistors. A substrate 11 composed of glass, silicon, or the like and an insulating layer 12 on top of the substrate 11 are provided. On the insulating layer 12, active elements such as TFTs 18 are disposed, and a gate electrode 13, a gate insulating film 14, and a semiconductor layer 15 of each of the active elements are disposed. Each of the TFTs 18 has a drain electrode 16 and a source electrode 17. An insulating film 19 is disposed on the TFTs 18. An anode 21 included in each of the organic light-emitting elements 26 is connected to the source electrode 17 through a contact hole 20.

The form of the electrical connection between the electrodes (anode 21 and cathode 23) included in each organic light-emitting element 26 and the electrodes (source electrode 17 and drain electrode 16) included in the corresponding one of the TFTs 18 is not limited to the form illustrated in FIG. 1B. In other words, it is sufficient that one of the anode 21 and the cathode 23 is electrically connected to one of the source electrode 17 and the drain electrode 16 of the TFT 18.

In the display apparatus 100 in FIG. 1B, an organic compound layer 22 is illustrated as if the organic compound layer 22 is formed of a single layer. Alternatively, the organic compound layer 22 may be formed of a plurality of layers. A first protective layer 24 and a second protective layer 25 for reducing deterioration of the organic light-emitting elements 26 are disposed over the cathodes 23.

Although transistors are used as the switching elements in the display apparatus 100 illustrated in FIG. 1B, other switching elements, such as metal-insulator-metal (MIM) elements, may be used instead of the transistors.

The transistors used in the display apparatus 100 illustrated in FIG. 1B are not limited to thin-film transistors having an active layer on an insulating surface of a substrate and may be transistors that use a single-crystal silicon wafer. Examples of the material of the active layer include single-crystal silicon, non-single-crystal silicon such as amorphous silicon and microcrystalline silicon, and non-single-crystal oxide semiconductors such as indium zinc oxide and indium gallium zinc oxide. Thin-film transistors are also referred to as TFT elements.

The transistors included in the display apparatus 100 illustrated in FIG. 1B may be formed inside a substrate such as a Si substrate. The expression "formed inside a substrate" as used herein means that transistors are produced by processing a substrate, such as a Si substrate, itself. In other words, having transistors inside a substrate can also be considered that a substrate and transistors are integrally formed.

In the organic light-emitting element according to this embodiment, the emission luminance is controlled with the TFTs, which are one example of switching elements. Thus, a plurality of organic light-emitting elements can be arranged in the plane to display an image at respective emission luminance levels. The switching elements according to this embodiment are not limited to TFTs and may be transistors formed of low-temperature polysilicon or active-matrix drivers formed on a substrate such as a Si substrate. The expression "on a substrate" can also be referred to as "inside the substrate". Whether transistors are formed inside a substrate or TFTs are used is selected on the basis of the size of the display unit. For example, when the size is about 0.5 inches, organic light-emitting elements can be disposed on a Si substrate.

Figure 2:
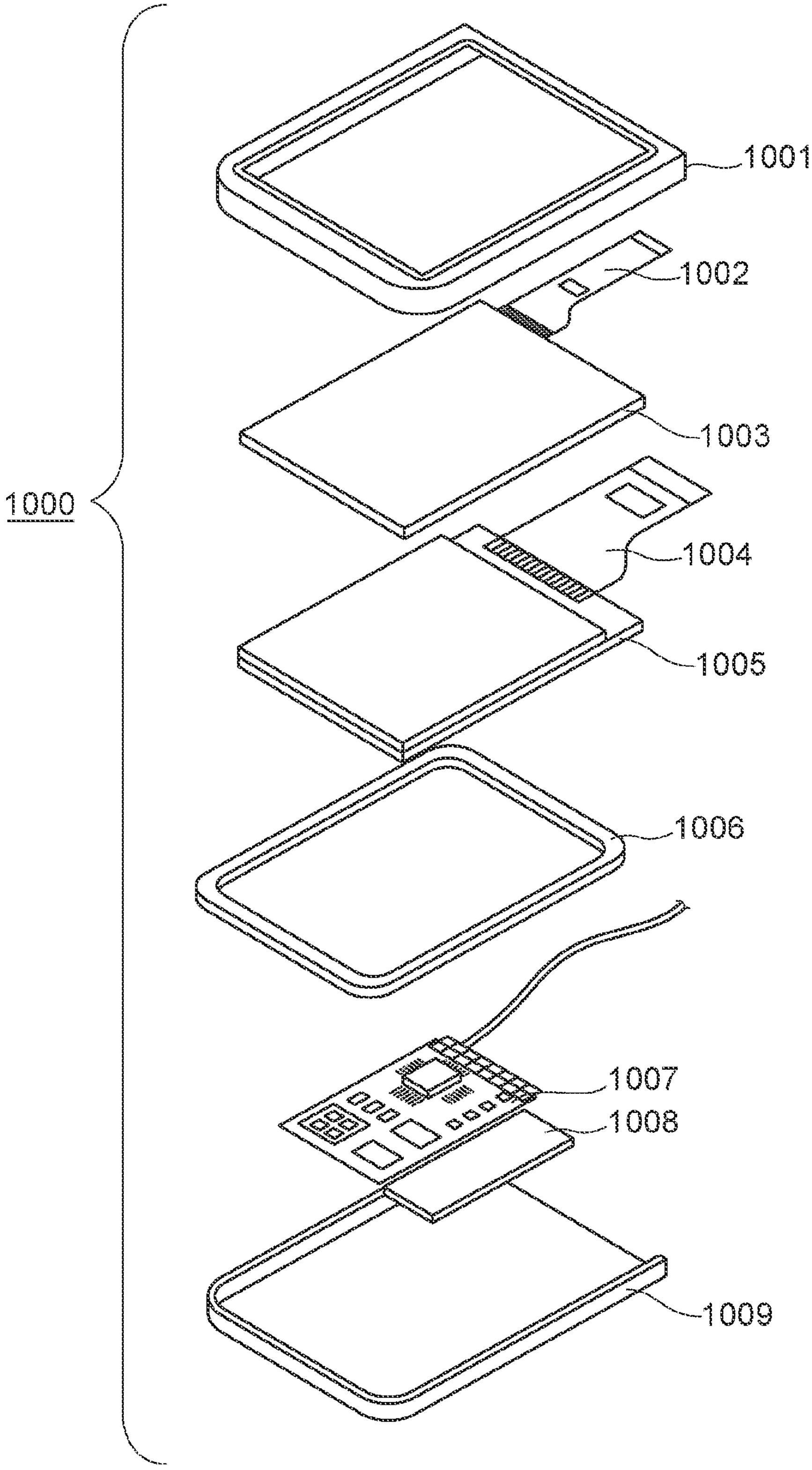
FIG. 2 is a schematic view illustrating an example of a display apparatus according to an embodiment of the present disclosure.

FIG. 2 is a schematic view illustrating an example of a display apparatus according to this embodiment. A display apparatus 1000 may include an upper cover 1001 and a lower cover 1009, and a touch panel 1003, a display panel 1005, a frame 1006, a circuit substrate 1007, and a battery 1008 that are disposed between the upper cover 1001 and the lower cover 1009. The touch panel 1003 and the display panel 1005 are connected to flexible printed circuits FPC 1002 and 1004, respectively. Transistors are printed on the circuit substrate 1007. The battery 1008 is not necessarily installed unless the display apparatus is a portable apparatus or may be installed in a different position even if the display apparatus is a portable apparatus.

The display apparatus according to this embodiment may include a color filter having red, green, and blue portions. The red, green, and blue portions of the color filter may be arranged in the delta arrangement.

The display apparatus according to this embodiment may be used in a display unit of a portable terminal. In such a case, the display apparatus may have both a display function and an operation function. Examples of the portable terminal include mobile phones such as smart phones, tablets, and head mount displays.

The display apparatus according to this embodiment may be used in a display unit of an image pickup apparatus including an optical unit that includes a plurality of lenses and an image pickup element configured to receive light that has passed through the optical unit. The image pickup apparatus may include a display unit configured to display information acquired by the image pickup element. The display unit may be a display unit exposed to the outside of the image pickup apparatus or a display unit disposed in a viewfinder. The image pickup apparatus may be a digital camera or a digital camcorder.

Figure 3A:
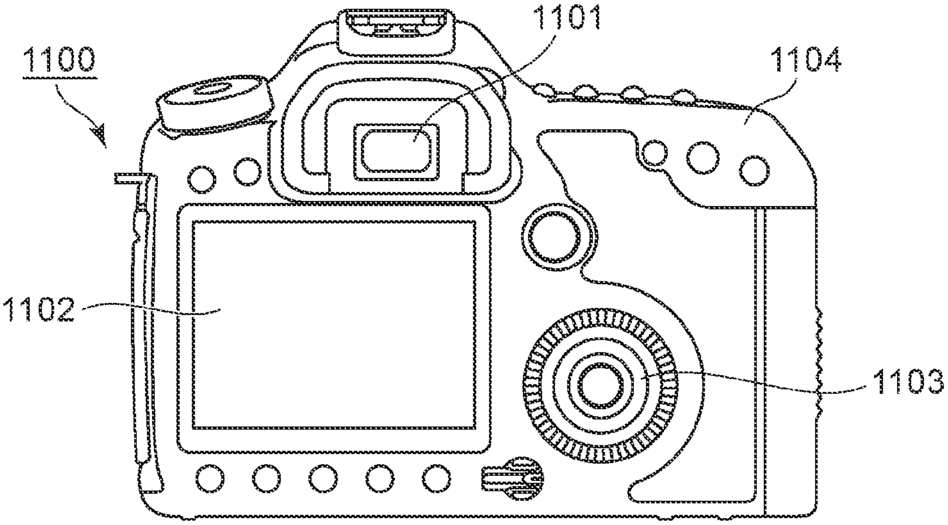
FIG. 3A is a schematic view illustrating an example of an image pickup apparatus according to an embodiment of the present disclosure.

FIG. 3A is a schematic view illustrating an example of an image pickup apparatus according to this embodiment. An image pickup apparatus 1100 may include a viewfinder 1101, a rear surface display 1102, an operation unit 1103, and a housing 1104. The viewfinder 1101 may include a display apparatus according to this embodiment. In such a case, the display apparatus may display not only an image to be captured but also, for example, environmental information and imaging instructions. The environmental information may include, for example, the intensity of external light, the direction of external light, the moving speed of the photographic subject, and the possibility that the photographic subject may hide behind an obstacle.

Since the suitable timing for capturing an image is a very short period of time, it is desirable to display information as quickly as possible. Accordingly, a display apparatus including the organic light-emitting element according to this embodiment can be used. This is because the organic light-emitting element has a high response speed. The display apparatus including an organic light-emitting element is more suitable than liquid crystal display apparatuses for use in apparatuses for which a high display speed is required.

The image pickup apparatus 1100 includes an optical unit not illustrated in the drawing. The optical unit includes a plurality of lenses and is configured to focus an image on an image pickup element contained in the housing 1104. The plurality of lenses can adjust the focal point by adjusting their relative positions. This operation can be automatically performed. The image pickup apparatus may also be referred to as a photoelectric conversion apparatus. The photoelectric conversion apparatus can employ, instead of a method of successively capturing images, image capturing methods such as a method of detecting a difference from the previous image and a method of extracting images from continuously recorded images.

Figure 3B:
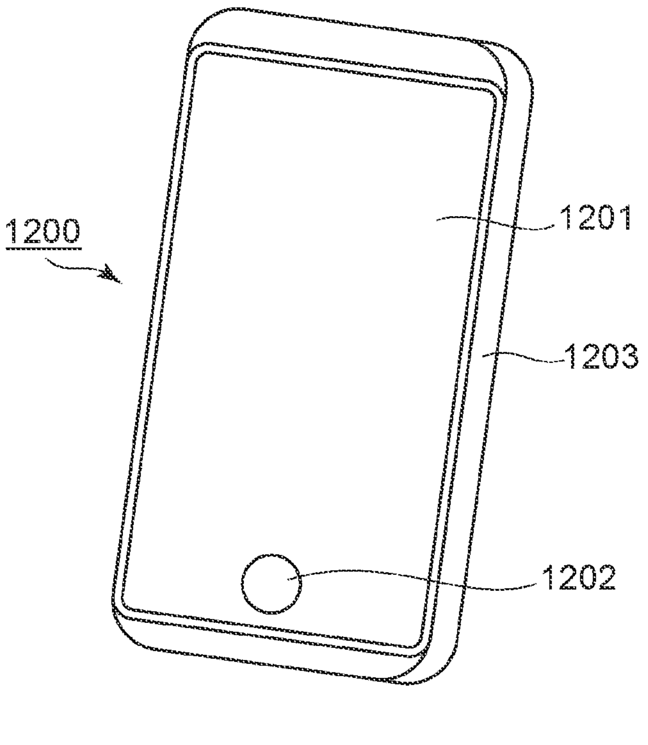
FIG. 3B is a schematic view illustrating an example of an electronic apparatus according to an embodiment of the present disclosure.

FIG. 3B is a schematic view illustrating an example of an electronic apparatus according to this embodiment. An electronic apparatus 1200 includes a display unit 1201, an operation unit 1202, and a housing 1203. The housing 1203 may include therein circuits, a print substrate having the circuits, a battery, and a communication unit. The operation unit 1202 may be a button or a touch panel-type responsive unit. The operation unit 1202 may be a biometric authentication unit configured to, for example, recognize the fingerprints and release the lock. The electronic apparatus that includes a communication unit can also be referred to as a communication apparatus. The electronic apparatus 1200 may include a lens and an image pickup element so as to further have a camera function. An image captured by the camera function is displayed on the display unit 1201. Examples of the electronic apparatus 1200 include smart phones and notebook computers.

Figure 4A:
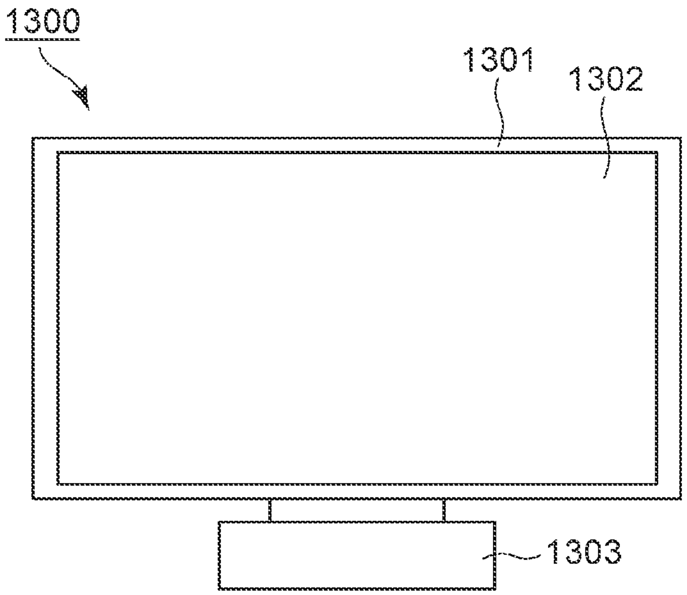
FIG. 4A is a schematic view illustrating an example of a display apparatus according to an embodiment of the present disclosure.
Figure 4B:
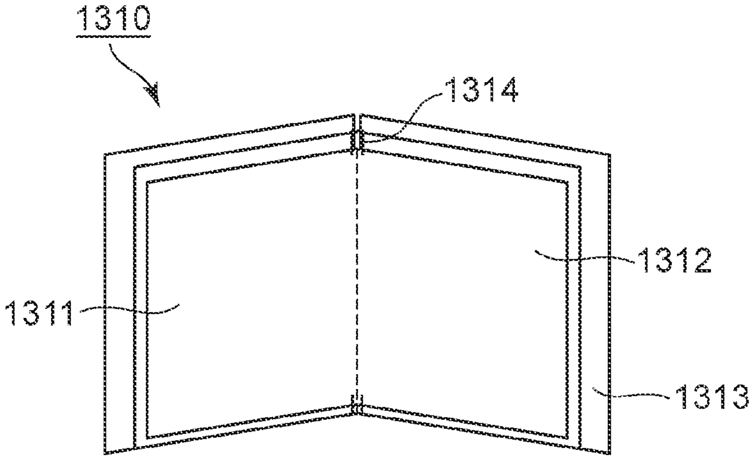
FIG. 4B is a schematic view illustrating an example of a foldable display apparatus.

FIGS. 4A and 4B are schematic views each illustrating an example of a display apparatus according to this embodiment. FIG. 4A illustrates a display apparatus such as a television monitor or a personal computer (PC) monitor. A display apparatus 1300 includes a frame 1301 and a display unit 1302. The light-emitting element according to this embodiment may be used in the display unit 1302. The display apparatus 1300 further includes a base 1303 configured to support the frame 1301 and the display unit 1302. The base 1303 is not limited to the form illustrated in FIG. 4A. The lower side of the frame 1301 may also function as the base. The frame 1301 and the display unit 1302 may be curved. The radius of curvature thereof may be 5,000 mm or more and 6,000 mm or less.

FIG. 4B is a schematic view illustrating another example of the display apparatus according to this embodiment. A display apparatus 1310 illustrated in FIG. 4B is configured to be foldable and is the so-called foldable display apparatus. The display apparatus 1310 includes a first display unit 1311, a second display unit 1312, a housing 1313, and an inflexion point 1314. Each of the first display unit 1311 and the second display unit 1312 may include the light-emitting element according to this embodiment. The first display unit 1311 and the second display unit 1312 may be designed as a single, seamless display apparatus. The first display unit 1311 and the second display unit 1312 can be separated at the inflexion point. The first display unit 1311 and the second display unit 1312 may display images that differ from each other. Alternatively, the first and second display units may collectively display a single image.

Figure 5A:
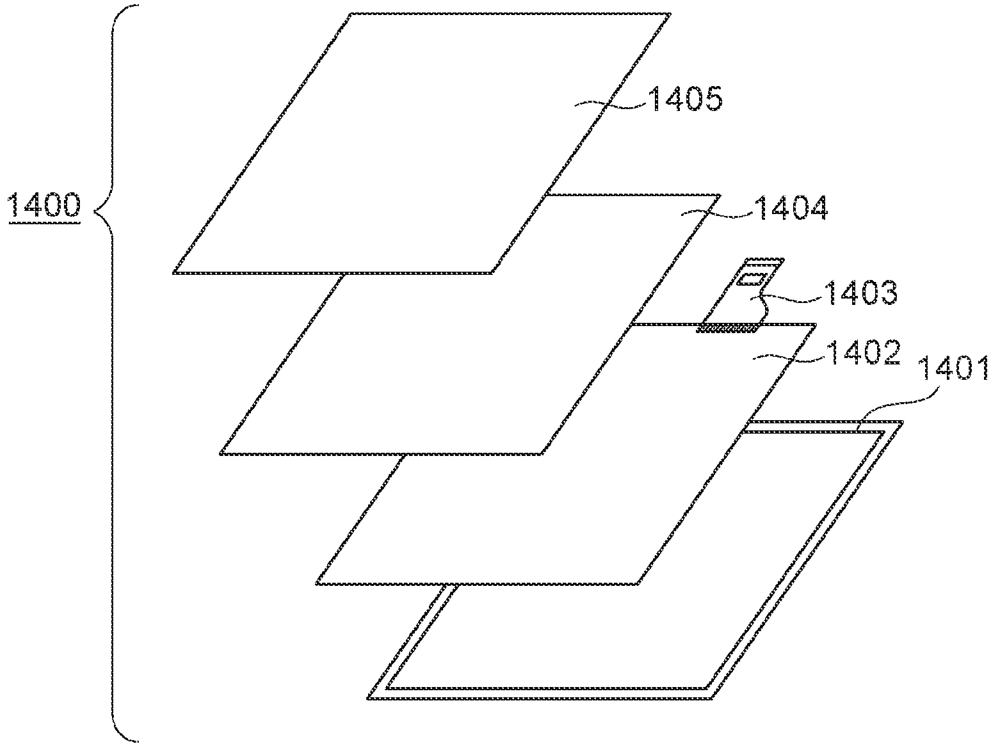
FIG. 5A is a schematic view illustrating an example of an illumination apparatus according to an embodiment of the present disclosure.

FIG. 5A is a schematic view illustrating an example of an illumination apparatus according to this embodiment. An illumination apparatus 1400 may include a housing 1401, a light source 1402, a circuit substrate 1403, and an optical filter 1404 and a light diffusion unit 1405 that are configured to transmit light emitted from the light source 1402. The light source 1402 may include the organic light-emitting element according to this embodiment. The optical filter 1404 may be a filter configured to improve the color rendering properties of the light source. The light diffusion unit 1405 can effectively diffuse light emitted from the light source and allow the light to reach a wide range, for example, for lighting up. The optical filter 1404 and the light diffusion unit 1405 may be disposed on the light-emitting side of the illumination. A cover may be optionally disposed on the outermost portion.

The illumination apparatus is, for example, an apparatus that illuminates a room. The illumination apparatus may emit light of a color such as white, neutral white, or any other color from blue to red. The illumination apparatus may have a light modulation circuit configured to modulate the light and a color control circuit configured to control the emission color. The illumination apparatus may include the organic light-emitting element according to this embodiment and a power supply circuit connected to the organic light-emitting element. The power supply circuit is a circuit configured to convert alternating current voltage to direct current voltage. The white is a color having a color temperature of 4,200 K, and the neutral white is a color having a color temperature of 5,000 K. The illumination apparatus may include a color filter.

The illumination apparatus according to this embodiment may include a heat dissipation unit. The heat dissipation unit dissipates heat in the apparatus to the outside of the apparatus. The heat dissipation unit may be formed of, for example, a metal having a high specific heat or liquid silicon.

Figure 5B:
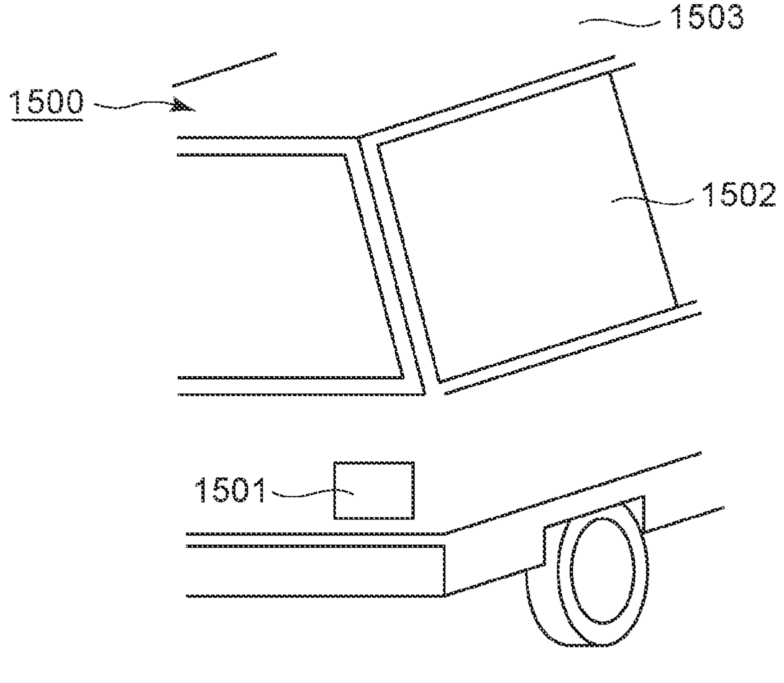
FIG. 5B is a schematic view illustrating an example of a moving object including a vehicle lighting fixture according to an embodiment of the present disclosure.

FIG. 5B is a schematic view of an automobile, which is an example of a moving object according to this embodiment. The automobile has a tail lamp, which is an example of a lighting fixture. An automobile 1500 has a tail lamp 1501, and the tail lamp 1501 may light up when, for example, the brakes are applied.

The tail lamp 1501 may include the organic light-emitting element according to this embodiment. The tail lamp 1501 may include a protective member that protects the organic light-emitting element. The protective member may be composed of any material that has high strength to a certain extent and is transparent, and can be composed of a polycarbonate or the like. The polycarbonate may be mixed with a furandicarboxylic acid derivative, an acrylonitrile derivative, or the like.

The automobile 1500 may include a car body 1503 and a window 1502 installed to the car body 1503. The window 1502 may be a transparent display unless it is a window for checking the front and rear of the automobile. The transparent display may include the organic light-emitting element according to this embodiment.

In such a case, the components, such as the electrodes, of the organic light-emitting element are formed of transparent members.

The moving object according to this embodiment may be, for example, a ship, an aircraft, or a drone. The moving object may include a body and a lighting fixture installed to the body. The lighting fixture may emit light to indicate the position of the body. The lighting fixture includes the organic light-emitting element according to this embodiment.

Examples of applications of the display apparatuses according to the above-described embodiments will be described with reference to FIGS. 6A and 6B. The display apparatuses are applicable to systems that can be worn as wearable devices, such as smart glasses, head mount displays (HMDs), and smart contact lenses. An imaging display apparatus used in such an example of the application includes an image pickup apparatus that can photoelectrically convert visible light and a display apparatus that can emit visible light.

Figure 6A:
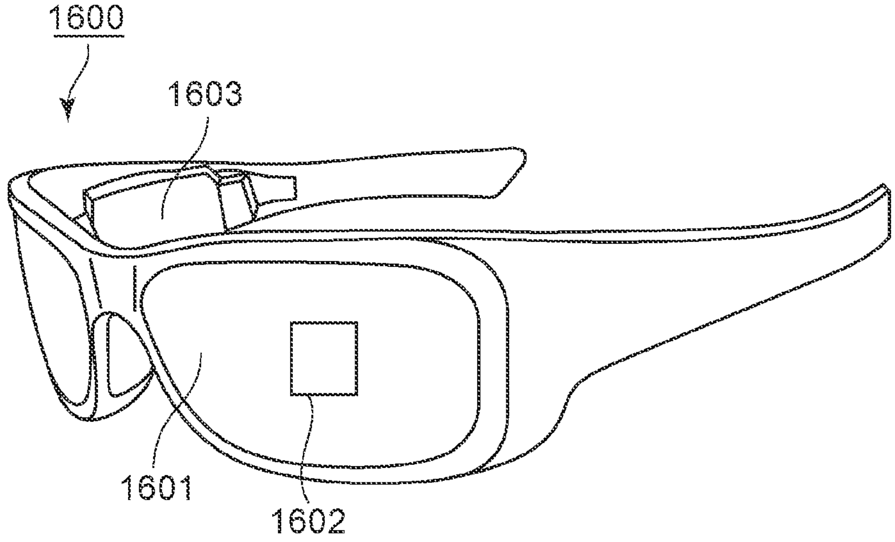
FIG. 6A is a schematic view illustrating an example of a wearable device according to an embodiment of the present disclosure.

FIG. 6A is a schematic view illustrating an example of a wearable device according to an embodiment of the present disclosure. Glasses 1600 (smart glasses) according to one example of applications will be described with reference to FIG. 6A. An image pickup apparatus 1602 such as a complementary metal-oxide semiconductor (CMOS) sensor or a single-photon avalanche diode (SPAD) is provided on the front surface side of a lens 1601 of the glasses 1600. The display apparatus according to any of the above-described embodiments is provided on the back surface side of the lens 1601.

The glasses 1600 further include a control unit 1603. The control unit 1603 functions as a power supply that supplies electric power to the image pickup apparatus 1602 and the display apparatus. The control unit 1603 controls the operation of the image pickup apparatus 1602 and the display apparatus. An optical system for focusing light on the image pickup apparatus 1602 is formed on the lens 1601.

Figure 6B:
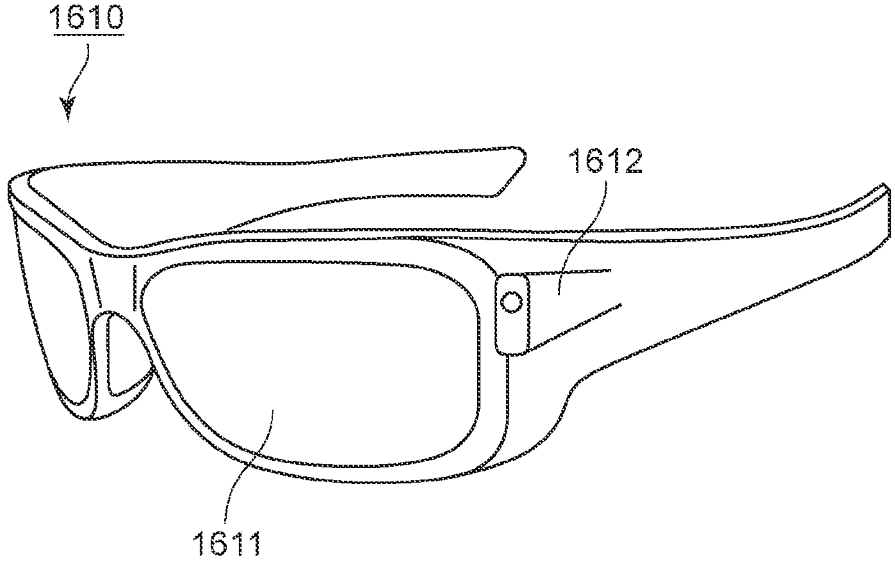
FIG. 6B is a schematic view illustrating another example of a wearable device according to an embodiment of the present disclosure.

FIG. 6B is a schematic view illustrating another example of a wearable device according to an embodiment of the present disclosure. Glasses 1610 (smart glasses) according to one example of applications will be described with reference to FIG. 6B. The glasses 1610 have a control unit 1612. The control unit 1612 includes an image pickup apparatus corresponding to the image pickup apparatus 1602 in FIG. 6A and a display apparatus. An optical system for projecting light emitted from the image pickup apparatus and the display apparatus in the control unit 1612 is formed on a lens 1611, and an image is projected on the lens 1611. The control unit 1612 functions as a power supply that supplies electric power to the image pickup apparatus and the display apparatus and controls the operation of the image pickup apparatus and the display apparatus.

The control unit 1612 may have a gaze detection unit that detects the gaze of the wearer. Infrared rays may be used to detect the gaze. An infrared light-emitting unit emits infrared light to an eyeball of the user who is gazing at a displayed image. The emitted infrared light is reflected by the eyeball, and the reflected light is detected by an image pickup unit including a light-receiving element to provide a captured image of the eyeball. A reduction unit configured to reduce light from the infrared light-emitting unit to a display unit in plan view is provided to reduce the deterioration of the image quality. The gaze of the user to the displayed image is detected from the captured image of the eyeball captured with the infrared light. Any publicly known method is applicable to the gaze detection using the captured image of the eyeball. As one example, a gaze detection method based on the Purkinje image formed by the reflection of irradiation light on the cornea can be employed. More specifically, a gaze detection process based on a pupil-corneal reflection method is performed. The gaze of the user is detected by calculating a gaze vector representing the direction (rotation angle) of the eyeball on the basis of the Purkinje image and a pupil image included in the captured image of the eyeball using the pupil-corneal reflection method.

A display apparatus according to an embodiment of the present disclosure may include an image pickup apparatus having a light-receiving element, and may control a displayed image of the display apparatus on the basis of the gaze information of the user from the image pickup apparatus. Specifically, the display apparatus determines, on the basis of the gaze information, a first field-of-view region at which the user gazes and a second field-of-view region other than the first field-of-view region. The first field-of-view region and the second field-of-view region may be determined by the control unit of the display apparatus or may be determined by receiving those determined by an external control unit. In the display region of the display apparatus, the display resolution of the first field-of-view region may be controlled to be higher than the display resolution of the second field-of-view region. That is, the resolution of the second field-of-view region may be controlled to be lower than that of the first field-of-view region.

The display region includes a first display region and a second display region different from the first display region. A region with a higher priority is determined from the first display region and the second display region on the basis of the gaze information. The first display region and the second display region may be determined by the control unit of the display apparatus or may be determined by receiving those determined by an external control unit. The resolution of the region with the higher priority may be controlled to be higher than the resolution of a region other than the region with the higher priority. That is, the region with a relatively low priority may have a lower resolution.

The first field-of-view region or a region with a higher priority may be determined by artificial intelligence (AI). The AI may be a model configured to estimate the angle of the gaze and the distance to a target object located in the gaze direction from images of the eyeball by using, as teaching data, images of the eyeball and the actual gaze direction of the eyeball in the images. The AI program may be stored in the display apparatus, the image pickup apparatus, or an external apparatus. When the AI program is stored in the external apparatus, the AI program is transmitted through communication to the display apparatus.

In the case of controlling the display on the basis of visual recognition detection, the display apparatus according to an embodiment of the present disclosure can be applied to smart glasses further including an image pickup apparatus that captures an external image. The smart glasses can display the captured external information in real time.

Figure 7A:
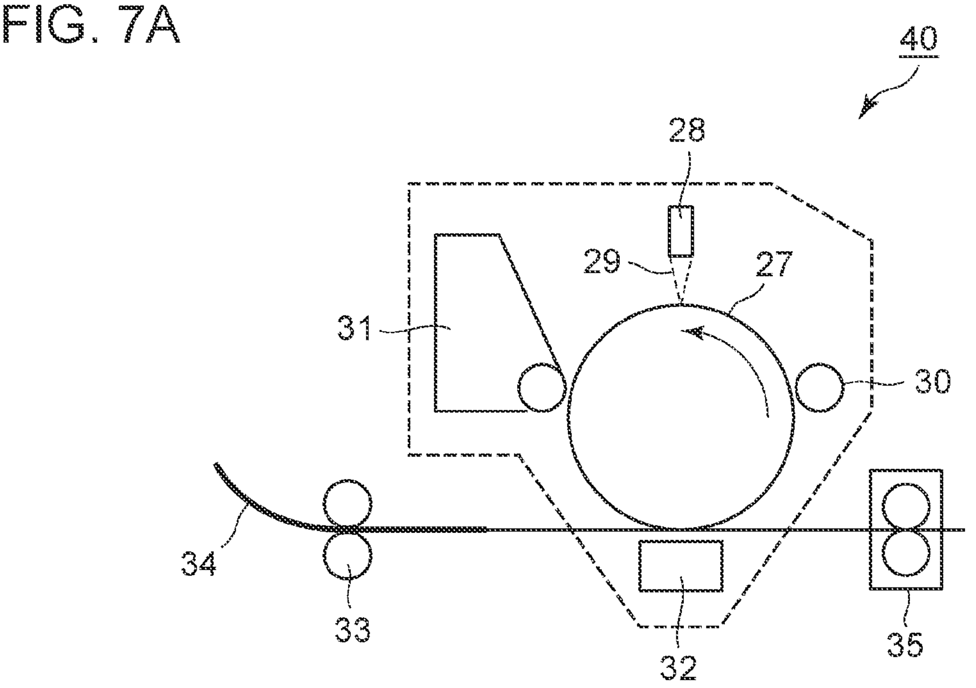
FIG. 7A is a schematic diagram illustrating an example of an image forming apparatus according to an embodiment of the present disclosure.

FIG. 7A is a schematic diagram illustrating an example of an image forming apparatus according to an embodiment of the present disclosure. An image forming apparatus 40 is an electrophotographic image forming apparatus and includes a photoreceptor 27, an exposure light source 28, a charging portion 30, a developing portion 31, a transfer unit 32, transport rollers 33, and a fixing unit 35. Light 29 is applied from the exposure light source 28, and an electrostatic latent image is formed on the surface of the photoreceptor 27. The exposure light source 28 includes the organic light-emitting element according to this embodiment. The developing portion 31 contains a toner and the like. The charging portion 30 charges the photoreceptor 27. The transfer unit 32 transfers a developed image to a recording medium 34. The transport rollers 33 transport the recording medium 34. The recording medium 34 is, for example, paper. The fixing unit 35 fixes the image formed on the recording medium 34.

Figure 7B:
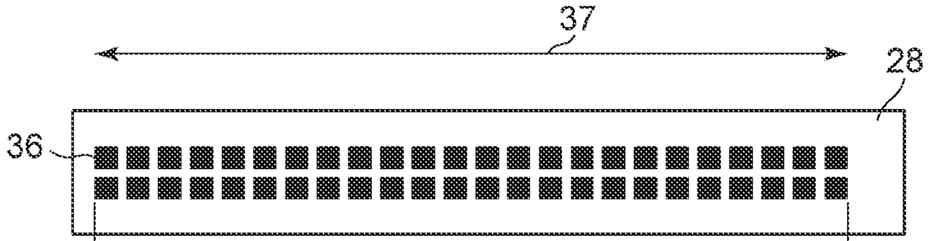
FIGS. 7B and 7C are schematic views illustrating an example of an exposure light source for an image forming apparatus according to an embodiment of the present disclosure.
Figure 7C:
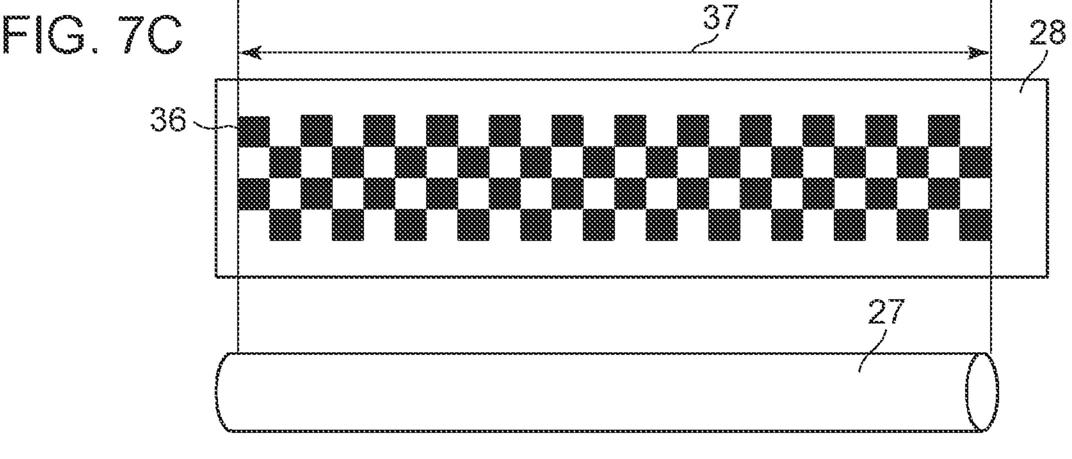

FIGS. 7B and 7C are views illustrating the exposure light source 28 and are schematic views illustrating a state in which a plurality of light-emitting portions 36 are arranged on a long substrate. An arrow 37 indicates a direction parallel to the axis of the photoreceptor, that is, a column direction in which organic light-emitting elements are arranged. This column direction is the same as the direction of the rotational axis of the photoreceptor 27. This direction may also be referred to as a major-axis direction of the photoreceptor 27. FIG. 7B illustrates a form in which the light-emitting portions 36 are arranged in the major-axis direction of the photoreceptor 27. FIG. 7C illustrates a form which is different from that in FIG. 7B and in which the light-emitting portions 36 are arranged in a staggered manner in a first column and a second column in the column direction. The first column and the second column are arranged at positions different in a row direction. In the first column, a plurality of light-emitting portions 36 are arranged at intervals. The second column has light-emitting portions 36 at positions corresponding to the spaces between the light-emitting portions 36 of the first column. That is, the plurality of light-emitting portions 36 are also arranged at intervals in the row direction. In other words, the arrangement in FIG. 7C corresponds to, for example, a state in which the light-emitting portions 36 are arranged in a lattice pattern, a state in which the light-emitting portions 36 are arranged in a houndstooth check pattern, or a checkered pattern.

As described above, the use of an apparatus including the organic light-emitting element according to this embodiment can achieve a stable display with a good image quality even for a long time.

EXEMPLARY EMBODIMENTS

Exemplary embodiments will be described below. However, the present disclosure is not limited to these exemplary embodiments.

Exemplary Embodiment 1 (Synthesis of Exemplary Compound A-1)

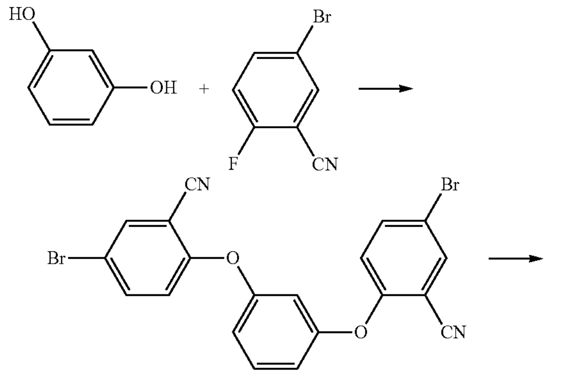

Int1-1

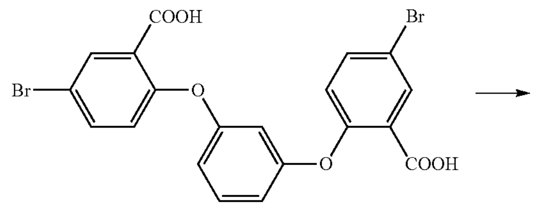

Int1-2

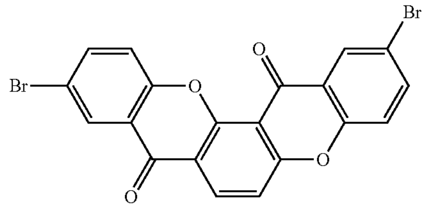

Int1-3

Reaction Step 1 (Synthesis of Intermediate Compound Int1-1)

The following reagents and solvent were placed in a 200 mL recovery flask.

Resorcinol (manufactured by Tokyo Chemical Industry Co., Ltd.): 5.00 g (45.4 mmol) 5-Bromo-2-fluorobenzonitrile (manufactured by Tokyo Chemical Industry Co., Ltd.): 19.8 g (98.8 mmol)

Potassium carbonate: 15.0 g (108 mmol)

Dimethyl sulfoxide: 62 mL

The resulting reaction solution was heated with stirring at 80° C. for 12 hours under nitrogen. After completion of the reaction, the reaction solution was cooled to room temperature and then poured into ice water, and stirring was performed for one hour. The precipitated solid was collected by filtration, washed with ion-exchange water, and then dried in a vacuum dryer at 80° C. for 12 hours. The resulting crude product was recrystallized with a dichloromethane/heptane solvent to obtain 18.1 g of intermediate compound Int1-1 (yield 85%).

Reaction Step 2 (Synthesis of Intermediate Compound Int1-2)

The following reagents and solvents were placed in a 200 mL recovery flask.

Int1-1: 5.00 g (10.6 Mmol)

Sodium Hydroxide: 5.32 g (133 Mmol)

Ion-Exchange Water: 21 mL

Ethanol: 80 Ml

The resulting reaction solution was heated under reflux with stirring for six hours under nitrogen. After completion of the reaction, the reaction solution was cooled to room temperature, and 2 N hydrochloric acid was then added dropwise to the reaction solution until the pH became 1 to 2. The precipitated solid was collected by filtration and then dried in a vacuum dryer at 80° C. for 12 hours to obtain 5.30 g of intermediate compound Int1-2 (yield 98%).

Reaction Step 3 (Synthesis of Intermediate Compound Int1-3)

The following reagent and solvent were placed in a 100 mL recovery flask.

Int1-2: 5.00 g (9.84 mmol)

Concentrated sulfuric acid: 17 mL

The resulting reaction solution was heated with stirring at 80° C. for 12 hours under nitrogen. After completion of the reaction, the reaction solution was cooled to room temperature and then poured into crushed ice, and stirring was performed for one hour. The precipitated solid was collected by filtration, washed with ion-exchange water, and then dried in a vacuum dryer at 80° C. for 12 hours.

The resulting crude product was recrystallized with a dichloromethane/methanol solvent to obtain 4.18 g of intermediate compound Int1-3 (yield 90%).

Reaction Step 4 (Synthesis of Exemplary Compound A-1)

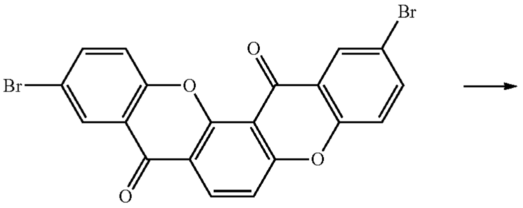

Int1-3

-continued

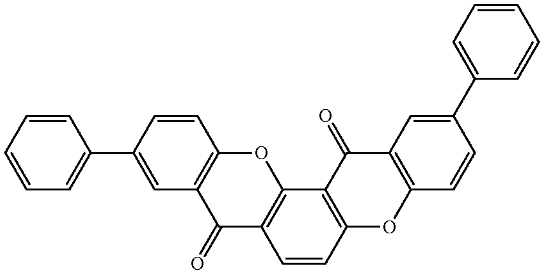

A-1

The following reagents and solvents were placed in a 50 mL recovery flask.

Int1-3: 0.500 g (1.06 mmol)
Phenylboronic acid (manufactured by Tokyo Chemical Industry Co., Ltd.): 0.284 g (2.33 mmol)
Sodium carbonate: 0.617 g (5.83 mmol)
Tetrakis(triphenylphosphine)palladium(0): 0.122 g (0.106 mmol)
Toluene: 10 mL
Ion-exchange water: 3 mL The resulting reaction solution was heated under reflux with stirring for 18 hours under nitrogen. After completion of the reaction, the reaction solution was cooled to room temperature, an organic layer was then separated and dried with magnesium sulfate, and filtration was performed. The solvent of the resulting filtrate was distilled off under reduced pressure, and the precipitated solid was purified with a silica gel column (chloroform:heptane=3:1). The resulting crystals were dried in a vacuum dryer at 80° C. for 12 hours to obtain 0.420 g of exemplary compound A-1 (yield 85%).

By matrix assisted laser desorption/ionization time of flight mass spectrometry (MALDI-TOF MS), 466.1, which was $M^+$ of this compound, was confirmed.

Exemplary Embodiments 2 to 6 (Synthesis of Exemplary Compounds)

Exemplary compounds shown in Table 2 were synthesized as in Exemplary Embodiment 1 except that phenylboronic acid was changed to the boronic acid compounds shown in Table 2 in the reaction step 4 of Exemplary Embodiment 1.

TABLE 2

| Exemplary | Exemplary compound | | |
|---|---|---|---|
| Embodiment | Number | Structure | Boronic acid compound |
| 2 | A-4 | 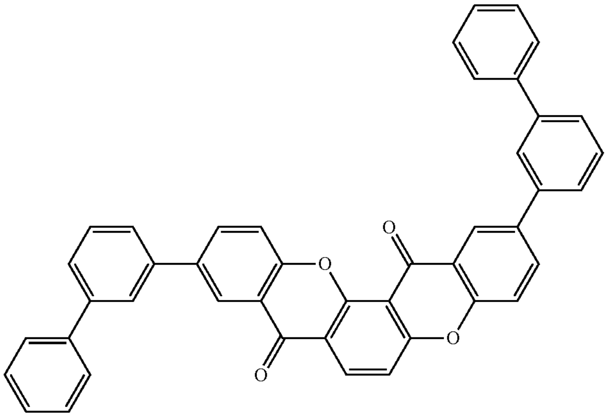 [SMILES: O=c1c2cc(-c3cccc(-c4ccccc4)c3)ccc2oc2c1ccc1oc3ccc(-c4cccc(-c5ccccc5)c4)cc3c(=O)c12] | 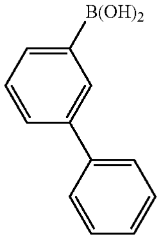 [SMILES: OB(O)c1cccc(-c2ccccc2)c1] |
| 3 | A-6 | 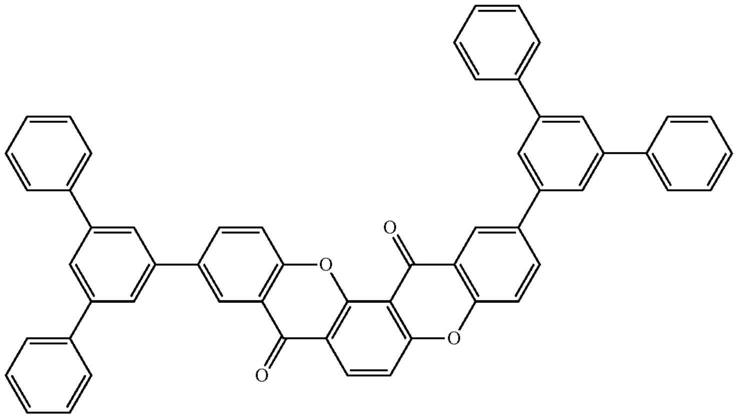 [SMILES: O=c1c2cc(-c3cc(-c4ccccc4)cc(-c4ccccc4)c3)ccc2oc2c1ccc1oc3ccc(-c4cc(-c5ccccc5)cc(-c5ccccc5)c4)cc3c(=O)c12] | 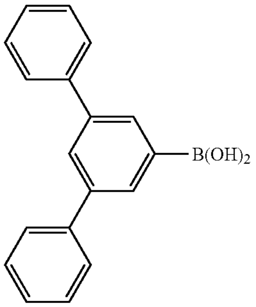 [SMILES: OB(O)c1cc(-c2ccccc2)cc(-c2ccccc2)c1] |

TABLE 2-continued
| Exemplary Embodiment | Exemplary compound Number | Exemplary compound Structure | Boronic acid compound |
|---|---|---|---|
| 4 | A-12 | 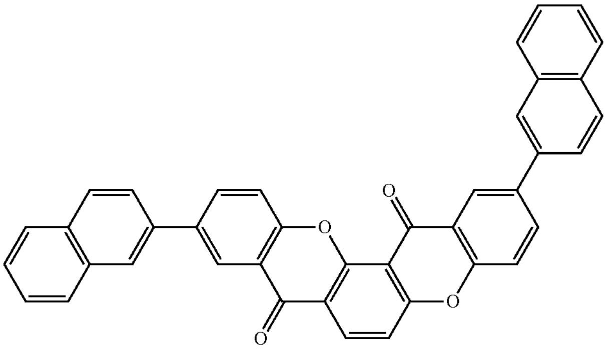 [SMILES: O=c1c2cc(-c3ccc4ccccc4c3)ccc2oc2c1ccc1oc3ccc(-c4ccc5ccccc5c4)cc3c(=O)c12] | 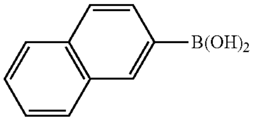 [SMILES: OB(O)c1ccc2ccccc2c1] |
| 5 | A-17 | 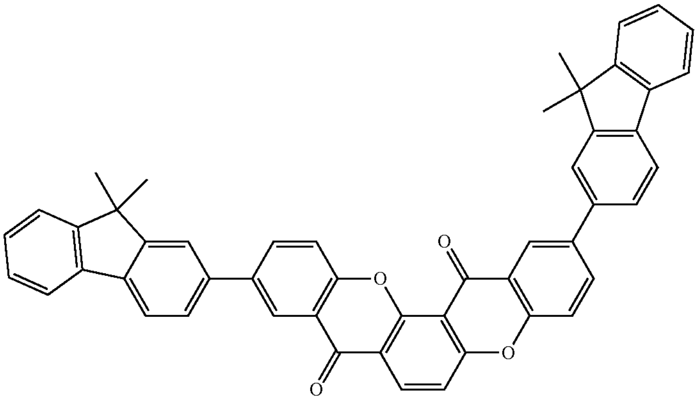 [SMILES: CC1(C)c2ccccc2-c2ccc(-c3ccc4oc5c(ccc6oc7ccc(-c8ccc9c(c8)C(C)(C)c8ccccc8-9)cc7c(=O)c65)c(=O)c4c3)cc21] | 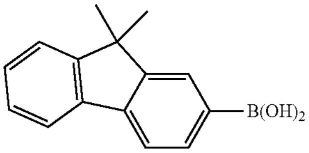 [SMILES: CC1(C)c2ccccc2-c2ccc(B(O)O)cc21] |
| 6 | A-18 | 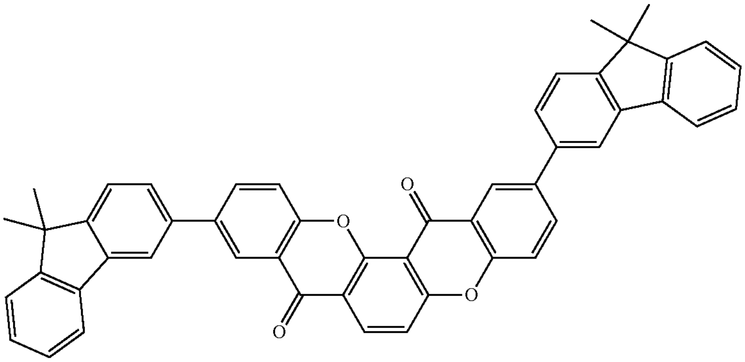 [SMILES: CC1(C)c2ccccc2-c2cc(-c3ccc4oc5c(ccc6oc7ccc(-c8ccc9c(c8)-c8ccccc8C9(C)C)cc7c(=O)c65)c(=O)c4c3)ccc21] | 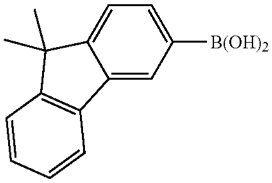 [SMILES: CC1(C)c2ccccc2-c2cc(B(O)O)ccc21] |

Exemplary Embodiment 7 (Synthesis of Exemplary Compound C-1)

Reaction Steps 1 to 3 (Synthesis of Intermediate Compounds Int2-1 to Int2-3)

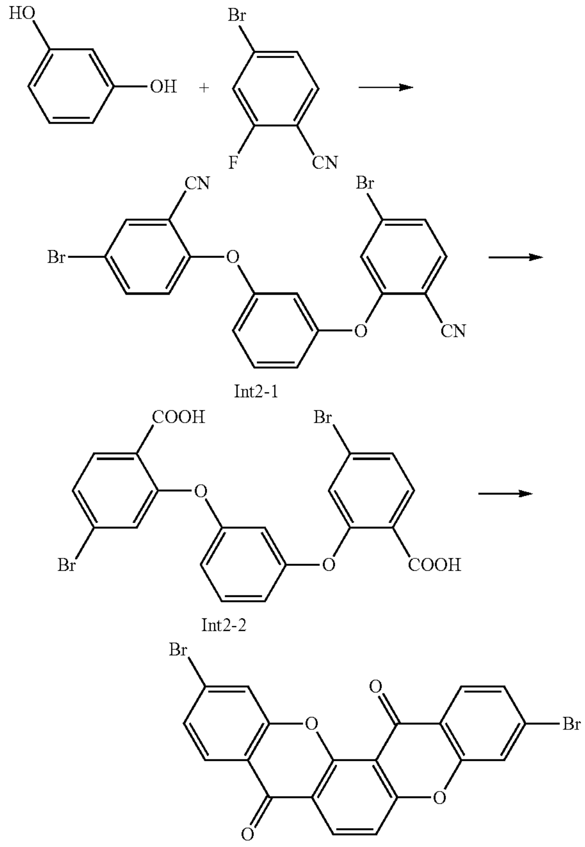

Int2-1

Int2-2

Int2-3

Intermediate compounds Int2-1 to Int2-3 were synthesized as in the reaction steps 1 to 3 of Exemplary Embodiment 1 except that 5-bromo-2-fluorobenzonitrile was changed to 4-bromo-2-fluorobenzonitrile in the reaction step 1 of Exemplary Embodiment 1.

Reaction Step 4 (Synthesis of Exemplary Compound C-1)

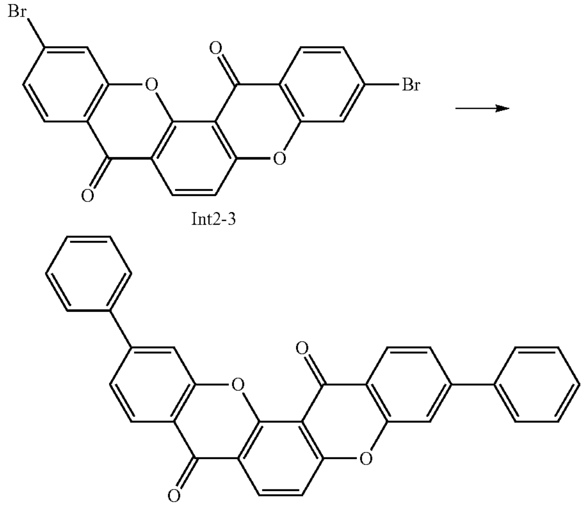

Int2-3

C-1

Exemplary compound C-1 was synthesized as in the reaction step 4 of Exemplary Embodiment 1 except that intermediate compound Int1-3 was changed to intermediate compound Int2-3 in the reaction step 4 of Exemplary Embodiment 1.

Exemplary Embodiments 8 to 12 (Synthesis of exemplary compounds) Exemplary compounds shown in Table 3 were synthesized as in Exemplary Embodiment 7 except that phenylboronic acid was changed to the boronic acid compounds shown in Table 3 in the reaction step 4 of Exemplary Embodiment 7.

TABLE 3

| Exemplary Embodiment | Exemplary compound Number | Exemplary compound Structure | Boronic acid compound |
|---|---|---|---|
| 8 | C-3 | 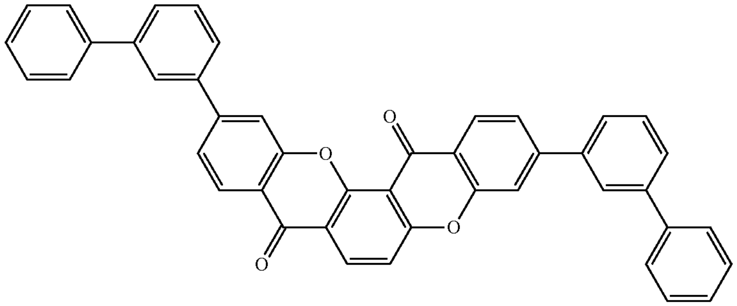 [SMILES: O=c1c2ccc(-c3cccc(-c4ccccc4)c3)cc2oc2c1ccc1oc3cc(-c4cccc(-c5ccccc5)c4)ccc3c(=O)c12] | 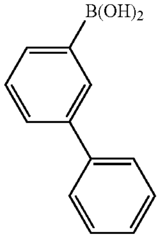 [SMILES: OB(O)c1cccc(-c2ccccc2)c1] |

TABLE 3-continued
| Exemplary Embodiment | Exemplary compound Number | Exemplary compound Structure | Boronic acid compound |
|---|---|---|---|
| 9 | C-5 | 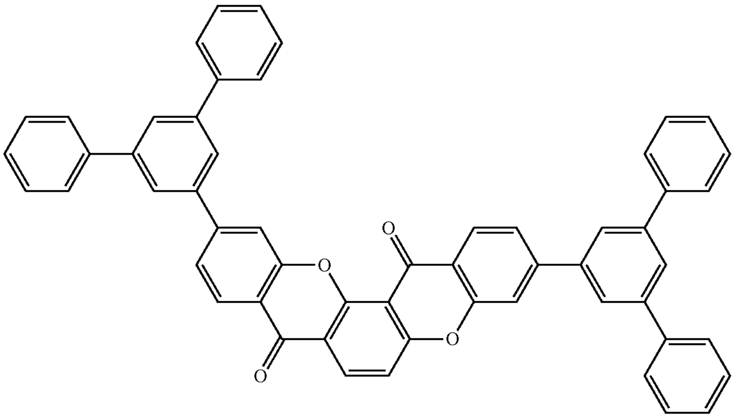 [SMILES: O=c1c2ccc(-c3cc(-c4ccccc4)cc(-c4ccccc4)c3)cc2oc2c1ccc1oc3cc(-c4cc(-c5ccccc5)cc(-c5ccccc5)c4)ccc3c(=O)c12] | 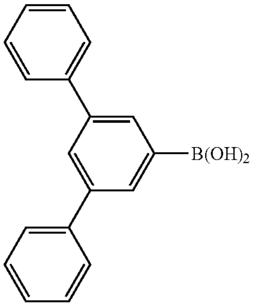 [SMILES: OB(O)c1cc(-c2ccccc2)cc(-c2ccccc2)c1] |
| 10 | C-9 | 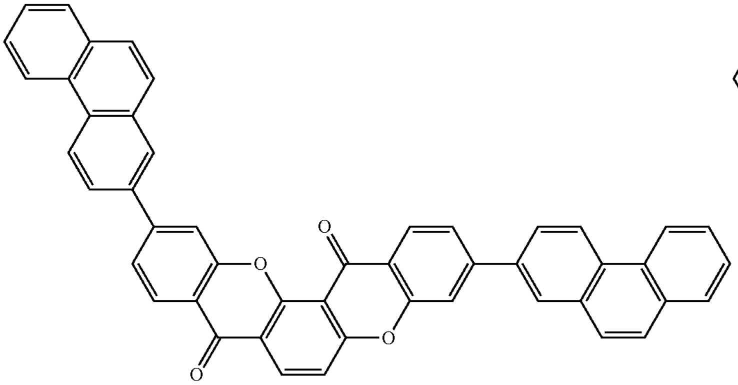 [SMILES: O=c1c2ccc(-c3ccc4c(ccc5ccccc54)c3)cc2oc2c1ccc1oc3cc(-c4ccc5c(ccc6ccccc65)c4)ccc3c(=O)c12] | 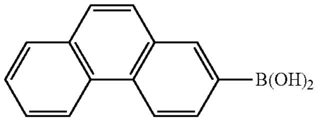 [SMILES: OB(O)c1ccc2c(ccc3ccccc32)c1] |
| 11 | C-10 | 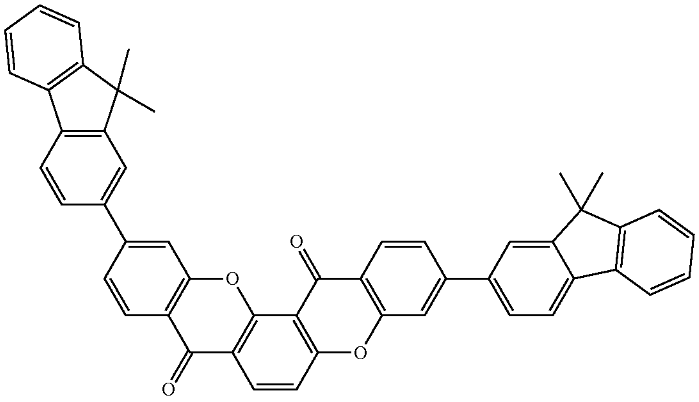 [SMILES: CC1(C)c2ccccc2-c2ccc(-c3ccc4c(=O)c5ccc6oc7cc(-c8ccc9c(c8)C(C)(C)c8ccccc8-9)ccc7c(=O)c6c5oc4c3)cc21] | 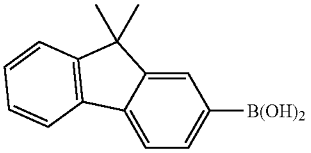 [SMILES: CC1(C)c2ccccc2-c2ccc(B(O)O)cc21] |

TABLE 3-continued

| Exemplary Embodiment | Exemplary compound Number | Exemplary compound Structure | Boronic acid compound |
|---|---|---|---|
| 12 | C-11 | 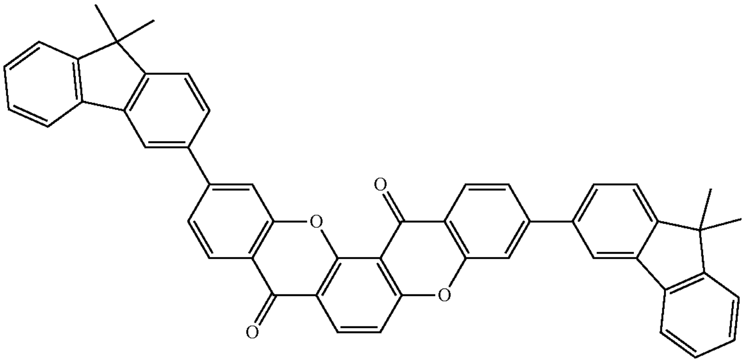 [SMILES: CC1(C)c2ccccc2-c2cc(-c3ccc4c(=O)c5ccc6oc7cc(-c8ccc9c(c8)-c8ccccc8C9(C)C)ccc7c(=O)c6c5oc4c3)ccc21] | 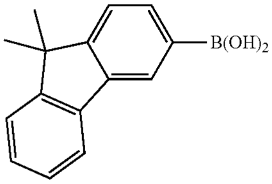 [SMILES: CC1(C)c2ccccc2-c2cc(B(O)O)ccc21] |

Exemplary Embodiments 13 and 14 (Synthesis of Exemplary Compounds A-40 and C-19)

Exemplary compounds A-40 and C-19 were synthesized as in the reaction steps 1 to 3 of Exemplary Embodiment 1 except that 5-bromo-2-fluorobenzonitrile was changed to 5-methyl-2-fluorobenzonitrile (manufactured by Tokyo Chemical Industry Co., Ltd.) or 4-methyl-2-fluorobenzonitrile (manufactured by Tokyo Chemical Industry Co., Ltd.) in the reaction step 1 of Exemplary Embodiment 1.

A-40

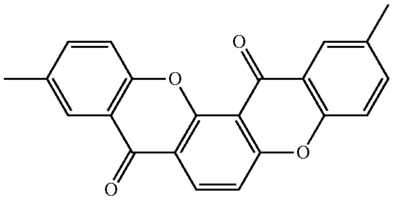

C-19

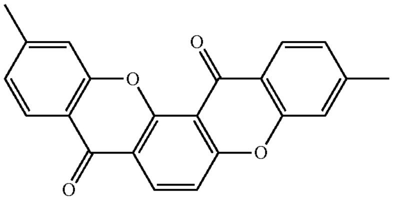

Comparative Example 1 (Synthesis of CXD)

CXD was synthesized as in the reaction steps 1 to 3 of Exemplary Embodiment 1 except that 5-bromo-2-fluorobenzonitrile was changed to 2-fluorobenzonitrile (manufactured by Tokyo Chemical Industry Co., Ltd.) in the reaction step 1 of Exemplary Embodiment 1.

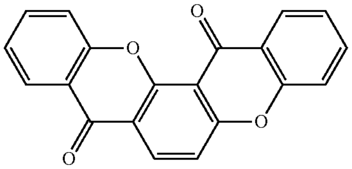

CXD

Exemplary Embodiment 15

A bottom-emission-type organic light-emitting element was produced in which an anode, a hole injection layer, a hole transport layer, an electron-blocking layer, a light-emitting layer, a hole-blocking layer, an electron transport layer, an electron injection layer, and a cathode were sequentially formed on a substrate.

First, ITO was deposited on a glass substrate, and the resulting ITO film was subjected to a desired pattering to form an ITO electrode (anode). The ITO electrode had a film thickness of 100 nm. The substrate on which the ITO electrode was formed in this manner was used as an ITO substrate in the following steps. Next, the organic compound layers and the electrode layer shown in Table 4 below were successively deposited on the ITO substrate by resistance-heating vacuum vapor deposition in a vacuum chamber at $1.33 \times 10^{-4}$ Pa. The area of the electrode (metal electrode layer, i.e., cathode) facing the anode was adjusted to 3 $mm^2$.

TABLE 4

| | Material | | | Thickness (nm) |
|---|---|---|---|---|
| Cathode | | Al | | 100 |
| Electron injection layer (EIL) | | LiF | | 1 |
| Electron transport layer (ETL) | | ET2 | | 20 |
| Hole-blocking layer (HBL) | | ET11 | | 20 |
| Light-emitting layer (EML) | Host | A-1 | Mass ratio | |
| | Guest | AA2 | A-1:AA2 = 90:10 | 20 |

TABLE 4-continued

| | Material | Thickness (nm) |
|---|---|---|
| Electron-blocking layer (EBL) | HT19 | 15 |
| Hole transport layer (HTL) | HT3 | 30 |
| Hole injection layer (HIL) | HT16 | 5 |

Characteristics of the element produced as described above were measured and evaluated. The light-emitting element had a maximum emission wavelength of 522 nm and a maximum external quantum efficiency (E.Q.E) of 13%.

Furthermore, a continuous driving test was conducted at a current density of 100 $mA/cm^2$ to measure the time taken for a luminance degradation rate to reach 5%. When the time taken for the luminance degradation rate to reach 5% in Comparative Example 2 was assumed to be a reference (1.0), this exemplary embodiment had a 5% luminance degradation time ratio of 1.4.

In this exemplary embodiment, with regard to measurement devices, specifically, the current-voltage characteristics were measured with a microammeter 4140B manufactured by Hewlett-Packard, and the emission luminance was measured with a luminance colorimeter BM7 manufactured by Topcon Corporation.

Exemplary Embodiments 16 to 24 and Comparative Example 2

Organic light-emitting elements were produced in the same manner as in Exemplary Embodiment 15 except that the host and the guest were changed to the compounds shown in Table 5. Characteristics of the resulting elements were measured and evaluated as in Exemplary Embodiment 15. The measurement results are shown in Table 5.

TABLE 5

| | EML | | E.Q.E | 5% Luminance degradation |
|---|---|---|---|---|
| | Host | Guest | [%] | time ratio |
| Exemplary Embodiment 16 | A-4 | AA2 | 13 | 1.5 |
| Exemplary Embodiment 17 | A-4 | AA24 | 14 | 1.4 |
| Exemplary Embodiment 18 | A-6 | AA2 | 13 | 1.4 |
| Exemplary Embodiment 19 | A-12 | AA2 | 13 | 1.1 |
| Exemplary Embodiment 20 | A-40 | AA2 | 11 | 1.1 |
| Exemplary Embodiment 21 | C-1 | AA2 | 12 | 1.2 |
| Exemplary Embodiment 22 | C-3 | AA2 | 13 | 1.5 |
| Exemplary Embodiment 23 | C-9 | AA2 | 13 | 1.4 |
| Exemplary Embodiment 24 | C-11 | AA2 | 12 | 1.1 |
| Comparative Example 2 | CXD | AA2 | 10 | 1.0 |

Exemplary Embodiment 25

An organic light-emitting element was produced in the same manner as in Exemplary Embodiment 15 except that the organic compound layers and the electrode layer shown in Table 6 were successively deposited.

TABLE 6

| | | Material | | Thickness (nm) |
|---|---|---|---|---|
| Cathode | | Al | | 100 |
| Electron injection layer (EIL) | | LiF | | 1 |
| Electron transport layer (ETL) | | ET2 | | 20 |
| Hole-blocking layer (HBL) | | ET11 | | 20 |
| Light-emitting layer (EML) | Host | A-1 | Mass ratio A-1:EM11:AA22 = 55:35:10 | 20 |
| | Assist (Second host) | EM11 | | |
| | Guest | AA22 | | |
| Electron-blocking layer (EBL) | | HT19 | | 15 |
| Hole transport layer (HTL) | | HT3 | | 30 |
| Hole injection layer (HIL) | | HT16 | | 5 |

Characteristics of the element produced as described above were measured and evaluated as in Exemplary Embodiment 15. The light-emitting element had a maximum emission wavelength of 522 nm and a maximum external quantum efficiency (E.Q.E) of 19%. Furthermore, when the time taken for the luminance degradation rate to reach 5% in Comparative Example 3 was assumed to be a reference (1.0), this exemplary embodiment had a 5% luminance degradation time ratio of 1.4.

Exemplary Embodiments 26 to 34 and Comparative Example 3

Organic light-emitting elements were produced in the same manner as in Exemplary Embodiment 25 except that the compounds shown in Table 7 were used. Characteristics of the resulting elements were measured and evaluated as in Exemplary Embodiment 25. The measurement results are shown in Table 7.

TABLE 7

| | EML | | | E.Q.E | 5% Luminance degradation |
|---|---|---|---|---|---|
| | Host | Assist | Guest | [%] | time ratio |
| Exemplary Embodiment 26 | A-4 | EM11 | AA2 | 19 | 1.5 |
| Exemplary Embodiment 27 | A-4 | EM11 | AA24 | 20 | 1.4 |
| Exemplary Embodiment 28 | A-6 | EM11 | AA2 | 18 | 1.6 |
| Exemplary Embodiment 29 | A-6 | EM34 | AA2 | 17 | 1.3 |
| Exemplary Embodiment 30 | A-17 | EM11 | AA2 | 16 | 1.3 |
| Exemplary Embodiment 31 | A-18 | EM11 | AA2 | 18 | 1.2 |
| Exemplary Embodiment 32 | C-5 | EM11 | AA2 | 17 | 1.5 |
| Exemplary Embodiment 33 | C-10 | EM11 | AA2 | 16 | 1.4 |
| Exemplary Embodiment 34 | C-19 | EM11 | AA2 | 15 | 1.2 |
| Comparative Example 3 | CXD | EM11 | AA2 | 14 | 1.0 |

As shown in Table 7, when the organic compounds according to this embodiment were used as the host, and materials having a carbazole skeleton, a triphenylene skeleton, or the like and being suitable for combinations with the organic compounds according to this embodiment were further used as the second host material, the light emission efficiency and durability characteristics of the elements were improved.

According to the present disclosure, an organic compound having good light emission efficiency and durability characteristics can be provided.

The organic compound according to the present disclosure can be used as a host molecule of a light-emitting layer to provide an organic light-emitting element having good light emission efficiency and durability characteristics.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-094225 filed Jun. 10, 2022, which is hereby incorporated by reference herein in its entirety.

What is claimed is:

1. An organic compound represented by formula [1]:

[1]

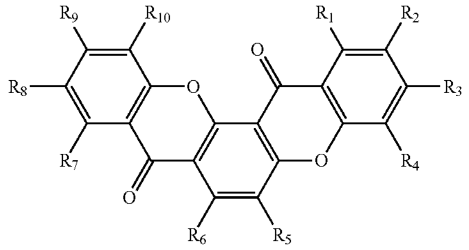

wherein, in formula [1], $R_1$ to $R_{10}$ are each independently selected from the group consisting of a hydrogen atom, a deuterium atom, a substituted or unsubstituted alkyl group, a substituted or unsubstituted aryl group, and a substituted or unsubstituted heterocyclic group, provided that $R_2$ and $R_8$ are selected from the group consisting of a substituted or unsubstituted alkyl group, a substituted or unsubstituted aryl group, and a substituted or unsubstituted heterocyclic group.

2. The organic compound according to claim 1, wherein at least one of $R_2$ and $R_8$ is selected from the group consisting of a substituted or unsubstituted aryl group and a substituted or unsubstituted heterocyclic group.

3. An organic light-emitting element comprising:

a pair of electrodes; and a light-emitting layer disposed between the pair of electrodes, wherein the light-emitting layer contains a first compound and a second compound, and the first compound is an organic compound represented by formula [1];

[1]

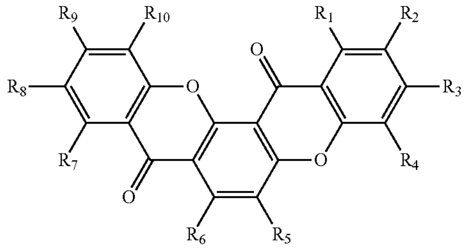

wherein, in formula [1], $R_1$ to $R_{10}$ are each independently selected from the group consisting of a hydrogen atom, a deuterium atom, a substituted or unsubstituted alkyl group, a substituted or unsubstituted aryl group, and a substituted or unsubstituted heterocyclic group, provided that at least one of $R_2$, $R_3$, $R_8$, and $R_9$ is selected from the group consisting of a deuterium atom, a substituted or unsubstituted alkyl group, a substituted or unsubstituted aryl group, and a substituted or unsubstituted heterocyclic group.

4. The organic light-emitting element according to claim 3, wherein the second compound is an organometallic complex represented by formula [2]:

$$M(L)_m(L')_n \quad [2]$$

in formula [2], M is selected from the group consisting of iridium and platinum;

L and L' represent bidentate ligands different from each other;

in a case that m is greater than 1, Ls may be the same or different, and in a case that n is greater than 1, L's may be the same or different;

m is an integer of 1 to 3, and n is an integer of 0 to 2, provided that when M is iridium, m+n=3, and when M is platinum, m+n=2;

a partial structure M (L) m is represented by formula [2-1]:

[2-1]

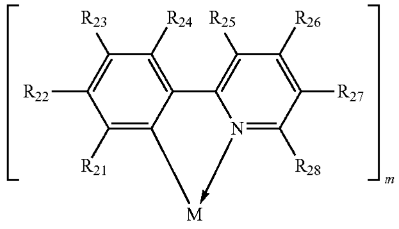

in formula [2-1], $R_{21}$ to $R_{28}$ are each independently selected from the group consisting of a hydrogen atom, a deuterium atom, a halogen atom, a substituted or unsubstituted alkyl group, a substituted or unsubstituted alkoxy group, a substituted or unsubstituted silyl group, a substituted or unsubstituted aryl group, a substituted or unsubstituted heterocyclic group, a substituted or unsubstituted amino group, a substituted or unsubstituted aryloxy group, a substituted or unsubstituted heteroaryloxy group, and a cyano group; adjacent $R_{21}$ to $R_{28}$ are optionally bonded together to form a ring; and a partial structure $M(L')_n$ is represented by formula [2-2]:

[2-2]

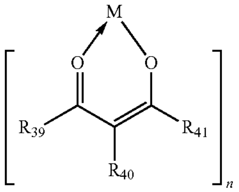

in formula [2-2], $R_{39}$ to $R_{41}$ are each independently selected from the group consisting of a hydrogen atom, a deuterium atom, a halogen atom, a substituted or unsubstituted alkyl group, a substituted or unsubstituted alkoxy group, a substituted or unsubstituted silyl group, a substituted or unsubstituted aryl group, a substituted or unsubstituted heterocyclic group, a substituted or unsubstituted amino group, a substituted or unsubstituted aryloxy group, a substituted or unsubstituted heteroaryloxy group, and a cyano group.

5. The organic light-emitting element according to claim 4, wherein M is iridium.

6. The organic light-emitting element according to claim 4, wherein the partial structure M (L) m has a fused ring including three or more rings.

7. The organic light-emitting element according to claim 6, wherein the fused ring including three or more rings is a ring selected from the group consisting of a phenanthrene ring, a triphenylene ring, a benzofluorene ring, a dibenzofuran ring, a dibenzothiophene ring, a benzonaphthofuran ring, a benzonaphthothiophene ring, a benzoisoquinoline ring, and a naphthoisoquinoline ring.

8. The organic light-emitting element according to claim 4, wherein, in formula [2-1], at least one of $R_{22}$, $R_{23}$, $R_{26}$, and $R_{27}$ is selected from the group consisting of a substituted or unsubstituted aryl group and a substituted or unsubstituted heterocyclic group.

9. The organic light-emitting element according to claim 3, wherein the light-emitting layer further contains a third compound.

10. The organic light-emitting element according to claim 9, wherein the third compound has at least a carbazole skeleton.

11. The organic light-emitting element according to claim 9, wherein the third compound has at least a triphenylene ring in a skeleton.

12. The organic light-emitting element according to claim 9, wherein the third compound has at least a dibenzothiophene skeleton.

13. The organic light-emitting element according to claim 3, further comprising:

another light-emitting layer stacked on the light-emitting layer, wherein the other light-emitting layer emits light of a color different from a color of light emitted from the light-emitting layer.

14. The organic light-emitting element according to claim 13, wherein the organic light-emitting element emits white light.

15. A display apparatus comprising a plurality of pixels, wherein at least one of the plurality of pixels includes the organic light-emitting element according to claim 7 and a transistor connected to the organic light-emitting element.

16. A photoelectric conversion apparatus comprising:

an optical unit that includes a plurality of lenses;

an image pickup element configured to receive light that has passed through the optical unit; and a display unit configured to display an image captured by the image pickup element, wherein the display unit includes the organic light-emitting element according to claim 3.

17. An electronic apparatus comprising:

a display unit including the organic light-emitting element according to claim 3;

a housing in which the display unit is disposed; and a communication unit that is disposed in the housing and configured to communicate with an external unit.

18. An illumination apparatus comprising:

a light source that includes the organic light-emitting element according to claim 3; and a light diffusion unit or an optical filter configured to transmit light emitted from the light source.

19. A moving object comprising:

a lighting fixture that includes the organic light-emitting element according to claim 3; and a body on which the lighting fixture is disposed.

20. An exposure light source for an electrophotographic image forming apparatus, the exposure light source comprising the organic light-emitting element according to claim 3.

* * * * *